(12) United States Patent
Becker et al.

(10) Patent No.: US 8,937,065 B2
(45) Date of Patent: Jan. 20, 2015

(54) COMPOSITIONS AND METHODS FOR MODULATING A KINASE

(75) Inventors: Oren M. Becker, Mevasseret Zion (IL); Itai Bloch, Rehovot (IL); Efrat Ben-Zeev, Kiryat Motzkin (IL); Alina Shitrit, Tel-Aviv (IL); Avihai Yacovan, Gedera (IL); Sharon Gazal, Rehovot (IL); Vered Behar, Moshav Bet Zayit (IL); Alexander Konson, Beersheba (IL); Nili Schutz, Tel-Aviv (IL); Sima Mirilashvili, Lod (IL); Gali Golan, Shoeva (IL)

(73) Assignee: Clevexel Pharma, Maisons-Alfrot Cedex (FR)

( * ) Notice: Subject to any disclaimer, the term of this patent is extended or adjusted under 35 U.S.C. 154(b) by 40 days.

(21) Appl. No.: 13/491,069

(22) Filed: Jun. 7, 2012

(65) Prior Publication Data
US 2012/0316148 A1 Dec. 13, 2012

Related U.S. Application Data

(60) Provisional application No. 61/520,256, filed on Jun. 7, 2011, provisional application No. 61/562,700, filed on Nov. 22, 2011, provisional application No. 61/640,139, filed on Apr. 30, 2012.

(51) Int. Cl.
| | | |
|---|---|---|
| *A61K 31/5377* | (2006.01) |
| *A61K 31/427* | (2006.01) |
| *C07D 413/14* | (2006.01) |
| *C07D 417/14* | (2006.01) |
| *C07D 417/12* | (2006.01) |
| *C07D 417/04* | (2006.01) |
| *C07D 471/04* | (2006.01) |
| *C07D 487/04* | (2006.01) |
| *C07D 491/113* | (2006.01) |
| *C07D 491/147* | (2006.01) |
| *C07D 495/04* | (2006.01) |
| *C07D 495/22* | (2006.01) |
| *C07D 513/04* | (2006.01) |

(52) U.S. Cl.
CPC ............ *C07D 417/04* (2013.01); *C07D 417/12* (2013.01); *A61K 31/427* (2013.01); *C07D 413/14* (2013.01); *A61K 31/5377* (2013.01); *C07D 417/14* (2013.01); *C07D 471/04* (2013.01); *C07D 487/04* (2013.01); *C07D 491/113* (2013.01); *C07D 491/147* (2013.01); *C07D 495/04* (2013.01); *C07D 495/22* (2013.01); *C07D 513/04* (2013.01)
USPC ........ 514/236.8; 514/365; 514/370; 544/133; 548/190; 548/204

(58) Field of Classification Search
CPC ............. A61K 31/5377; A61K 31/427; C07D 417/12; C07D 417/14; C07D 413/14
USPC ........... 548/204, 190; 544/133; 514/365, 370, 514/236.8
See application file for complete search history.

(56) References Cited

PUBLICATIONS

Registry No. 1225040-09-4, STN File Registry, entered STN May 25, 2010.*
Sawhney et al., Indian Journal of Chemistry,, 15(8), 1977, pp. 727-730.*

* cited by examiner

*Primary Examiner* — Rebecca Anderson
(74) *Attorney, Agent, or Firm* — Porzio, Bromberg & Newman, P.C.

(57) ABSTRACT

The invention relates to compounds and methods for modulating one or more components of a kinase signaling cascade.

11 Claims, 19 Drawing Sheets

COMPOSITIONS AND METHODS FOR MODULATING A KINASE

RELATED APPLICATIONS

This application claims priority under 35 U.S.C. 119(e) to U.S. Provisional Application Nos. 61/520,256, filed Jun. 7, 2011; 61/562,700, filed Nov. 22, 2011; and 61/640,139, filed Apr. 30, 2012. The entire teachings of the above applications are incorporated herein by reference.

BACKGROUND OF THE INVENTION

Signal transduction is any process by which a cell converts one kind of signal or stimulus into another. Signal transduction processes often involve a sequence of biochemical reactions inside the cell, which are carried out by enzymes and linked through second messengers. In many transduction processes, an increasing number of enzymes and other molecules become engaged in the events that proceed from the initial stimulus. In such cases the chain of steps is referred to as a "signaling cascade" or a "second messenger pathway" and often results in a small stimulus eliciting a large response. One class of molecules involved in signal transduction is the kinase family of enzymes. The largest group of kinases is protein kinases, which act on and modify the activity of specific proteins. These are used extensively to transmit signals and control complex processes in cells.

Protein kinases are a large class of enzymes which catalyze the transfer of the α-phosphate from ATP to the hydroxyl group on the side chain of Ser/Thr or Tyr in proteins and peptides and are intimately involved in the control of various important cell functions, perhaps most notably: growth, proliferation, differentiation, survival, adhesion, migration. There are estimated to be about 2,000 distinct protein kinases in the human body, and although each of these phosphorylate particular protein/peptide substrates, they all bind the same second substrate, ATP, in a highly conserved pocket. Protein phosphatases catalyze the transfer of phosphate in the opposite direction.

A tyrosine kinase is an enzyme that can transfer a phosphate group from ATP to a tyrosine residue in a protein. Phosphorylation of proteins by kinases is an important mechanism in signal transduction for regulation of enzyme activity. The tyrosine kinases are divided into two groups; those that are cytoplasmic proteins and the transmembrane receptor-linked kinases. In humans, there are 32 cytoplasmic protein tyrosine kinases and 58 receptor-linked protein-tyrosine kinases. The hormones and growth factors that act on cell surface tyrosine kinase-linked receptors are generally growth-promoting and function to stimulate cell division (e.g., insulin, insulin-like growth factor 1, epidermal growth factor).

Inhibitors of various known protein kinases or protein phosphatases have a variety of therapeutic applications. One promising potential therapeutic use for protein kinase or protein phosphatase inhibitors is as anti-cancer agents. About 50% of the known oncogene products are protein tyrosine kinases (PTKs) and their kinase activity has been shown to lead to cell transformation.

Because kinases are involved in the regulation of a wide variety of normal cellular signal transduction pathways (e.g., cell growth, proliferation, differentiation, survival, adhesion, migration, etc.), kinases are thought to play a role in a variety of diseases and disorders. Thus, modulation of kinase signaling cascades may be an important way to treat or prevent such diseases and disorders.

SUMMARY OF THE INVENTION

Compounds of the invention may be useful for modulating one or more components involved in a normal cellular signal transduction pathway (e.g., cell growth, proliferation, differentiation, survival, adhesion, migration, etc.), or one involved in a disease or disorder. Such diseases and disorders include, without limitation, cell proliferative disorders including, cancers; inflammatory disorders; immune disorders including, autoimmune disorders, immune system dysfunction, and transplant rejection, and dry eye disease (xerophthalmia). For example, compounds of the invention may be useful as modulators (e.g., inhibitors) of a tyrosine kinase e.g., one or more components of a kinase signaling cascade, such as JAK, SYK, and/or BTK.

Compounds of the invention may also be useful in treating diseases and disorders that are modulated by a signal transduction pathway, such as a pathway modulated by a spleen tyrosine kinase (SYK) e.g., the BCR signaling pathway. For example, compounds of the invention may be useful in treating diseases and disorders that are modulated by SYK inhibition. Compounds of the invention may also be useful in treating diseases and disorders that are additionally or alternatively, modulated by a signal transduction pathway that does not include a spleen tyrosine kinase.

Compounds of the invention may also be useful in treating diseases and disorders that are modulated by a signal transduction pathway, such as a pathway modulated by a Bruton's tyrosine kinase (BTK). For example, compounds of the invention may be useful in treating diseases and disorders that are modulated by BTK inhibition. Compounds of the invention may also be useful in treating diseases and disorders that are additionally or alternatively, modulated by a signal transduction pathway that does not include a Bruton's tyrosine kinase.

Compounds of the invention may also be useful in treating diseases and disorders that are modulated by a signal transduction pathway, such as a pathway modulated by a Janus kinase (JAK). For example, compounds of the invention may be useful in treating diseases and disorders that are modulated by JAK inhibition (e.g., JAK3). Compounds of the invention may also be useful in treating diseases and disorders that are additionally or alternatively, modulated by a signal transduction pathway that does not include a Janus kinase.

For example, the compounds of the invention may be useful as anti-proliferative agents, for treating mammals, such as for treating humans and animals. Compounds of the invention may be used without limitation, for example, as anti-cancer, anti-inflammatory and/or immunosuppressive agents.

In one aspect, the invention includes a compound of Formula I:

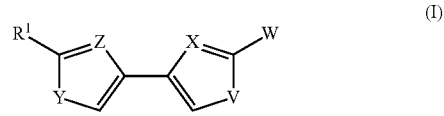

(I)

or a pharmaceutically acceptable salt, solvate, polymorph, or prodrug thereof, wherein $R^1$, Y, Z, X, V, and W are as described herein.

In one aspect, a compound of the invention may be used as a pharmaceutical agent. For example, a compound of the invention is used as an anti-proliferative agent, for treating humans and/or animals, such as for treating humans and/or other mammals. A compound of the invention may be used without limitation, for example, as anti-cancer, anti-inflammatory and/or immunosuppressive agents. Additionally, a compound of the invention may be used for cell proliferation-related disorders and autoimmune disorders. A compound of the invention may be used for dry eye disease.

In one aspect, a compound of the invention may be used to treat or prevent a cell proliferation disorder in a subject. In one aspect, the cell proliferation disorder is pre-cancer or cancer. In another aspect, the cell proliferation disorder is a hyperproliferative disorder. In certain embodiments, prevention or treatment of the cell proliferation disorder, cancer or hyperproliferative disorder occurs through the inhibition of a tyrosine kinase, such as JAK (JAK3), SYK, or BTK. In certain embodiments, the subject is a mammal, e.g., a human.

In one aspect, the invention includes methods of treating or preventing cancers and/or cell proliferation disorders in a subject by administering a pharmaceutical composition that includes an effective amount of a compound of the invention. For example, the cancer or cell proliferation disorder is cancer, pre-cancer or a hyperproliferative disorder. In some embodiments, the foregoing methods are monotherapies for preventing or treating cancer and/or cell proliferation disorder. In some embodiments, the foregoing methods are part of a combination therapy with other therapeutic agents (e.g., a cancer metabolism modulators or a cytotoxic agent) and/or non-drug therapies (e.g., surgery, immunotherapy or radiation treatment). In some embodiments of the combination therapy, the additional therapy is conducted substantially simultaneously or concurrently with the administration of the pharmaceutical composition. In some embodiments, the administration of the pharmaceutical composition is conducted prior to the additional therapy of the combination therapy. In some embodiments, the administration of the pharmaceutical composition is conducted subsequent to the additional therapy. In some embodiments, the pharmaceutical composition is administered chronically (e.g., as part of a maintenance therapy). In some embodiments, the cancer and/or cell proliferation disorder is a cell proliferative disorder of the hematologic system (e.g., leukemia or lymphoma). In some embodiments, the cancer of the hematologic system is leukemia. In some embodiments, the leukemia is myelofibrosis. In some embodiments, the leukemia is acute myelogenous leukemia (AML). In some embodiments, the cell proliferation disorder is selected from polycythaemia vera (erythremia) and essential thrombocythemia. In some embodiments, the cancer and/or cell proliferation disorder is a cell proliferative disorder of the lung (e.g., lung cancer). In some embodiments, the cancer and/or cell proliferation disorder is a cell proliferative disorder of the colon (e.g., colon cancer). In some embodiments, the cancer and/or cell proliferation disorder is a cell proliferative disorder of the pancreas (e.g., pancreatic cancer). In some embodiments, the cancer and/or cell proliferation disorder is a cell proliferative disorder of the prostate (e.g., prostate cancer). In some embodiments, the cancer and/or cell proliferation disorder is a cell proliferative disorder of the skin (e.g., a skin cancer). In some embodiments, the cancer and/or cell proliferation disorder is a cell proliferative disorder of the ovary (e.g., ovarian cancer). In some embodiments, the cancer and/or cell proliferation disorder is a cell proliferative disorder of the breast (e.g., breast cancer).

In one aspect, the invention includes a method of regulating immune system activity in a subject comprising administering a compound of the invention. For example, modulating immune system activity includes modulating autoimmune diseases such as transplant rejection (e.g., kidney, heart, lung, liver, pancreas, skin, host versus graft reaction (HVGR), etc.), rheumatoid arthritis, psoriatic arthritis, and amyotrophic lateral sclerosis. In one embodiment, the autoimmune disease is selected from psoriasis, rheumatoid arthritis, and psoriatic arthritis. In one aspect, the invention includes use of a compound of the invention in the manufacture of a medicament to regulate immune system activity. In certain embodiments, regulation of the immune system occurs through the inhibition of lymphocyte proliferation. In certain embodiments, regulation of the immune system occurs through the inhibition of lymphocyte activation. For example, T-cell proliferation and/or activation is inhibited. Additionally or alternatively, B-cell proliferation and/or activation is inhibited. In certain embodiments, the subject is a mammal, e.g., a human. In one aspect, the invention includes use of a compound of the invention in the manufacture of a medicament to treat or prevent an inflammatory disorder or disease. In one embodiment, the inflammatory disease is selected from inflammatory bowel disease and ankylosing spondylitis. In one embodiment the inflammatory bowel disease is selected from ulcerative colitis and Crohn's disease. In one aspect, the invention includes use of a compound of the invention in the manufacture of a medicament to treat or prevent dry eye disease.

In one aspect, administration of a compound of the invention is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one aspect, a compound of the invention is administered with a pharmaceutically acceptable carrier. In one aspect, a compound of the invention is administered before the onset of immune system irregularity. In one aspect, a compound of the invention is administered after the onset of immune system irregularity.

The application is also directed to certain polymorphs of 2-morpholino-N-(3-(4-(5-(pyrrolidine-1-carbonyl)-1H-pyrrol-3-yl)thiazol-2-yl)phenyl)acetamide and of the hydrochloric acid salt of 2-morpholino-N-(3-(4-(5-(pyrrolidine-1-carbonyl)-1H-pyrrol-3-yl)thiazol-2-yl)phenyl)acetamide and pharmaceutical compositions thereof.

The compound 2-morpholino-N-(3-(4-(5-(pyrrolidine-1-carbonyl)-1H-pyrrol-3-yl)thiazol-2-yl)phenyl)acetamide or a pharmaceutically acceptable salt thereof or a polymorph of the compound or salt is useful for modulating one or more components involved in a normal signal transduction pathway (e.g., cell growth, proliferation, differentiation, survival, adhesion, migration, etc.) More specifically, this compound modulates one or more components of a kinase signaling pathway, such as a pathway modulated by Janus kinase (JAK e.g., JAK3), spleen tyrosine kinase (SYK) and/or Bruton's tyrosine kinase (BTK). This compound is useful in treating diseases and disorders that are modulated by a signal transduction pathway. For example, 2-morpholino-N-(3-(4-(5-(pyrrolidine-1-carbonyl)-1H-pyrrol-3-yl)thiazol-2-yl)phenyl)acetamide hydrochloride salt is useful in the treatment of cell proliferative disorders, including cancers; inflammatory disorders; immune disorders, including autoimmune disorders, immune system dysfunction, and transplant rejection; and dry eye disease.

No polymorph forms of 2-morpholino-N-(3-(4-(5-(pyrrolidine-1-carbonyl)-1H-pyrrol-3-yl)thiazol-2-yl)phenyl)acetamide or of a pharmaceutically acceptable salt thereof have been disclosed. However, the crystalline form of a drug may affect, among other physical and mechanical properties, solubility, dissolution rate, hardness, compressability, and melting point. Because these properties may, in turn, affect a drug's manufacture and its utility, there is an existing need in the chemical and therapeutic arts for identification of crystalline forms of drugs and ways of making them. It is disclosed herein that 2-morpholino-N-(3-(4-(5-(pyrrolidine-1-carbonyl)-1H-pyrrol-3-yl)thiazol-2-yl)phenyl)acetamide and the hydrochloride salt of 2-morpholino-N-(3-(4-(5-(pyrrolidine-1-carbonyl)-1H-pyrrol-3-yl)thiazol-2-yl)phenyl)acetamide can each exist as a novel crystalline form. The polymorphs of the present invention exhibit properties that render them superior to previously known compounds and pharmaceutically acceptable salts thereof.

It is contemplated that whenever appropriate, any embodiment of the present invention can be combined with one or more other embodiments of the present invention, even though the embodiments are described under different aspects of the present invention.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION OF THE INVENTION

Figure 1:
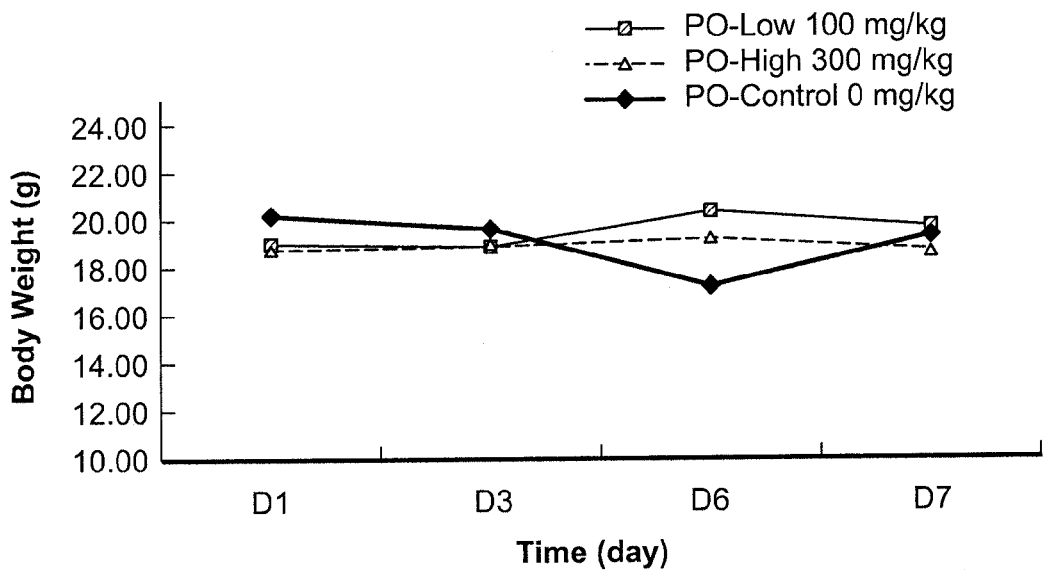
FIG. 1 is a line graph which shows changes in body weight in a 6-day safety study of animals dosed orally with control or compound 7A (100 mg/kg and 300 mg/kg).

The details of one or more embodiments of the invention are set forth in the accompanying description below. Although any methods and materials similar or equivalent to those described herein can be used in the practice or testing of the present invention, some of the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

Because kinases are involved in the regulation of a wide variety of normal cellular signal transduction pathways (e.g., cell growth, proliferation, differentiation, survival, adhesion, migration, etc.), kinases are thought to play a role in a variety of diseases and disorders. Thus, modulation of kinase signaling cascades may be an important way to treat or prevent such diseases and disorders. Such diseases and disorders include, for example, cell proliferative disorders including, cancers; inflammatory disorders; immune disorders including autoimmune disorders, immune system dysfunction, and transplant rejection, and dry eye disease (xerophthalmia).

In one aspect, a compound of the invention may be useful for modulating one or more components involved in a signal transduction pathway to prevent or to treat a disease or disorder in which the pathway plays a role, such as a pathway modulated by a tyrosine kinase e.g., JAK, SYK, and/or BTK. In one aspect, a compound of the invention may be useful for treating such diseases and disorders including, without limitation, cell proliferative disorders including, cancers; inflammatory disorders, immune disorders including, autoimmune disorders, immune system dysfunction, and transplant rejection, and dry eye disease (xerophthalmia).

Janus Kinases

In one aspect, a compound of the invention may be useful for modulating one or more components involved in a signal transduction pathway to prevent or to treat a disease or disorder in which the pathway plays a role, such as a pathway modulated by a Janus kinase (JAK).

The Janus kinases (JAK) are a family of intracellular non-receptor tyrosine kinases consisting of JAK1, JAK2, JAK3 and tyrosine kinase 2 (TYK2). The JAKs play a crucial role in cytokine signaling. The downstream substrates of the JAK family of kinases include the signal transducer activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, 1999, Mol. Med. 5:432:456 and Seidel et al., 2000, Oncogene 19:2645-2656.

JAK3 is a member of the Janus family of protein kinases. Although the other members of this family are expressed by essentially all tissues, JAK3 expression is limited to hematopoietic cells and transduces a signal in response to its activation via tyrosine phosphorylation by interleukin receptors. JAK3 is involved in signal transduction by non-covalent association with receptors that employ the common gamma chain (γC) of the type I cytokine receptor family (e.g. IL-2R, IL-4R, IL-7R, IL-9R, IL-15R, and IL-21R). Mutations that abrogate JAK3 function cause an autosomal SCID (severe combined immunodeficiency disease), suggesting that blocking JAK3 should result with immunosuppression. These observations were supported by animal data which indicated that JAK3 not only plays a role in B and T cell maturation, but it is also required to maintain T cell function (Fujimoto, M. et al., 2000. J. Immunol. 165:1799-806, Baird et al., 2000. J. Immunol. 165:3680-3688).

JAK3 is associated with a variety of human cancers. Individuals with Down syndrome (DS) are predisposed to develop acute megakaryoblastic leukemia (AMKL). The subsequent development of leukemia in DS is often preceded earlier on in life by a transient myeloproliferative disorder (TMD). Acquired mutations in JAK3 have been reported in both DS patients with TMD, and non-DS patients with AMKL (Walters D K, et al., 2006. Cancer Cell. 10:65-75, De Vita S., et al., 2007. Br. J. Haematol. 137:337-341). Further analysis revealed that a point mutation in JAK3 affects its pseudokinase domain and renders the kinase constitutively active. Further support was gained from animal studies where murine bone marrow transfected with different mutations of JAK3 induced several forms of leukemia, leading to a T cell lymphoproliferative disorder or myeloproliferative disease. Modulation or inhibition via this mechanism, therefore, can prove effective for the treatment of immune proliferative disorders, such as autoimmune diseases (e.g., rheumatoid arthritis) or different forms of leukemia. There is thus a need in the art for, inter alia, modulators of signal transduction pathways, such as inhibitors of JAK3.

In one aspect, a compound of the invention may be useful as modulators (e.g., inhibitors) of one or more components of a JAK kinase signaling cascade, such as JAK3. In one aspect, a compound of the invention may be useful in modulation of more than one component of a JAK kinase signaling cascade. In one aspect, a compound of the invention may also be useful in treating diseases and disorders that are additionally or alternatively, modulated by a signal transduction pathway that does not include a Janus kinase.

The phrase "modulates one or more components of a JAK kinase signaling cascade" means that one or more components of the JAK kinase signaling cascade are affected such that the functioning of a cell changes. Components of a protein kinase signaling cascade include any proteins involved directly or indirectly in a JAK kinase signaling pathway including second messengers and upstream and downstream targets.

Spleen Tyrosine Kinase

In one aspect, a compound of the invention may be useful for modulating one or more components involved in a signaling pathway to prevent or to treat a disease or disorder in which the pathway plays a role, such as a pathway involving spleen tyrosine kinase (SYK).

Spleen tyrosine kinase (SYK) is a member of the SYK family of tyrosine protein kinases, a family of cytoplasmic tyrosine kinases characterized by the presence of two SH2 domains in the amino terminal of a single kinase domain. Homologs of the SYK family of protein kinases have been identified in a number of species, including the human ZAP-70. SYK has been reported to be involved in several cellular signaling events. For example, SYK participates in immunoreceptor signaling, integrin signaling, and G proteincoupled receptor signaling. SYK is known to be expressed in hematopoietic cells as wells as in fibroblasts, epithelial cells, hepatocytes, neuronal cells, endothelial cells and mast cells. SYK is also involved in hematopoietic responses such as proliferation, for example, SYK inhibitors have been suggested as modulators of thrombin-induced ASM cell proliferation, differentiation, and phagocytosis.

In addition, SYK inhibitors have also been demonstrated to be important in non-hematopoietic cells as well, such as in fibroblasts, epithelial cells, breast tissue, hepatocytes, neuronal cells, and vascular endothelial cells. Accordingly, SYK has been implicated as playing a critical role in endothelial cell functions, including morphogenesis cell growth, migration, and survival, and as contributing to maintaining vascular integrity in vivo. For further review, see Yanagi et al., Biochem. Biophys. Res. Comm. 288:495-498 (2001).

Both SYK antisense and specific inhibitors have been shown to have some activity in asthma models and SYK is thought to be a target for the treatment of asthma and other airway diseases, as well as for allergies, inflammation, and autoimmunity. SYK has also been suggested as a target for the development of agonists in cancer therapy, due to its role in cell growth.

SYK is essential for B-cell activation through BCR signaling. SYK become activated upon binding to phosphoryated BCR and thus initiates the early signaling events following BCR activation. Mice deficient in SYK exhibit an early block in B-cell development (Cheng et al. Nature 378:303, 1995; Turner et al. Nature 378:298, 1995). Therefore inhibition of SYK enzymatic activity in cells is proposed as a treatment for autoimmune disease through its effects on autoantibody production.

In one aspect, a compound of the invention may be useful as modulators (e.g., inhibitors) of SYK. Some compounds may be useful in modulation of more than one component of a signaling cascade involving SYK. In one aspect, a compound of the invention may also be useful in treating diseases and disorders that are additionally or alternatively, modulated by a signaling pathway that does not include BTK.

Bruton's Tyrosine Kinase (BTK)

In one aspect, a compound of the invention may be useful for modulating one or more components involved in a signaling pathway to prevent or to treat a disease or disorder in which the pathway plays a role, such as a pathway modulated by BTK.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes.

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl Clin. Exp. Immunol. 1993 94:459). A selective BTK inhibitor has been demonstrated dose-dependent efficacy in a mouse arthritis model (Z. Pan et al., Chem. Med. Chem. 2007 2:58-61).

BTK is also expressed by cells other than B-cells that may be involved in disease processes. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 2003 197:1603). Therefore TNF alpha mediated inflammation could be modulated by small molecular Btk inhibitors. Also, Btk has been reported to play a role in apoptosis (Islam and Smith Immunol. Rev. 2000 178:49,) and thus BTK inhibitors would be useful for the treatment of certain B-cell lymphomas and leukemias (Feldhahn et al. J. Exp. Med. 2005 201:1837).

In one aspect, a compound of the invention may be useful as modulators (e.g., inhibitors) of BTK. In one aspect, a compound of the invention may be useful in modulation of more than one component of a signaling cascade involving BTK. In one aspect, a compound of the invention may also be useful in treating diseases and disorders that are additionally or alternatively, modulated by a signaling pathway that does not include BTK.

In one aspect, a compound of the invention is useful as a pharmaceutical agent, for example, as therapeutic agent for treating humans and animals. In one aspect, a compound of the invention may be used without limitation, for example, as anti-cancer, anti-inflammatory, and/or immunosuppressive agents. In one aspect, a compound of the invention may be used for other cell proliferation-related disorders and autoimmune disorders.

In one aspect, a compound of the invention may be used to regulate immune system activity in a subject, thereby protecting against or preventing autoimmune disease, e.g., lupus, transplant rejection (e.g., kidney, heart, lung, liver, pancreas, skin, host versus graft reaction (HVGR), etc.), rheumatoid arthritis, psoriatic arthritis, and amyotrophic lateral sclerosis, sepsis, T-cell mediated autoimmune diseases such as multiple sclerosis, psoriasis and Sjogren's syndrome, and hypersensitivity reactions. In one aspect, a compound of the invention may also be used to protect against or prevent solid and hematologic malignancies, e.g., leukemia and lymphomas. In one aspect, the invention includes a compound of the invention in the manufacture of a medicament to regulate the immune system. In one aspect, a compound of the invention may be used to treat autoimmune disease in a subject. In one aspect, the invention includes use of a compound of the invention in the manufacture of a medicament to protect against or treat solid and hematologic malignancies. For example, a compound of the invention may result in reduction in the severity of symptoms or halt impending progression of the autoimmune disease, or solid or hematologic malignancy in a subject. In certain embodiments, regulation of the immune system occurs through the inhibition of lymphocyte proliferation. In certain embodiments, regulation of the immune system occurs through the inhibition of lymphocyte activation. For example, T-cell proliferation and/or activation is inhibited. Additionally or alternatively, B-cell proliferation and/or activation is inhibited. In certain embodiments, the subject is a mammal, e.g., a human.

In one aspect, a compound of the invention may be involved in modulating a kinase signaling cascade, e.g., a Janus kinase (JAK) inhibitor such as a JAK1, JAK2, JAK3 or TYK2 inhibitor. Thus, without wishing to be bound by theory, it is hypothesized that the administration of a compound of the invention modulates ones or more members of the JAK kinase family (e.g., JAK1, JAK2, JAK3, or TYK2) and is useful for the treatment of immune mediated diseases, e.g., hypersensitivity reactions, transplant rejection (e.g., acute and chronic transplant rejection), allergies, rheumatoid arthritis, psoriatic arthritis, amyotrohopic lateral sclerosis, and malignanices, e.g., leukemia and lymphoma. In one aspect, a compound of the invention used in the methods of treating, preventing or ameliorating immune mediated disease is an inhibitor of a tyrosine kinase. In one aspect, a compound of the invention used in the methods of treating, prevention or ameliorating immune mediated disease is an inhibitor of a tyrosine kinease selected from JAK (JAK3), SYK, and BTK.

JAK3 kinase binds the common gamma chain of cytokinetic receptors. This common gamma chain, which is involved in both ligand binding and signal transduction, is a shared subunit of the multichain receptor for cytokines IL-2, IL-4, IL-7, IL-9, IL-15 and IL-21. Without intending to be bound by theory, because the JAK3 kinase binds the common gamma chain of these receptors, in one aspect, a compound of the invention may be used to regulate, and in particular inhibit, these and other cytokine receptor signaling cascades which utilize the common gamma chain. Thus, in one aspect, the invention includes methods of regulating, and in particular inhibiting, signal transduction cascades in which a JAK kinase plays a role, such as signal transduction cascades of cytokine receptors utilizing the common gamma chain, including, but not limited to, the IL-2, IL-4, IL-7, IL-9, IL-15 and IL-21 signal transduction cascades. In one aspect, the methods generally involve contacting a JAK-dependent receptor, or a cell expressing a JAK-dependent receptor, with an amount of a compound of the invention effective to regulate or inhibit the signal transduction cascade. The methods may also be used to regulate, and in particular inhibit, downstream processes or cellular responses elicited by activation of the particular JAK-dependent signal transduction cascade. The methods may be practiced to regulate any signal transduction cascade where JAK kinase is now known or later discovered to play a role. The methods may be practiced in in vitro contexts or in in vivo contexts as a therapeutic approach towards the treatment or prevention of diseases characterized by, caused by or associated with activation of the JAK-dependent signal transduction cascade. Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, psoriatic arthritis, and amyotrophic lateral sclerosis, multiple sclerosis, psoriasis and Sjogren' syndrome, Type II inflammatory disease such as vascular inflammation (including vasculitis, ateritis, atherosclerosis and coronary artery disease), chronic inflammatory diseases such as ankylosing spondylitis (also known as Bekhterev's disease, Bekhterev syndrome, and Marie-Strumpell diseases), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas.

In one aspect, a compound of the invention may be involved in modulating a kinase signaling cascade, e.g., a spleen tyrosine kinase (SYK) inhibitor such as a SYK or Zap-70 inhibitor. Thus, without wishing to be bound by theory, it is hypothesized that the administration of a compound of the invention modulates ones or more members of the SYK kinase family (e.g., SYK or Zap-70) and is useful for the treatment of immune mediated diseases, e.g., hypersensitivity reactions, transplant rejection (e.g., acute and chronic transplant rejection), allergies, rheumatoid arthritis, psoriatic arthritis, amyotrohopic lateral sclerosis, and malignanices, e.g., leukemia and lymphoma. In one aspect, a compound of the invention used in the methods of treating, preventing or ameliorating immune mediated disease is an inhibitor of a tyrosine kinase. In one aspect, a compound of the invention used in the methods of treating, prevention or ameliorating immune mediated disease is an inhibitor of a tyrosine kinease selected from JAK (JAK3), SYK, and BTK.

The Syk family of tyrosine kinases includes e.g., SYK and Zap-70. SYK plays a role in the signaling cascades from a certain cell surface receptors (e.g., CD74, Fc Receptor, and integrins). Without intending to be bound by theory, because the SYK kinase binds the cell surface receptors such as CD74, Fc Receptor, and integrins, in one aspect, a compound of the invention may be used to regulate, and in particular inhibit, these and similar receptors. Thus, in one aspect, the invention includes methods of regulating, and in particular inhibiting, signal transduction cascades in which a SYK kinase plays a role. In one aspect, the methods generally involve contacting a SYK-dependent receptor, or a cell expressing a SYK-dependent receptor, with an amount of a compound of the invention effective to regulate or inhibit the signal transduction cascade. The methods may also be used to regulate, and in particular inhibit, downstream processes or cellular responses elicited by activation of the particular SYK-dependent signal transduction cascade. The methods may be practiced to regulate any signal transduction cascade where SYK kinase is now known or later discovered to play a role. The methods may be practiced in in vitro contexts or in in vivo contexts as a therapeutic approach towards the treatment or prevention of diseases characterized by, caused by or associated with activation of the SYK-dependent signal transduction cascade. Examples of diseases that are mediated, at least in part, by SYK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, psoriatic arthritis, and amyotrophic lateral sclerosis, multiple sclerosis, psoriasis and Sjogren' syndrome, Type II inflammatory disease such as vascular inflammation (including vasculitis, ateritis, atherosclerosis and coronary artery disease), chronic inflammatory diseases such as ankylosing spondylitis (also known as Bekhterev's disease, Bekhterev syndrome, and Marie-Strumpell diseases), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas.

Furthermore, and without wishing to be bound by theory, compounds of the invention are shown in the Examples below to modulate other pathways in addition to a JAK-dependent signal transduction cascade, such as those found in lymphocytes (e.g., B-cells and T-cells). Without intending to be bound by theory, compounds described herein may be used to regulate, and in particular inhibit, lymphocyte proliferation and/or activation (e.g., T-cell proliferation and/or activation and/or B-cell proliferation and/or activation).

Compounds

In one aspect, the invention includes a compound according to Formula I:

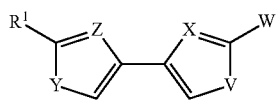

(I)

or a pharmaceutically acceptable salt, solvate, polymorph, or prodrug thereof,
wherein:
Y and V are each independently selected from O, S or NH;
Z and X are each independently selected from CH or N;
W is either $CONR^2R^3$ or $NR^2R^3$, with the proviso that when W is $NR^2R^3$ then $R^1$ is an aryl or a substituted aryl,
$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl,
wherein said alkyl, alkenyl, alkynyl, heteroalkyl, cycloalkyl, cycloalkenyl, heterocycloalkyl, aryl, amine or heteroaryl is unsubstituted or substituted with one or more $R^a$,
wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$,
or together two $R^a$ with the atoms to which they are attached, form a five or six membered heterocycloalkyl, an aryl, or heteroaromatic ring;
wherein $R^b$ and $R^c$ are, each independently, hydrogen or a group selected from halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;
wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;
or together two $R^b$ with the atoms to which they are attached, form a five or six membered heterocycloalkyl ring;
$R^2$ and $R^3$ either
(i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, $C_3$-$C_8$ cycloalkenyl, or heterocycloalkyl;
or
(ii) together with the nitrogen atom to which they are attached, form a five, six, or seven membered heterocycloalkyl or heteroaromatic ring, wherein said heterocycloalkyl or heteroaromatic ring is unsubstituted.

In one aspect, a compound of the invention includes a compound of Formula I or a salt, solvate, or prodrug thereof, wherein:
Y and V are each independently selected from O, S or NH;
Z and X are each independently selected from CH or N;
W is either $CONR^2R^3$ or $NR^2R^3$, with the proviso that when W is $NR^2R^3$ then $R^1$ is an aryl or a substituted aryl,
$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl,
wherein said alkyl, alkenyl, alkynyl, heteroalkyl, cycloalkyl, cycloalkenyl, heterocycloalkyl, aryl, amine or heteroaryl is unsubstituted or substituted with one or more $R^a$,
wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_2$-$C_6$ alkynyl, d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$
wherein $R^b$ and $R^c$ are, each independently, hydrogen or a group selected from halogen, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, or heterocycloalkyl, an aryl and a heteroaryl;
wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl, and a heteroaryl;
$R^2$ and $R^3$ either
(i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, or heterocycloalkyl;
or
(ii) collectively, together with the nitrogen atom to which they are attached, form a five to seven membered heterocycloalkyl or heteroaromatic ring.

In some embodiments, V is NH. In some embodiments, V is O. In some embodiments, V is S. In some embodiments, Z is N. In some embodiments, Z is CH. In some embodiments, V is NH and Z is N. In some embodiments, Y is NH. In some embodiments, Y is O. In some embodiments, Y is S. In some embodiments, X is N. In some embodiments, X is CH. In some embodiments, Y and V are not both S.

In some embodiments, W is $CONR^2R^3$. In some embodiments, W is $NR^2R^3$. In some embodiments, W is $NR^2R^3$ and one of $R^2$ and $R^3$ is $COR^e$ while the other is hydrogen.

In one aspect, the invention includes a compound according to Formula II:

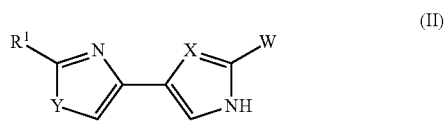

(II)

or a pharmaceutically acceptable salt, solvate, polymorph, or prodrug thereof,
wherein:
Y is selected from O or S;
X is selected from CH or N;
W is either $CONR^2R^3$ or $NR^2R^3$, with the proviso that when W is $NR^2R^3$ then $R^1$ is an aryl or a substituted aryl,
$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl,
wherein said alkyl, alkenyl, alkynyl, heteroalkyl, cycloalkyl, cycloalkenyl, heterocycloalkyl, aryl, amine or heteroaryl is unsubstituted or substituted with one or more $R^a$,
wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_3$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$, m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$,
  or together two $R^a$ with the atoms to which they are attached, form a five or six membered heterocycloalkyl, an aryl, or heteroaromatic ring;
  wherein $R^b$ and $R^c$ are, each independently, hydrogen or a group selected from halogen, $C(O)CH_3$, $CF_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl and a heteroaryl;
  wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl, a dialkylamine, a monoalkylamine, and a heteroaryl;
  or together two $R^b$ with the atoms to which they are attached, form a five or six membered heterocycloalkyl ring;
$R^2$ and $R^3$ either
  (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, or heterocycloalkyl;
  or
  (ii) together with the nitrogen atom to which they are attached, form a five, six, or seven membered heterocycloalkyl or heteroaromatic ring, wherein said heterocycloalkyl or heteroaromatic ring is unsubstituted.

In one aspect, the invention includes a compound of Formula II or a salt, solvate, or prodrug thereof, wherein:
Y is selected from O or S;
X is selected from CH or N;
W is either $CONR^2R^3$ or $NR^2R^3$, with the proviso that when W is $NR^2R^3$ then $R^1$ is an aryl or a substituted aryl,
$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a saturated or unsaturated $C_3$-$C_8$ cycloalkyl or heterocycloalkyl, an amine, an aryl and a heteroaryl,
  wherein said alkyl, alkenyl, alkynyl, heteroalkyl, cycloalkyl, heterocycloalkyl, aryl, amine or heteroaryl is unsubstituted or substituted with one or more $R^a$, wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
  wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$),
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$
  wherein $R^b$ and $R^c$ are, each independently, hydrogen or a group selected from halogen, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;
  wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, $C_3$-$C_8$ cycloalkenyl, a heterocycloalkyl, an aryl, and a heteroaryl;
$R^2$ and $R^3$ either
  (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, and a heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, or heterocycloalkyl;

or (ii) collectively, together with the nitrogen atom to which they are attached, form a five to seven membered heterocycloalkyl or heteroaromatic ring.

In some embodiments, Y is O. In some embodiments, Y is S. In some embodiments, X is N. In some embodiments, X is CH.

In some embodiments, W is $CONR^2R^3$. In some embodiments, W is $NR^2R^3$. In some embodiments, W is $NR^2R^3$ and one of $R^2$ and $R^3$ is $COR^e$ while the other is hydrogen.

In one aspect, the invention includes a compound according to Formula III:

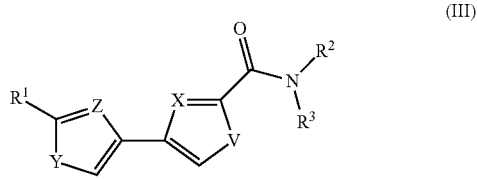

(III)

or a pharmaceutically acceptable salt, solvate, polymorph, or prodrug thereof, wherein:

Y and V are each independently selected from O, S or NH;

Z and X are each independently selected from CH or N;

$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl, wherein said alkyl, alkenyl, alkynyl, heteroalkyl, cycloalkyl, cycloalkenyl, heterocycloalkyl, aryl, amine or heteroaryl is unsubstituted or substituted with one or more $R^a$, wherein $R^a$ is independently at each occurrence selected from the group consisting of:

a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl, wherein said alkyl, alkenyl, alkynyl, and aryl in a)-h) is unsubstituted or substituted independently at each occurrence with one or more $R^b$, i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$, or together two $R^a$ with the atoms to which they are attached, form a five or six membered heterocycloalkyl, an aryl, or heteroaromatic ring;

wherein $R^b$ and $R^c$ are, each independently, hydrogen or a group selected from halogen, $C(O)CH_3$, $CF_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl and a heteroaryl;

wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl, a dialkylamine, a monoalkylamine, and a heteroaryl;

or together two $R^b$ with the atoms to which they are attached, form a five or six membered heterocycloalkyl ring;

$R^2$ and $R^3$ either (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ alkenyl, and a heterocycloalkyl;

or (ii) together with the nitrogen atom to which they are attached, form a five, six, or seven membered heterocycloalkyl or heteroaromatic ring, wherein said heterocycloalkyl or heteroaromatic ring is unsubstituted.

In one aspect, the invention includes a compound of Formula III or a salt, solvate, or prodrug thereof, wherein:

Y and V are each independently selected from O, S or NH;

Z and X are each independently selected from CH or N;

$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl, wherein said alkyl, alkenyl, alkynyl, heteroalkyl, cycloalkyl, cycloalkenyl, heterocycloalkyl, aryl, amine or heteroaryl is unsubstituted or substituted with one or more $R^a$, wherein $R^a$ is independently at each occurrence selected from the group consisting of:

a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl, e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$
wherein $R^b$ and $R^c$ are, each independently, hydrogen or a group selected from halogen, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl and a heteroaryl;
wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, and a heteroaryl;
$R^2$ and $R^3$ either
(i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, and a heterocycloalkyl;
or
(ii) collectively, together with the nitrogen atom to which they are attached, form a five to seven membered heterocycloalkyl or heteroaromatic ring.
In some embodiments, V is NH. In some embodiments, V is O. In some embodiments, V is S. In some embodiments, Z is N. In some embodiments, Z is CH. In some embodiments, V is NH and Z is N. In some embodiments, Y is NH. In some embodiments, Y is O. In some embodiments, Y is S. In some embodiments, X is N. In some embodiments, X is CH. In some embodiments, Y and V are not both S.

In one aspect, the invention includes a compound according to Formula IV:

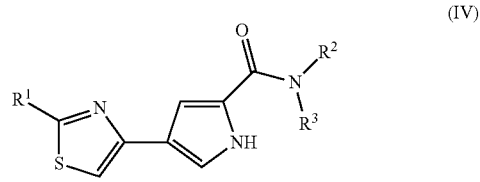

or a pharmaceutically acceptable salt, solvate, polymorph, or prodrug thereof,
wherein:
$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, a heterocycloalkyl, an amine, an aryl and a heteroaryl,
wherein said alkyl, alkenyl, alkynyl, heteroalkyl, cycloalkyl, cycloalkenyl, heterocycloalkyl, aryl, amine or heteroaryl is unsubstituted or substituted with one or more $R^a$,
wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$, and
w) $NR^bR^c$ or together two $R^a$ with the atoms to which they are attached, form a five or six membered heterocycloalkyl, an aryl, or heteroaromatic ring;

wherein $R^b$ and $R^c$ are, each independently, hydrogen or a group selected from halogen, $C(O)CH_3$, $CF_3$, a linear or branched $C_1$-$C_6$ alkyl, a linear or branched $C_2$-$C_6$ akenyl, a linear or branched $C_2$-$C_6$ alkynyl, a $C_3$-$C_8$ cycloalkyl, a $C_3$-$C_8$ cycloalkenyl, a heterocycloalkyl, an aryl and a heteroaryl;

wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ akenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;

or together two $R^b$ with the atoms to which they are attached, form a five or six membered heterocycloalkyl ring;

$R^2$ and $R^3$ either
  (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, and a heterocycloalkyl;
  or
  (ii) together with the nitrogen atom to which they are attached, form a five, six, or seven membered heterocycloalkyl or heteroaromatic ring, wherein said ring is unsubstituted.

In one aspect, the invention includes a compound of Formula IV or a salt, solvate, or prodrug thereof, wherein:

$R^1$ is selected from the group consisting of a linear or branched $C_1$-$C_6$ alkyl, a linear or branched $C_2$-$C_6$ alkenyl, a linear or branched $C_2$-$C_6$ alkynyl, or heteroalkyl, a $C_3$-$C_8$ cycloalkyl, a $C_3$-$C_8$ cycloalkenyl, heterocycloalkyl, an amine, an aryl and a heteroaryl, wherein said alkyl, alkenyl, alkynyl, heteroalkyl, cycloalkyl, cycloalkenyl, heterocycloalkyl, aryl, amine or heteroaryl is unsubstituted or substituted with one or more $R^a$, wherein $R^a$ is independently at each occurrence selected from the group consisting of:
a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl,
wherein said alkyl, alkenyl, alkynyl, and aryl in a)-h) is unsubstituted or substituted independently at each occurrence with one or more $R^b$,
i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^C$,
v) $NHCOR^b$, and
w) $NR^bR^c$
  wherein $R^b$ and $R^c$ are, each independently, hydrogen or a group selected from halogen, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl and a heteroaryl;
  wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, and a heteroaryl;

$R^2$ and $R^3$ either
  (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_6$ cycloalkyl, a $C_3$-$C_6$ cycloalkenyl, and heterocycloalkyl;
  or
  (ii) collectively, together with the nitrogen atom to which they are attached, form a five to seven membered heterocycloalkyl or heteroaromatic ring.

In one aspect, the invention includes a compound according to Formula V:

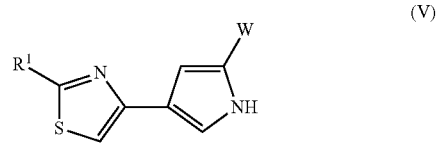

(V)

or a pharmaceutically acceptable salt, solvate, polymorph, or prodrug thereof, wherein
W is $CONR^2R^3$; $R^1$ is selected from
1) $NR^aR^a$, wherein a) one $R^a$ is H and one $R^a$ is phenyl substituted with one or more $R^b$ and b) one $R^a$ is a linear or branched $C_1$-$C_6$ alkyl and one $R^a$ is unsubstituted phenyl or phenyl substituted with one or more $R^b$, and
2) phenyl substituted with one or more $NHCOR^b$, wherein $R^b$ is a) unsubstituted phenyl or phenyl substituted with one or more $R^d$ or b) is a linear or branched $C_1$-$C_6$ alkyl, wherein said alkyl is substituted with five, six, or seven membered heterocycloalkyl optionally substituted with a linear or branched $C_1$-$C_6$ alkyl, provided that the heterocycloalkyl is not morpholine, $R^2$ and $R^3$ together with the nitrogen atom to which they are attached form a five, six, or seven membered heterocycloalkyl or heteroaromatic ring;

$R^b$ is selected from halogen, $C(O)CH_3$, $CF_3$, a linear or branched $C_1$-$C_6$ alkyl, a linear or branched $C_2$-$C_6$ alkenyl, a linear or branched $C_2$-$C_6$ alkynyl, a $C_3$-$C_8$cycloalkyl, a $C_3$-$C_8$ cycloalkenyl, a heterocycloalkyl, an aryl and a heteroaryl; wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, an aryl, a dialkylamine, a monoalkylamine, and a heteroaryl.

In one aspect, $R^1$ is NRaRa and one $R^a$ is H. In one aspect, $R^1$ is $NR^aR^a$ and one $R^a$ is H and one $R^a$ is phenyl substituted with one or more $R^b$. In one aspect, $R^1$ is $NR^aR^a$ and one $R^a$ is H and one $R^a$ is phenyl substituted with one or more halogen or $C(O)CH_3$.

In one aspect, $R^1$ is $NR^aR^a$ and one $R^a$ is $CH_3$. In one aspect, $R^1$ is $NR^aR^a$ and one $R^a$ is $CH_3$ and one $R^a$ is unsubstituted phenyl.

In one aspect, $R^1$ is phenyl substituted with one $NHCOR^b$. In one aspect, $R^1$ is phenyl substituted with one $NHCOR^b$ and $R^b$ is unsubstituted phenyl. In one aspect, $R^1$ is phenyl substituted with one $NHCOR^b$ and $R^b$ is linear $C_1$-$C_6$ alkyl. In one aspect, $R^1$ is phenyl substituted with one $NHCOR^b$ and $R^b$ is $CH_2$ substituted with heterocycloalkyl. In one aspect, $R^1$ is phenyl substituted with one $NHCOR^b$ and $R^b$ is $C_1$-$C_6$ alkyl substituted with piperazine, wherein said piperazine is substituted with methyl.

In one aspect, the $R^2$ and $R^3$ together with the nitrogen to which they are attached from a five-membered heterocycloalkyl.

In one aspect, the invention includes a compound of formula VI:

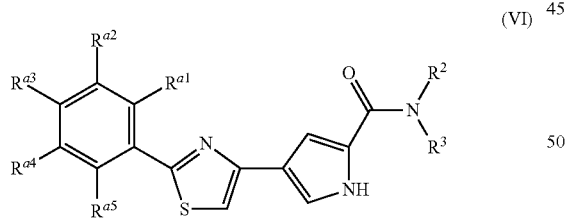

(VI)

or a pharmaceutically acceptable salt, solvate, or polymorph, or prodrug thereof, wherein $R^2$ and $R^3$ are as described for formula I or further herein; $R^{a1}$, $R^{a2}$, $R^{a3}$, $R^{a4}$, and $R^{a5}$ are each independently selected from the group consisting of:

a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl,
h) a linear or branched, saturated or unsaturated $C_1$-$C_6$ thioalkyl or thioaryl, wherein said alkyl, alkenyl, alkynyl, and aryl in a)-h) is unsubstituted or substituted independently at each occurrence with one or more $R^b$, i) a $C_3$-$C_8$ cycloalkyl, wherein said cycloalkyl is unsubstituted or substituted independently at each occurrence with one or more $R^b$,
j) a $C_3$-$C_8$ cycloalkenyl, wherein said cycloalkenyl is unsubstituted or substituted independently at each occurrence with one or more $R^b$,
k) an aryl, wherein said aryl is unsubstituted or substituted independently at each occurrence with one or more $R^b$,
l) a heteroaryl, wherein said heteroaryl is unsubstituted or substituted independently at each occurrence with one or more $R^b$,
m) a heterocycloalkyl, wherein said heterocycloalkyl is unsubstituted or substituted independently at each occurrence with one or more $R^b$,
n) hydroxyl,
o) cyano,
p) amino,
q) nitro,
r) halogen,
s) $COR^b$,
t) $COOR^b$,
u) $CONR^bR^c$,
v) $NHCOR^b$,
w) $NR^bR^c$, and
x) hydrogen, or two of $R^{a1}$, $R^{a2}$, $R^{a3}$, $R^{a4}$, $R^{a6}$, and $R^{a7}$ together with the atoms to which they are attached, form a five or six membered heterocycloalkyl, an aryl, or heteroaromatic ring;

wherein $R^b$ and $R^c$ are, each independently, hydrogen or a group selected from halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;

wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;

two $R^b$ with the atoms to which they are attached, form a five or six membered heterocycloalkyl ring.

In one aspect, the invention includes a compound of formula VII:

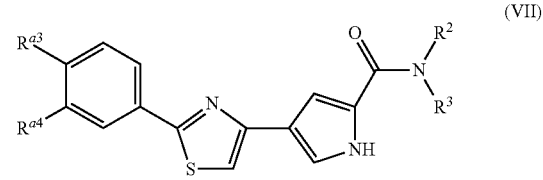

(VII)

or a pharmaceutically acceptable salt, solvate, polymorph, or prodrug thereof, wherein $R^{a3}$, $R^{a4}$, $R^2$, and $R^3$ are as described for formulae VI and I and further herein.

In one aspect, the invention includes a compound of formula VIII:

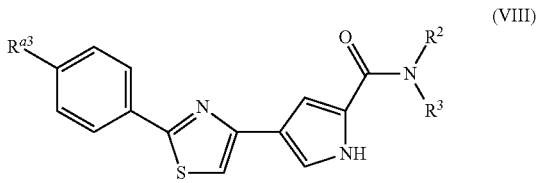

(VIII)

or a pharmaceutically acceptable salt, solvate, polymorph, or prodrug thereof, wherein Ra3, R2 and R3 are as described for formulae VI and I and further herein.

In one aspect, the invention includes a compound of formula IX:

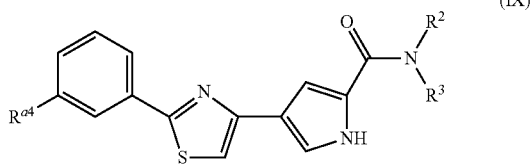

(IX)

or a pharmaceutically acceptable salt, solvate, polymorph, or prodrug thereof, wherein Ra4, R2 and R3 are as described for formulae VI and I and further herein.

In one aspect, the invention includes a compound of formula X:

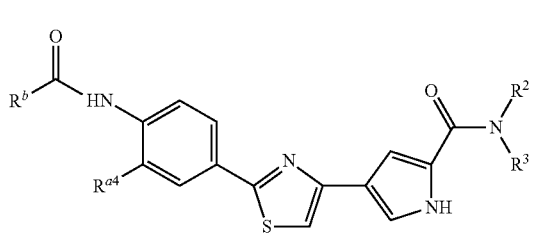

(X)

or a pharmaceutically acceptable salt, solvate, polymorph, or prodrug thereof, wherein Ra4, Rb, R2 and R3 are as described for formulae VI and I and further herein.

In one aspect, the invention includes a compound of formula XI:

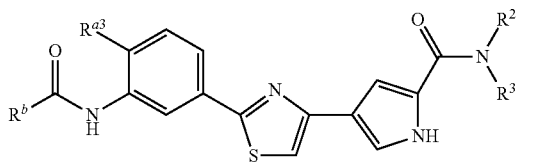

(XI)

or a pharmaceutically acceptable salt, solvate, polymorph, or prodrug thereof, wherein $R^{a3}$, $R^b$, $R^2$ and R3 are as described for formulae VI and I and further herein.

In one aspect, the invention includes a compound of formula XII:

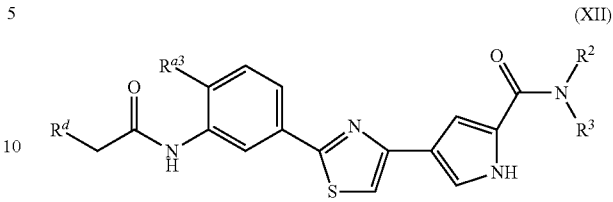

(XII)

or a pharmaceutically acceptable salt, solvate, polymorph, or prodrug thereof, wherein $R^{a3}$, $R^d$, $R^2$ and $R^3$ are as described for formulae VI and I and further herein.

In one aspect, the invention includes a compound of formula XIII:

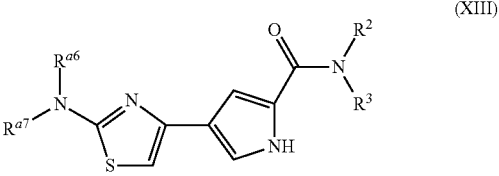

(XIII)

or a pharmaceutically acceptable salt, solvate, polymorph, prodrug thereof, wherein, wherein $R^2$ and $R^3$ are as described for formula I and further herein;

$R^{a6}$ and $R^{a7}$ are each independently selected from the group consisting of:
  a) a linear or branched $C_1$-$C_6$ alkyl,
  b) a linear or branched $C_2$-$C_6$ alkenyl,
  c) a linear or branched $C_2$-$C_6$ alkynyl,
  d) a linear or branched, saturated or unsaturated $C_1$-$C_6$ haloalkyl,
  e) a linear or branched, saturated or unsaturated $C_1$-$C_6$ alkoxy or aryloxy,
  f) a linear or branched, saturated or unsaturated $C_1$-$C_6$ haloalkoxy,
  g) a linear or branched, saturated or unsaturated $C_1$-$C_6$ alkylsulfonyl,
  h) a linear or branched, saturated or unsaturated $C_1$-$C_6$ thioalkyl or thioaryl,
  wherein said alkyl, alkenyl, alkynyl, and aryl in a)-h) is unsubstituted or substituted independently at each occurrence with one or more $R^b$,
  i) a $C_3$-$C_8$ cycloalkyl, wherein said cycloalkyl is unsubstituted or substituted independently at each occurrence with one or more $R^b$,
  j) a $C_3$-$C_8$ cycloalkenyl, wherein said cycloalkenyl is unsubstituted or substituted independently at each occurrence with one or more $R^b$,
  k) an aryl, wherein said aryl is unsubstituted or substituted independently at each occurrence with one or more $R^b$,
  l) a heteroaryl, wherein said heteroaryl is unsubstituted or substituted independently at each occurrence with one or more $R^b$,
  m) a heterocycloalkyl, wherein said heterocycloalkyl is unsubstituted or substituted independently at each occurrence with one or more $R^b$,
  n) hydroxyl,
  o) cyano,
  p) amino, q) nitro,
r) halogen,
s) $COR^b$,
t) $COOR^b$,
u) $CONR^bR^c$,
v) $NHCOR^b$,
w) $NR^bR^c$, and
x) hydrogen,
or $R^{a6}$ and $R^{a7}$ together with the atoms to which they are attached, form a five or six membered heterocycloalkyl, an aryl, or heteroaromatic ring;
wherein $R^b$ and $R^c$ are, each independently, hydrogen or a group selected from halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;
wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;
two $R^b$ with the atoms to which they are attached, form a five or six membered heterocycloalkyl ring.

In one aspect, the invention includes a compound of formula XIV:

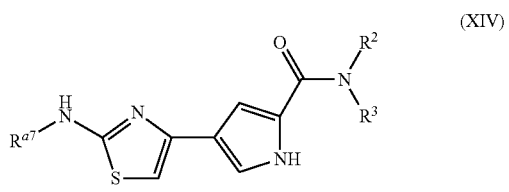

(XIV)

or a pharmaceutically acceptable salt, solvate, polymorph, or prodrug thereof, wherein $R^{a7}$, $R^2$ and $R^3$ are as described for formulae XIII and I and further herein.

In one aspect, the invention includes a compound of formula XV:

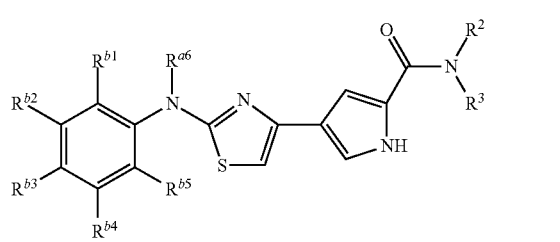

(XV)

or a pharmaceutically acceptable salt, solvate, polymorph, or prodrug thereof, wherein $R^2$ and $R^3$ are as described for formula I and further herein; $R^{b1}$, $R^{b2}$, $R^{b3}$, $R^{b4}$, and $R^{b5}$ are each independently selected from hydrogen, halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl; wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl; or two of $R^{b1}$, $R^{b2}$, $R^{b3}$, $R^{b4}$, or $R^{b5}$ together with the atoms to which they are attached, form a five or six membered heterocycloalkyl ring.

In one aspect, the invention includes a compound of formula XVI:

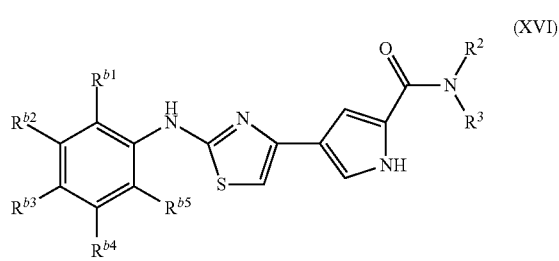

(XVI)

or a pharmaceutically acceptable salt, solvate, polymorph, or prodrug thereof, wherein $R^{b1}$, $R^{b2}$, $R^{b3}$, $R^{b4}$, $R^{b5}$, $R^2$ and $R^3$ are as described for formulae XV and I and further herein.

In one aspect, the invention includes a compound of formula XVII:

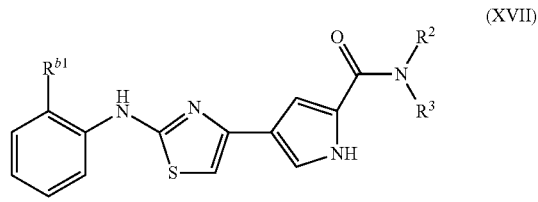

(XVII)

or a pharmaceutically acceptable salt, solvate, polymorph, or prodrug thereof, wherein $R^{b1}$, $R^2$ and $R^3$ are as described for formulae XVII and I and further herein.

In one aspect, the invention includes a compound of formula XVIII:

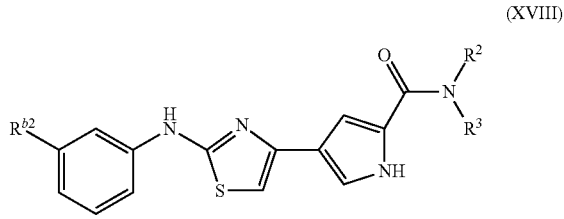

(XVIII)

or a pharmaceutically acceptable salt, solvate, polymorph, or prodrug thereof, wherein $R^{b2}$, $R^2$ and $R^3$ are as described for formulae XV and I and further herein.

In one aspect, the invention includes a compound of formula XIX:

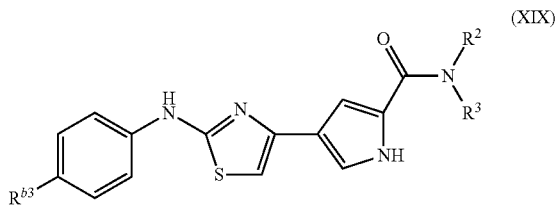

or a pharmaceutically acceptable salt, solvate, polymorph, or prodrug thereof, wherein $R^{b3}$, $R^2$ and $R^3$ are as described for formulae XV and I and further herein.

While all of the compounds of this invention are useful, certain classes are preferred. The following paragraphs recite such preferred classes:

1) In one aspect, the invention includes a compound of formulae I, II, III, IV, V, VI, VII, VIII, IX, X, XI, XII, XIII, XIV, XV, XV, XVI, XVII, XVIII, or XIX, wherein $R^2$ and $R^3$ are each independently selected from a linear or branched $C_1$-$C_6$ alkyl, hydrogen, and $C_3$-$C_a$ cycloalkyl, or $R^2$ and $R^3$ together with the nitrogen atom to which they are attached form a five, six, or seven membered heterocycloalkyl.

2) In one aspect, the invention includes a compound of formulae I, II, III, IV, V, VI, VII, VIII, IX, X, XI, XII, XIII, XIV, XV, XV, XVI, XVII, XVIII, or XIX, wherein $R^2$ and $R^3$ together with the nitrogen atom to which they are attached, form a five, six, or seven membered heterocycloalkyl ring.

3) In one aspect, the invention includes a compound of formulae I, II, III, IV, V, VI, VII, VIII, IX, X, XI, XII, XIII, XIV, XV, XV, XVI, XVII, XVIII, or XIX), wherein $R^2$ and $R^3$ together with the nitrogen atom to which they are attached, form a five or six membered heterocycloalkyl ring.

4) In one aspect, the invention includes a compound of formulae I, II, III, IV, V, VI, VII, VIII, IX, X, XI, XII, XIII, XIV, XV, XV, XVI, XVII, XVIII, or XIX, wherein $R^2$ and $R^3$ together with the nitrogen atom to which they are attached, form a five membered heterocycloalkyl ring.

5) In one aspect, the invention includes a compound of formulae I, II, III, IV, V, VI, VII, VIII, IX, X, XI, XII, XIII, XIV, XV, XV, XVI, XVII, XVIII, or XIX, wherein $R^2$ and $R^3$ together with the nitrogen atom to which they are attached, form a pyrrolidine or piperidine ring.

6) In one aspect, the invention includes a compound of formulae I, II, III, IV, V, VI, VII, VIII, IX, X, XI, XII, XIII, XIV, XV, XV, XVI, XVII, XVIII, or XIX, wherein $R^2$ and $R^3$ together with the nitrogen atom to which they are attached, form a pyrrolidine ring.

7) In one aspect, the invention includes a compound of formulae VI, wherein $R^{a1}$, $R^{a2}$, $R^{a3}$, $R^{a4}$, and $R^{a5}$ are each independently selected from hydrogen, $NHCOR^b$, $C_1$-$C_6$ alkoxy, halogen, hydroxyl, $C_1$-$C_6$ alkyl, $CF_3$, and $NR^bR^c$.

8) In one aspect, the invention includes a compound of formulae VI, wherein one of $R^{a1}$, $R^{a2}$, $R^{a3}$, $R^{a4}$, and $R^{a5}$ is $NHCOR^b$ and the remaining $R^{a1}$, $R^{a2}$, $R^{a3}$, $R^{a4}$, and $R^{a5}$ are hydrogen.

9) In one aspect, the invention includes a compound of formulae VI, wherein one of $R^{a1}$, $R^{a2}$, $R^{a3}$, $R^{a4}$, and $R^{a5}$ is halogen and the remaining $R^{a1}$, $R^{a2}$, $R^{a3}$, $R^{a4}$, and $R^{a5}$ are hydrogen.

10) In one aspect, the invention includes a compound of formulae VI, wherein one of $R^{a1}$, $R^{a2}$, $R^{a3}$, $R^{a4}$, and $R^{a5}$ is fluorine or chlorine and the remaining $R^{a1}$, $R^{a2}$, $R^{a3}$, $R^{a4}$, and $R^{a5}$ are hydrogen.

11) In one aspect, the invention includes a compound of formulae VI, wherein one of $R^{a1}$, $R^{a2}$, $R^{a3}$, $R^{a4}$, and $R^{a5}$ is $C_1$-$C_6$ alkoxy and the remaining $R^{a1}$, $R^{a2}$, $R^{a3}$, $R^{a4}$, and $R^{a5}$ are hydrogen.

12) In one aspect, the invention includes a compound of formula VI, wherein one of $R^{a2}$, $R^{a3}$, $R^{a4}$, and $R^{a5}$ is methoxy or ethoxy and the remaining $R^{a1}$, $R^{a2}$, $R^{a3}$, $R^{a4}$, and $R^{a5}$ are hydrogen.

13) In one aspect, the invention includes a compound of formulae VI, wherein one of $R^{a1}$, $R^{a2}$, $R^{a3}$, $R^{a4}$, and $R^{a5}$ is $CF_3$ and the remaining $R^{a1}$, $R^{a2}$, $R^{a3}$, $R^{a4}$, and $R^{a5}$ are hydrogen.

14) In one aspect, the invention includes a compound of formula VI, wherein one or two of $R^{a1}$, $R^{a2}$, $R^{a3}$, $R^{a4}$, and $R^{a5}$ are $C_1$-$C_6$ alkyl and the remaining $R^{a1}$, $R^{a2}$, $R^{a3}$, $R^{a4}$, and $R^{a5}$ are hydrogen.

15) In one aspect, the invention includes a compound of formula VI, wherein one or two of $R^{a1}$, $R^{a2}$, $R^{a3}$, $R^{a4}$, and $R^{a5}$ are methyl and the remaining $R^{a1}$, $R^{a2}$, $R^{a3}$, $R^{a4}$, and $R^{a5}$ are hydrogen.

16) In one aspect, the invention includes a compound of formula VI, wherein $R^{a1}$ and $R^{a3}$ are not hydrogen.

17) In one aspect, the invention includes a compound of formula VI, wherein $R^{a5}$ is not hydrogen.

18) In one aspect, the invention includes a compound of formula VI, wherein $R^{a4}$ is not hydrogen.

19) In one aspect, the invention includes a compound of formula VI, wherein $R^{a3}$ is not hydrogen.

20) In one aspect, the invention includes a compound of formulae VI or VII, wherein $R^{a3}$ and $R^{a4}$ are each independently selected from hydrogen, $NHCOR^b$, $C_1$-$C_6$ alkoxy, halogen, hydroxyl, a linear $C_1$-$C_6$ alkyl, and $NR^bR^c$.

21) In one aspect, the invention includes a compound of formulae VI or VII, wherein one of $R^{a3}$ and $R^{a4}$ is $NHCOR^b$, and the remaining $R^{a3}$ or $R^{a4}$ is selected from $C_1$-$C_6$ alkoxy, halogen, hydroxyl, a linear $C_1$-$C_6$ alkyl, and $NR^bR^c$.

22) In one aspect, the invention includes a compound of formulae VI or VII, wherein one of $R^{a3}$ and $R^{a4}$ is $NHCOR^b$ and the remaining $R^{a3}$ or $R^{a4}$ is selected from hydrogen, $C_1$-$C_6$ alkoxy, and halogen.

23) In one aspect, the invention includes a compound of formulae VI, VII, VIII, XI, or XII, wherein $R^{a1}$ is selected from hydrogen, $NHCOR^b$, $C_1$-$C_6$ alkoxy, halogen, hydroxyl, a linear or branched $C_1$-$C_6$ alkyl, and $NR^bR^c$.

24) In one aspect, the invention includes a compound of formulae VI, VII, VIII, XI, or XII, wherein $R^{a3}$ is selected from hydrogen, $NHCOR^b$, methoxy, ethoxy, fluorine, chlorine, hydroxyl, methyl, and dimethylamine.

25) In one aspect, the invention includes a compound of formulae VI, VII, VIII, XI, or XII, wherein $R^{a1}$ is selected from hydrogen, methoxy, ethoxy, fluorine, chlorine, hydroxyl, methyl, and dimethylamine.

26) In one aspect, the invention includes a compound of formulae VI, VII, VIII, XI, or XII, wherein $R^{a3}$ is hydrogen.

27) In one aspect, the invention includes a compound of formulae VI, VII, IX or X, wherein $R^{a4}$ is selected from hydrogen, $NHCOR^b$, $C_1$-$C_6$ alkoxy, halogen, hydroxyl, a linear or branched $C_1$-$C_6$ alkyl, and $NR^bR^c$.

28) In one aspect, the invention includes a compound of formulae VI, VII, IX, or X, wherein $R^{a4}$ is selected from hydrogen, $NHCOR^b$, methoxy, methyl, and chlorine.

29) In one aspect, the invention includes a compound of formulae VI, VII, IX, or X, wherein $R^{a4}$ is selected from hydrogen, methoxy, methyl, and chlorine.

30) In one aspect, the invention includes a compound of formulae VI, VII, IX, or X, wherein $R^{a4}$ is hydrogen.

31) In one aspect, the invention includes a compound of formulae VI, VII, IX, or X, wherein $R^b$ is selected from a linear or branched $C_1$-$C_6$ alkyl, unsubstituted $C_3$-$C_8$ cycloalkyl, unsubstituted aryl and unsubstituted heterocycloalkyl, wherein said $C_1$-$C_6$ alkyl is unsubstituted or substituted with one or more $R^d$.

32) In one aspect, the invention includes a compound of formulae VI, VII, VIII, IX, X, or XI, wherein $R^b$ is selected from —$CH_2R^d$, a linear or branched unsubstituted $C_1$-$C_6$ alkyl, unsubstituted heterocycloalkyl, and unsubstituted $C_3$-$C_8$ cycloalkyl.

33) In one aspect, the invention includes a compound of formulae VI, VII, VIII, IX, X, or XI, wherein $R^b$ is methyl.

34) In one aspect, the invention includes a compound of formulae VI, VII, VIII, IX, X, or XI, wherein $R^b$ is —$CH_2R^d$.

35) In one aspect, the invention includes a compound of formulae VI, VII, VIII, IX, X, or XI, wherein $R^b$ is not cyclopropyl or

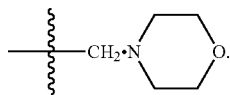

36) In one aspect, the invention includes a compound of formulae VI, VII, VIII, IX, X, XI, or XII, wherein $R^d$ is selected from heterocycloalkyl, dialkylamine, monoalkylamine, and $C_3$-$C_8$ cycloalkyl.

37) In one aspect, the invention includes a compound of formulae VI, VII, VIII, IX, X, XI, or XII, wherein $R^d$ is selected from methylpiperazine, piperidine, dimethylamine, morpholine, dimethylamine, and cyclopropyl.

38) In one aspect, the invention includes a compound of formulae I, II, III, IV, V, VI, VII, VIII, IX, X, XI, or XII, wherein $R^d$ is not morpholine or cyclopropyl.

39) In one aspect, the invention includes a compound of formulae I, II, III, IV, V, VI, VII, VIII, IX, X, XI, and XII, wherein $R^d$ is methylpiperazine.

40) In one aspect, the invention includes a compound of formulae I, II, III, IV, V, VI, VII, VIII, IX, X, XI, and XII, wherein $R^d$ is piperidine.

41) In one aspect, the invention includes a compound of formulae I, II, III, IV, V, VI, VII, VIII, IX, X, XI, and XII, wherein $R^d$ is dimethylamine.

42) In one aspect, the invention includes a compound of formulae I, II, III, IV, V, VI, VII, VIII, IX, X, XI, and XII, wherein $R^d$ is morpholine.

43) In one aspect, the invention includes a compound of formulae I, II, III, IV, V, VI, VII, VIII, IX, X, XI, or XII, wherein $R^d$ is $C_3$-$C_8$ cycloalkyl.

44) In one aspect, the invention includes a compound of formulae I, II, III, IV, V, VI, VII, VIII, IX, X, XI, or XII, wherein $R^d$ is cyclopropyl.

45) In one aspect, the invention includes a compound of formulae I, II, III, IV, V, VI, VII, VIII, IX, X, XI, or XII, provided that $R^2$ and $R^3$ together with the nitrogen atom to which they are attached do not form a pyrrolidine ring.

46) In one aspect, the invention includes a compound of formula XIII, wherein $R^{a6}$ and $R^{a7}$ are each independently selected from hydrogen, a linear $C_1$-$C_6$ alkyl, an aryl, $C_3$-$C_5$ cycloalkyl, and heterocycloalkyl, wherein said aryl or alkyl is unsubstituted or substituted with one or more $R^b$, or $R^{a6}$ and $R^{a7}$ together with the atoms to which they are attached, form a five or six membered heterocycloalkyl.

47) In one aspect, the invention includes a compound of formula XIII, wherein $R^{a6}$ and $R^{a7}$ are each independently selected from hydrogen, methyl, phenyl, cyclopropyl, cyclopentyl, and cyclohexyl, wherein said methyl or phenyl is unsubstituted or substituted with one or more $R^b$, or taken together $R^{a6}$ and $R^{a7}$ form a methylpiperazine or morpholine.

48) In one aspect, the invention includes a compound of formulae XIII or XIV, wherein $R^{a7}$ is selected from a phenyl, cyclopropyl, cyclopentyl, and cyclohexyl, wherein said methyl or phenyl is unsubstituted or substituted with one or more $R^b$.

49) In one aspect, the invention includes a compound of formulae XIII of XIV, wherein $R^{a7}$ is selected from unsubstituted phenyl or phenyl substituted with one or more $R^b$.

50) In one aspect, the invention includes a compound of formulae XIII or XV, wherein $R^{a6}$ is methyl.

51) In one aspect, the invention includes a compound of formulae XV or XVI, wherein $R^{b1}$, $R^{b2}$, $R^{b3}$, $R^{b4}$, and $R^{b5}$ are each independently selected from hydrogen, halogen, C(O)$CH_3$, a linear $C_1$-$C_6$ alkyl, $CF_3$, and $C_1$-$C_6$ alkoxy, or $R^{b3}$ and $R^{b4}$ taken together form a five- or six membered heterocycloalkyl ring.

52) In one aspect, the invention includes a compound of formulae XV or XVI, wherein $R^{b1}$, $R^{b2}$, $R^{b3}$, $R^{b4}$, and $R^{b5}$ are each independently selected from hydrogen, fluorine, C(O)$CH_3$, unsubstituted morpholine, methyl, $CF_3$, and methoxy, or $R^{b3}$ and $R^{b4}$ taken together form a dioxane ring.

53) In one aspect, the invention includes a compound of formulae XV or XVI, wherein $R^{b1}$, $R^{b2}$, $R^{b3}$, and $R^{b5}$ are each independently selected from hydrogen, fluorine, C(O)$CH_3$, and unsubstituted morpholine.

54) In one aspect, the invention includes a compound of formulae XV or XVI, wherein $R^{b2}$ and $R^{b4}$ are hydrogen.

55) In one aspect, the invention includes a compound of formulae XV or XVI, wherein $R^{b1}$, $R^{b3}$, and $R^{b5}$ are fluorine.

56) In one aspect, the invention includes a compound of formulae XV or XVI, wherein $R^{b1}$, $R^{b2}$, $R^{b3}$, $R^{b4}$, and $R^{b5}$ are each independently selected from hydrogen, halogen, C(O)$CH_3$, heterocycloalkyl, provided that when one of $R^{b1}$, $R^{b2}$, $R^{b3}$, $R^{b4}$, and $R^{b5}$ is fluorine, the remaining $R^{b1}$, $R^{b2}$, $R^{b3}$, $R^{b4}$, and $R^{b5}$ are hydrogen.

57) In one aspect, the invention includes a compound of formulae XV, XVI, or XVII, wherein $R^{b1}$ is selected from hydrogen, halogen, C(O)$CH_3$, heterocycloalkyl, a linear $C_1$-$C_6$ alkyl, $CF_3$, $C_1$-$C_6$ alkoxy, and $C_3$-$C_8$ cycloalkyl.

58) In one aspect, the invention includes a compound of formulae XV, XVI, or XVII, wherein $R^{b1}$ is selected from hydrogen, fluorine, C(O)$CH_3$, unsubstituted morpholine, methyl, $CF_3$, and methoxy, and cyclopropyl.

59) In one aspect, the invention includes a compound of formulae XV, XVI, or XVII, wherein $R^{b1}$ is selected from hydrogen, fluorine, C(O)$CH_3$, and unsubstituted morpholine.

60) In one aspect, the invention includes a compound of formulae XV, XVI, or XVII, wherein $R^{b1}$ is fluorine.

61) In one aspect, the invention includes a compound of formulae XV, XVI, or XVII, wherein $R^{b1}$ is methoxy.

62) In one aspect, the invention includes a compound of formulae XV, XVI, or XVII, wherein $R^{b1}$ is $CF_3$.

63) In one aspect, the invention includes a compound of formulae XV, XVI, or XVII, wherein $R^{b2}$ is selected from hydrogen, halogen, C(O)$CH_3$, heterocycloalkyl, a linear $C_1$-$C_6$ alkyl, $CF_3$, $C_1$-$C_6$ alkoxy, and $C_3$-$C_8$ cycloalkyl.

64) In one aspect, the invention includes a compound of formulae XV, XVI, or XVII, wherein $R^{b2}$ is selected from hydrogen, fluorine, C(O)$CH_3$, unsubstituted morpholine, methyl, $CF_3$, and methoxy, and cyclopropyl.

65) In one aspect, the invention includes a compound of formulae XV, XVI, or XVII, wherein $R^{b2}$ is selected from hydrogen, fluorine, C(O)$CH_3$, and unsubstituted morpholine.

66) In one aspect, the invention includes a compound of formulae XV, XVI, or XVII, wherein $R^{b2}$ is chlorine or fluorine.

67) In one aspect, the invention includes a compound of formulae XV, XVI, or XVII, wherein $R^{b2}$ is methoxy.

68) In one aspect, the invention includes a compound of formulae XV, XVI, or XIX, wherein $R^{b3}$ is selected from hydrogen, halogen, C(O)CH$_3$, heterocycloalkyl, a linear C$_1$-C$_6$ alkyl, CF$_3$, C$_1$-C$_6$ alkoxy, and C$_3$-C$_8$ cycloalkyl.

69) In one aspect, the invention includes a compound of formulae XV, XVI, or XIX, wherein $R^{b3}$ is selected from hydrogen, fluorine, C(O)CH$_3$, unsubstituted morpholine, methyl, CF$_3$, and methoxy, and cyclopropyl.

70) In one aspect, the invention includes a compound of formulae XV, XVI, or XIX, wherein $R^{b3}$ is selected from hydrogen, fluorine, C(O)CH$_3$, and unsubstituted morpholine.

71) In one aspect, the invention includes a compound of formulae XV, XVII, or XIX, wherein $R^{b3}$ is selected from fluorine, C(O)CH$_3$, and methoxy, unsubstituted morpholine, methoxy, and methyl.

72) In one aspect, the invention includes a compound of formulae XV, XVII, or XIX, wherein $R^{3b}$ is fluorine.

73) In one aspect, the invention includes a compound of formulae XV, XVII, or XIX, wherein $R^{3b}$ is methoxy.

74) In one aspect, the invention includes a compound of formulae XIII, XIV, XV, XVI, XVII, XVIII, or XIX, wherein $R^2$ and $R^3$ together with the nitrogen atom to which they are attached do not form a pyrrolidine ring.

It will be understood that the above classes may be combined to form additional preferred classes, as for example the combination of preferred selections for two or more substituents.

In one aspect, the invention includes a compound of Table A. In one aspect, the invention includes a compound of Table B. In one aspect, the invention includes a compound of Table C. In one aspect, the invention includes the use of a compound of Table B or Table C. In one aspect, the invention does not include the compounds of Table B and C.

TABLE A

| Compound Name | Structure |
|---|---|
| 16A | 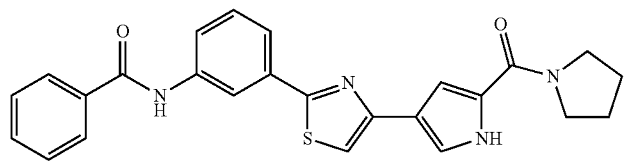 [SMILES: O=C(Nc1cccc(-c2nc(-c3c[nH]c(C(=O)N4CCCC4)c3)cs2)c1)c1ccccc1] |
| 17A | 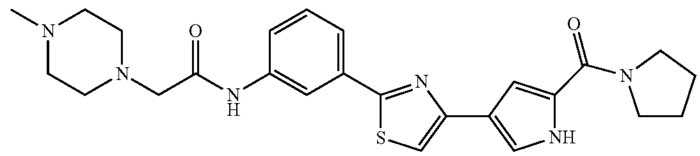 [SMILES: CN1CCN(CC(=O)Nc2cccc(-c3nc(-c4c[nH]c(C(=O)N5CCCC5)c4)cs3)c2)CC1] |
| 13A | 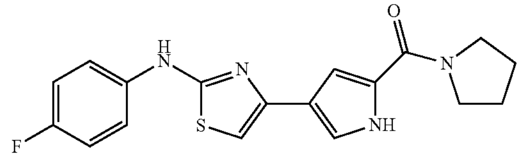 [SMILES: O=C(c1cc(-c2csc(Nc3ccc(F)cc3)n2)c[nH]1)N1CCCC1] |
| 15A | 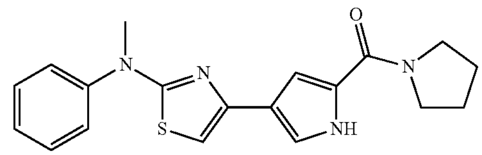 [SMILES: CN(c1ccccc1)c1nc(-c2c[nH]c(C(=O)N3CCCC3)c2)cs1] |
| 14A | 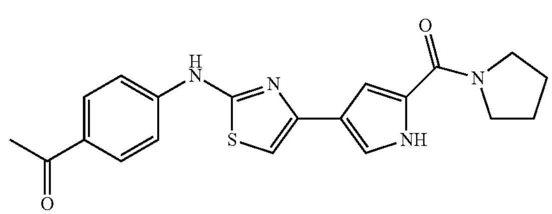 [SMILES: CC(=O)c1ccc(Nc2nc(-c3c[nH]c(C(=O)N4CCCC4)c3)cs2)cc1] |
| 18A | 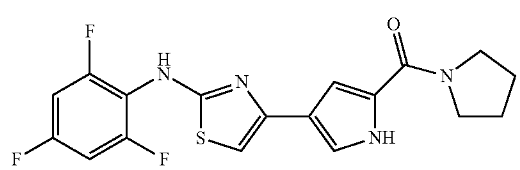 [SMILES: O=C(c1cc(-c2csc(Nc3c(F)cc(F)cc3F)n2)c[nH]1)N1CCCC1] |

TABLE A-continued

| Compound Name | Structure |
|---|---|
| 19A | 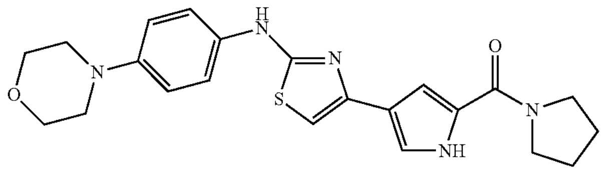 [SMILES: O=C(c1cc(-c2csc(Nc3ccc(N4CCOCC4)cc3)n2)c[nH]1)N1CCCC1] |
| 20A | 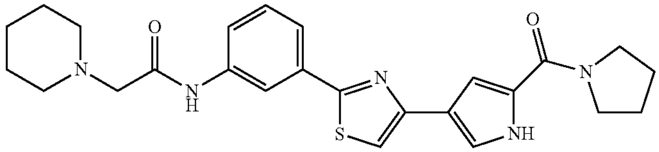 [SMILES: O=C(CN1CCCCC1)Nc1cccc(-c2nc(-c3c[nH]c(C(=O)N4CCCC4)c3)cs2)c1] |
| 21A | 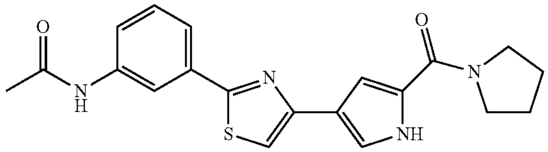 [SMILES: CC(=O)Nc1cccc(-c2nc(-c3c[nH]c(C(=O)N4CCCC4)c3)cs2)c1] |
| 22A | 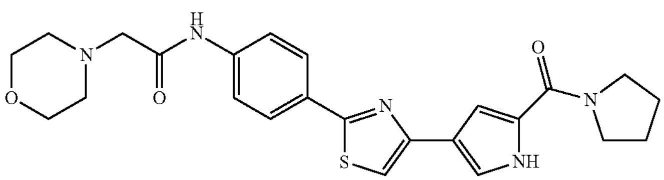 [SMILES: O=C(CN1CCOCC1)Nc1ccc(-c2nc(-c3c[nH]c(C(=O)N4CCCC4)c3)cs2)cc1] |
| 23A | 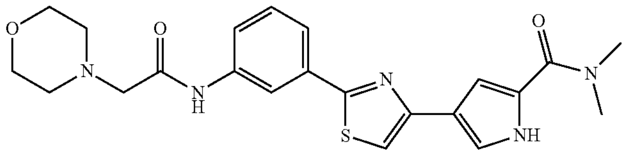 [SMILES: CN(C)C(=O)c1cc(-c2csc(-c3cccc(NC(=O)CN4CCOCC4)c3)n2)c[nH]1] |
| 24A | 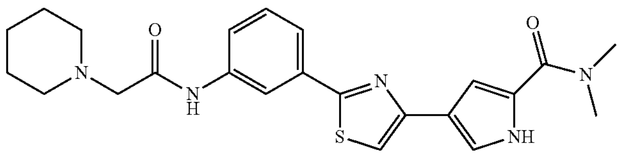 [SMILES: CN(C)C(=O)c1cc(-c2csc(-c3cccc(NC(=O)CN4CCCCC4)c3)n2)c[nH]1] |
| 25A | 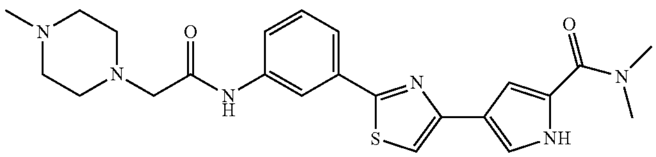 |
| 26A | 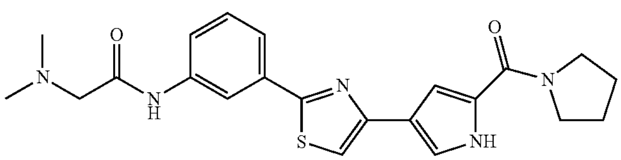 [SMILES: CN(C)CC(=O)Nc1cccc(-c2nc(-c3c[nH]c(C(=O)N4CCCC4)c3)cs2)c1] |
| 27A | 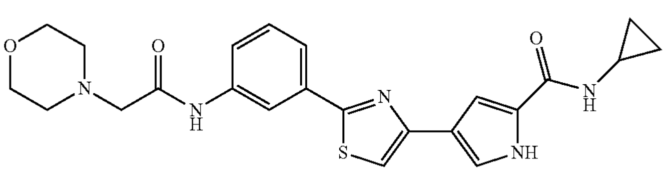 [SMILES: O=C(CN1CCOCC1)Nc1cccc(-c2nc(-c3c[nH]c(C(=O)NC4CC4)c3)cs2)c1] |

TABLE A-continued

| Compound Name | Structure |
|---|---|
| 28A | 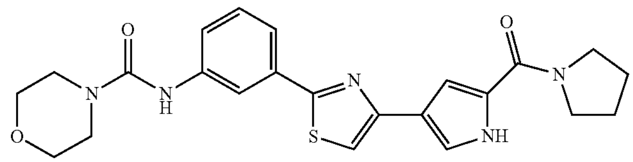 [SMILES: O=C(Nc1cccc(-c2nc(-c3c[nH]c(C(=O)N4CCCC4)c3)cs2)c1)N1CCOCC1] |
| 29A | 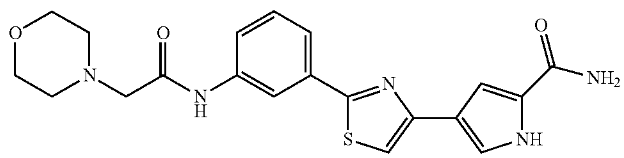 [SMILES: NC(=O)c1cc(-c2csc(-c3cccc(NC(=O)CN4CCOCC4)c3)n2)c[nH]1] |
| 30A | 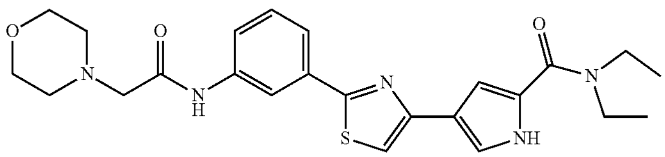 [SMILES: CCN(CC)C(=O)c1cc(-c2csc(-c3cccc(NC(=O)CN4CCOCC4)c3)n2)c[nH]1] |
| 31A | 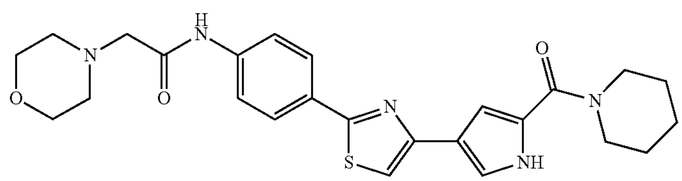 [SMILES: O=C(CN1CCOCC1)Nc1ccc(-c2nc(-c3c[nH]c(C(=O)N4CCCCC4)c3)cs2)cc1] |
| 32A | 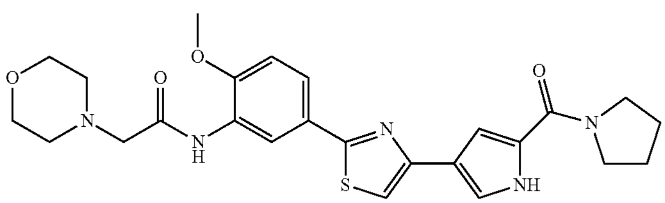 [SMILES: COc1ccc(-c2nc(-c3c[nH]c(C(=O)N4CCCC4)c3)cs2)cc1NC(=O)CN1CCOCC1] |
| 33A | 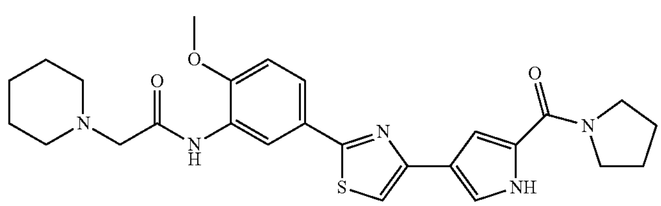 [SMILES: COc1ccc(-c2nc(-c3c[nH]c(C(=O)N4CCCC4)c3)cs2)cc1NC(=O)CN1CCCCC1] |
| 34A | 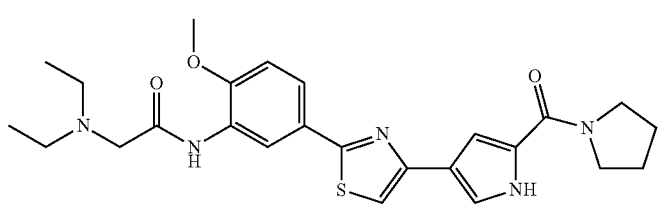 [SMILES: CCN(CC)CC(=O)Nc1cc(-c2nc(-c3c[nH]c(C(=O)N4CCCC4)c3)cs2)ccc1OC] |
| 35A | 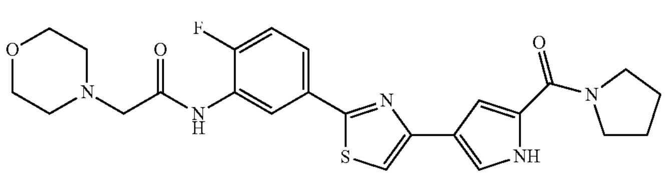 [SMILES: O=C(CN1CCOCC1)Nc1cc(-c2nc(-c3c[nH]c(C(=O)N4CCCC4)c3)cs2)ccc1F] |

TABLE A-continued

| Compound Name | Structure |
|---|---|
| 36A | (structure) |
| 37A | (structure) |
| 38A | (structure) |

TABLE B

| Compound Name | Structure |
|---|---|
| 7A | (structure) |
| 12A | (structure) |
| 8A | (structure) |
| 5A | (structure) |
| 10A | (structure) |

TABLE B-continued

| Compound Name | Structure |
|---|---|
| 9A | 4-(2-(4-ethoxy-3-methoxyphenyl)thiazol-4-yl)-1H-pyrrol-2-yl)(pyrrolidin-1-yl)methanone |
| 3A | N-(3-(4-(5-(pyrrolidine-1-carbonyl)-1H-pyrrol-3-yl)thiazol-2-yl)phenyl)cyclopropanecarboxamide |
| 2A | (4-(2-(4-fluorophenyl)thiazol-4-yl)-1H-pyrrol-2-yl)(pyrrolidin-1-yl)methanone |
| 4A | (4-(2-(4-ethoxyphenyl)thiazol-4-yl)-1H-pyrrol-2-yl)(pyrrolidin-1-yl)methanone |
| 11A | (4-(2-phenylthiazol-4-yl)-1H-pyrrol-2-yl)(pyrrolidin-1-yl)methanone |
| 39A | (4-(2-((3-(trifluoromethyl)phenyl)amino)thiazol-4-yl)-1H-pyrrol-2-yl)(pyrrolidin-1-yl)methanone |
| 40A | (4-(2-((3-methoxyphenyl)amino)thiazol-4-yl)-1H-pyrrol-2-yl)(pyrrolidin-1-yl)methanone |
| 41A | (4-(2-((4-methoxyphenyl)amino)thiazol-4-yl)-1H-pyrrol-2-yl)(pyrrolidin-1-yl)methanone |
| 42A | (4-(2-(cyclopropylamino)thiazol-4-yl)-1H-pyrrol-2-yl)(pyrrolidin-1-yl)methanone |

TABLE B-continued

| Compound Name | Structure |
| --- | --- |
| 43A | 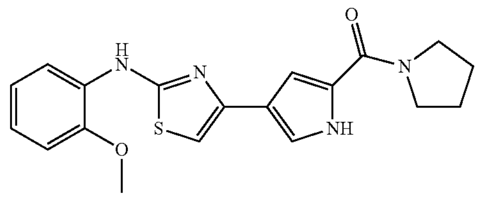 [SMILES: COc1ccccc1Nc1nc(-c2c[nH]c(C(=O)N3CCCC3)c2)cs1] |
| 44A | 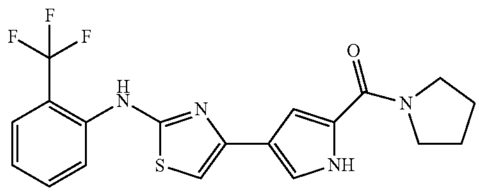 [SMILES: O=C(c1cc(-c2csc(Nc3ccccc3C(F)(F)F)n2)c[nH]1)N1CCCC1] |
| 45A | 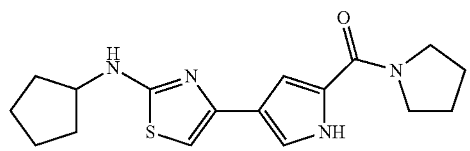 [SMILES: O=C(c1cc(-c2csc(NC3CCCC3)n2)c[nH]1)N1CCCC1] |
| 46A | 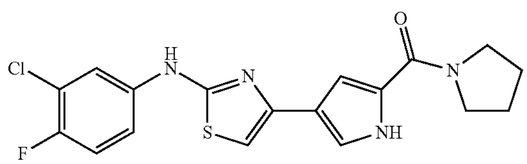 [SMILES: O=C(c1cc(-c2csc(Nc3ccc(F)c(Cl)c3)n2)c[nH]1)N1CCCC1] |
| 47A | 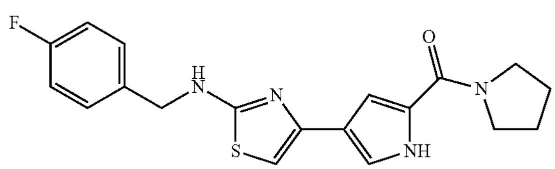 [SMILES: O=C(c1cc(-c2csc(NCc3ccc(F)cc3)n2)c[nH]1)N1CCCC1] |
| 48A | 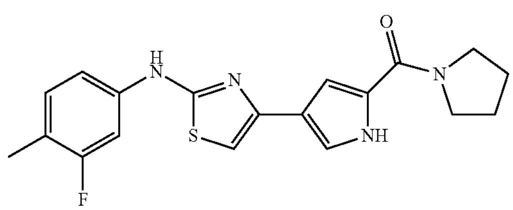 [SMILES: Cc1ccc(Nc2nc(-c3c[nH]c(C(=O)N4CCCC4)c3)cs2)cc1F] |
| 49A | 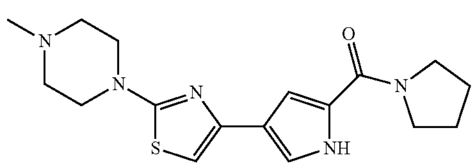 [SMILES: CN1CCN(c2nc(-c3c[nH]c(C(=O)N4CCCC4)c3)cs2)CC1] |
| 50A | 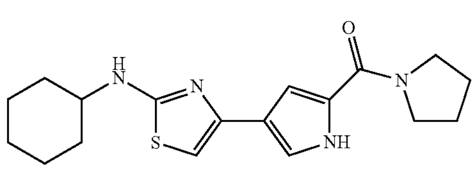 [SMILES: O=C(c1cc(-c2csc(NC3CCCCC3)n2)c[nH]1)N1CCCC1] |

TABLE B-continued
| Compound Name | Structure |
|---|---|
| 51A | 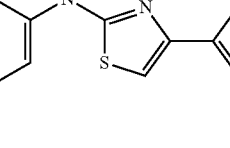 |
| 52A | 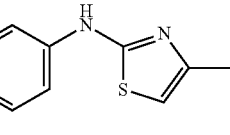 |
| 53A | 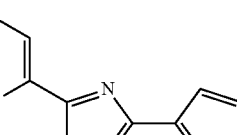 |
| 54A | 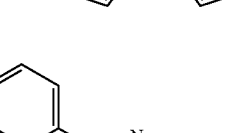 |
| 55A | 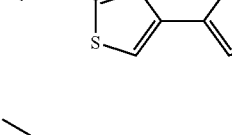 |
| 56A | 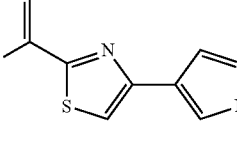 |
| 57A | 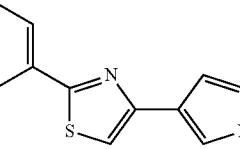 |
| 58A | 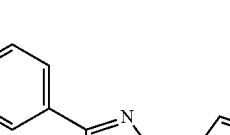 |

TABLE B-continued
| Compound Name | Structure |
|---|---|
| 59A | 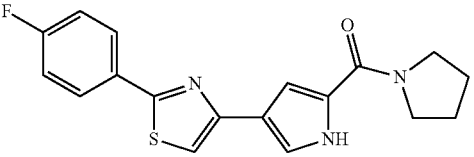 [SMILES: O=C(c1cc(-c2csc(-c3ccc(F)cc3)n2)c[nH]1)N1CCCC1] |
| 60A | 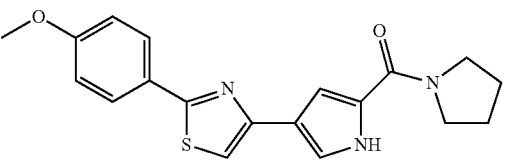 [SMILES: COc1ccc(-c2nc(-c3c[nH]c(C(=O)N4CCCC4)c3)cs2)cc1] |
| 61A | 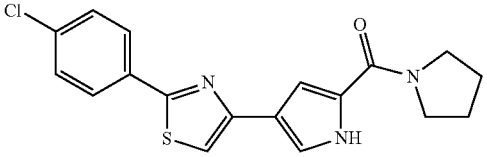 [SMILES: O=C(c1cc(-c2csc(-c3ccc(Cl)cc3)n2)c[nH]1)N1CCCC1] |
| 62A | 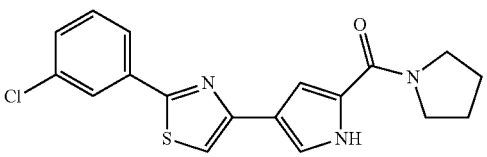 [SMILES: O=C(c1cc(-c2csc(-c3cccc(Cl)c3)n2)c[nH]1)N1CCCC1] |
| 63A | 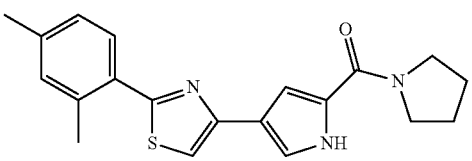 [SMILES: Cc1ccc(-c2nc(-c3c[nH]c(C(=O)N4CCCC4)c3)cs2)c(C)c1] |
| 64A | 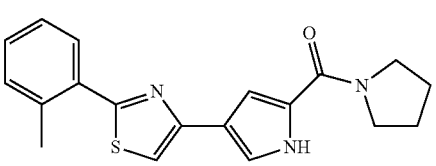 [SMILES: Cc1ccccc1-c1nc(-c2c[nH]c(C(=O)N3CCCC3)c2)cs1] |
| 6A | 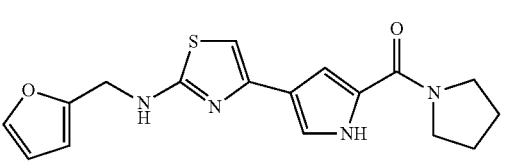 [SMILES: O=C(c1cc(-c2csc(NCc3ccco3)n2)c[nH]1)N1CCCC1] |

TABLE C
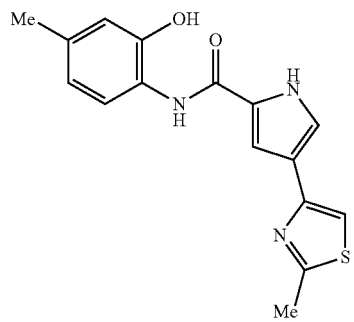 [SMILES: Cc1ccc(NC(=O)c2cc(-c3csc(C)n3)c[nH]2)c(O)c1]
1B
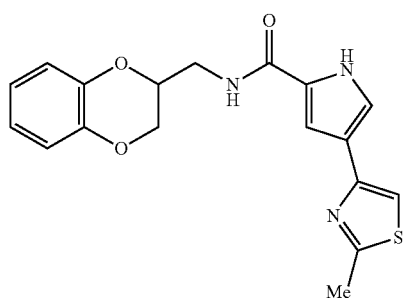 [SMILES: Cc1nc(-c2c[nH]c(C(=O)NCC3COc4ccccc4O3)c2)cs1]
2B
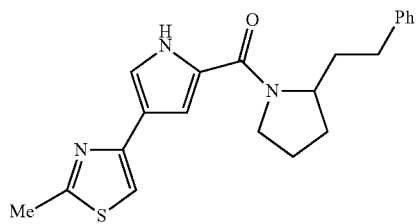 [SMILES: Cc1nc(-c2c[nH]c(C(=O)N3CCCC3CCc3ccccc3)c2)cs1]
3B
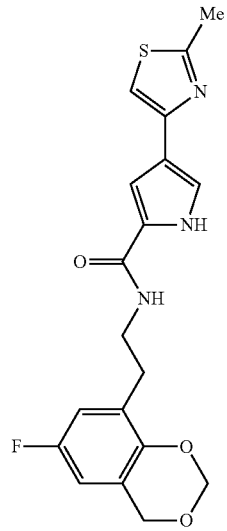 [SMILES: Cc1nc(-c2c[nH]c(C(=O)NCCc3cc(F)cc4c3OCOC4)c2)cs1]
4B

TABLE C-continued
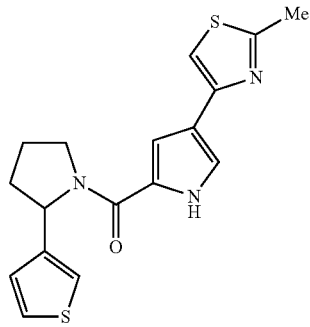 [SMILES: Cc1nc(-c2c[nH]c(C(=O)N3CCCC3c3ccsc3)c2)cs1] 5B
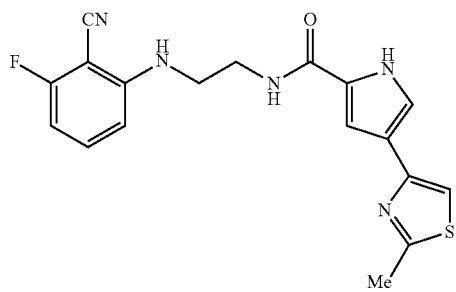 [SMILES: Cc1nc(-c2c[nH]c(C(=O)NCCNc3cccc(F)c3C#N)c2)cs1] 6B
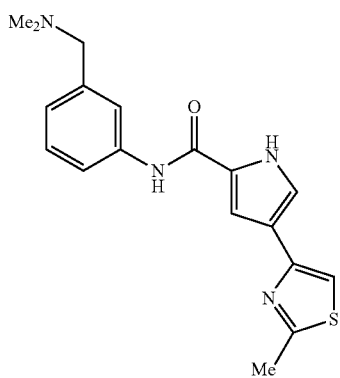 [SMILES: Cc1nc(-c2c[nH]c(C(=O)Nc3cccc(CN(C)C)c3)c2)cs1] 7B
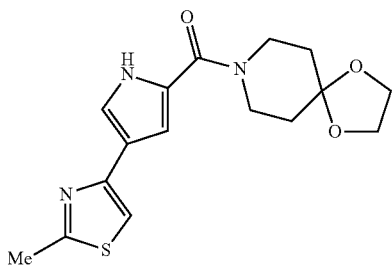 [SMILES: Cc1nc(-c2c[nH]c(C(=O)N3CCC4(CC3)OCCO4)c2)cs1] 8B
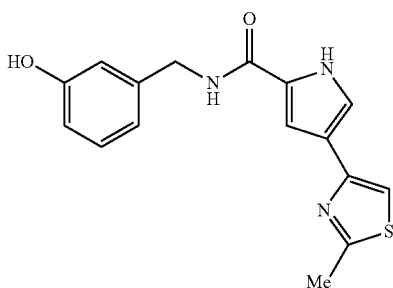 [SMILES: Cc1nc(-c2c[nH]c(C(=O)NCc3cccc(O)c3)c2)cs1] 9B TABLE C-continued
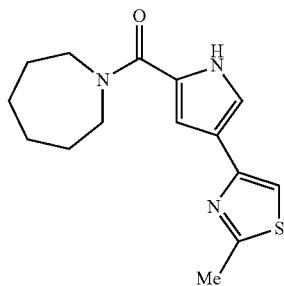 [SMILES: Cc1nc(-c2c[nH]c(C(=O)N3CCCCCC3)c2)cs1]
10B
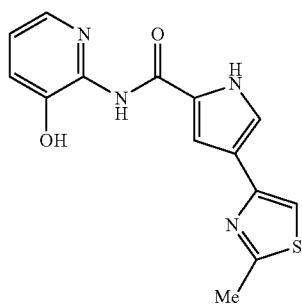 [SMILES: Cc1nc(-c2c[nH]c(C(=O)Nc3ncccc3O)c2)cs1]
11B
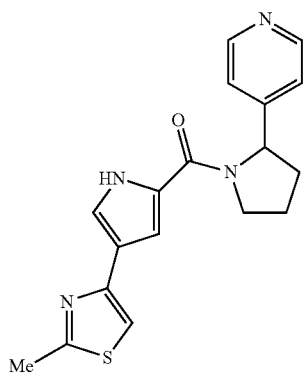 [SMILES: Cc1nc(-c2c[nH]c(C(=O)N3CCCC3c3ccncc3)c2)cs1]
12B
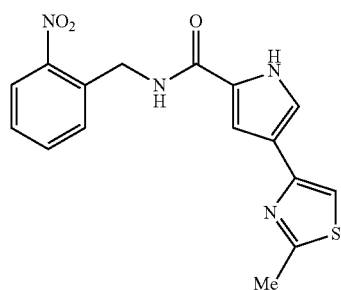 [SMILES: Cc1nc(-c2c[nH]c(C(=O)NCc3ccccc3[N+](=O)[O-])c2)cs1]
13B
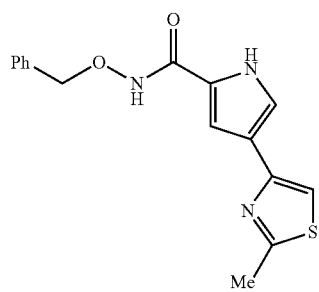 [SMILES: Cc1nc(-c2c[nH]c(C(=O)NOCc3ccccc3)c2)cs1]
14B TABLE C-continued
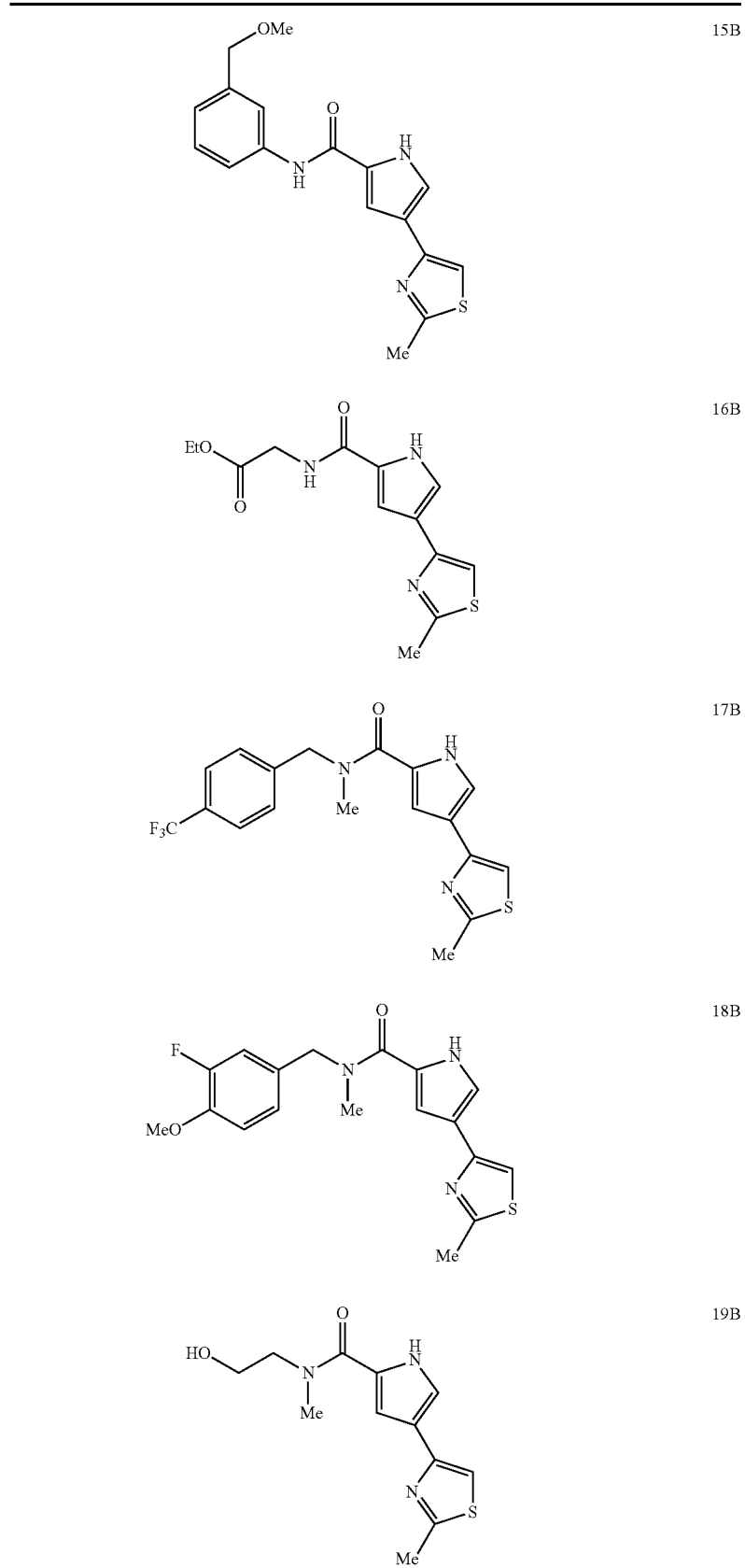

TABLE C-continued
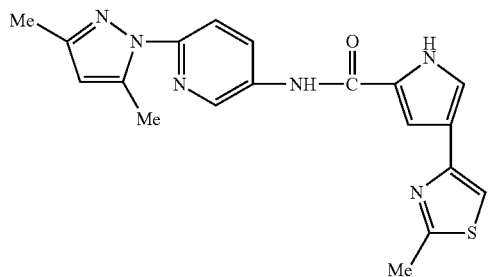 [SMILES: Cc1cc(C)n(-c2ccc(NC(=O)c3cc(-c4csc(C)n4)c[nH]3)cn2)n1]
20B
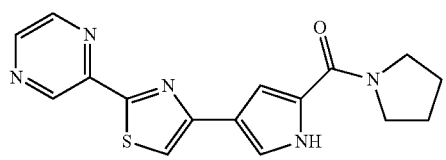
21B
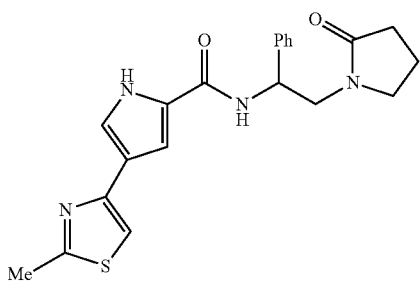 [SMILES: Cc1nc(-c2c[nH]c(C(=O)NC(CN3CCCC3=O)c3ccccc3)c2)cs1]
22B
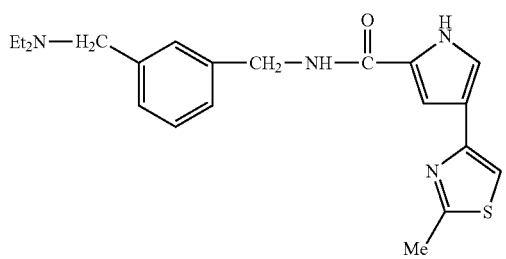
23B
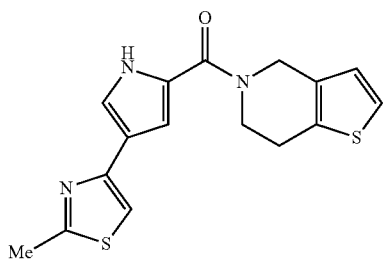 [SMILES: Cc1nc(-c2c[nH]c(C(=O)N3CCc4sccc4C3)c2)cs1]
24B
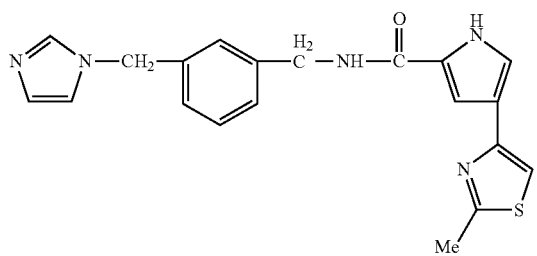 [SMILES: Cc1nc(-c2c[nH]c(C(=O)NCc3cccc(Cn4ccnc4)c3)c2)cs1]
25B TABLE C-continued
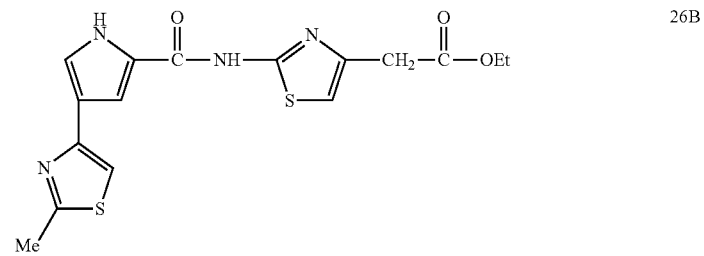 26B
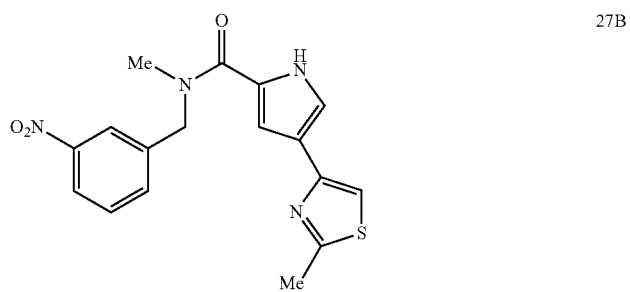 27B
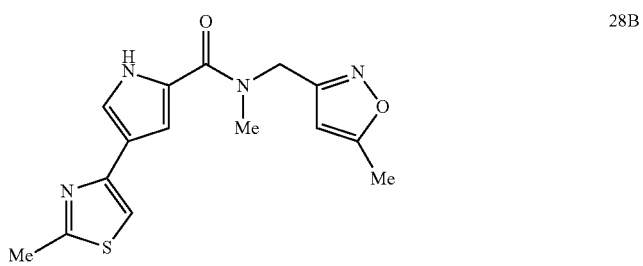 28B
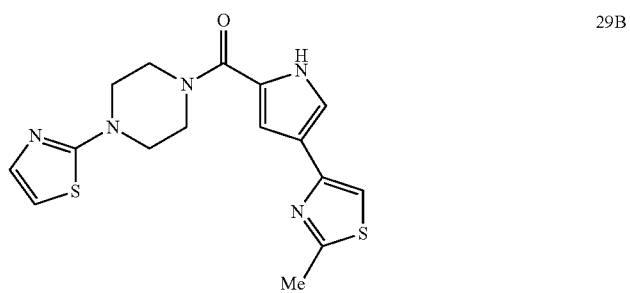 29B
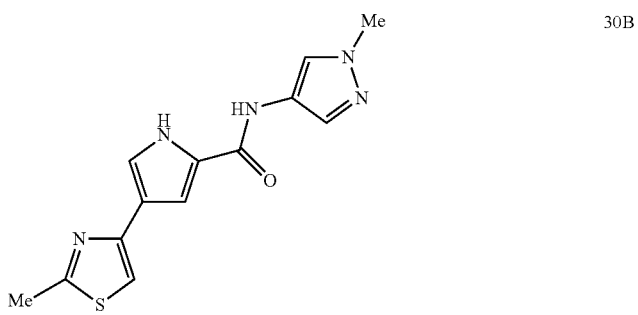 30B TABLE C-continued
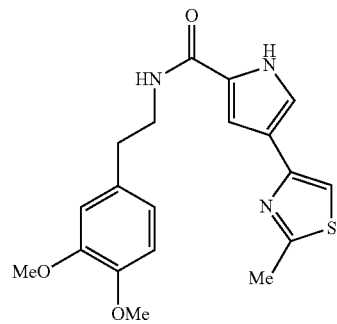 [SMILES: COc1ccc(CCNC(=O)c2cc(-c3csc(C)n3)c[nH]2)cc1OC]
31B
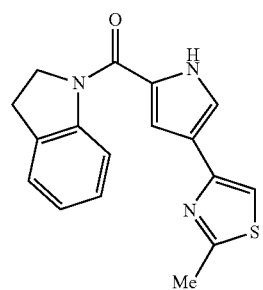 [SMILES: Cc1nc(-c2c[nH]c(C(=O)N3CCc4ccccc43)c2)cs1]
32B
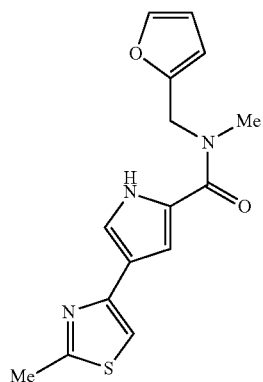 [SMILES: Cc1nc(-c2c[nH]c(C(=O)N(C)Cc3ccco3)c2)cs1]
33B
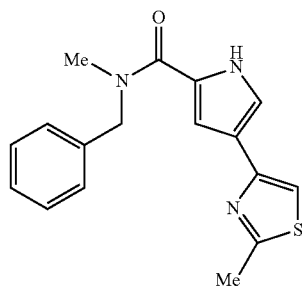 [SMILES: Cc1nc(-c2c[nH]c(C(=O)N(C)Cc3ccccc3)c2)cs1]
34B
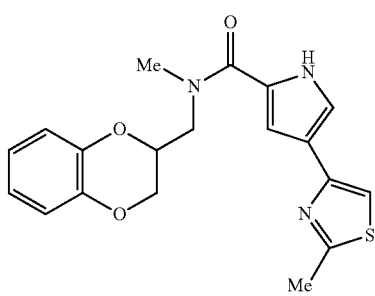 [SMILES: Cc1nc(-c2c[nH]c(C(=O)N(C)CC3COc4ccccc4O3)c2)cs1]
35B TABLE C-continued
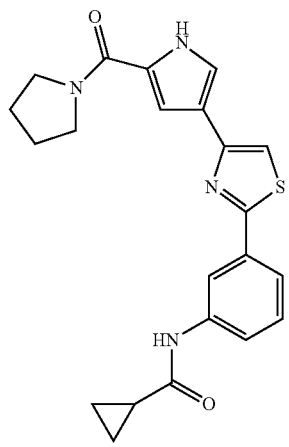 [SMILES: O=C(Nc1cccc(-c2nc(-c3c[nH]c(C(=O)N4CCCC4)c3)cs2)c1)C1CC1]
36B
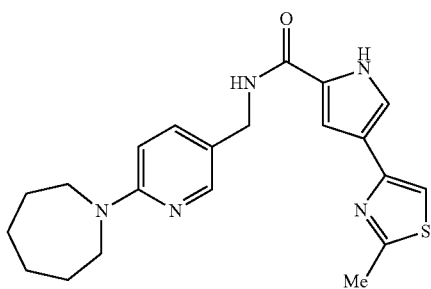 [SMILES: Cc1nc(-c2c[nH]c(C(=O)NCc3ccc(N4CCCCCC4)nc3)c2)cs1]
37B
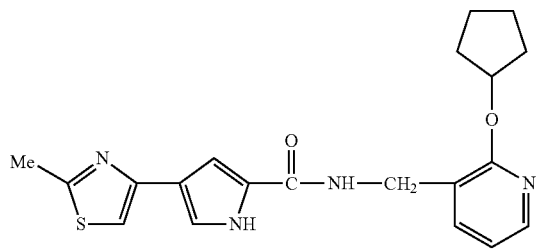 [SMILES: Cc1nc(-c2c[nH]c(C(=O)NCc3cccnc3OC3CCCC3)c2)cs1]
38B
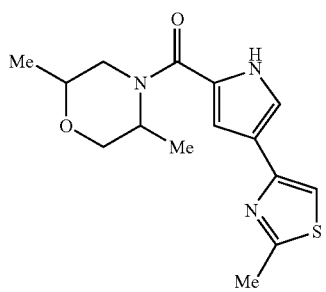 [SMILES: Cc1nc(-c2c[nH]c(C(=O)N3CC(C)OCC3C)c2)cs1]
39B
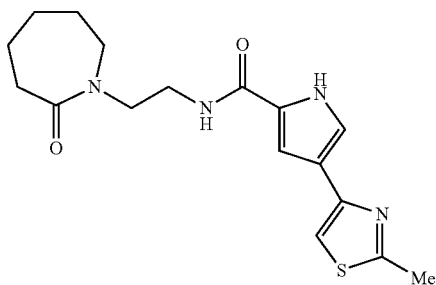 [SMILES: Cc1nc(-c2c[nH]c(C(=O)NCCN3CCCCCC3=O)c2)cs1]
40B TABLE C-continued
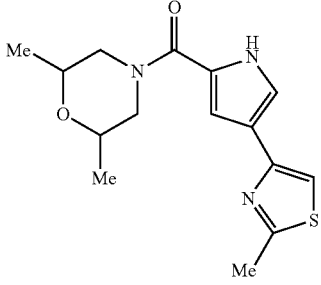 [SMILES: Cc1nc(-c2c[nH]c(C(=O)N3CC(C)OC(C)C3)c2)cs1] 41B
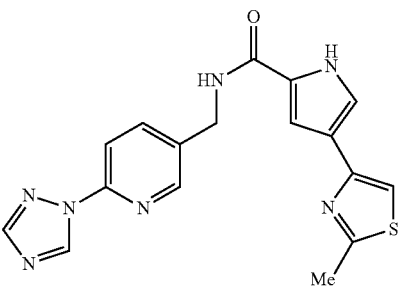 [SMILES: Cc1nc(-c2c[nH]c(C(=O)NCc3ccc(-n4cncn4)nc3)c2)cs1] 42B
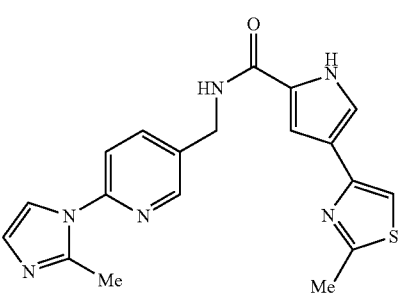 [SMILES: Cc1nc(-c2c[nH]c(C(=O)NCc3ccc(-n4ccnc4C)nc3)c2)cs1] 43B
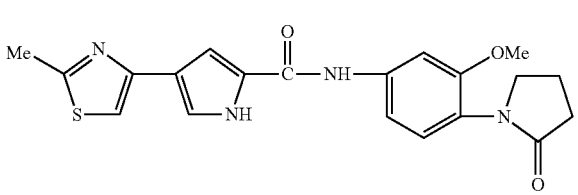 [SMILES: COc1cc(NC(=O)c2cc(-c3csc(C)n3)c[nH]2)ccc1N1CCCC1=O] 44B
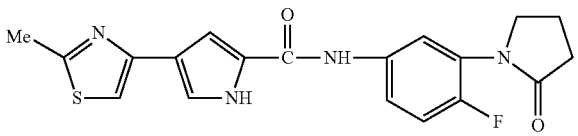 [SMILES: Cc1nc(-c2c[nH]c(C(=O)Nc3ccc(F)c(N4CCCC4=O)c3)c2)cs1] 45B
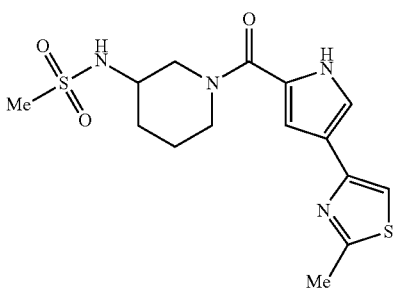 [SMILES: Cc1nc(-c2c[nH]c(C(=O)N3CCCC(NS(C)(=O)=O)C3)c2)cs1] 46B TABLE C-continued
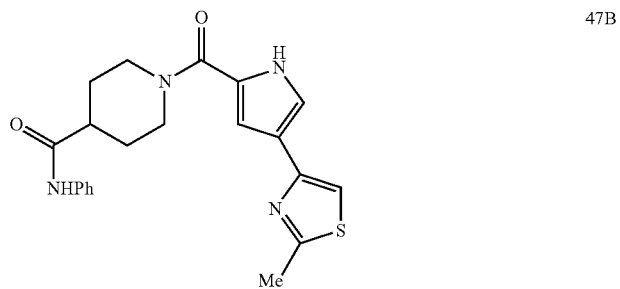
47B
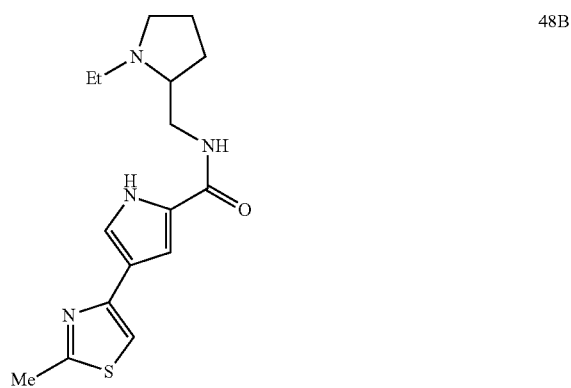
48B
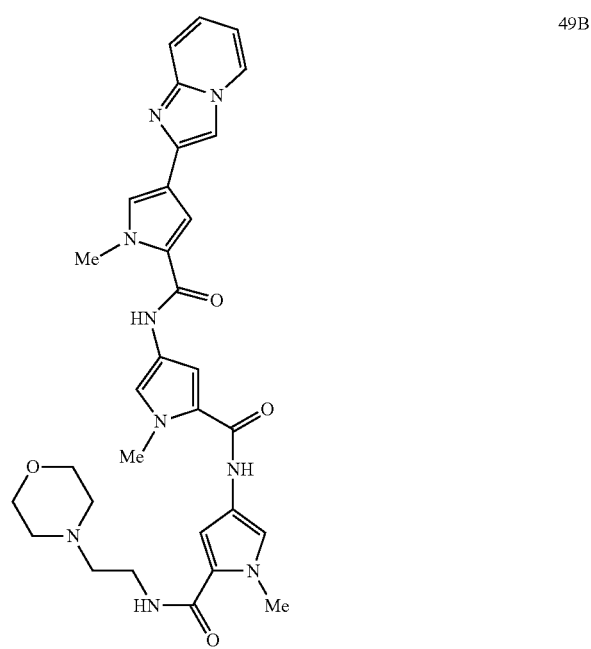
49B TABLE C-continued
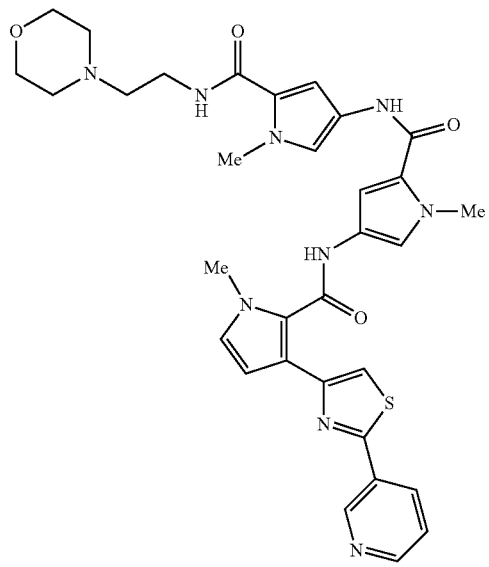 [SMILES: Cn1cc(NC(=O)c2cc(NC(=O)c3c(-c4csc(-c5cccnc5)n4)ccn3C)cn2C)cc1C(=O)NCCN1CCOCC1]
50B
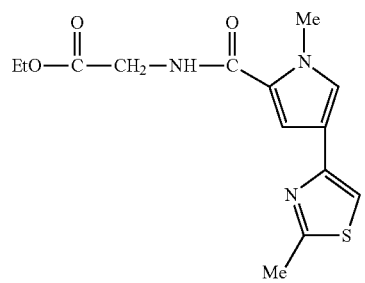 [SMILES: CCOC(=O)CNC(=O)c1cc(-c2csc(C)n2)cn1C]
51B
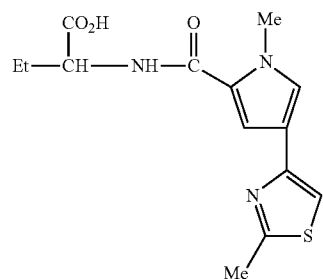 [SMILES: CCC(NC(=O)c1cc(-c2csc(C)n2)cn1C)C(=O)O]
52B
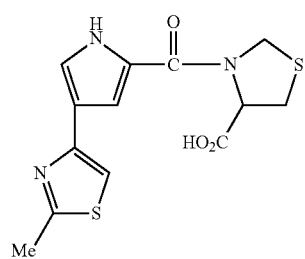 [SMILES: Cc1nc(-c2c[nH]c(C(=O)N3CSCC3C(=O)O)c2)cs1]
53B TABLE C-continued
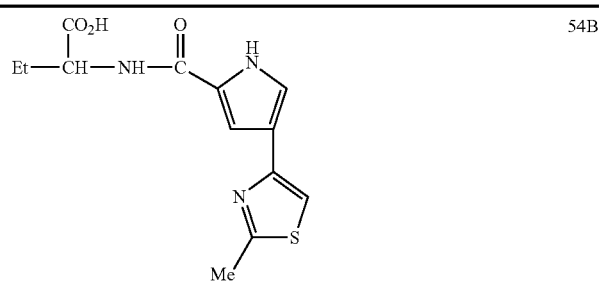
54B
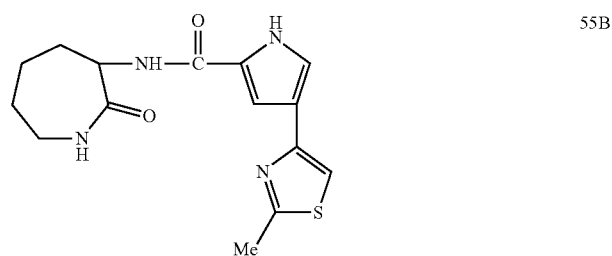
55B
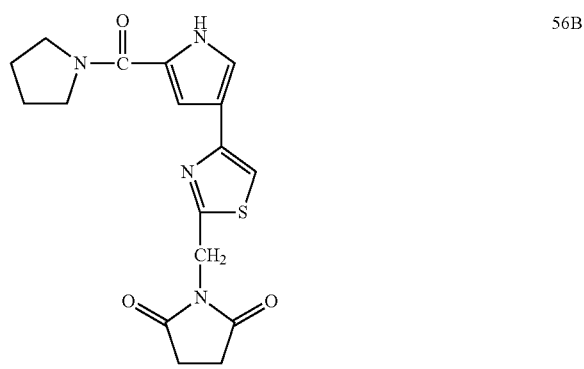
56B
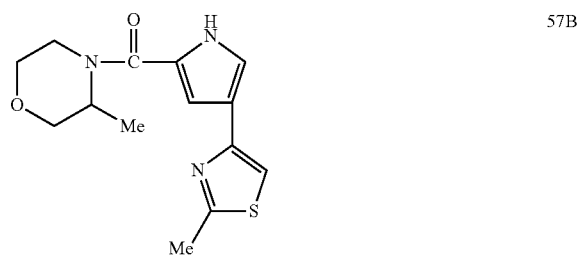
57B
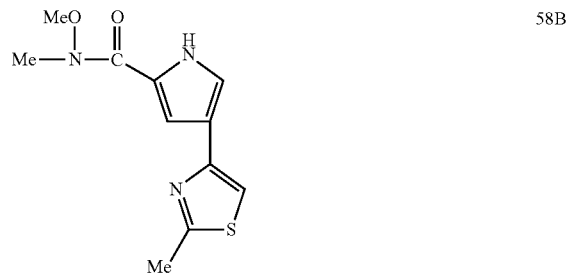
58B TABLE C-continued
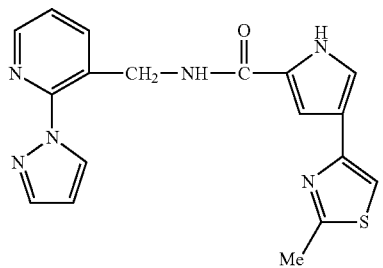 [SMILES: Cc1nc(-c2c[nH]c(C(=O)NCc3cccnc3-n3cccn3)c2)cs1]
59B
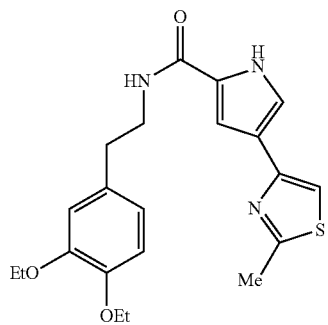 [SMILES: CCOc1ccc(CCNC(=O)c2cc(-c3csc(C)n3)c[nH]2)cc1OCC]
60B
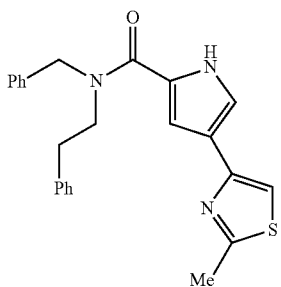 [SMILES: Cc1nc(-c2c[nH]c(C(=O)N(CCc3ccccc3)Cc3ccccc3)c2)cs1]
61B
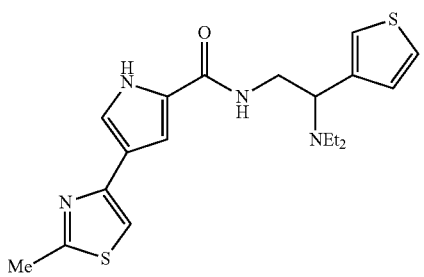
62B
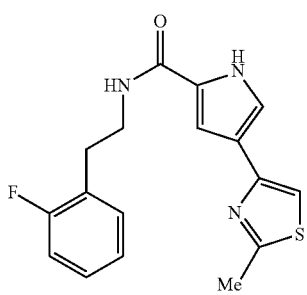 [SMILES: Cc1nc(-c2c[nH]c(C(=O)NCCc3ccccc3F)c2)cs1]
63B TABLE C-continued
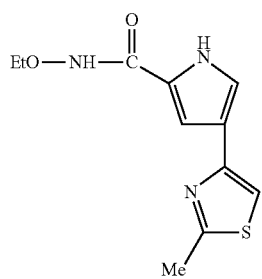 [SMILES: CCONC(=O)c1cc(-c2csc(C)n2)c[nH]1]
64B
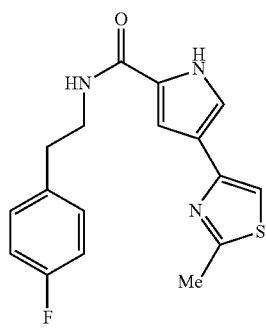 [SMILES: Cc1nc(-c2c[nH]c(C(=O)NCCc3ccc(F)cc3)c2)cs1]
65B
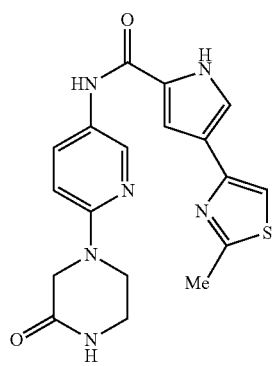 [SMILES: Cc1nc(-c2c[nH]c(C(=O)Nc3ccc(N4CCNC(=O)C4)nc3)c2)cs1]
66B
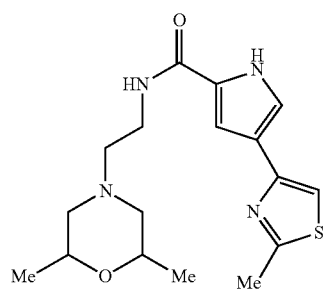 [SMILES: Cc1nc(-c2c[nH]c(C(=O)NCCN3CC(C)OC(C)C3)c2)cs1]
67B
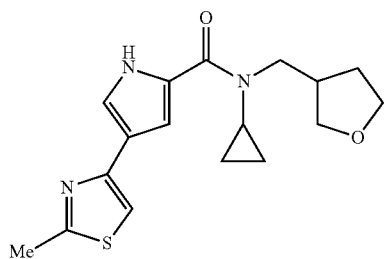 [SMILES: Cc1nc(-c2c[nH]c(C(=O)N(CC3CCOC3)C3CC3)c2)cs1]
68B TABLE C-continued
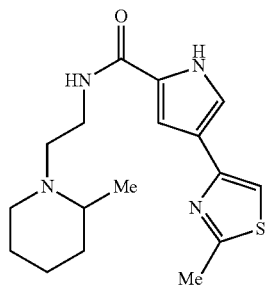 [SMILES: Cc1nc(-c2c[nH]c(C(=O)NCCN3CCCCC3C)c2)cs1]
69B
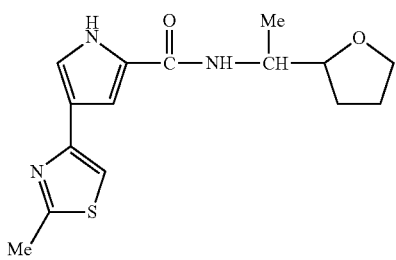 [SMILES: Cc1nc(-c2c[nH]c(C(=O)NC(C)C3CCCO3)c2)cs1]
70B
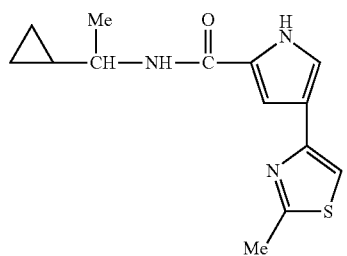 [SMILES: Cc1nc(-c2c[nH]c(C(=O)NC(C)C3CC3)c2)cs1]
71B
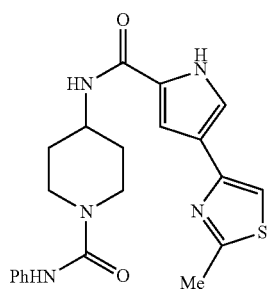
72B
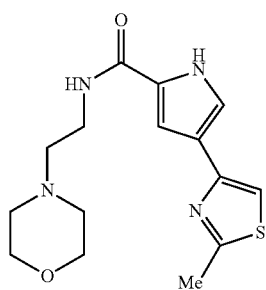 [SMILES: Cc1nc(-c2c[nH]c(C(=O)NCCN3CCOCC3)c2)cs1]
73B TABLE C-continued
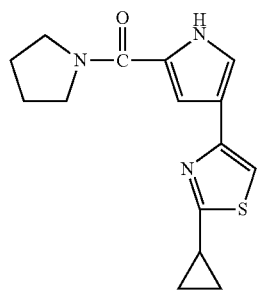 [SMILES: O=C(c1cc(-c2csc(C3CC3)n2)c[nH]1)N1CCCC1]
74B
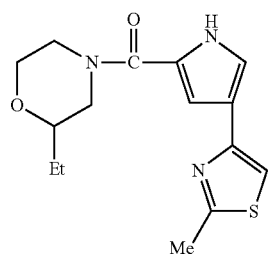 [SMILES: CCC1CN(C(=O)c2cc(-c3csc(C)n3)c[nH]2)CCO1]
75B
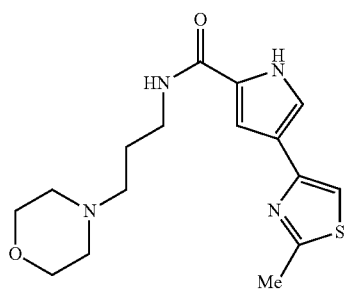 [SMILES: Cc1nc(-c2c[nH]c(C(=O)NCCCN3CCOCC3)c2)cs1]
76B
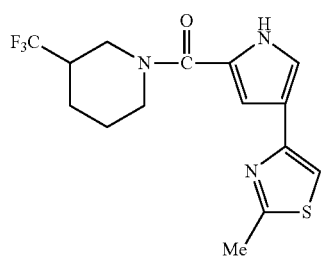 [SMILES: Cc1nc(-c2c[nH]c(C(=O)N3CCCC(C(F)(F)F)C3)c2)cs1]
77B
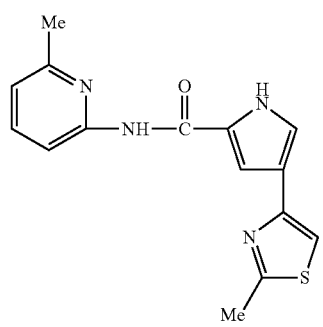 [SMILES: Cc1cccc(NC(=O)c2cc(-c3csc(C)n3)c[nH]2)n1]
78B TABLE C-continued
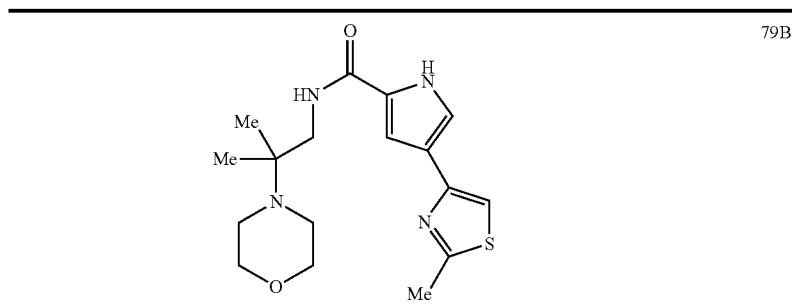
79B
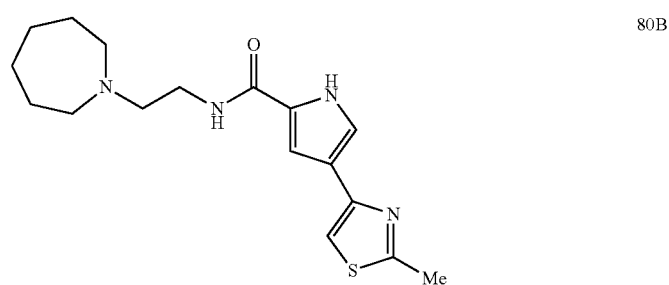
80B
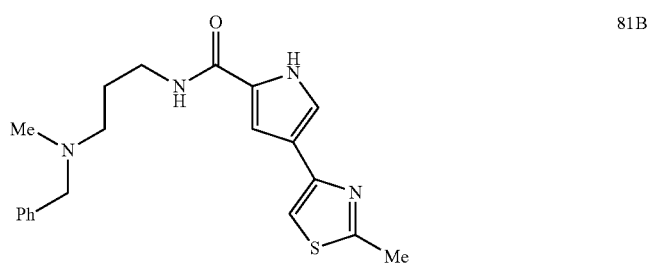
81B
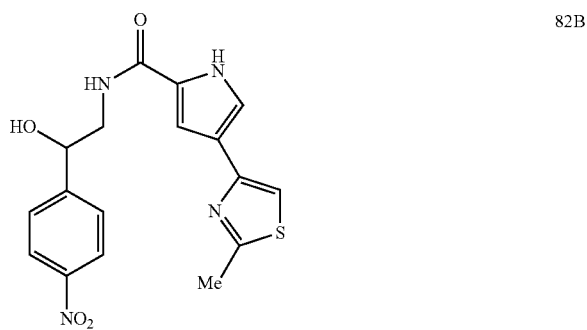
82B
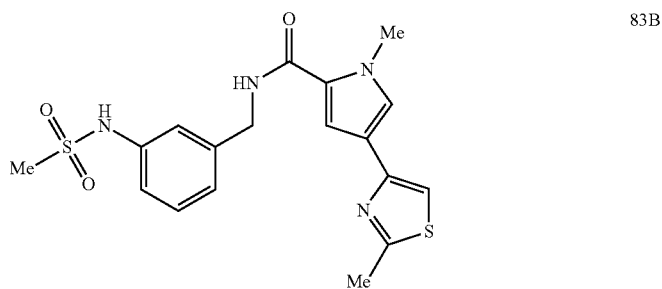
83B TABLE C-continued
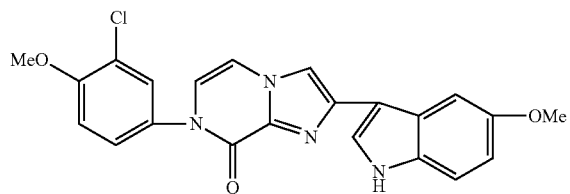 [SMILES: COc1ccc2[nH]cc(-c3cn4ccn(-c5ccc(OC)c(Cl)c5)c(=O)c4n3)c2c1]
84B
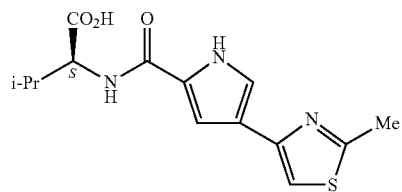
85B
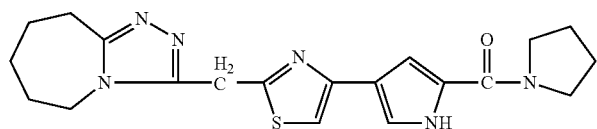 [SMILES: O=C(c1cc(-c2csc(Cc3nnc4n3CCCCC4)n2)c[nH]1)N1CCCC1]
86B
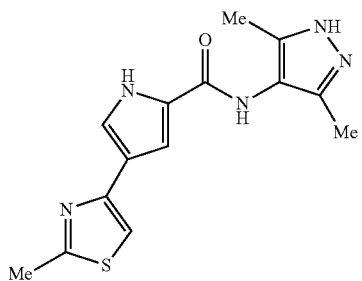 [SMILES: Cc1nc(-c2c[nH]c(C(=O)Nc3c(C)n[nH]c3C)c2)cs1]
87B
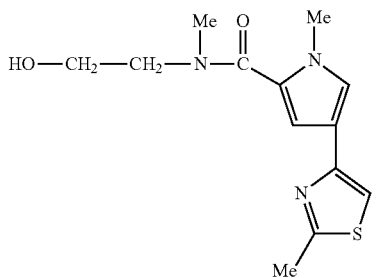 [SMILES: Cc1nc(-c2cc(C(=O)N(C)CCO)n(C)c2)cs1]
88B
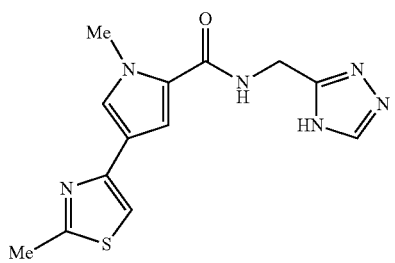 [SMILES: Cc1nc(-c2cc(C(=O)NCc3nnc[nH]3)n(C)c2)cs1]
89B TABLE C-continued
| | |
|---|---|
| 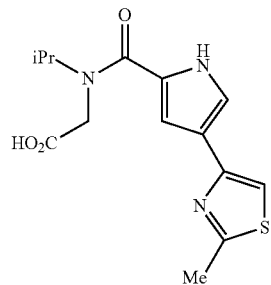 [SMILES: Cc1nc(-c2c[nH]c(C(=O)N(CC(=O)O)C(C)C)c2)cs1] | 90B |
| 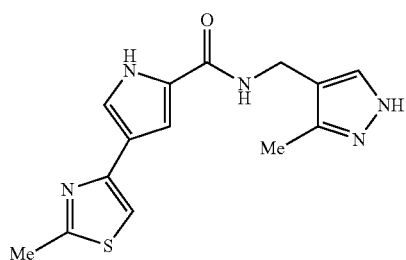 [SMILES: Cc1nc(-c2c[nH]c(C(=O)NCc3c[nH]nc3C)c2)cs1] | 91B |
| 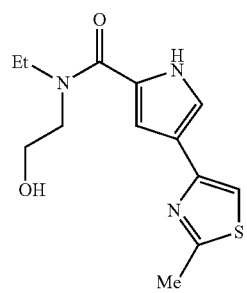 [SMILES: CCN(CCO)C(=O)c1cc(-c2csc(C)n2)c[nH]1] | 92B |
| 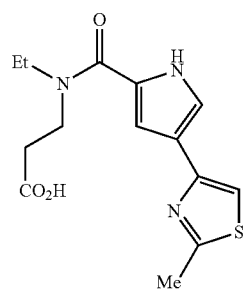 [SMILES: CCN(CCC(=O)O)C(=O)c1cc(-c2csc(C)n2)c[nH]1] | 93B |
| 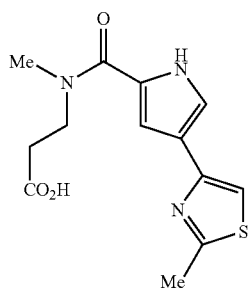 [SMILES: Cc1nc(-c2c[nH]c(C(=O)N(C)CCC(=O)O)c2)cs1] | 94B |

TABLE C-continued
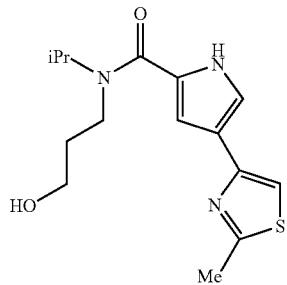 [SMILES: Cc1nc(-c2c[nH]c(C(=O)N(CCCO)C(C)C)c2)cs1]
95B
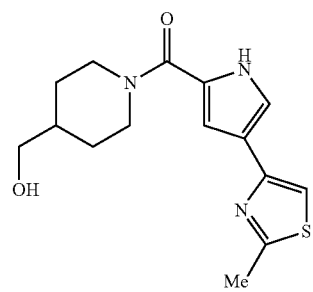 [SMILES: Cc1nc(-c2c[nH]c(C(=O)N3CCC(CO)CC3)c2)cs1]
96B
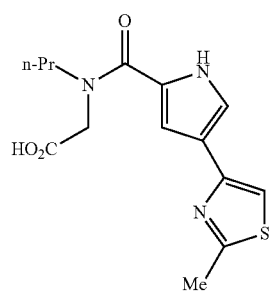
97B
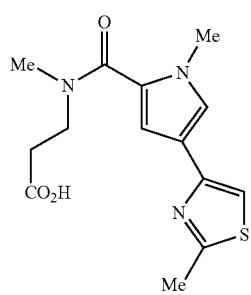 [SMILES: Cc1nc(-c2cc(C(=O)N(C)CCC(=O)O)n(C)c2)cs1]
98B
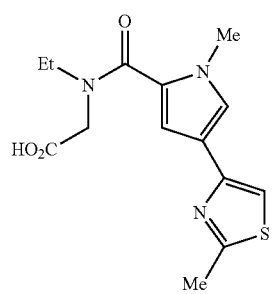 [SMILES: CCN(CC(=O)O)C(=O)c1cc(-c2csc(C)n2)cn1C]
99B TABLE C-continued
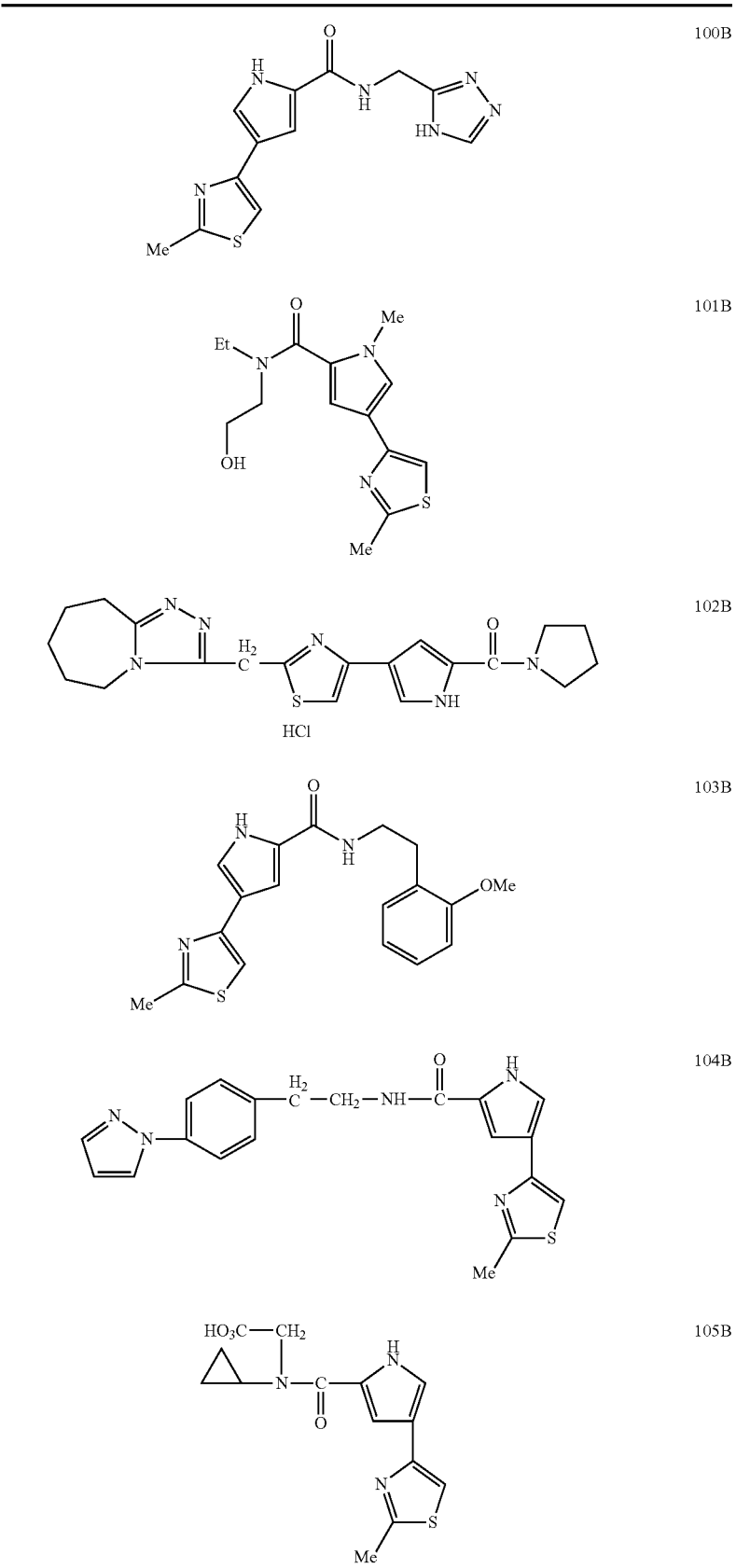

TABLE C-continued
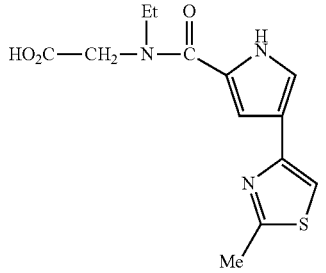 [SMILES: CCN(CC(=O)O)C(=O)c1cc(-c2csc(C)n2)c[nH]1] 106B
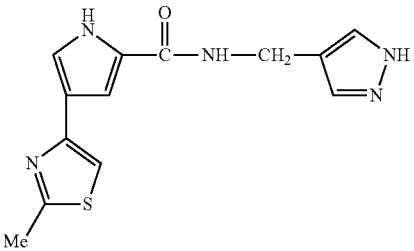 [SMILES: Cc1nc(-c2c[nH]c(C(=O)NCc3cn[nH]c3)c2)cs1] 107B
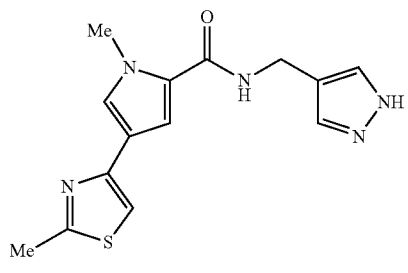 [SMILES: Cc1nc(-c2cc(C(=O)NCc3cn[nH]c3)n(C)c2)cs1] 108B
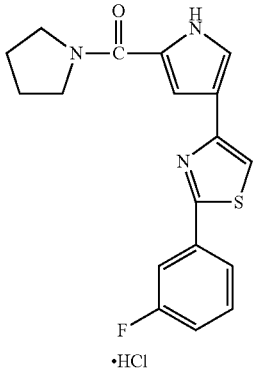 [SMILES: O=C(c1cc(-c2csc(-c3cccc(F)c3)n2)c[nH]1)N1CCCC1 ; Cl] 109B
·HCl
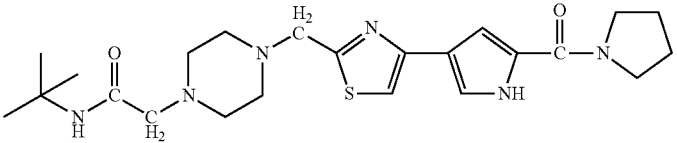 110B
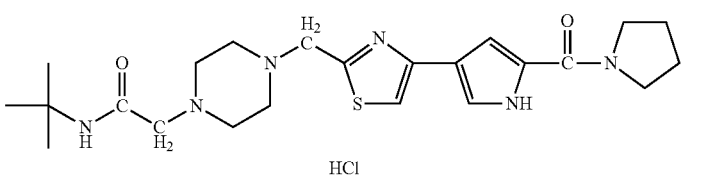 [SMILES: CC(C)(C)NC(=O)CN1CCN(Cc2nc(-c3c[nH]c(C(=O)N4CCCC4)c3)cs2)CC1 ; Cl] 111B
HCl TABLE C-continued
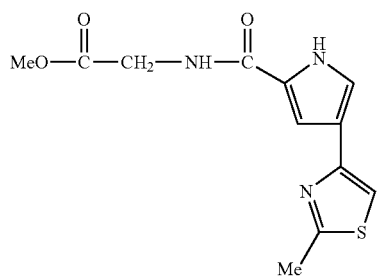 [SMILES: COC(=O)CNC(=O)c1cc(-c2csc(C)n2)c[nH]1]
112B
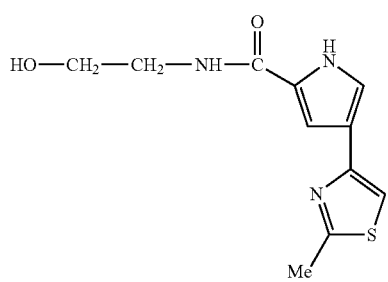 [SMILES: Cc1nc(-c2c[nH]c(C(=O)NCCO)c2)cs1]
113B
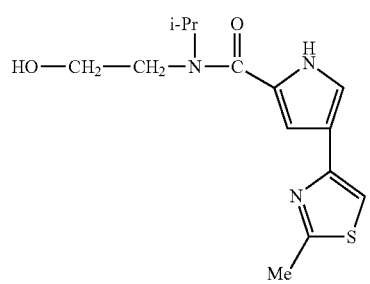 [SMILES: Cc1nc(-c2c[nH]c(C(=O)N(CCO)C(C)C)c2)cs1]
114B
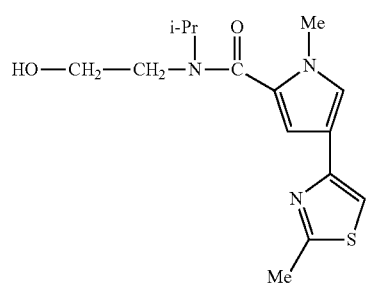 [SMILES: Cc1nc(-c2cc(C(=O)N(CCO)C(C)C)n(C)c2)cs1]
115B
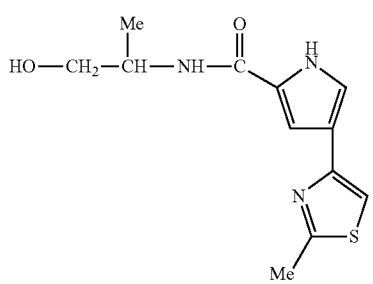 [SMILES: Cc1nc(-c2c[nH]c(C(=O)NC(C)CO)c2)cs1]
116B TABLE C-continued
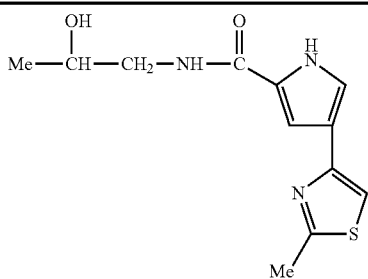
117B
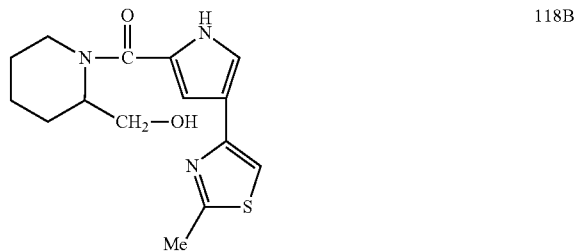
118B
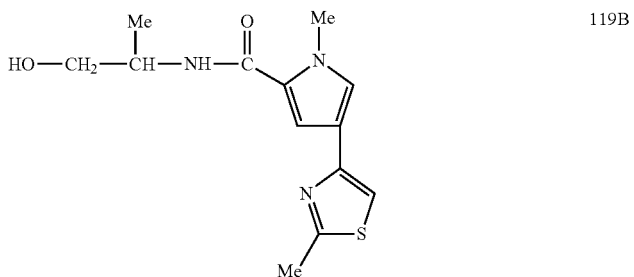
119B
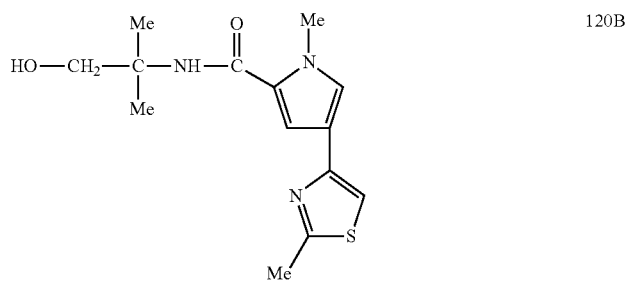
120B
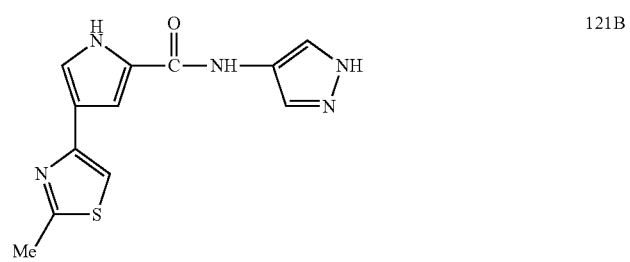
121B
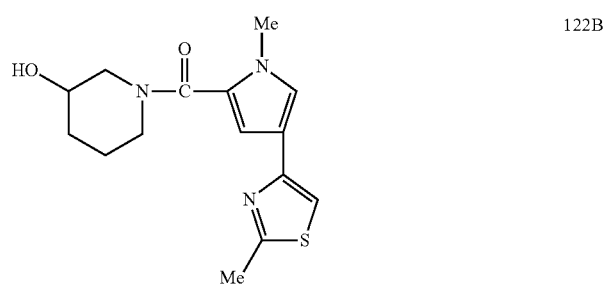
122B TABLE C-continued
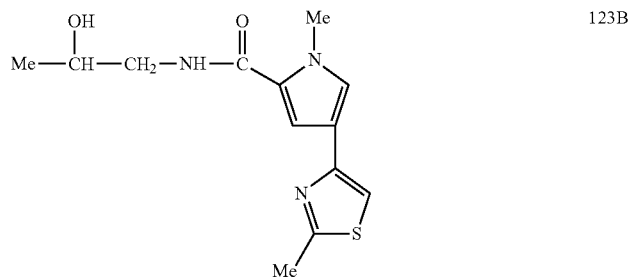
123B
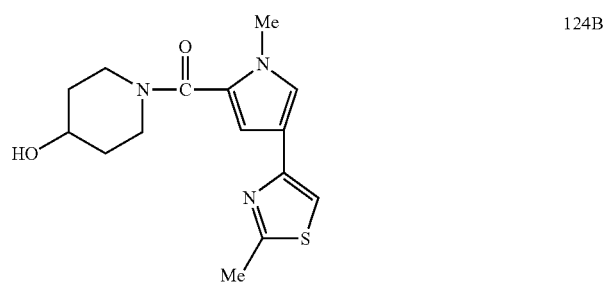
124B
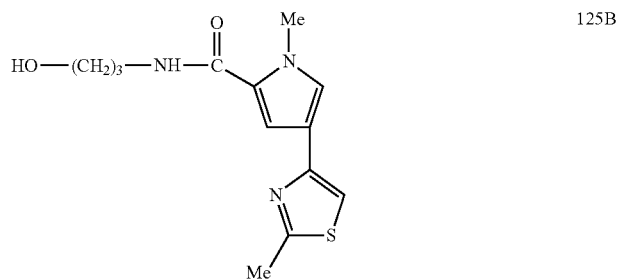
125B
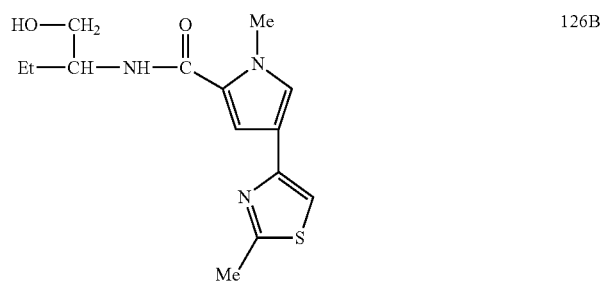
126B
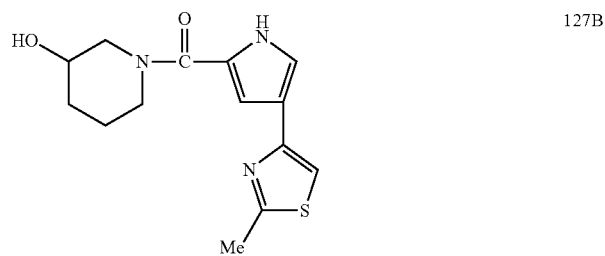
127B TABLE C-continued
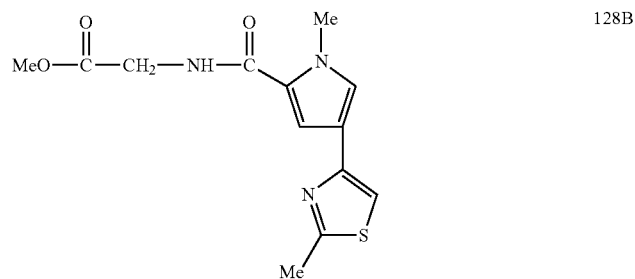 128B
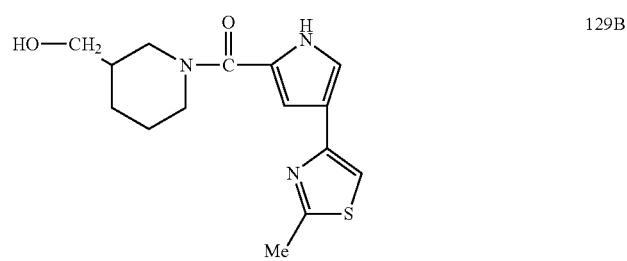 129B
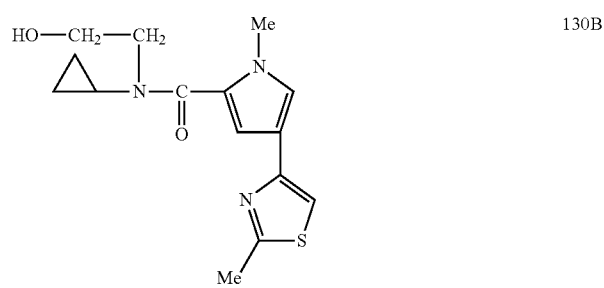 130B
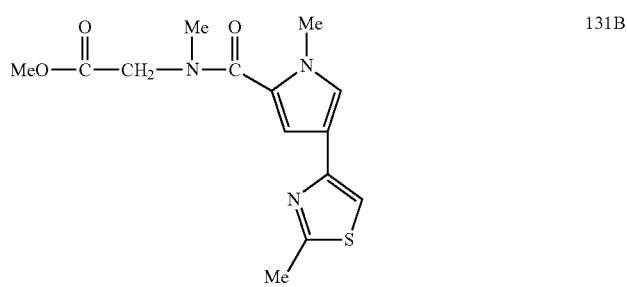 131B
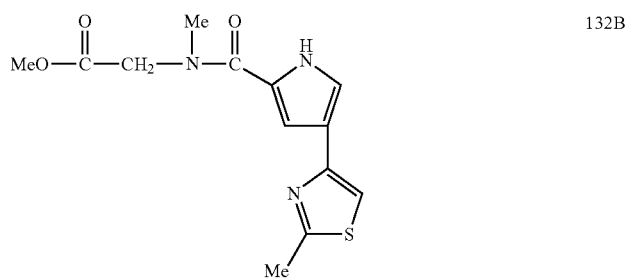 132B TABLE C-continued

| | |
|---|---|
| (structure) | 133B |
| (structure) | 134B |
| (structure) | 135B |
| (structure) | 136B |
| (structure) | 137B |
| (structure) | 138B |

TABLE C-continued
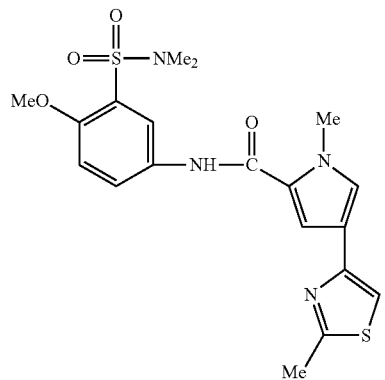 [SMILES: COc1ccc(NC(=O)c2cc(-c3csc(C)n3)cn2C)cc1S(=O)(=O)N(C)C] 139B
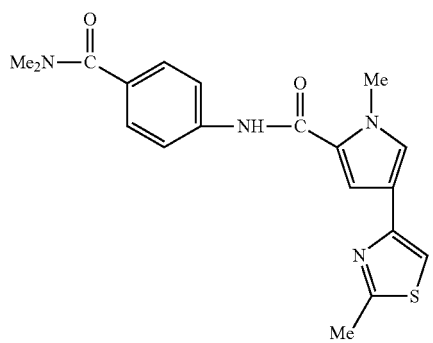 [SMILES: Cc1nc(-c2cc(C(=O)Nc3ccc(C(=O)N(C)C)cc3)n(C)c2)cs1] 140B
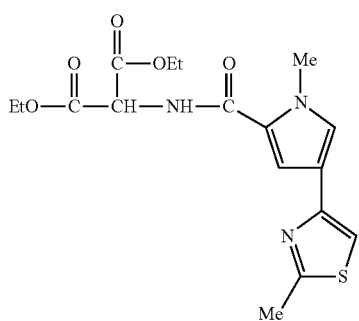 [SMILES: CCOC(=O)C(NC(=O)c1cc(-c2csc(C)n2)cn1C)C(=O)OCC] 141B
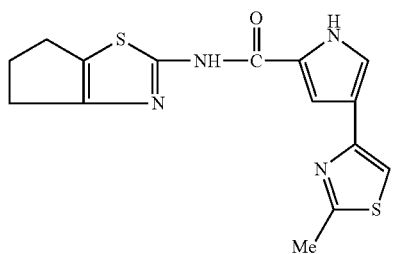 [SMILES: Cc1nc(-c2c[nH]c(C(=O)Nc3nc4c(s3)CCC4)c2)cs1] 142B
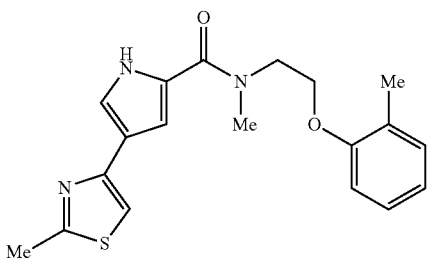 [SMILES: Cc1nc(-c2c[nH]c(C(=O)N(C)CCOc3ccccc3C)c2)cs1] 143B TABLE C-continued
| | |
|---|---|
| 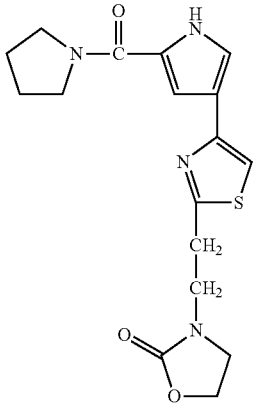 [SMILES: O=C1OCCN1CCc1nc(-c2c[nH]c(C(=O)N3CCCC3)c2)cs1] | 144B |
| 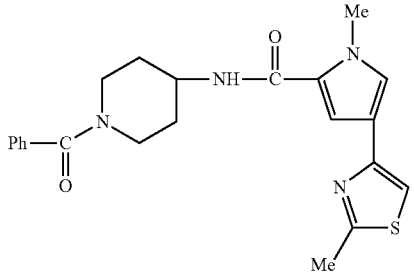 [SMILES: Cc1nc(-c2cc(C(=O)NC3CCN(C(=O)c4ccccc4)CC3)n(C)c2)cs1] | 145B |
| 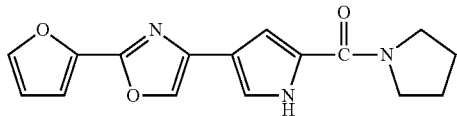 [SMILES: O=C(c1cc(-c2coc(-c3ccco3)n2)c[nH]1)N1CCCC1] | 146B |
| 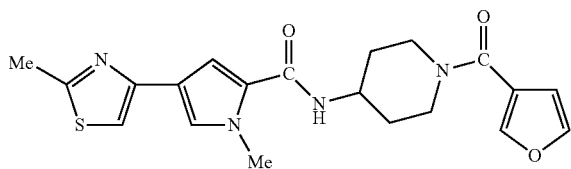 [SMILES: Cc1nc(-c2cc(C(=O)NC3CCN(C(=O)c4ccoc4)CC3)n(C)c2)cs1] | 147B |
| 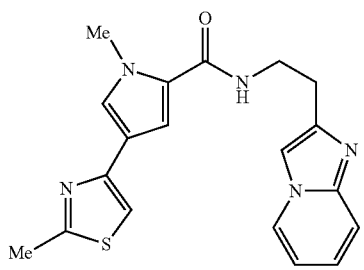 [SMILES: Cc1nc(-c2cc(C(=O)NCCc3cn4ccccc4n3)n(C)c2)cs1] | 148B |
| 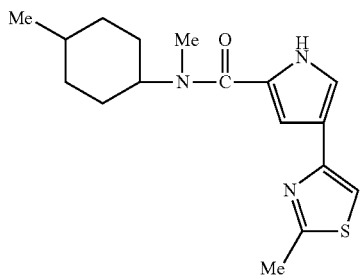 [SMILES: Cc1nc(-c2c[nH]c(C(=O)N(C)C3CCC(C)CC3)c2)cs1] | 149B |

TABLE C-continued
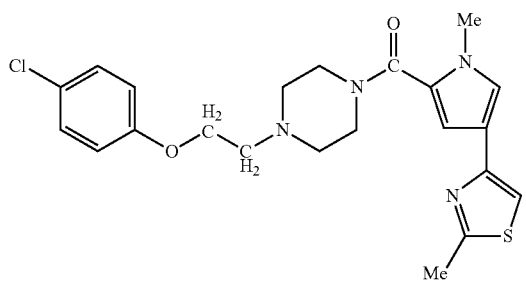 [SMILES: Cc1nc(-c2cc(C(=O)N3CCN(CCOc4ccc(Cl)cc4)CC3)n(C)c2)cs1]
150B
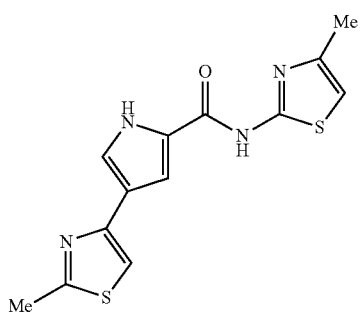 [SMILES: Cc1csc(NC(=O)c2cc(-c3csc(C)n3)c[nH]2)n1]
151B
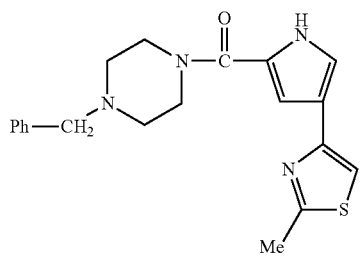 [SMILES: Cc1nc(-c2c[nH]c(C(=O)N3CCN(Cc4ccccc4)CC3)c2)cs1]
152B
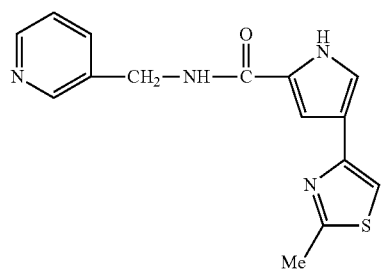 [SMILES: Cc1nc(-c2c[nH]c(C(=O)NCc3cccnc3)c2)cs1]
153B
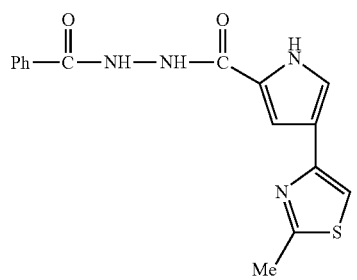 [SMILES: Cc1nc(-c2c[nH]c(C(=O)NNC(=O)c3ccccc3)c2)cs1]
154B TABLE C-continued
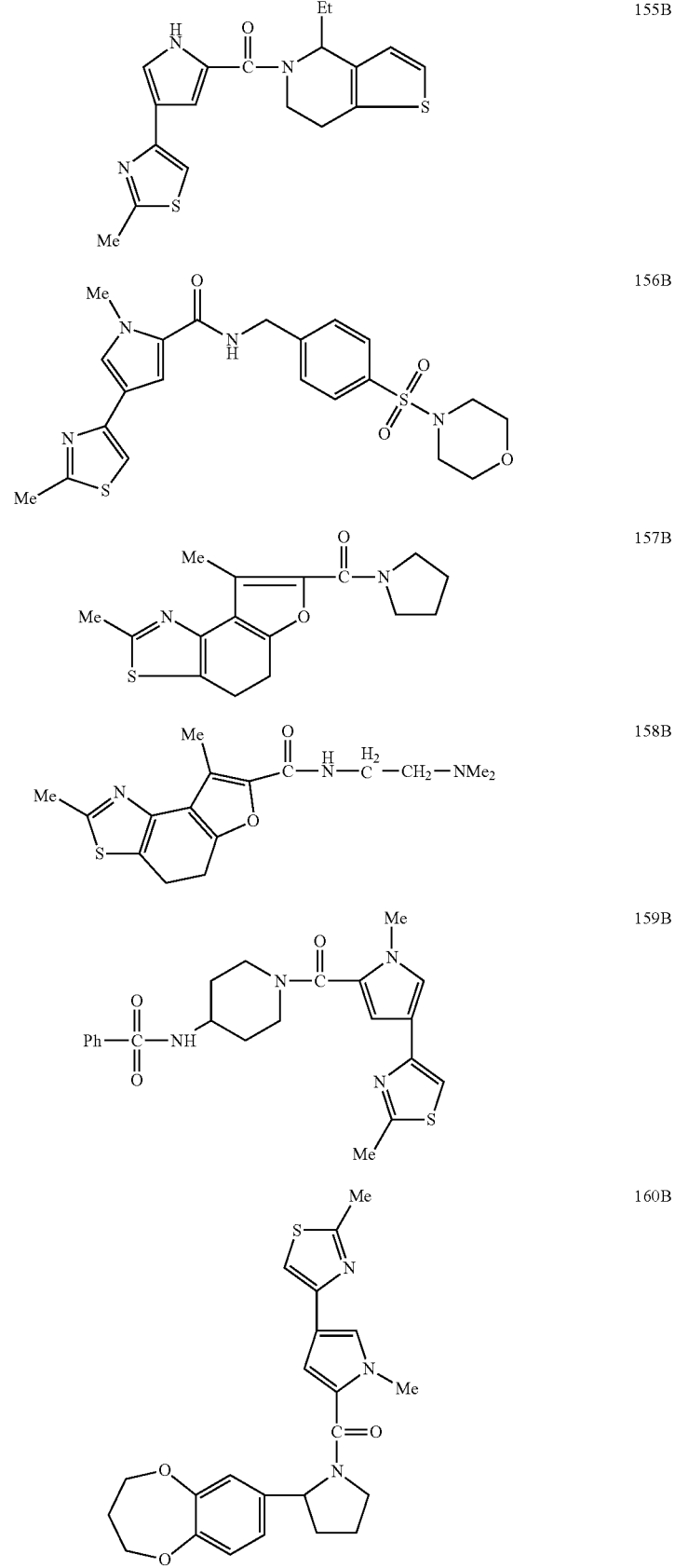
155B
156B
157B
158B
159B
160B TABLE C-continued
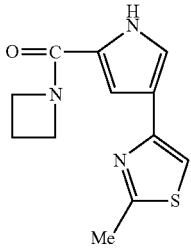 [SMILES: Cc1nc(-c2c[nH]c(C(=O)N3CCC3)c2)cs1]
161B
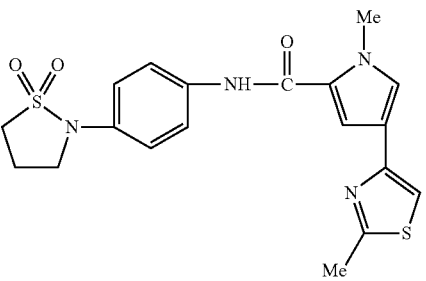 [SMILES: Cc1nc(-c2cc(C(=O)Nc3ccc(N4CCCS4(=O)=O)cc3)n(C)c2)cs1]
162B
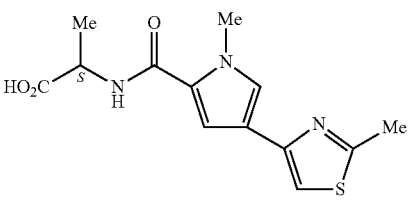
163B
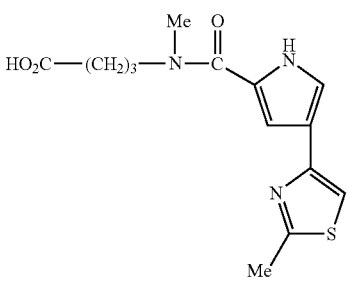
164B
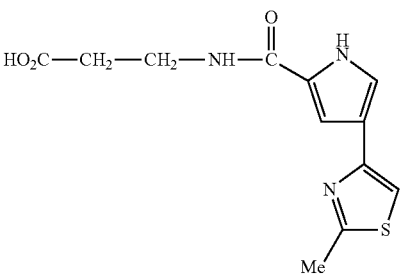 [SMILES: Cc1nc(-c2c[nH]c(C(=O)NCCC(=O)O)c2)cs1]
165B
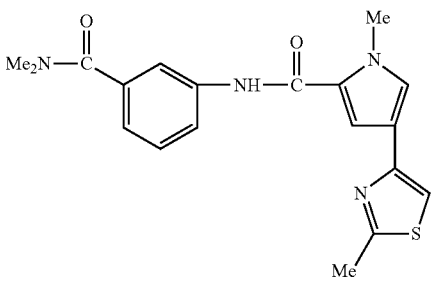 [SMILES: Cc1nc(-c2cc(C(=O)Nc3cccc(C(=O)N(C)C)c3)n(C)c2)cs1]
166B

TABLE C-continued
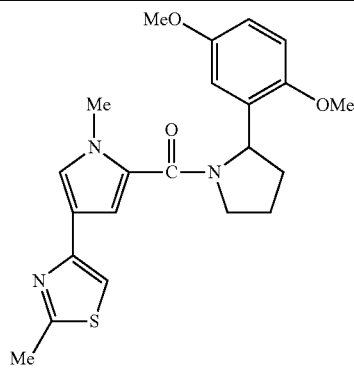
167B
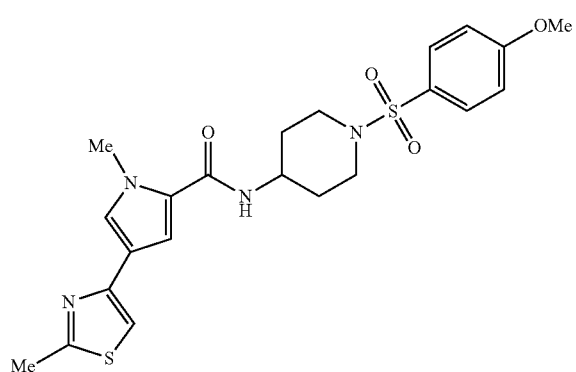 [SMILES: COc1ccc(S(=O)(=O)N2CCC(NC(=O)c3cc(-c4csc(C)n4)cn3C)CC2)cc1]
168B
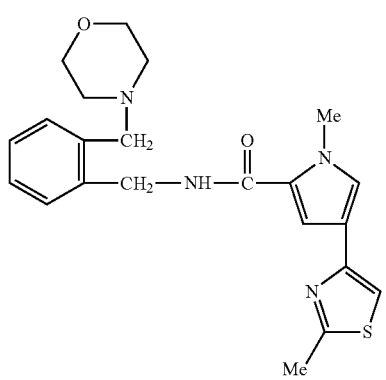 [SMILES: Cc1nc(-c2cc(C(=O)NCc3ccccc3CN3CCOCC3)n(C)c2)cs1]
169B
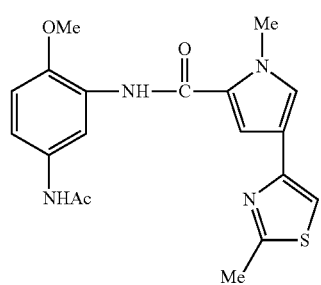 [SMILES: COc1ccc(NC(C)=O)cc1NC(=O)c1cc(-c2csc(C)n2)cn1C]
170B TABLE C-continued
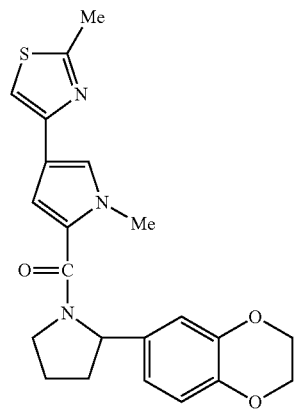 [SMILES: Cc1nc(-c2cc(C(=O)N3CCCC3c3ccc4c(c3)OCCO4)n(C)c2)cs1]
171B
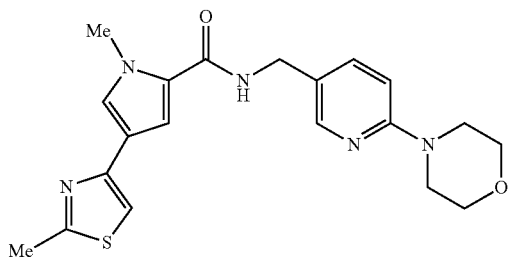 [SMILES: Cc1nc(-c2cc(C(=O)NCc3ccc(N4CCOCC4)nc3)n(C)c2)cs1]
172B
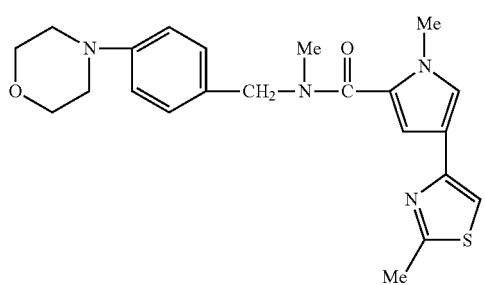 [SMILES: Cc1nc(-c2cc(C(=O)N(C)Cc3ccc(N4CCOCC4)cc3)n(C)c2)cs1]
173B
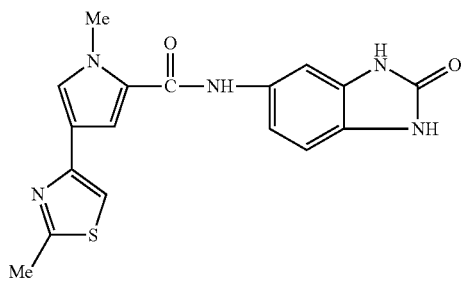 [SMILES: Cc1nc(-c2cc(C(=O)Nc3ccc4[nH]c(=O)[nH]c4c3)n(C)c2)cs1]
174B
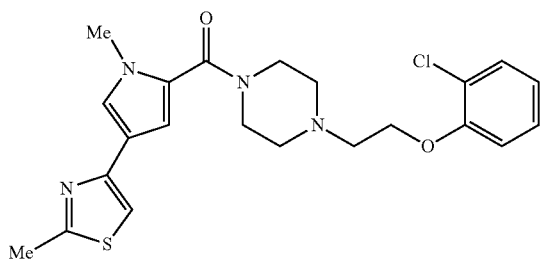 [SMILES: Cc1nc(-c2cc(C(=O)N3CCN(CCOc4ccccc4Cl)CC3)n(C)c2)cs1]
175B TABLE C-continued
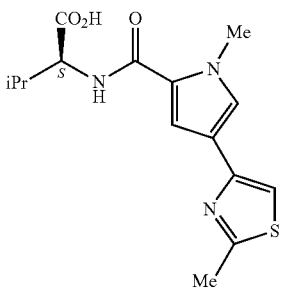
176B
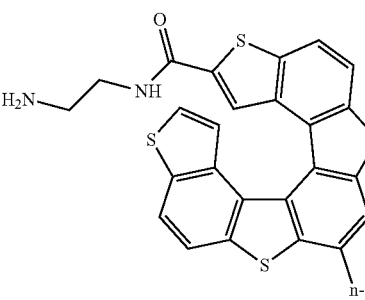
177B
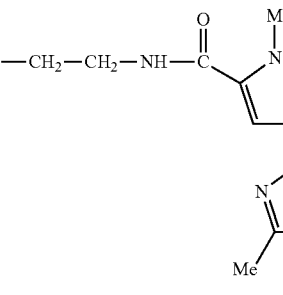
178B
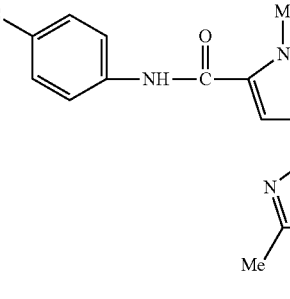
179B
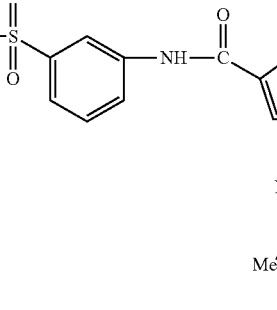
180B TABLE C-continued
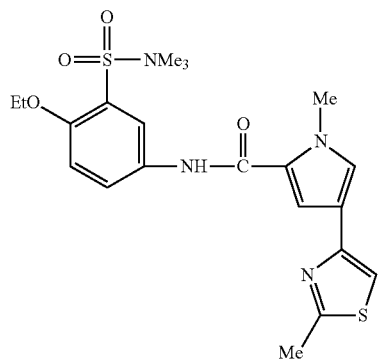
181B
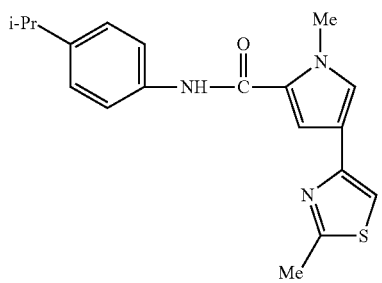 [SMILES: Cc1nc(-c2cc(C(=O)Nc3ccc(C(C)C)cc3)n(C)c2)cs1]
182B
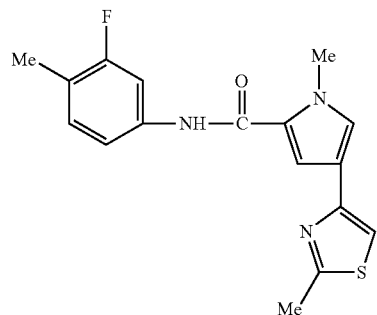
183B
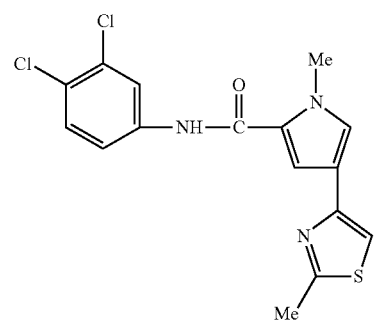 [SMILES: Cc1nc(-c2cc(C(=O)Nc3ccc(Cl)c(Cl)c3)n(C)c2)cs1]
184B
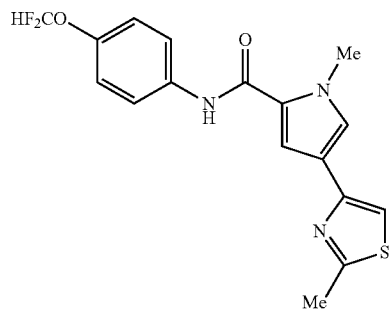
185B TABLE C-continued
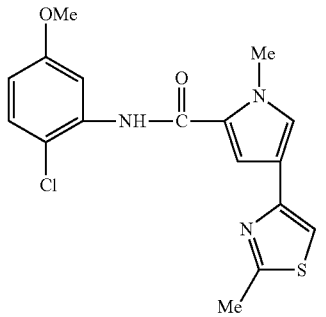 [SMILES: COc1ccc(Cl)c(NC(=O)c2cc(-c3csc(C)n3)cn2C)c1] 186B
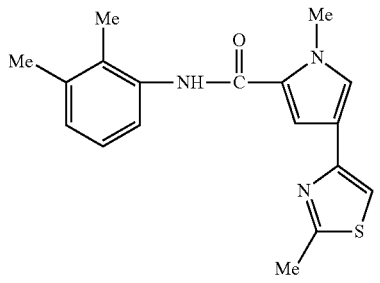 [SMILES: Cc1nc(-c2cc(C(=O)Nc3cccc(C)c3C)n(C)c2)cs1] 187B
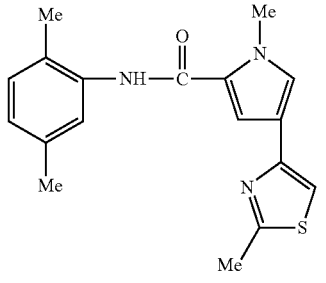 [SMILES: Cc1ccc(C)c(NC(=O)c2cc(-c3csc(C)n3)cn2C)c1] 188B
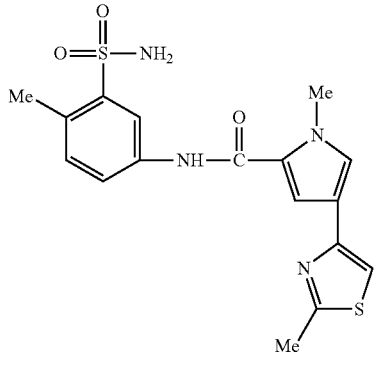 [SMILES: Cc1nc(-c2cc(C(=O)Nc3ccc(C)c(S(N)(=O)=O)c3)n(C)c2)cs1] 189B
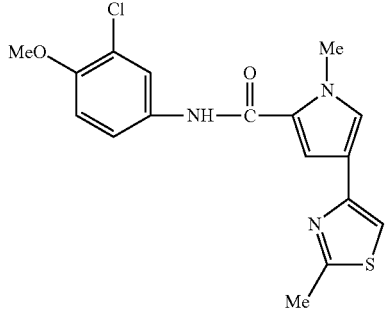 [SMILES: COc1ccc(NC(=O)c2cc(-c3csc(C)n3)cn2C)cc1Cl] 190B TABLE C-continued
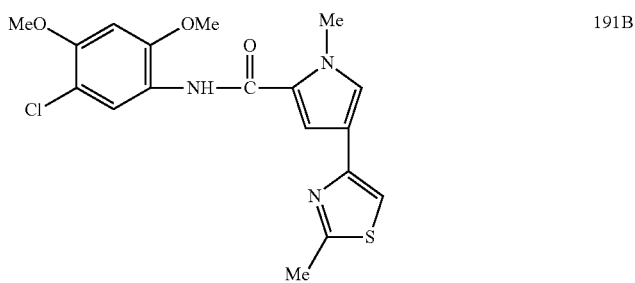
191B
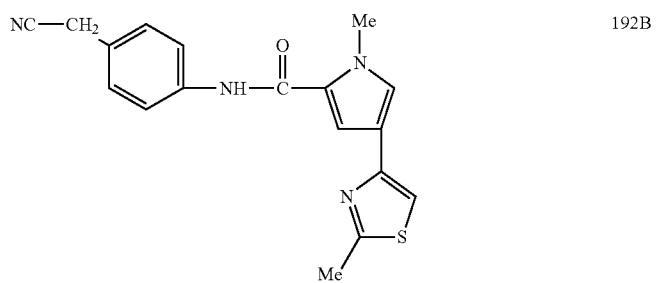
192B
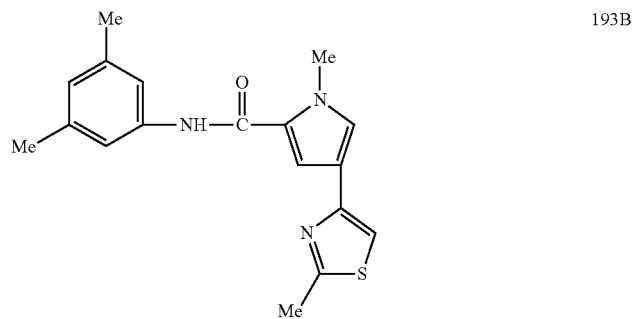
193B
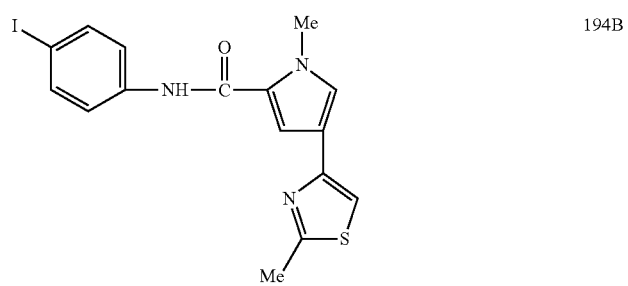
194B
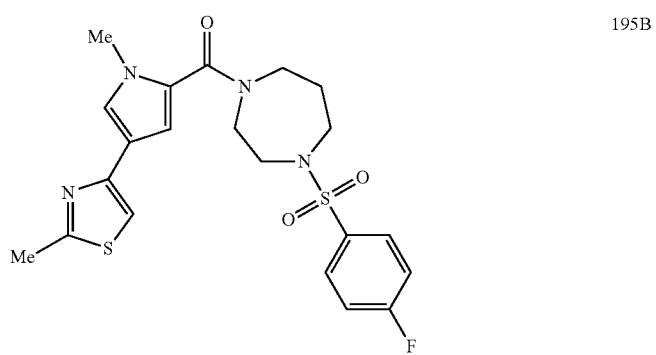
195B TABLE C-continued
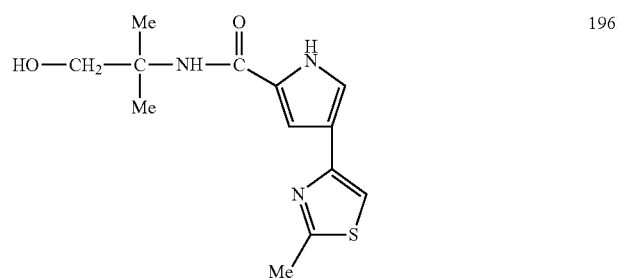 196B
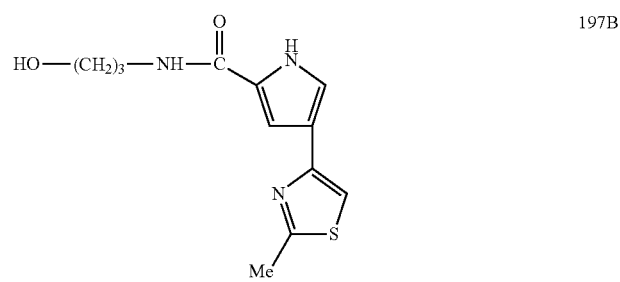 197B
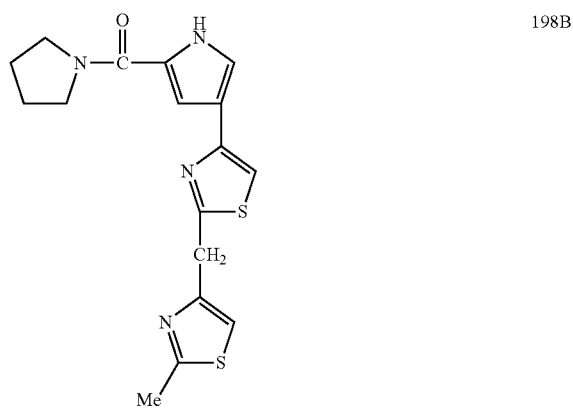 198B
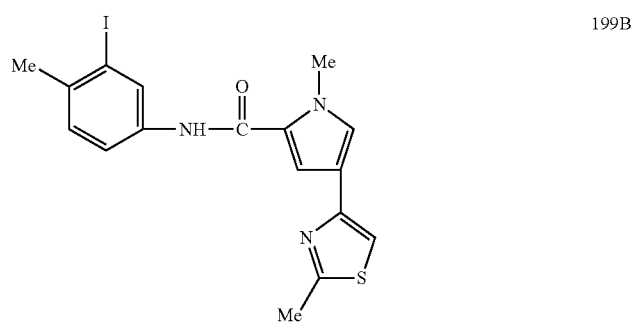 199B
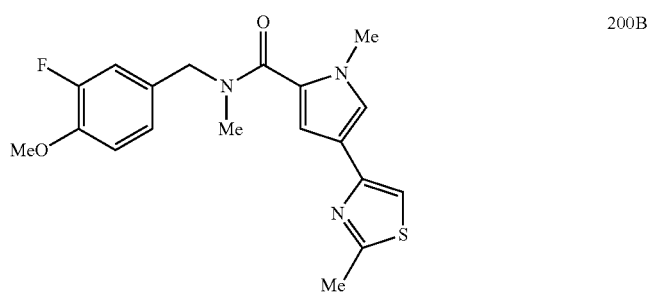 200B TABLE C-continued
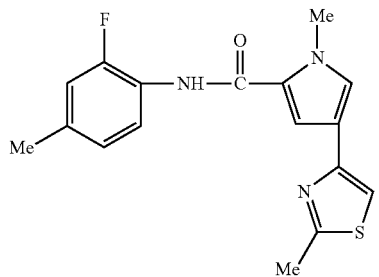 [SMILES: Cc1ccc(NC(=O)c2cc(-c3csc(C)n3)cn2C)c(F)c1]
201B
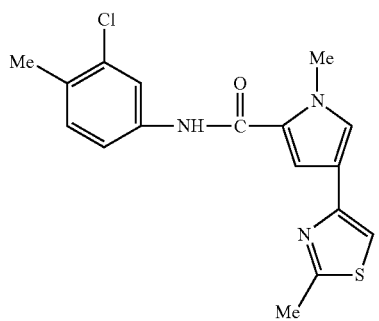 [SMILES: Cc1nc(-c2cc(C(=O)Nc3ccc(C)c(Cl)c3)n(C)c2)cs1]
202B
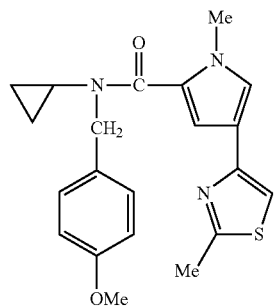 [SMILES: COc1ccc(CN(C(=O)c2cc(-c3csc(C)n3)cn2C)C2CC2)cc1]
203B
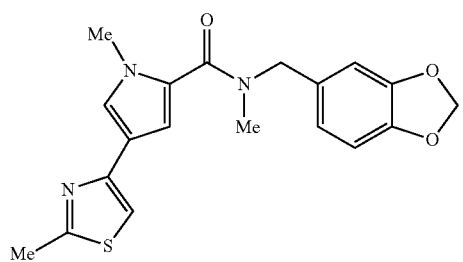 [SMILES: Cc1nc(-c2cc(C(=O)N(C)Cc3ccc4c(c3)OCO4)n(C)c2)cs1]
204B
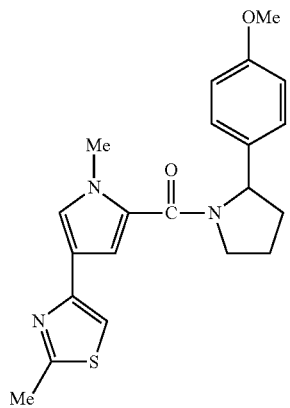 [SMILES: COc1ccc(C2CCCN2C(=O)c2cc(-c3csc(C)n3)cn2C)cc1]
205B TABLE C-continued
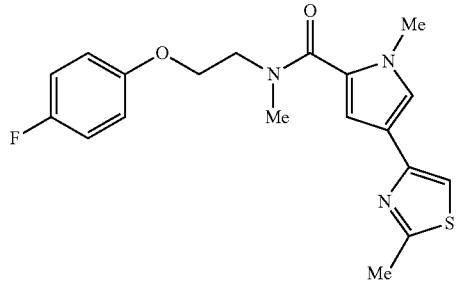 [SMILES: Cc1nc(-c2cc(C(=O)N(C)CCOc3ccc(F)cc3)n(C)c2)cs1]
206B
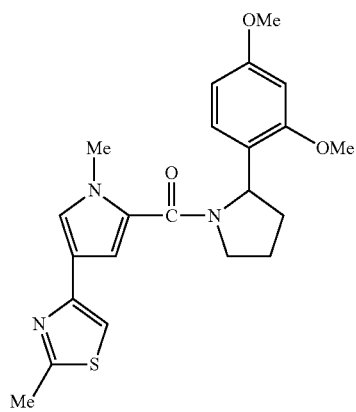 [SMILES: COc1ccc(C2CCCN2C(=O)c2cc(-c3csc(C)n3)cn2C)c(OC)c1]
207B
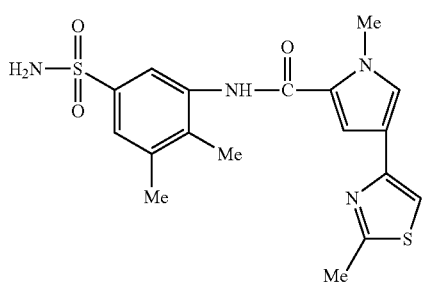 [SMILES: Cc1nc(-c2cc(C(=O)Nc3cc(S(N)(=O)=O)cc(C)c3C)n(C)c2)cs1]
208B
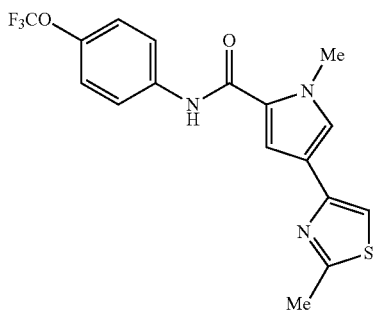 [SMILES: Cc1nc(-c2cc(C(=O)Nc3ccc(OC(F)(F)F)cc3)n(C)c2)cs1]
209B TABLE C-continued
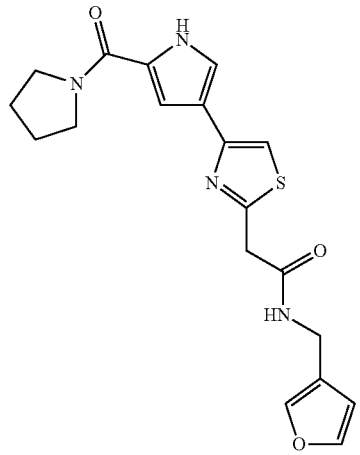 [SMILES: O=C(Cc1nc(-c2c[nH]c(C(=O)N3CCCC3)c2)cs1)NCc1ccoc1]
210B
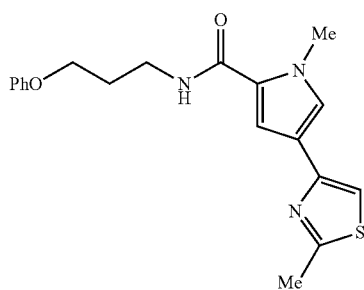 [SMILES: Cc1nc(-c2cc(C(=O)NCCCOc3ccccc3)n(C)c2)cs1]
211B
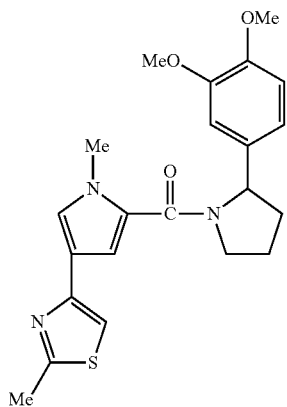 [SMILES: COc1ccc(C2CCCN2C(=O)c2cc(-c3csc(C)n3)cn2C)cc1OC]
212B
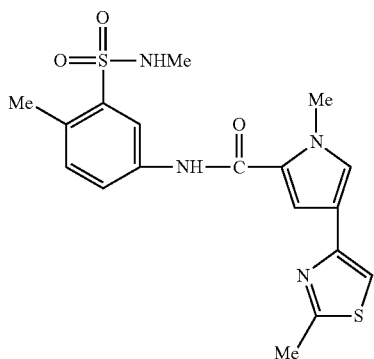 [SMILES: CNS(=O)(=O)c1cc(NC(=O)c2cc(-c3csc(C)n3)cn2C)ccc1C]
213B TABLE C-continued
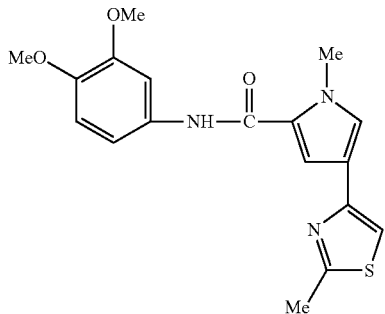 [SMILES: COc1ccc(NC(=O)c2cc(-c3csc(C)n3)cn2C)cc1OC] 214B
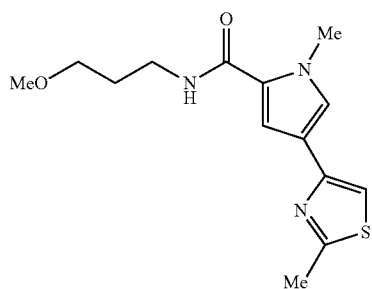 [SMILES: COCCCNC(=O)c1cc(-c2csc(C)n2)cn1C] 215B
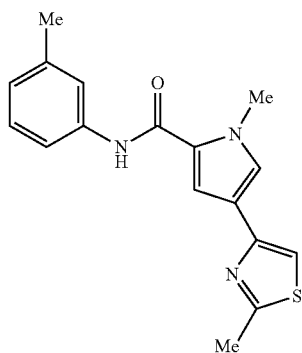 [SMILES: Cc1cccc(NC(=O)c2cc(-c3csc(C)n3)cn2C)c1] 216B
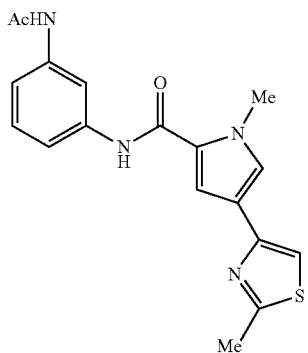 [SMILES: CC(=O)Nc1cccc(NC(=O)c2cc(-c3csc(C)n3)cn2C)c1] 217B
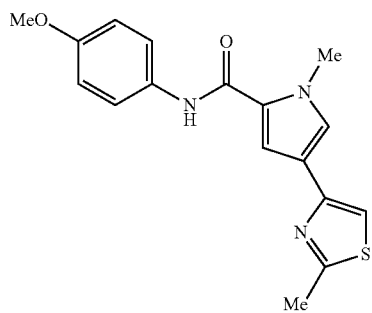 [SMILES: COc1ccc(NC(=O)c2cc(-c3csc(C)n3)cn2C)cc1] 218B TABLE C-continued
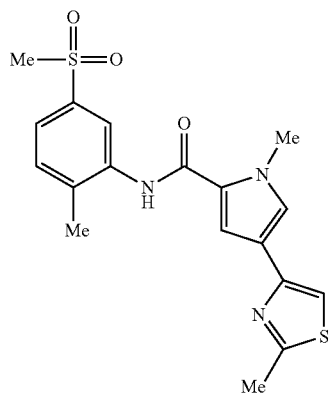 [SMILES: Cc1nc(-c2cc(C(=O)Nc3cc(S(C)(=O)=O)ccc3C)n(C)c2)cs1]
219B
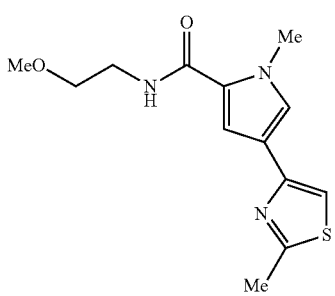 [SMILES: COCCNC(=O)c1cc(-c2csc(C)n2)cn1C]
220B
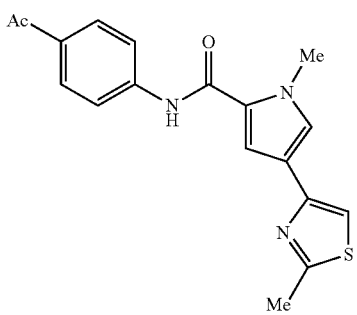
221B
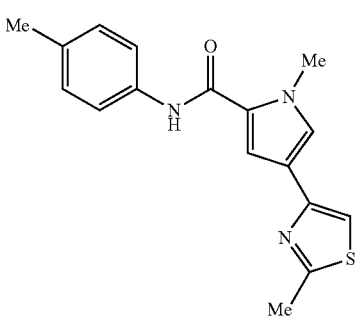 [SMILES: CC(=O)c1ccc(NC(=O)c2cc(-c3csc(C)n3)cn2C)cc1]
222B
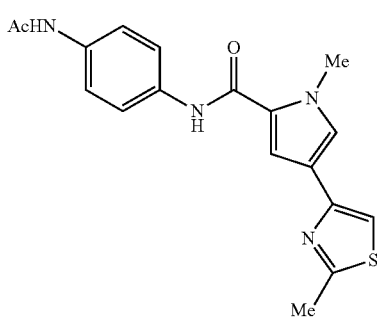 [SMILES: CC(=O)Nc1ccc(NC(=O)c2cc(-c3csc(C)n3)cn2C)cc1]
223B TABLE C-continued
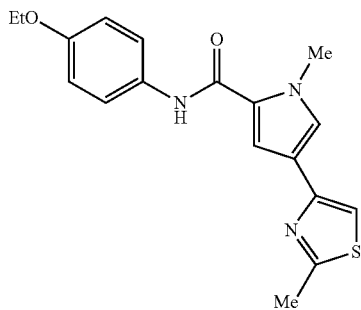 [SMILES: CCOc1ccc(NC(=O)c2cc(-c3csc(C)n3)cn2C)cc1] 224B
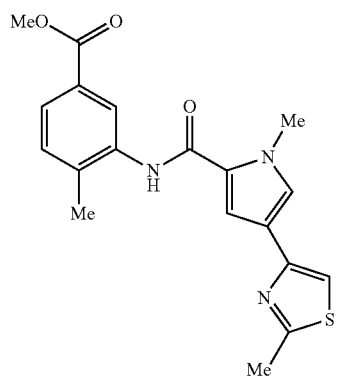 [SMILES: COC(=O)c1ccc(C)c(NC(=O)c2cc(-c3csc(C)n3)cn2C)c1] 225B
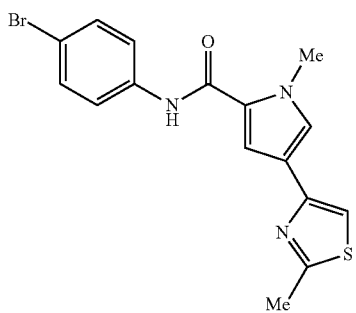 [SMILES: Cc1nc(-c2cc(C(=O)Nc3ccc(Cl)cc3)n(C)c2)cs1] 226B
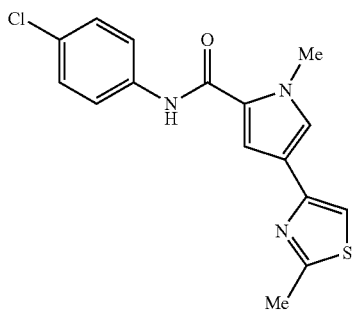 227B
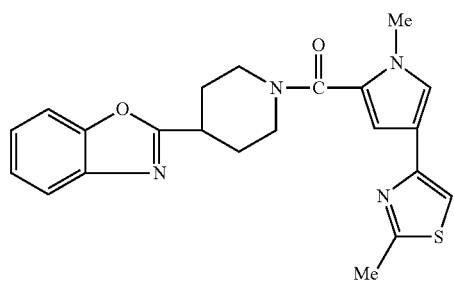 [SMILES: Cc1nc(-c2cc(C(=O)N3CCC(c4nc5ccccc5o4)CC3)n(C)c2)cs1] 228B TABLE C-continued
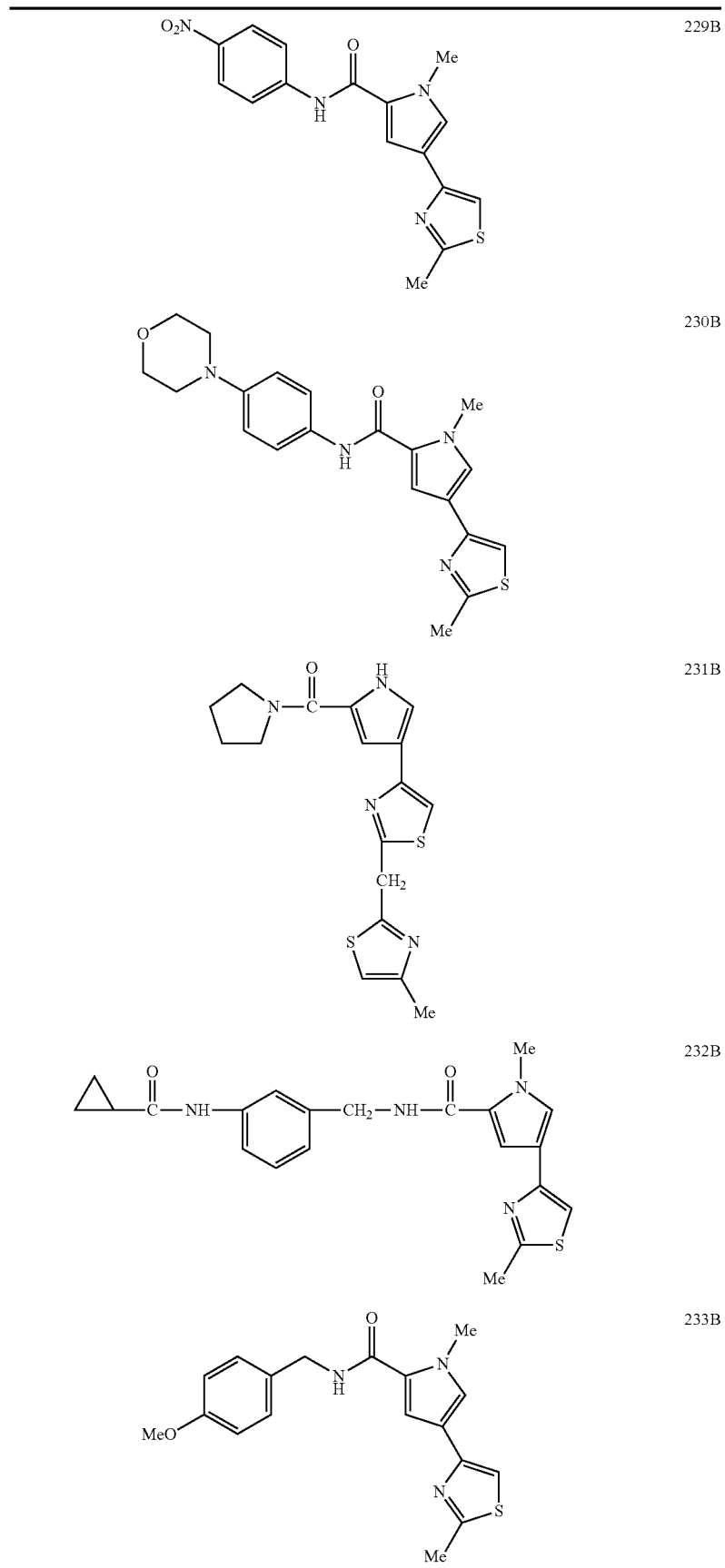

TABLE C-continued
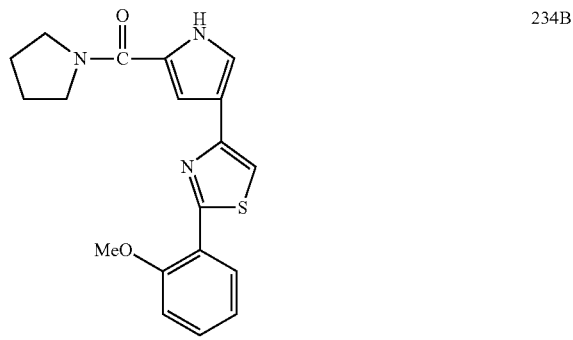
234B
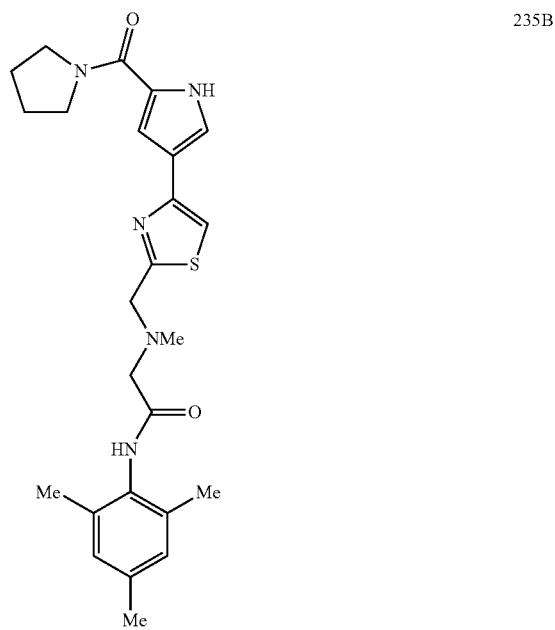
235B
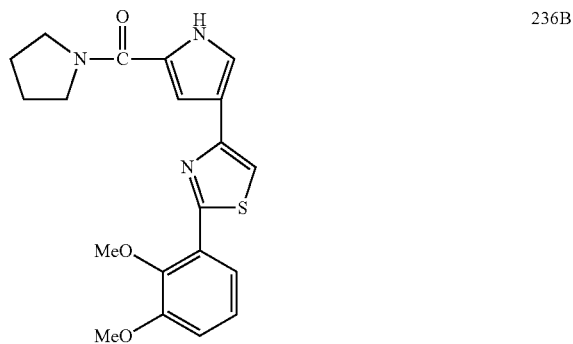
236B

TABLE C-continued
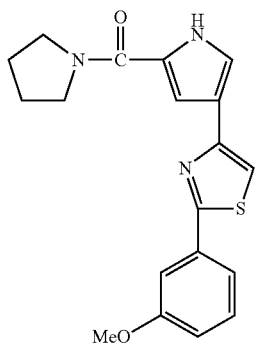 [SMILES: COc1cccc(-c2nc(-c3c[nH]c(C(=O)N4CCCC4)c3)cs2)c1]
237B
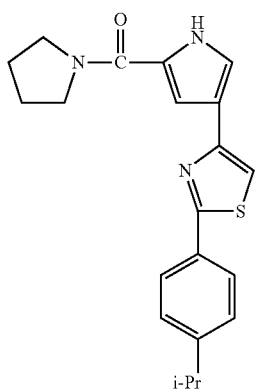 [SMILES: CC(C)c1ccc(-c2nc(-c3c[nH]c(C(=O)N4CCCC4)c3)cs2)cc1]
238B
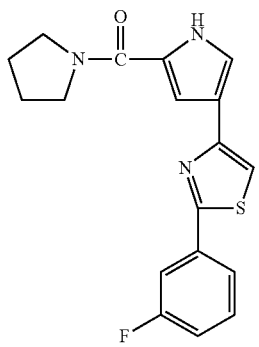 [SMILES: O=C(c1cc(-c2csc(-c3cccc(F)c3)n2)c[nH]1)N1CCCC1]
239B
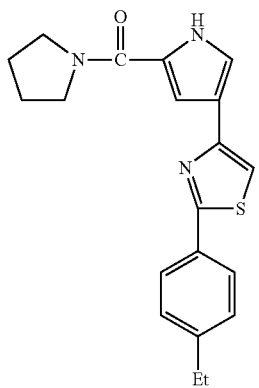 [SMILES: CCc1ccc(-c2nc(-c3c[nH]c(C(=O)N4CCCC4)c3)cs2)cc1]
240B TABLE C-continued
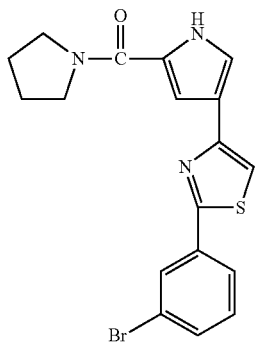 241B
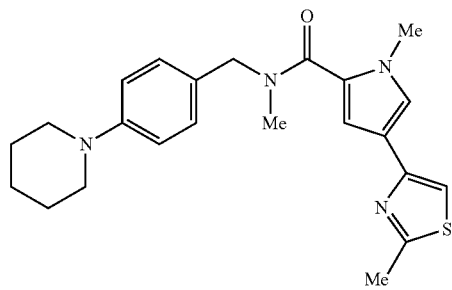 [SMILES: Cc1nc(-c2cc(C(=O)N(C)Cc3ccc(N4CCCCC4)cc3)n(C)c2)cs1] 242B
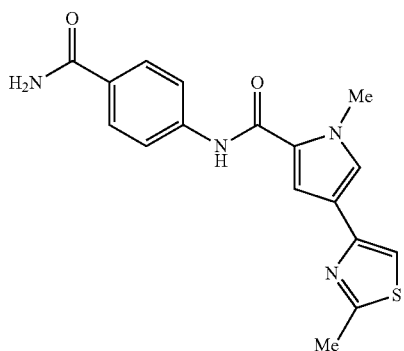 [SMILES: Cc1nc(-c2cc(C(=O)Nc3ccc(C(N)=O)cc3)n(C)c2)cs1] 243B
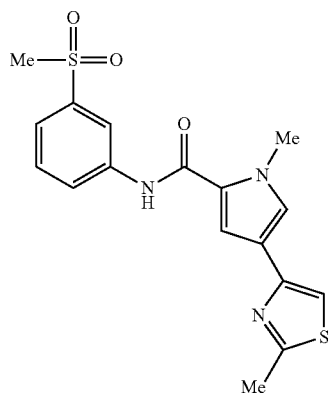 [SMILES: Cc1nc(-c2cc(C(=O)Nc3cccc(S(C)(=O)=O)c3)n(C)c2)cs1] 244B
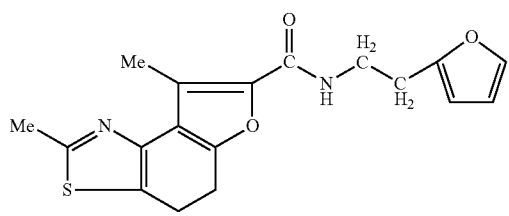 [SMILES: Cc1nc2c(s1)CCc1oc(C(=O)NCCc3ccco3)c(C)c1-2] 245B TABLE C-continued
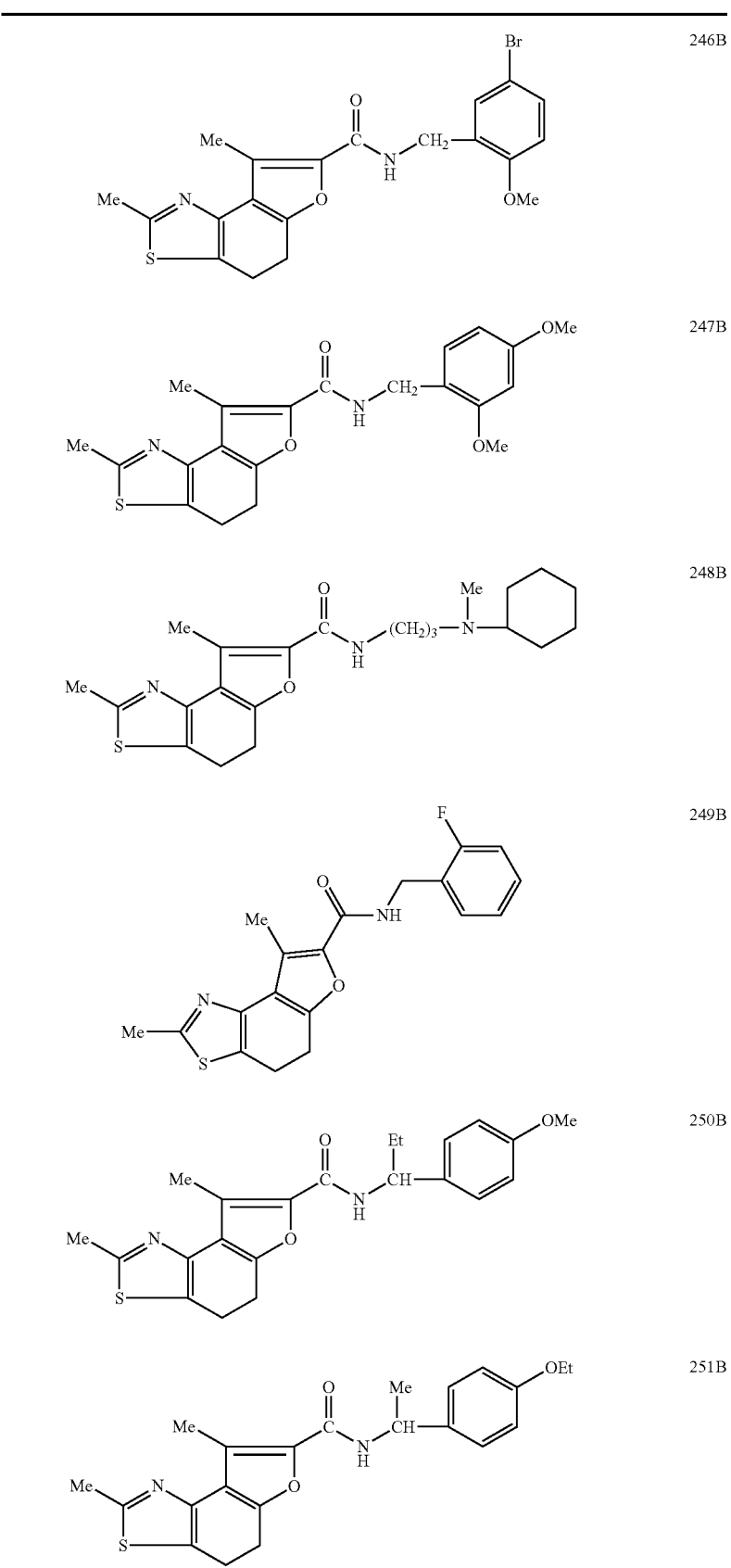

TABLE C-continued
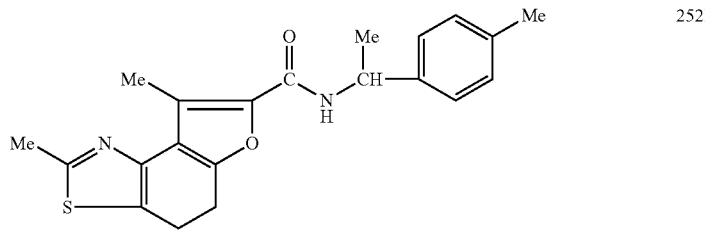
252B
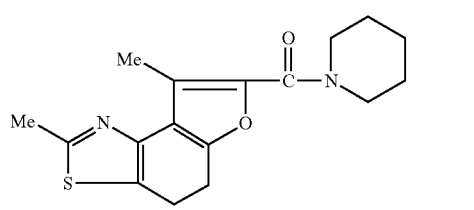 [SMILES: Cc1nc2c(s1)CCc1oc(C(=O)N3CCCCC3)c(C)c1-2]
253B
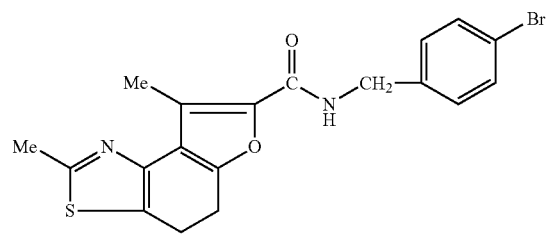 [SMILES: Cc1nc2c(s1)CCc1oc(C(=O)NCc3ccc(Br)cc3)c(C)c1-2]
254B
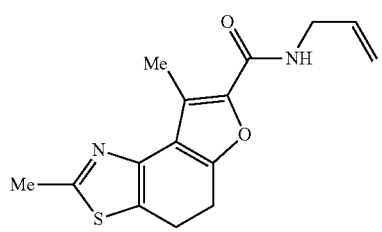 [SMILES: C=CCNC(=O)c1oc2c(c1C)-c1nc(C)sc1CC2]
255B
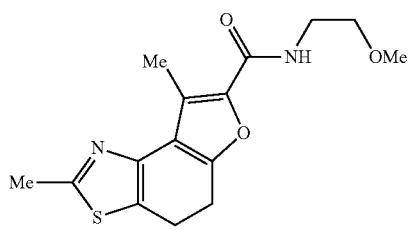 [SMILES: COCCNC(=O)c1oc2c(c1C)-c1nc(C)sc1CC2]
256B
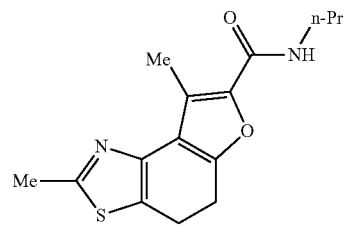
257B TABLE C-continued
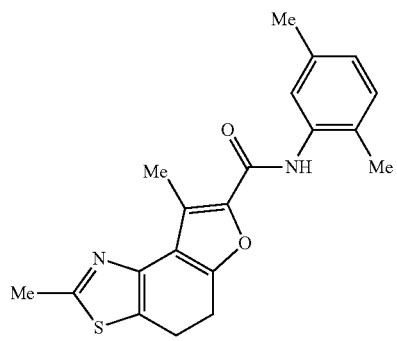 [SMILES: Cc1ccc(C)c(NC(=O)c2oc3c(c2C)-c2nc(C)sc2CC3)c1]
258B
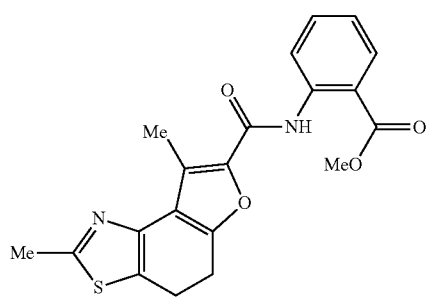 [SMILES: COC(=O)c1ccccc1NC(=O)c1oc2c(c1C)-c1nc(C)sc1CC2]
259B
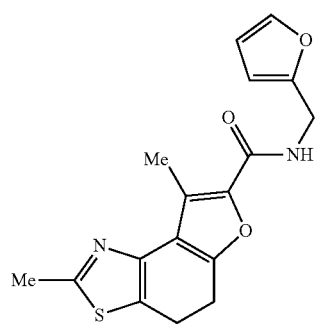 [SMILES: Cc1nc2c(s1)CCc1oc(C(=O)NCc3ccco3)c(C)c1-2]
260B
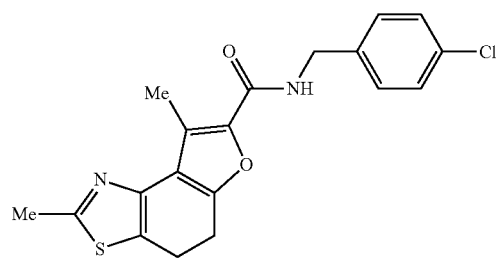 [SMILES: Cc1nc2c(s1)CCc1oc(C(=O)NCc3ccc(Cl)cc3)c(C)c1-2]
261B
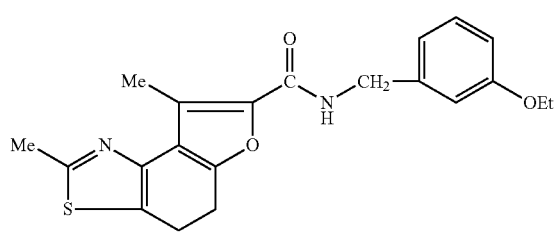 [SMILES: CCOc1cccc(CNC(=O)c2oc3c(c2C)-c2nc(C)sc2CC3)c1]
262B TABLE C-continued
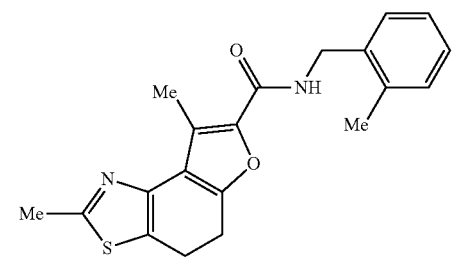 [SMILES: Cc1nc2c(s1)CCc1oc(C(=O)NCc3ccccc3C)c(C)c1-2]
263B
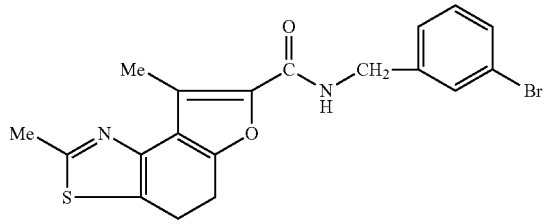
264B
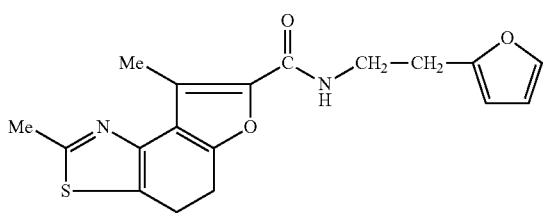 [SMILES: Cc1nc2c(s1)CCc1oc(C(=O)NCCc3ccco3)c(C)c1-2]
265B
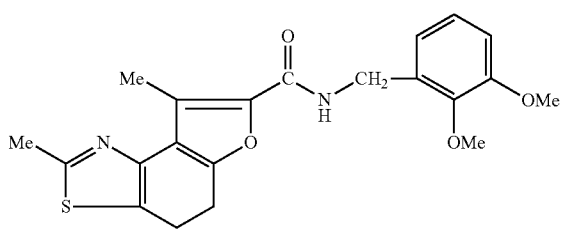 [SMILES: COc1cccc(CNC(=O)c2oc3c(c2C)-c2nc(C)sc2CC3)c1OC]
266B
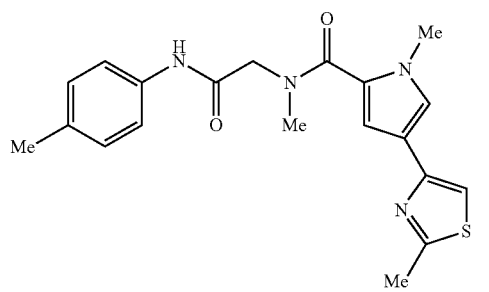 [SMILES: Cc1ccc(NC(=O)CN(C)C(=O)c2cc(-c3csc(C)n3)cn2C)cc1]
267B
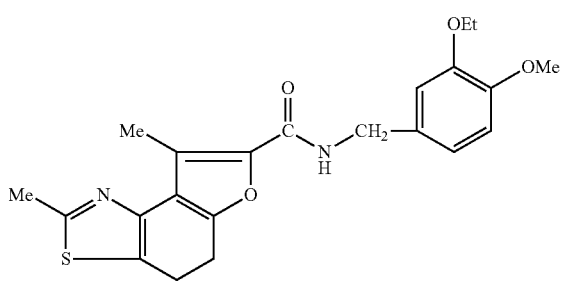 [SMILES: CCOc1cc(CNC(=O)c2oc3c(c2C)-c2nc(C)sc2CC3)ccc1OC]
268B TABLE C-continued
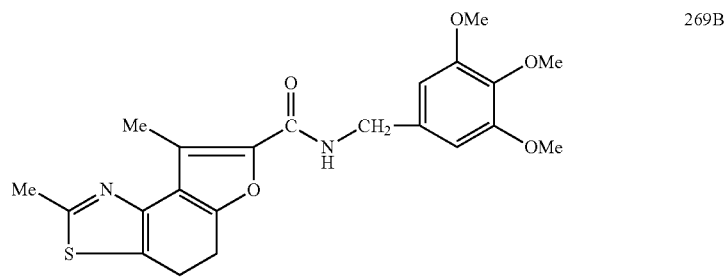 269B
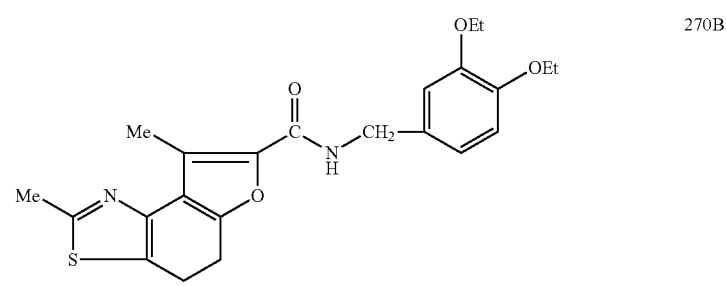 270B
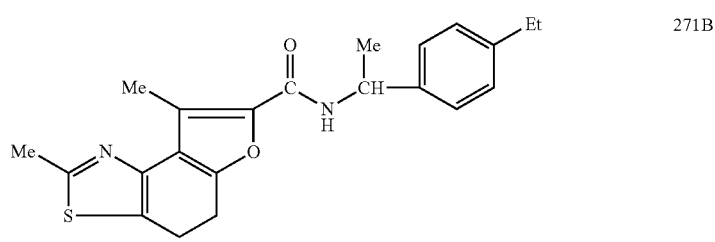 271B
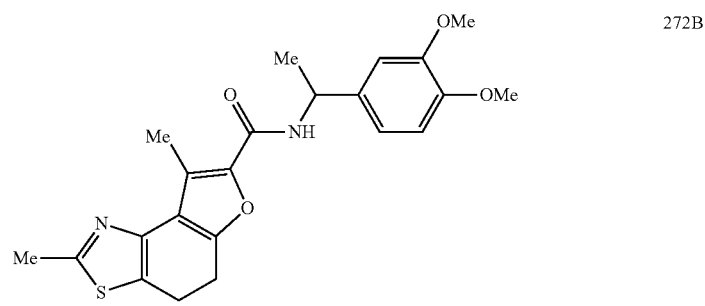 272B
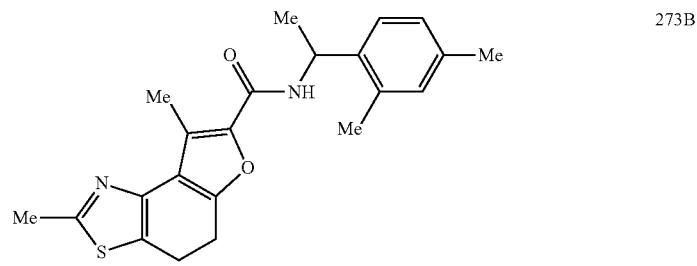 273B TABLE C-continued
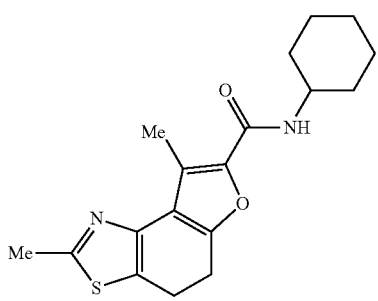 [SMILES: Cc1nc2c(s1)CCc1oc(C(=O)NC3CCCCC3)c(C)c1-2]
274B
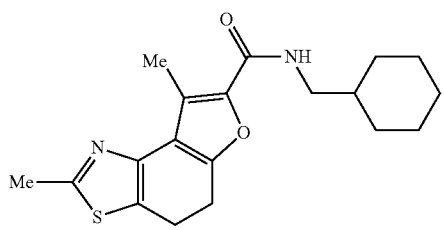 [SMILES: Cc1nc2c(s1)CCc1oc(C(=O)NCC3CCCCC3)c(C)c1-2]
275B
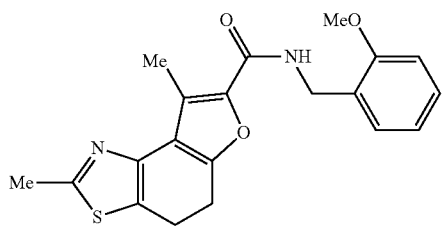 [SMILES: COc1ccccc1CNC(=O)c1oc2c(c1C)-c1nc(C)sc1CC2]
276B
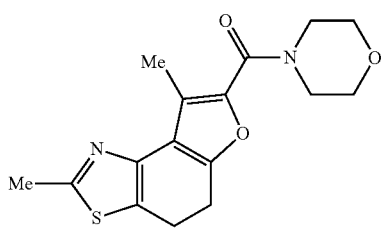 [SMILES: Cc1nc2c(s1)CCc1oc(C(=O)N3CCOCC3)c(C)c1-2]
277B
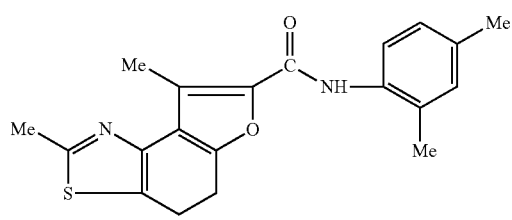 [SMILES: Cc1ccc(NC(=O)c2oc3c(c2C)-c2nc(C)sc2CC3)c(C)c1]
278B
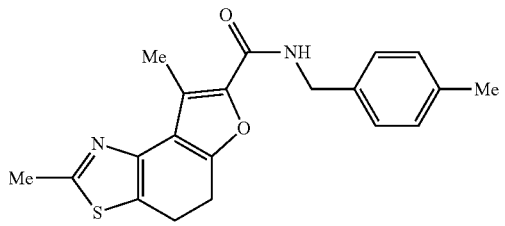 [SMILES: Cc1ccc(CNC(=O)c2oc3c(c2C)-c2nc(C)sc2CC3)cc1]
279B TABLE C-continued
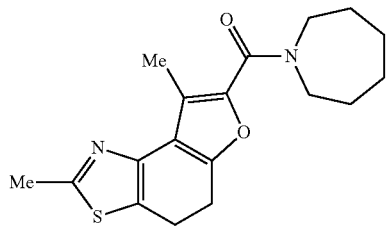 [SMILES: Cc1nc2c(s1)CCc1oc(C(=O)N3CCCCCC3)c(C)c1-2]
280B
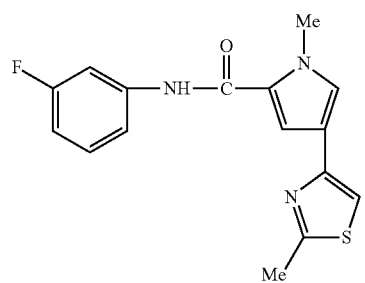 [SMILES: Cc1nc(-c2cc(C(=O)Nc3cccc(F)c3)n(C)c2)cs1]
281B
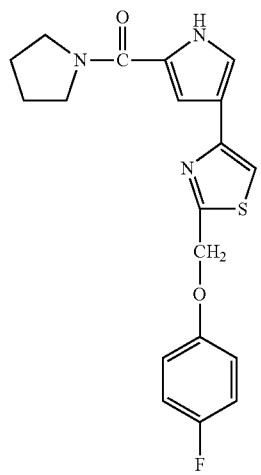 [SMILES: O=C(c1cc(-c2csc(COc3ccc(F)cc3)n2)c[nH]1)N1CCCC1]
282B
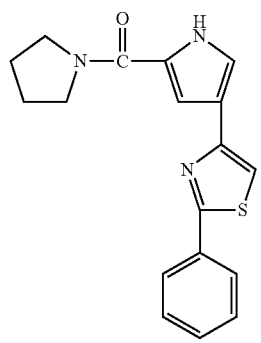 [SMILES: O=C(c1cc(-c2csc(-c3ccccc3)n2)c[nH]1)N1CCCC1]
283B
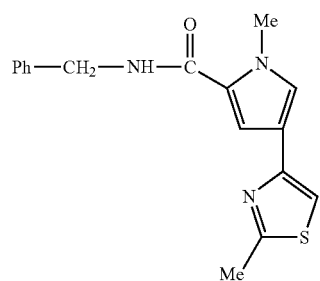 [SMILES: Cc1nc(-c2cc(C(=O)NCc3ccccc3)n(C)c2)cs1]
284B TABLE C-continued
| | |
|---|---|
| 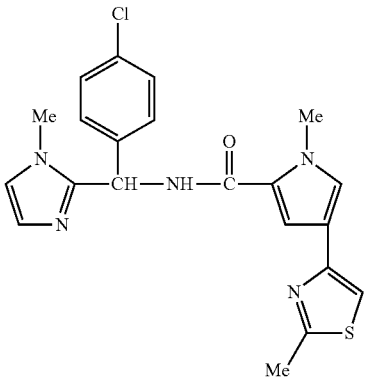 [SMILES: Cc1nc(-c2cc(C(=O)NC(c3ccc(Cl)cc3)c3nccn3C)n(C)c2)cs1] | 285B |
| 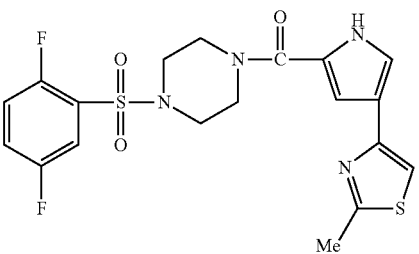 [SMILES: Cc1nc(-c2c[nH]c(C(=O)N3CCN(S(=O)(=O)c4cc(F)ccc4F)CC3)c2)cs1] | 286B |
| 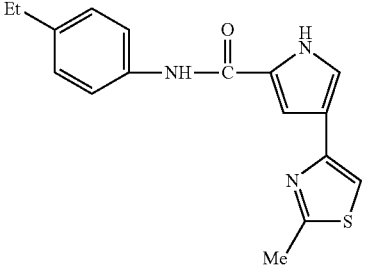 [SMILES: CCc1ccc(NC(=O)c2cc(-c3csc(C)n3)c[nH]2)cc1] | 287B |
| 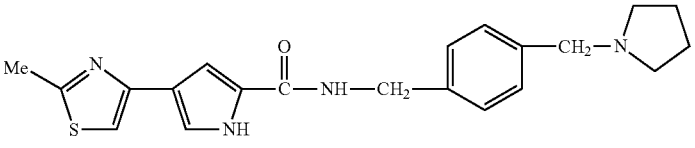 [SMILES: Cc1nc(-c2c[nH]c(C(=O)NCc3ccc(CN4CCCC4)cc3)c2)cs1] | 288B |
| 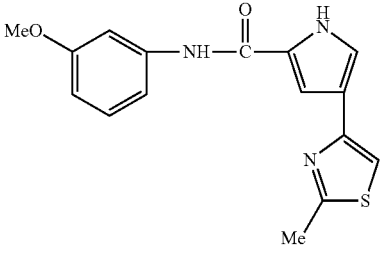 [SMILES: COc1cccc(NC(=O)c2cc(-c3csc(C)n3)c[nH]2)c1] | 289B |
| 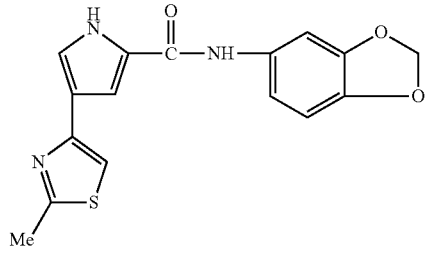 [SMILES: Cc1nc(-c2c[nH]c(C(=O)Nc3ccc4c(c3)OCO4)c2)cs1] | 290B |

TABLE C-continued
| | |
|---|---|
| 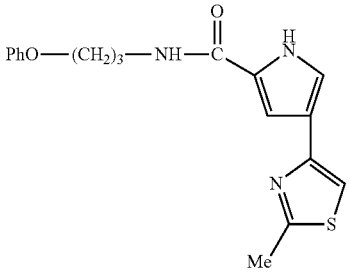 | 291B |
| 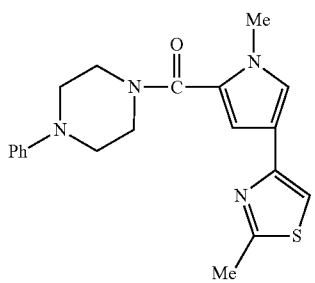 [SMILES: Cc1nc(-c2cc(C(=O)N3CCN(c4ccccc4)CC3)n(C)c2)cs1] | 292B |
| 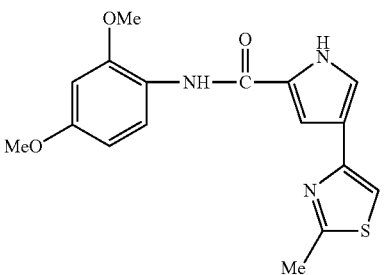 [SMILES: COc1ccc(NC(=O)c2cc(-c3csc(C)n3)c[nH]2)c(OC)c1] | 293B |
| 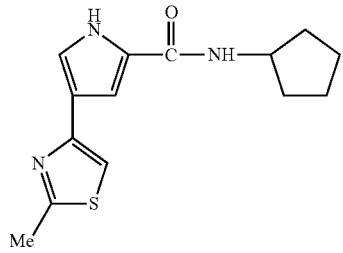 [SMILES: Cc1nc(-c2c[nH]c(C(=O)NC3CCCC3)c2)cs1] | 294B |
| 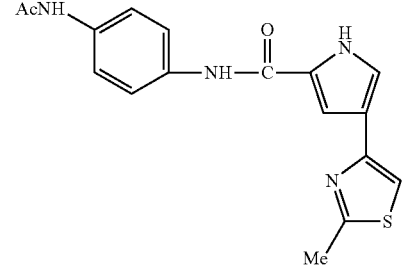 | 295B |
| 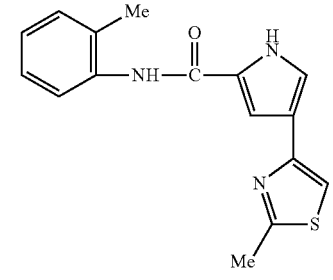 [SMILES: Cc1nc(-c2c[nH]c(C(=O)Nc3ccccc3C)c2)cs1] | 296B |

TABLE C-continued
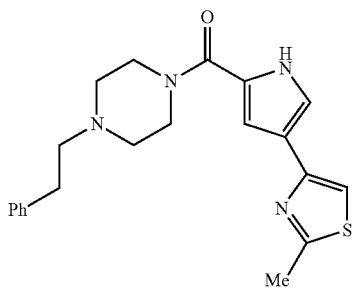 [SMILES: Cc1nc(-c2c[nH]c(C(=O)N3CCN(CCc4ccccc4)CC3)c2)cs1]
297B
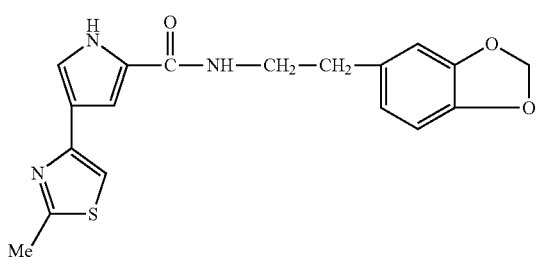 [SMILES: Cc1nc(-c2c[nH]c(C(=O)NCCc3ccc4c(c3)OCO4)c2)cs1]
298B
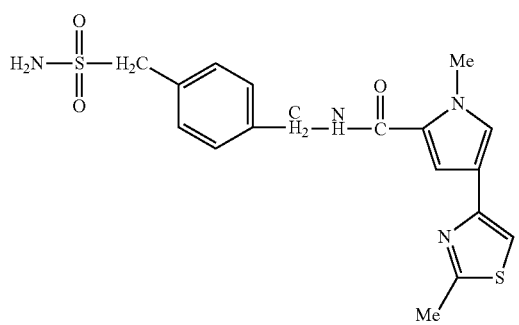 [SMILES: Cc1nc(-c2cc(C(=O)NCc3ccc(CS(N)(=O)=O)cc3)n(C)c2)cs1]
299B
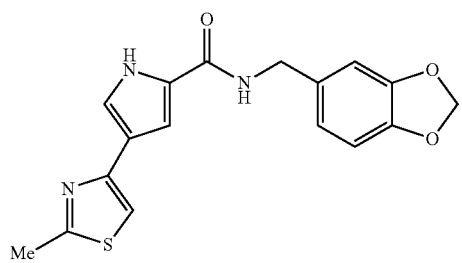 [SMILES: Cc1nc(-c2c[nH]c(C(=O)NCc3ccc4c(c3)OCO4)c2)cs1]
300B
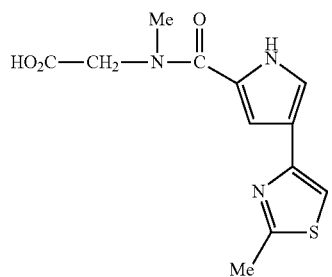 [SMILES: Cc1nc(-c2c[nH]c(C(=O)N(C)CC(=O)O)c2)cs1]
301B TABLE C-continued
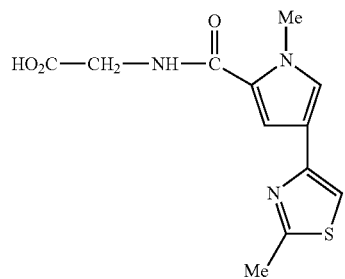 [SMILES: Cc1nc(-c2cc(C(=O)NCC(=O)O)n(C)c2)cs1]
302B
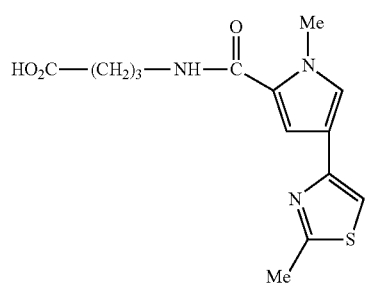
303B
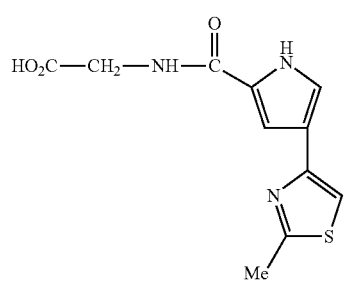 [SMILES: Cc1nc(-c2c[nH]c(C(=O)NCC(=O)O)c2)cs1]
304B
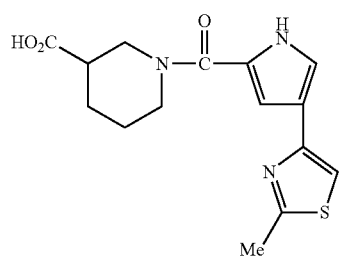 [SMILES: Cc1nc(-c2c[nH]c(C(=O)N3CCCC(C(=O)O)C3)c2)cs1]
305B
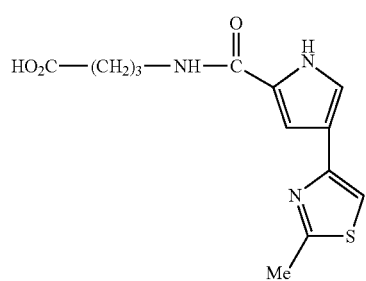
306B TABLE C-continued
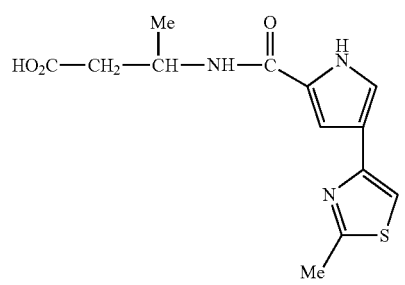 [SMILES: Cc1nc(-c2c[nH]c(C(=O)NC(C)CC(=O)O)c2)cs1]
307B
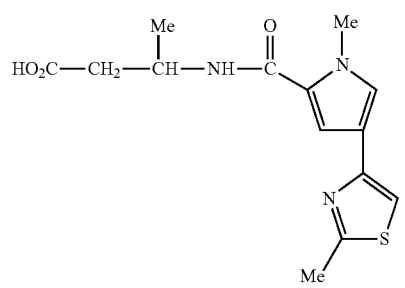 [SMILES: Cc1nc(-c2cc(C(=O)NC(C)CC(=O)O)n(C)c2)cs1]
308B
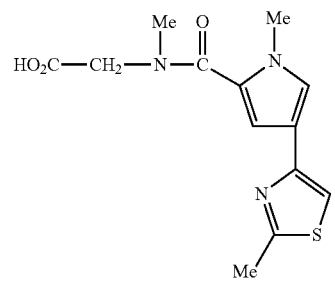 [SMILES: Cc1nc(-c2cc(C(=O)N(C)CC(=O)O)n(C)c2)cs1]
309B
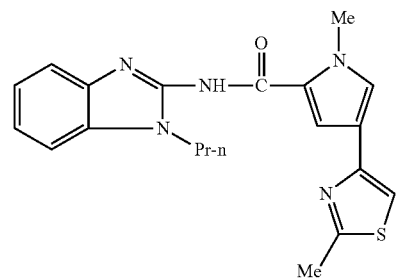
310B
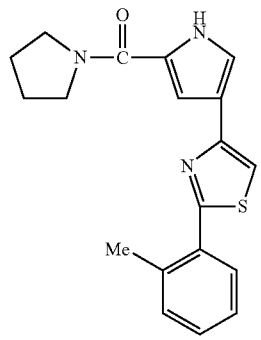 [SMILES: Cc1ccccc1-c1nc(-c2c[nH]c(C(=O)N3CCCC3)c2)cs1]
311B TABLE C-continued
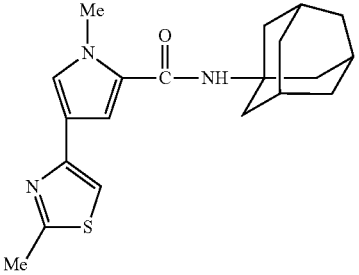 [SMILES: Cc1nc(-c2cc(C(=O)NC34CC5CC(CC(C5)C3)C4)n(C)c2)cs1] 312B
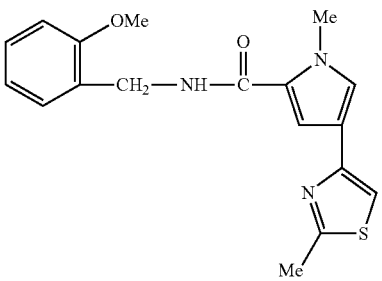 [SMILES: COc1ccccc1CNC(=O)c1cc(-c2csc(C)n2)cn1C] 313B
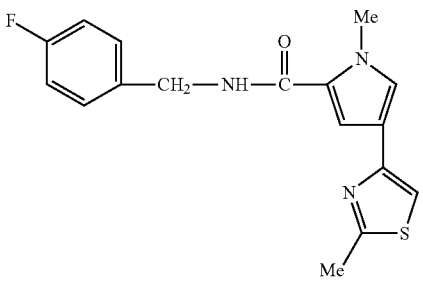 [SMILES: Cc1nc(-c2cc(C(=O)NCc3ccc(F)cc3)n(C)c2)cs1] 314B
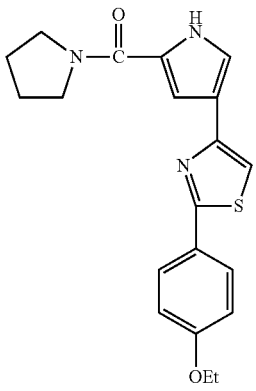 [SMILES: CCOc1ccc(-c2nc(-c3c[nH]c(C(=O)N4CCCC4)c3)cs2)cc1] 315B
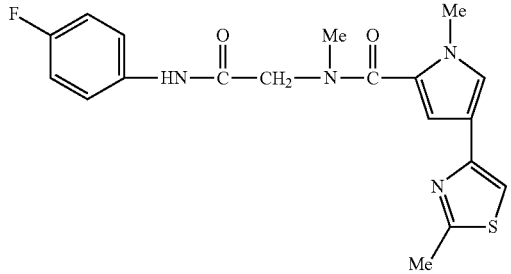 [SMILES: Cc1nc(-c2cc(C(=O)N(C)CC(=O)Nc3ccc(F)cc3)n(C)c2)cs1] 316B TABLE C-continued
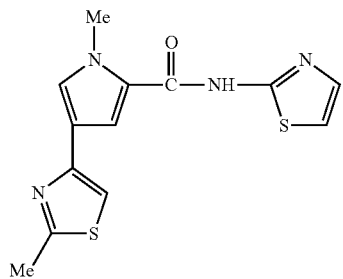 [SMILES: Cc1nc(-c2cc(C(=O)Nc3nccs3)n(C)c2)cs1]
317B
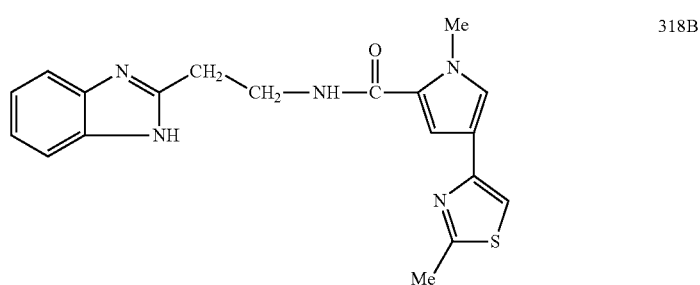
318B
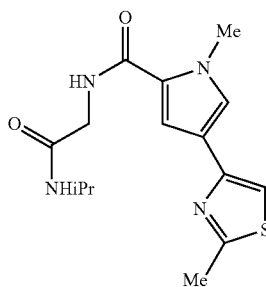
319B
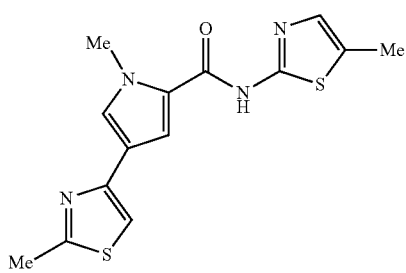 [SMILES: Cc1cnc(NC(=O)c2cc(-c3csc(C)n3)cn2C)s1]
320B
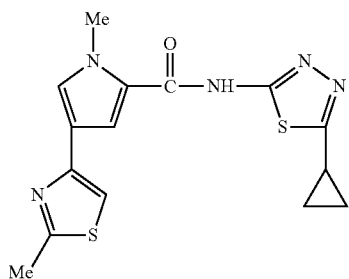 [SMILES: Cc1nc(-c2cc(C(=O)Nc3nnc(C4CC4)s3)n(C)c2)cs1]
321B TABLE C-continued
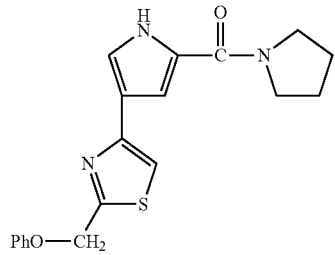 [SMILES: O=C(c1cc(-c2csc(COc3ccccc3)n2)c[nH]1)N1CCCC1]
322B
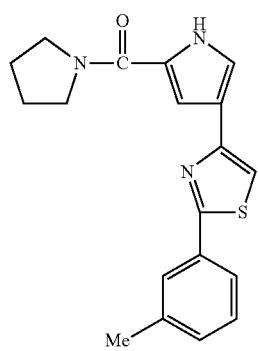
323B
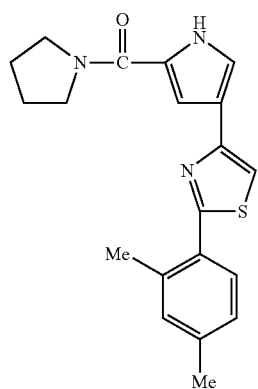 [SMILES: Cc1ccc(-c2nc(-c3c[nH]c(C(=O)N4CCCC4)c3)cs2)c(C)c1]
324B
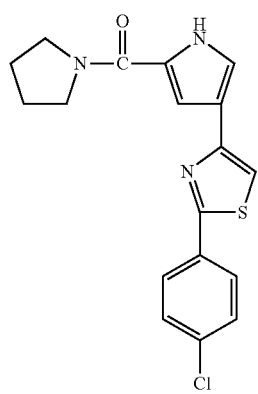 [SMILES: O=C(c1cc(-c2csc(-c3ccc(Cl)cc3)n2)c[nH]1)N1CCCC1]
325B TABLE C-continued
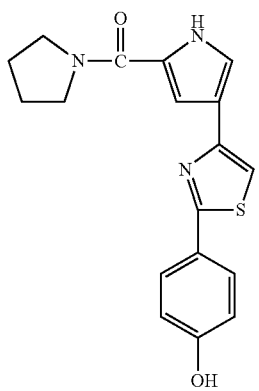 [SMILES: O=C(c1cc(-c2csc(-c3ccc(O)cc3)n2)c[nH]1)N1CCCC1] 326B
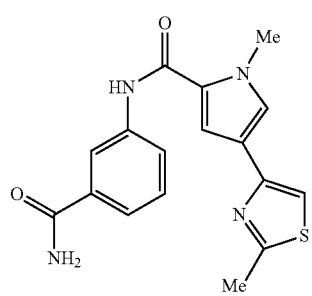 [SMILES: Cc1nc(-c2cc(C(=O)Nc3cccc(C(N)=O)c3)n(C)c2)cs1] 327B
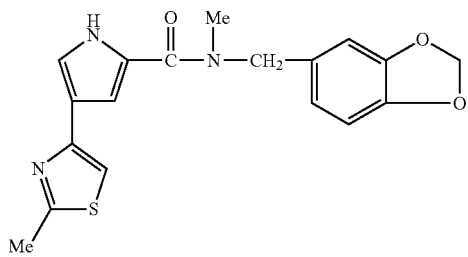 [SMILES: Cc1nc(-c2c[nH]c(C(=O)N(C)Cc3ccc4c(c3)OCO4)c2)cs1] 328B
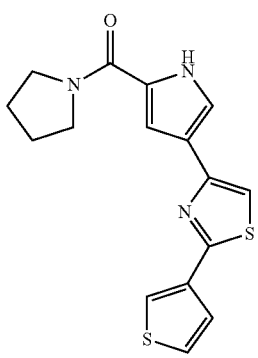 [SMILES: O=C(c1cc(-c2csc(-c3ccsc3)n2)c[nH]1)N1CCCC1] 329B
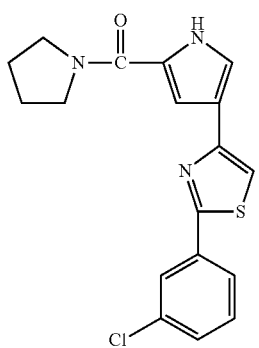 [SMILES: O=C(c1cc(-c2csc(-c3cccc(Cl)c3)n2)c[nH]1)N1CCCC1] 330B TABLE C-continued
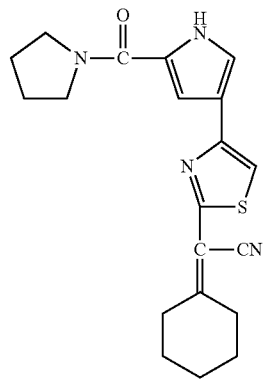 [SMILES: N#CC(=C1CCCCC1)c1nc(-c2c[nH]c(C(=O)N3CCCC3)c2)cs1]
331B
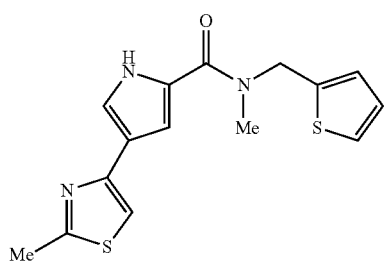 [SMILES: Cc1nc(-c2c[nH]c(C(=O)N(C)Cc3cccs3)c2)cs1]
332B
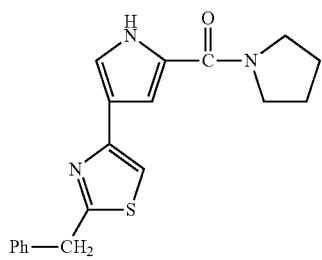 [SMILES: O=C(c1cc(-c2csc(Cc3ccccc3)n2)c[nH]1)N1CCCC1]
333B
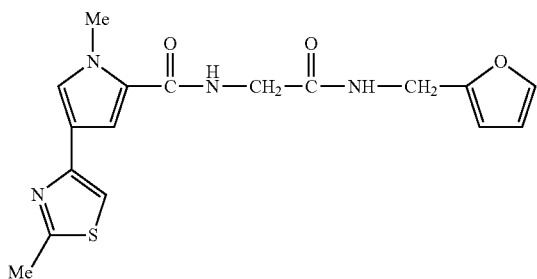 [SMILES: Cc1nc(-c2cc(C(=O)NCC(=O)NCc3ccco3)n(C)c2)cs1]
334B
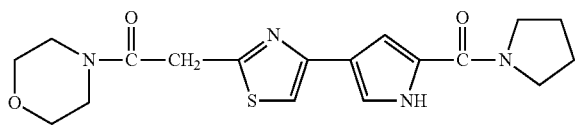 [SMILES: O=C(Cc1nc(-c2c[nH]c(C(=O)N3CCCC3)c2)cs1)N1CCOCC1]
335B
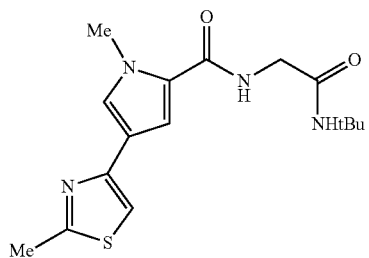
336B TABLE C-continued
| | |
|---|---|
| 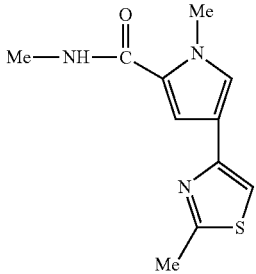 [SMILES: CNC(=O)c1cc(-c2csc(C)n2)cn1C] | 337B |
| 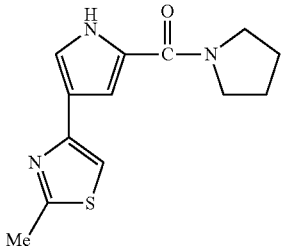 [SMILES: Cc1nc(-c2c[nH]c(C(=O)N3CCCC3)c2)cs1] | 338B |
| 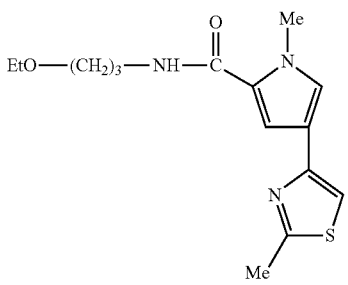 | 339B |
| 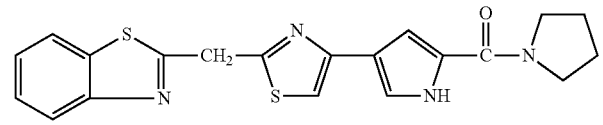 [SMILES: O=C(c1cc(-c2csc(Cc3nc4ccccc4s3)n2)c[nH]1)N1CCCC1] | 340B |
| 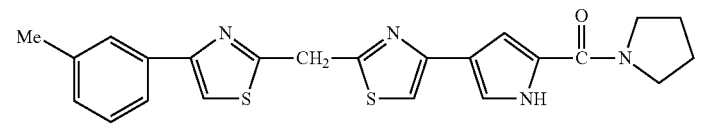 [SMILES: Cc1cccc(-c2csc(Cc3nc(-c4c[nH]c(C(=O)N5CCCC5)c4)cs3)n2)c1] | 341B |
| 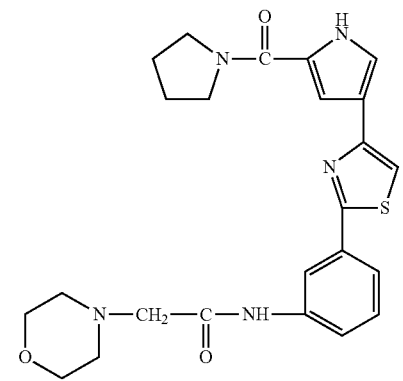 [SMILES: O=C(CN1CCOCC1)Nc1cccc(-c2nc(-c3c[nH]c(C(=O)N4CCCC4)c3)cs2)c1] | 342B |

TABLE C-continued
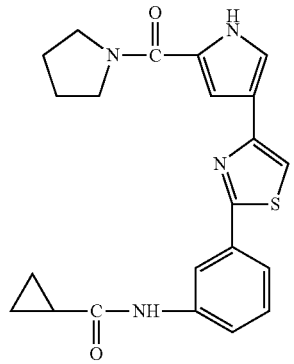 [SMILES: O=C(Nc1cccc(-c2nc(-c3c[nH]c(C(=O)N4CCCC4)c3)cs2)c1)C1CC1]
343B
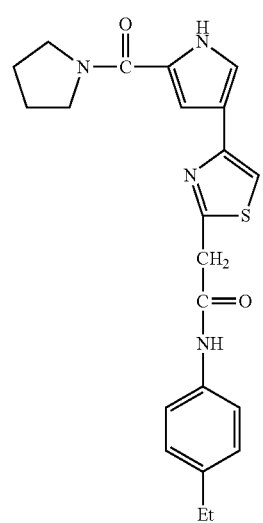 [SMILES: CCc1ccc(NC(=O)Cc2nc(-c3c[nH]c(C(=O)N4CCCC4)c3)cs2)cc1]
344B
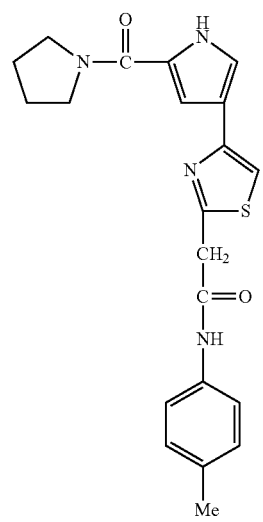 [SMILES: Cc1ccc(NC(=O)Cc2nc(-c3c[nH]c(C(=O)N4CCCC4)c3)cs2)cc1]
345B
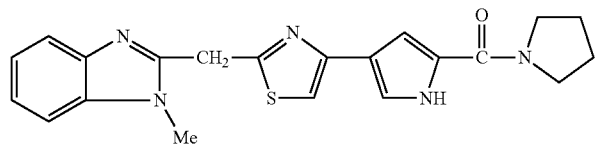 [SMILES: Cn1c(Cc2nc(-c3c[nH]c(C(=O)N4CCCC4)c3)cs2)nc2ccccc21]
346B TABLE C-continued
| | |
|---|---|
| 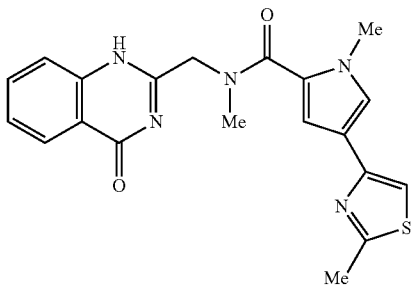 [SMILES: Cc1nc(-c2cc(C(=O)N(C)Cc3nc(=O)c4ccccc4[nH]3)n(C)c2)cs1] | 347B |
| 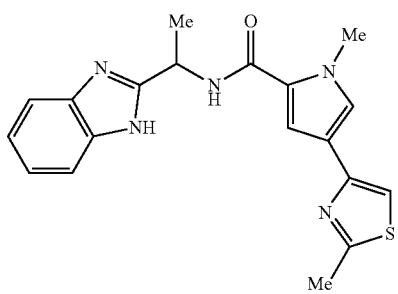 [SMILES: Cc1nc(-c2cc(C(=O)NC(C)c3nc4ccccc4[nH]3)n(C)c2)cs1] | 348B |
| 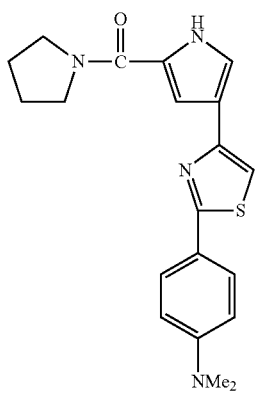 [SMILES: CN(C)c1ccc(-c2nc(-c3c[nH]c(C(=O)N4CCCC4)c3)cs2)cc1] | 349B |
| 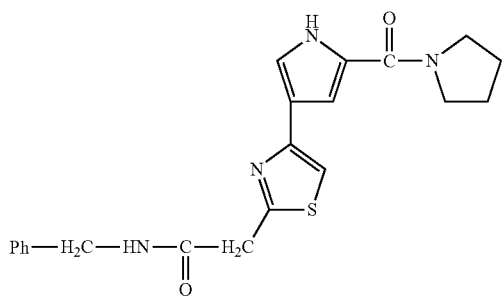 [SMILES: O=C(Cc1nc(-c2c[nH]c(C(=O)N3CCCC3)c2)cs1)NCc1ccccc1] | 350B |
| 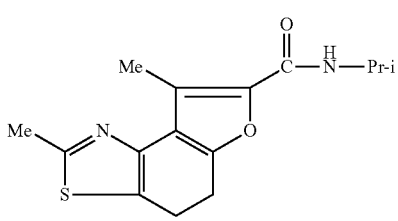 | 351B |

TABLE C-continued
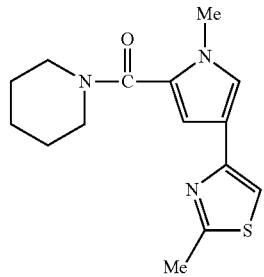 [SMILES: Cc1nc(-c2cc(C(=O)N3CCCCC3)n(C)c2)cs1] 352B
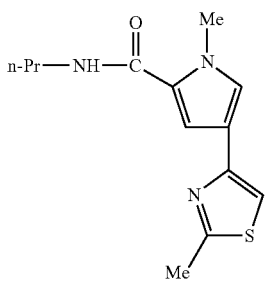 353B
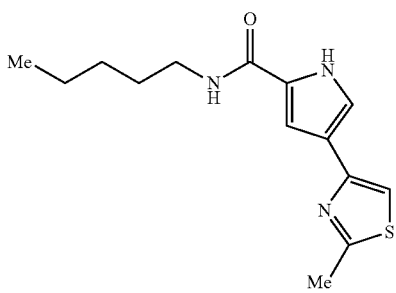 [SMILES: CCCCCNC(=O)c1cc(-c2csc(C)n2)c[nH]1] 354B
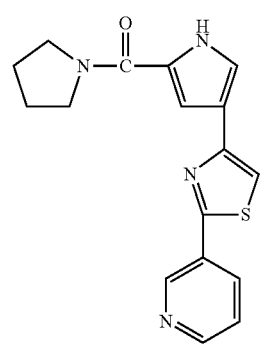 [SMILES: O=C(c1cc(-c2csc(-c3cccnc3)n2)c[nH]1)N1CCCC1] 355B
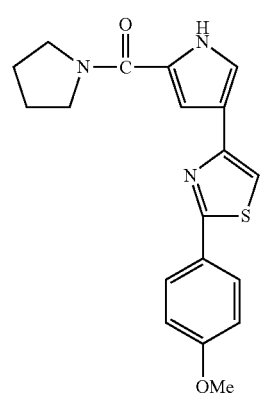 356B TABLE C-continued
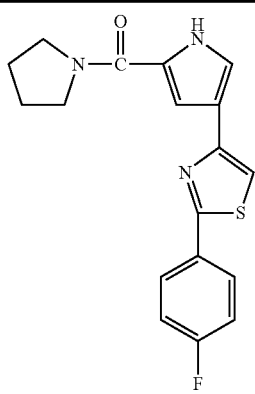
357B
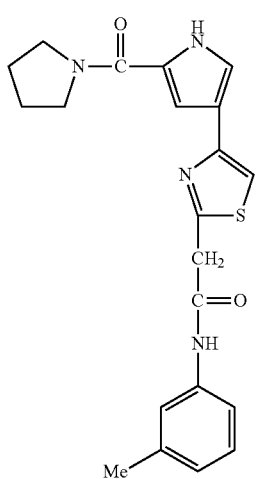 [SMILES: Cc1cccc(NC(=O)Cc2nc(-c3c[nH]c(C(=O)N4CCCC4)c3)cs2)c1]
358B
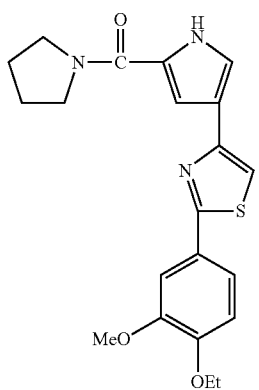 [SMILES: CCOc1ccc(-c2nc(-c3c[nH]c(C(=O)N4CCCC4)c3)cs2)cc1OC]
359B
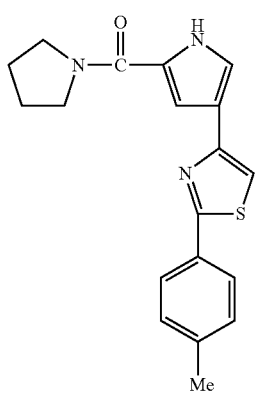 [SMILES: Cc1ccc(-c2nc(-c3c[nH]c(C(=O)N4CCCC4)c3)cs2)cc1]
360B TABLE C-continued
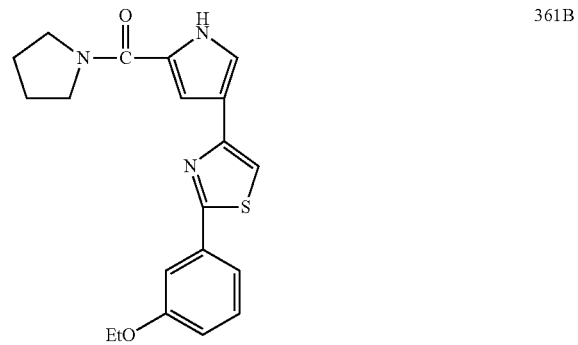
361B
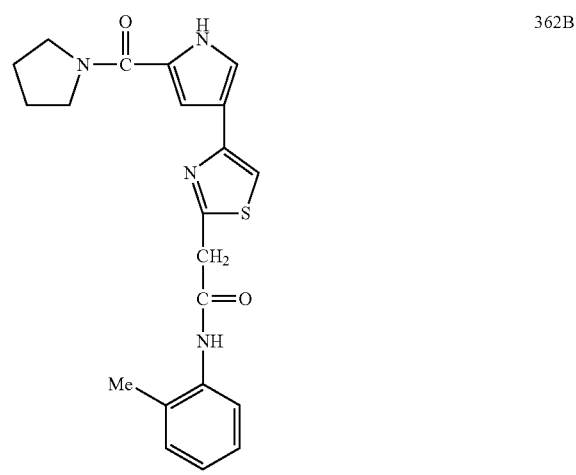
362B
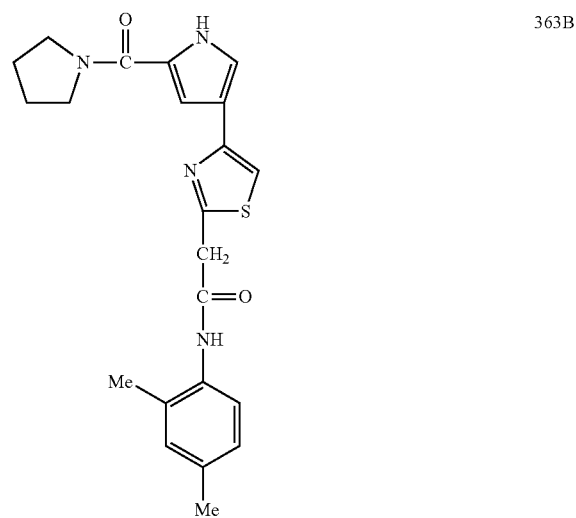
363B
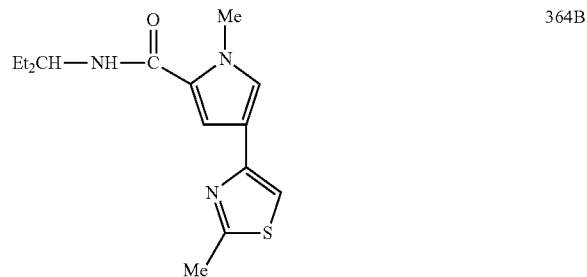
364B TABLE C-continued
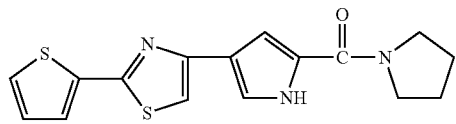 [SMILES: O=C(c1cc(-c2csc(-c3cccs3)n2)c[nH]1)N1CCCC1]
365B
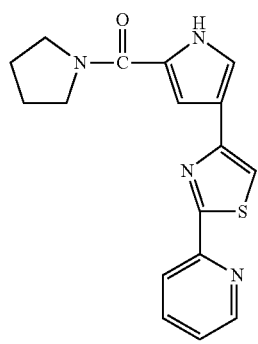 [SMILES: O=C(c1cc(-c2csc(-c3ccccn3)n2)c[nH]1)N1CCCC1]
366B
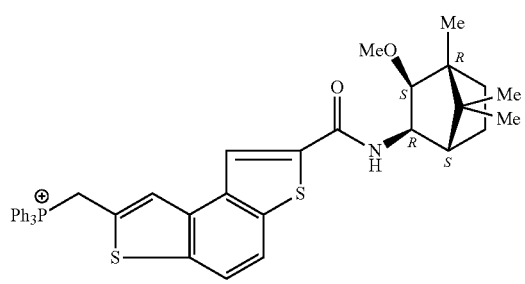
367B
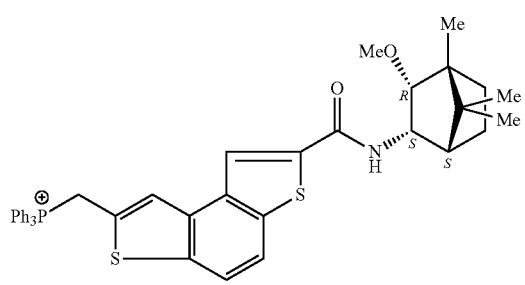
368B TABLE C-continued
| | |
|---|---|
| 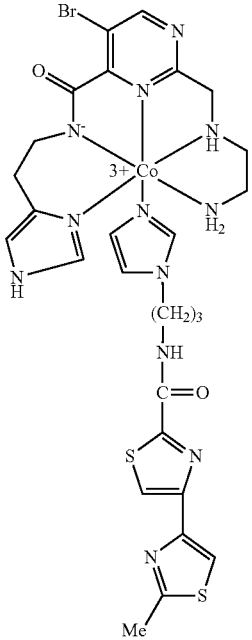 | 369B |
| 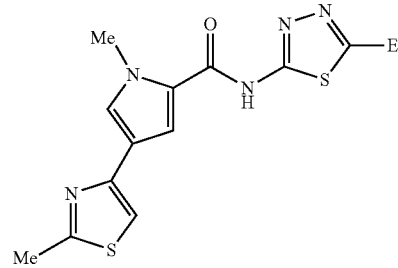 [SMILES: CCc1nnc(NC(=O)c2cc(-c3csc(C)n3)cn2C)s1] | 370B |
| 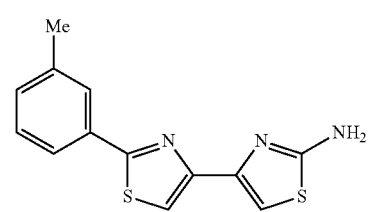 [SMILES: Cc1cccc(-c2nc(-c3csc(N)n3)cs2)c1] | 371B |
| 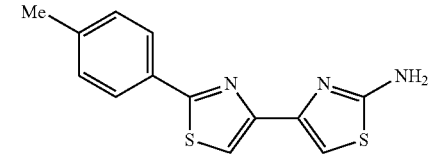 [SMILES: Cc1ccc(-c2nc(-c3csc(N)n3)cs2)cc1] | 372B |
| 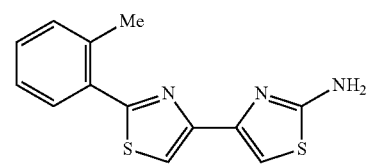 [SMILES: Cc1ccccc1-c1nc(-c2csc(N)n2)cs1] | 374B |
| 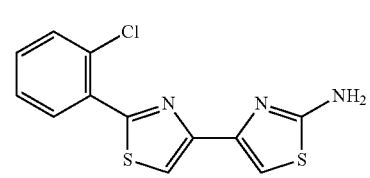 [SMILES: Nc1nc(-c2csc(-c3ccccc3Cl)n2)cs1] | 375B |

TABLE C-continued

376B

[Structure: a fused polycyclic compound with Me, HN-Ph, NH2, S, O, N substituents]

In one aspect, the invention includes a compound selected from Compound 13A, 14A, 15A, 16A, 17A, and 18A.

In one aspect, the invention includes a solvate of a compound of the invention. In one aspect, the invention includes a solvate, wherein the solvate is a hydrate of a compound of the invention. In one aspect, the invention includes an acid addition salt of a compound of the invention e.g., a hydrochloride salt. In one aspect, the invention includes a pharmaceutically acceptable salt of a compound of the invention. In one aspect, the invention includes a pharmaceutical composition comprising a compound of the invention and at least one pharmaceutically acceptable excipient.

In one aspect, the invention includes any of the compounds listed in Table C or a salt, solvate or prodrug thereof, wherein the compound inhibits a tyrosine kinase by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, a compound of the invention inhibits a tyrosine kinase by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, the invention includes any of the compounds listed in Table C or a salt, solvate, or prodrug thereof, wherein the compound inhibits JAK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more. In one aspect, JAK is JAK3.

In one aspect, a compound of the invention inhibits a JAK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more. In one aspect, JAK is JAK3.

In one aspect, the invention includes any of the compounds listed in Table C or a salt, solvate, or prodrug thereof, wherein the compound inhibits SYK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, a compound of the invention inhibits a SYK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, the invention includes any of the compounds listed in Table C or a salt, solvate, or prodrug thereof, wherein the compound inhibits BTK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, a compound of the invention inhibits BTK by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

The compounds of the invention are synthesized using methods known to one skilled in the art.

Formula V-1

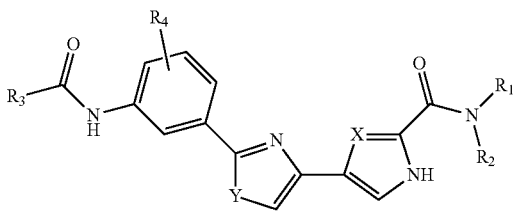

For example, compounds according to formula V-I shown above can be synthesized described below. In one aspect, the values for formula V-1 shown above: $R_3$, $R^4$, Y, X, $R_1$ and $R_2$ correspond to the values recited for formula VI: $R_3$ is $R^b$, $R^4$ is $R^{a1}$—$R^{a5}$, Y is S, X is CH, $R_1$ and $R_2$ are $R^2$ and $R^3$. The starting material ethyl 4-acetyl-1H-pyrrole-2-carboxylate may be prepared from the commercially available compound ethyl 1H-pyrrole-2-carboxylate according to the published procedure (See, e.g., Journal of the American Chemical Society, 129(11), 3078-3079; 2007; Chemical & Pharmaceutical Bulletin, 44(1), 48-54; 1996; Heterocycles, 27(8), 1855-60; 1988) using acyl chloride as acylating agent. Alternatively, it may be prepared starting from 4-acetyl-1H-pyrrole-2-carboxylic acid, also a commercially available compound (Scheme 1).

Scheme 1

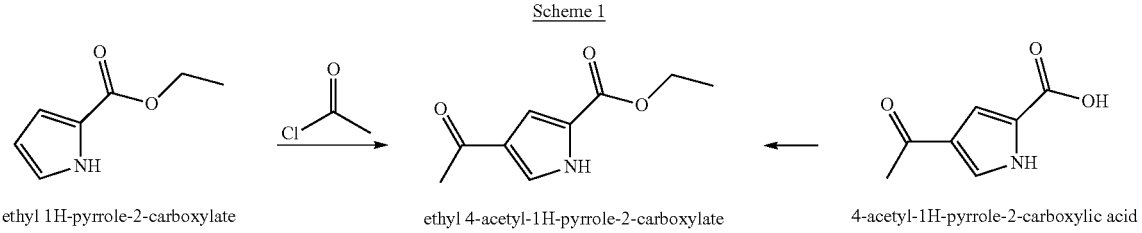

ethyl 1H-pyrrole-2-carboxylate → ethyl 4-acetyl-1H-pyrrole-2-carboxylate ← 4-acetyl-1H-pyrrole-2-carboxylic acid Similarly, the imidazole analog may be prepared starting from commercially available ethyl 1H-imidazole-2-carboxylate (Scheme 2).

Scheme 2

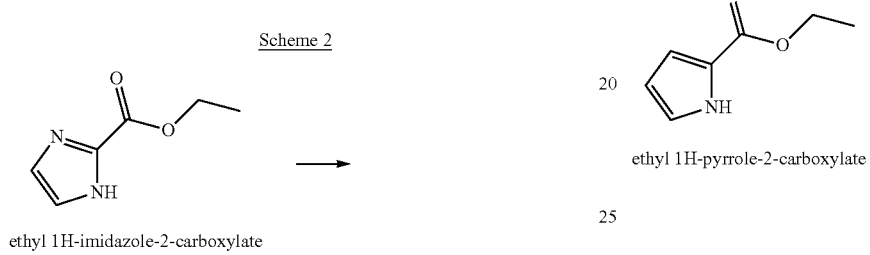

ethyl 1H-imidazole-2-carboxylate ethyl 4-acetyl-1H-imidazole-2-carboxylate

The next step is protecting the pyrrole or imidazole nitrogen and then acetyl bromination (Scheme 3) according to published procedures (See, e.g., Heterocycles, 55(8), 1475-1486; 2001; Journal of Medicinal Chemistry, 33(2), 543-52; 1990; Eur. Pat. Appl., 259085, 9 Mar. 1988).

Scheme 3

X = C or N
PG = protecting group

Alternatively the above starting materials may undergo acylation reaction with 2-bromoacetylbromide to give directly the desire product (See, e.g., Scheme 4).

Scheme 4 ethyl 1H-pyrrole-2-carboxylate ethyl 4-(2-bromoacetyl)-1H-pyrrole-2-carboxylate
[1]

At the next step, the intermediate ethyl 4-(2-bromoacetyl)-1H-pyrrole-2-carboxylate, or its imidazole analog, undergo a condensation reaction with 3-substitutedbenzothiazole derivatives to give the thiazole compound [2] (Scheme 5).

Scheme 5

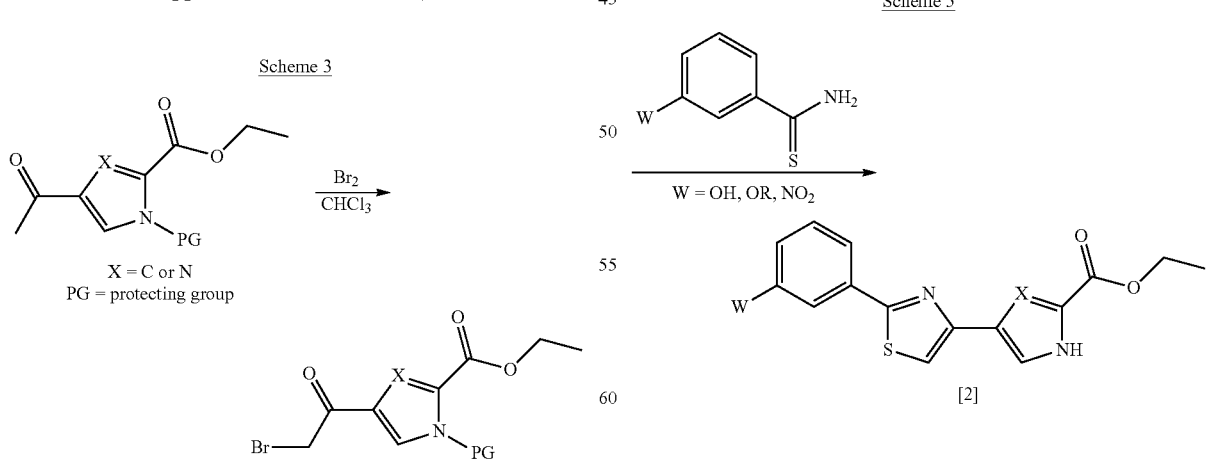

W = OH, OR, NO₂

[2]

The thioamides derivatives used in Scheme 5 may be prepared using BF₃-etherate assisted conversion of nitriles into thioamides with Lawesson's reagent (See, e.g., Synthesis, (24), 4012-4018; 2008; Farmaco, 54(8), 533-541; 1999) (Scheme 6).

Scheme 6

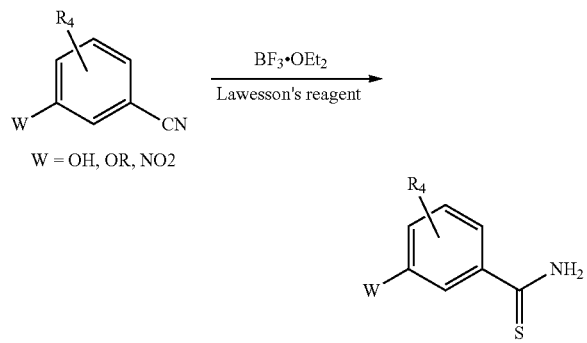

Alternatively condensation of intermediate [1] with 3-substitutedbezamide derivatives will give the oxazole compound [3] (Scheme 7) (Letters in Drug Design & Discovery, 6(1), 21-28; 2009; Journal of Heterocyclic Chemistry, 18(5), 885-8; 1981).

Scheme 7

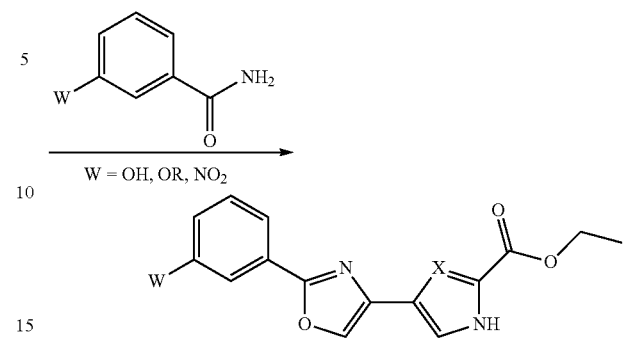

Referring to Scheme 8, the obtained intermediate [3] undergoes amidation reactions on both sides, one on the ethyl ester moiety and the second one on the amine obtained after reduction of the nitro group. When W is hydroxyl, it may undergo an alkylation reaction.

Scheme 8

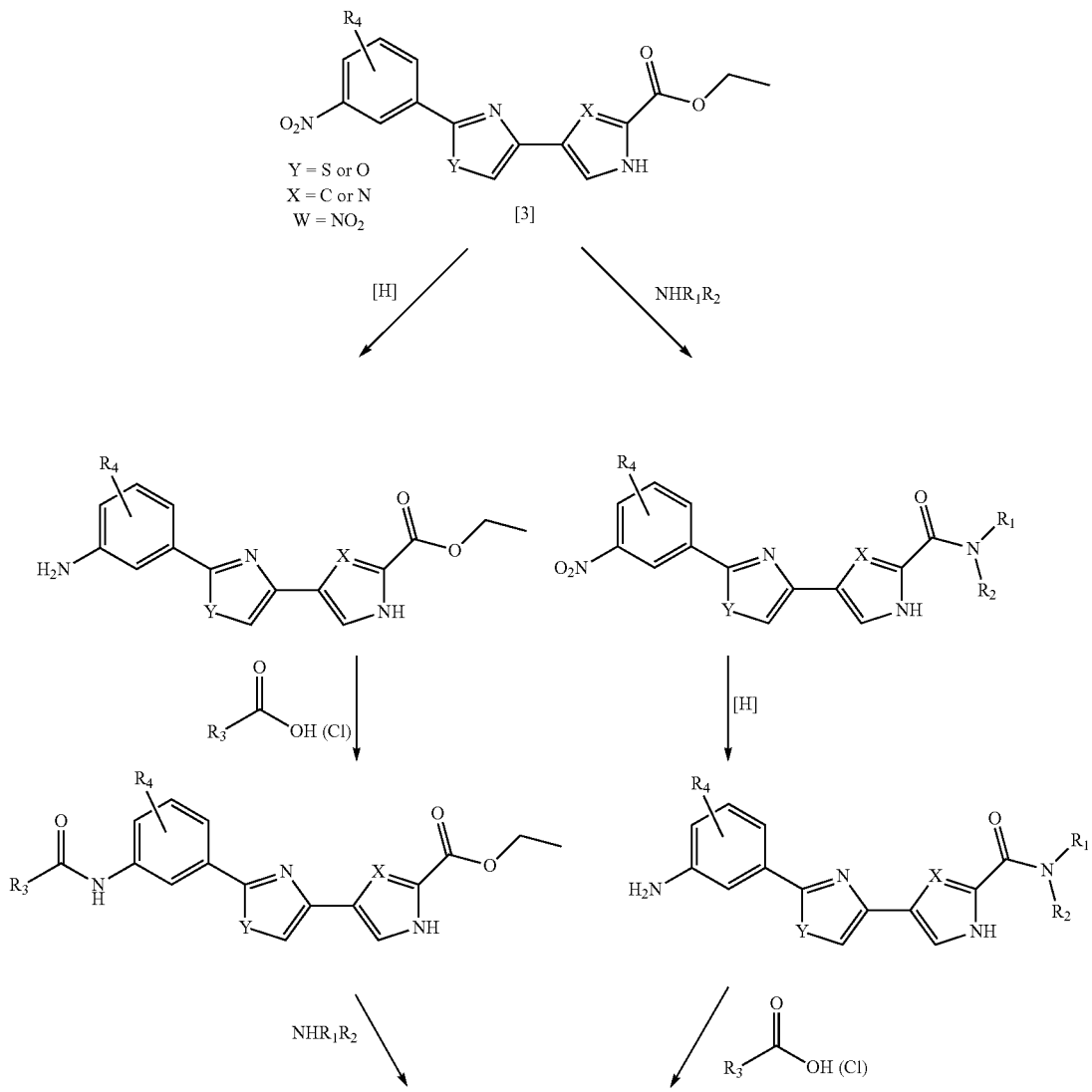

-continued

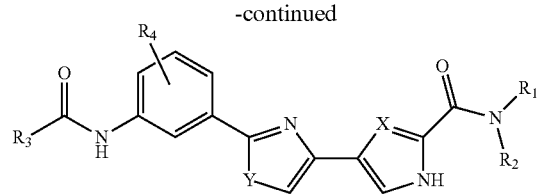

[4]

Crystalline Hydrochloride Salt of 2-Morpholino-N-(3-(4-(5-(pyrrolidine-1-carbonyl)-1H-pyrrol-3-yl)thiazol-2-yl)phenyl)acetamide The present invention includes crystalline 2-morpholino-N-(3-(4-(5-(pyrrolidine-1-carbonyl)-1H-pyrrol-3-yl)thiazol-2-yl)phenyl)acetamide hydrochloride salt (Form I) characterized by X-ray diffraction pattern, methods of making, pharmaceutical compositions comprising this polymorph and methods of treating diseases and disorders that are modulated by a signal transduction pathway. For example, 2-morpholino-N-(3-(4-(5-(pyrrolidine-1-carbonyl)-1H-pyrrol-3-yl)thiazol-2-yl)phenyl)acetamide hydrochloride salt Form I is useful in the treatment of cell proliferative disorders, including cancers; inflammatory disorders; immune disorders, including autoimmune disorders, immune system dysfunction, and transplant rejection; and dry eye disease.

The hydrochloride salt may be prepared under a variety of different conditions. However, in accordance with the present invention, the certain polymorph 2-morpholino-N-(3-(4-(5-(pyrrolidine-1-carbonyl)-1H-pyrrol-3-yl)thiazol-2-yl)phenyl)acetamide hydrochloride salt Form I is prepared as follows: the free base 2-morpholino-N-(3-(4-(5-(pyrrolidine-1-carbonyl)-1H-pyrrol-3-yl)thiazol-2-yl)phenyl)acetamide is dissolved in toluene (by heating) and HCl in EtOH is added dropwise. When the addition is complete, the precipitate is collected by filtration, washed, and dried in vacuum to afford crystalline 2-morpholino-N-(3-(4-(5-(pyrrolidine-1-carbonyl)-1H-pyrrol-3-yl)thiazol-2-yl)phenyl)acetamide hydrochloride salt (Form I).

Alternatively, 2-morpholino-N-(3-(4-(5-(pyrrolidine-1-carbonyl)-1H-pyrrol-3-yl)thiazol-2-yl)phenyl)acetamide (compound 8) can be recrystallized in ethanol or methanol to afford N-(3-(4-(5-(pyrrolidine-1-carbonyl)-1H-pyrrol-3-yl)thiazol-2-yl)phenyl)acetamide hydrochloride salt (Form I).

The 2-morpholino-N-(3-(4-(5-(pyrrolidine-1-carbonyl)-1H-pyrrol-3-yl)thiazol-2-yl)phenyl)acetamide hydrochloride salt (Form I) has characteristics combined with inertness toward common excipients used in pharmaceutical formulations that make it highly suitable for pharmaceutical formulation use. Furthermore, 2-morpholino-N-(3-(4-(5-(pyrrolidine-1-carbonyl)-1H-pyrrol-3-yl)thiazol-2-yl)phenyl)acetamide hydrochloride salt (Form I) exhibits superior solubility.

Figure 8:
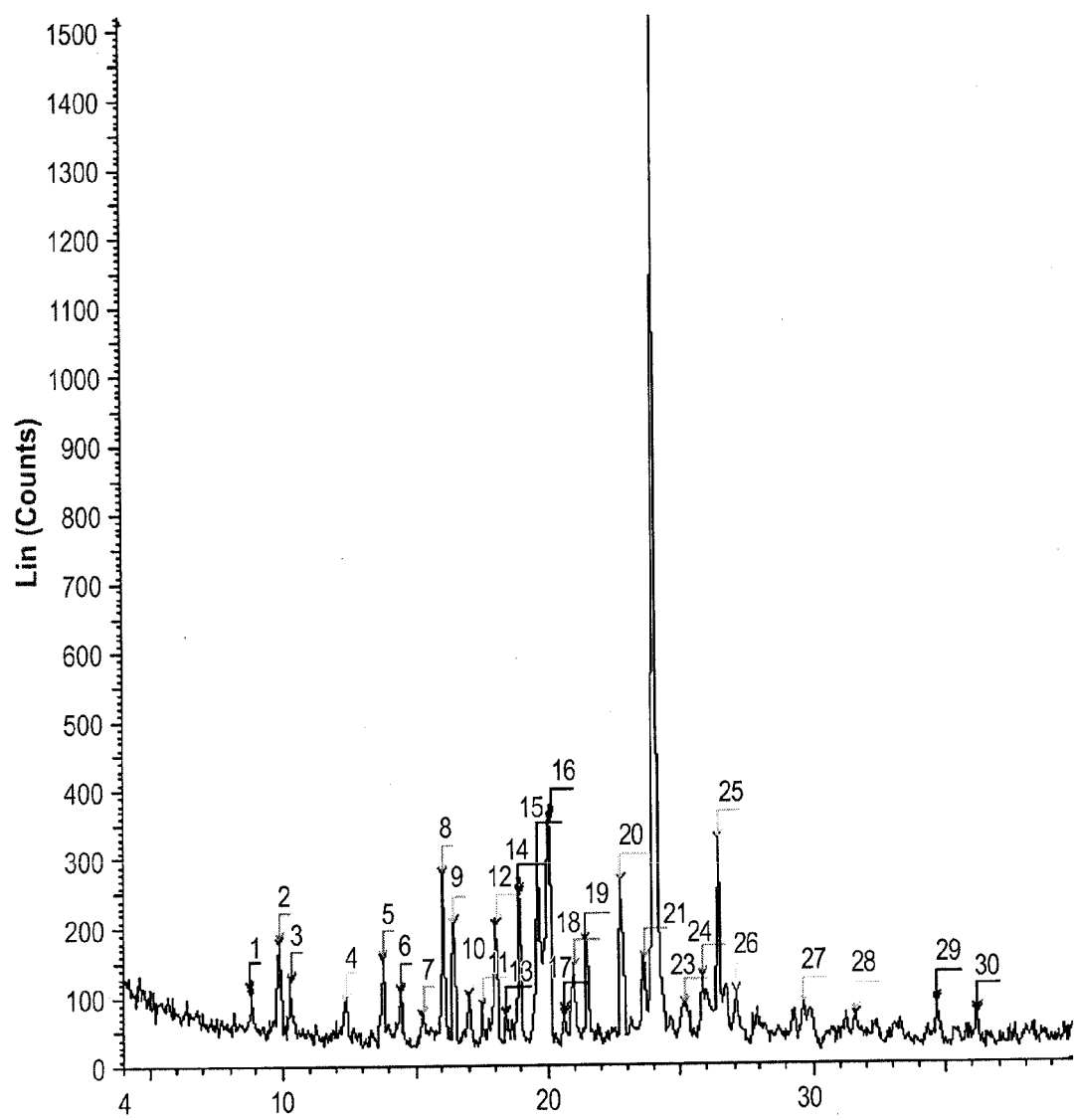
FIG. 8 is a characteristic X-ray diffraction pattern of 2-morpholino-N-(3-(4-(5-(pyrrolidine-1-carbonyl)-1H-pyrrol-3-yl)thiazol-2-yl)phenyl)acetamide hydrochloride salt (Form I), compound 9X (sample 1).
Figure 10:
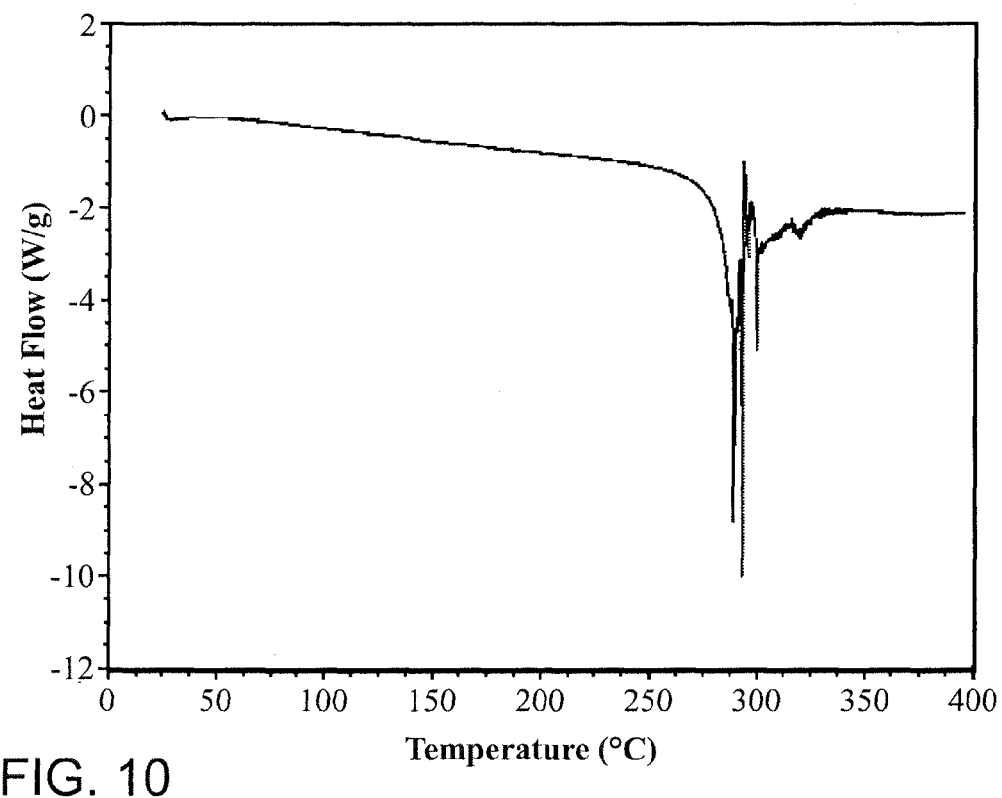
FIG. 10 is a DSC thermogram for 2-morpholino-N-(3-(4-(5-(pyrrolidine-1-carbonyl)-1H-pyrrol-3-yl)thiazol-2-yl)phenyl)acetamide hydrochloride salt (Form I), compound 9X (sample 1) (Example 14).
Figure 11:
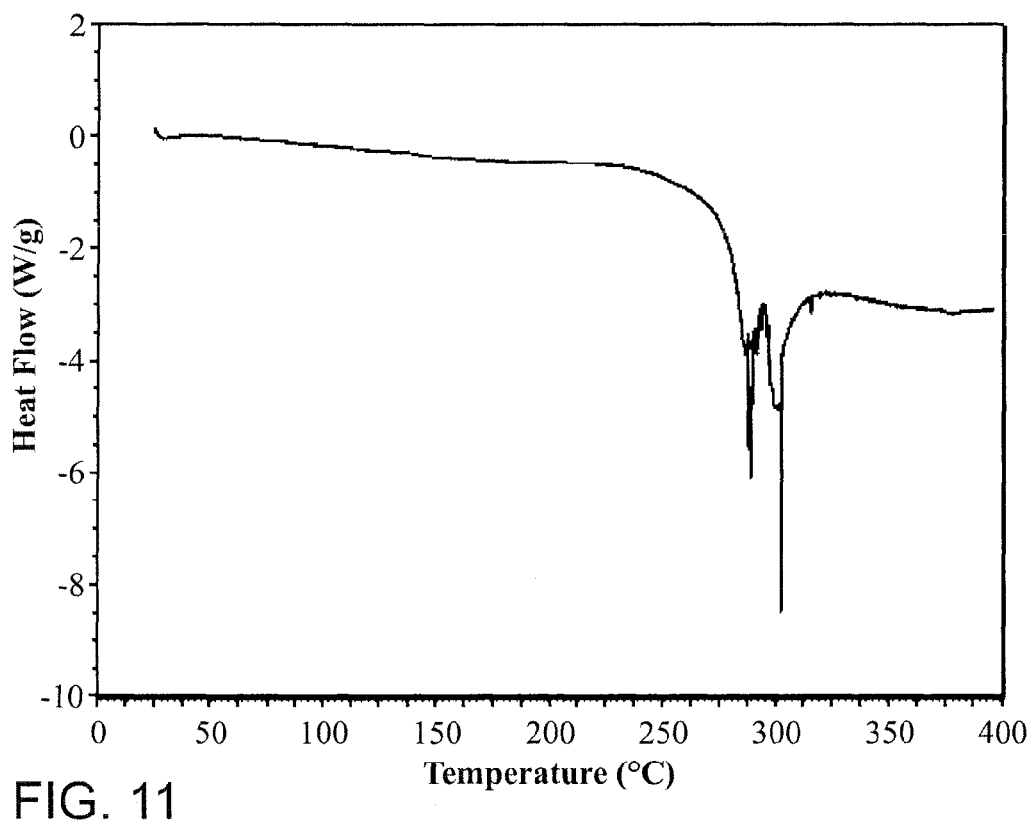
FIG. 11 is a DSC thermogram for 2-morpholino-N-(3-(4-(5-(pyrrolidine-1-carbonyl)-1H-pyrrol-3-yl)thiazol-2-yl)phenyl)acetamide hydrochloride salt (Form I) compound 9X (sample 2) (Example 14).
Figure 12:
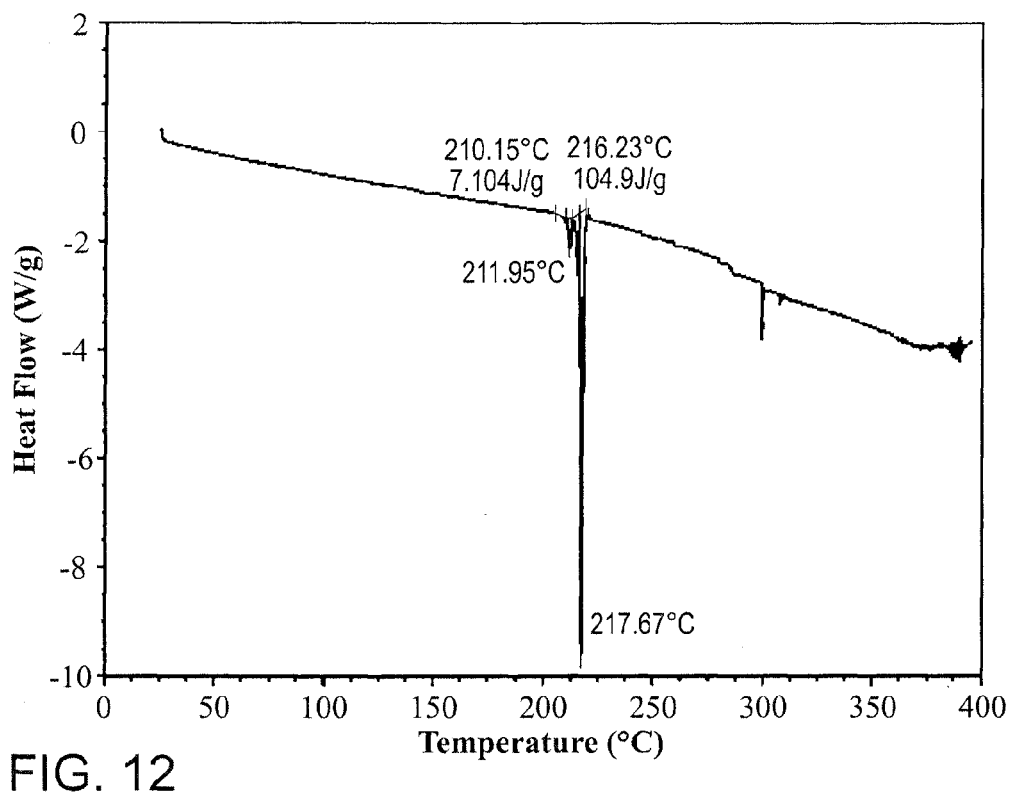
FIG. 12 is a DSC thermogram for 2-morpholino-N-(3-(4-(5-(pyrrolidine-1-carbonyl)-1H-pyrrol-3-yl)thiazol-2-yl)phenyl)acetamide (Example 14).

In one aspect, the invention provides a polymorph 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

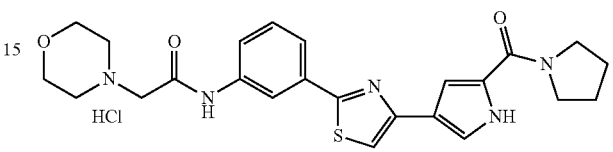

wherein, said polymorph is characterized by at least one of the following: an X-ray diffraction pattern characterized by an X-ray diffraction peak pattern substantially similar to that set forth in FIG. 8 or a Differential Scanning Calorimetry (DSC) thermogram having a decomposition trace substantially similar to that set forth in FIG. 10.

In one aspect, the invention provides a polymorph 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

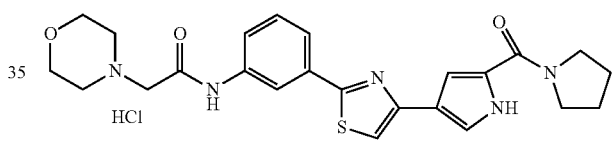

wherein, said polymorph characterized by at least one of the following: an X-ray diffraction pattern characterized by an X-ray diffraction peak pattern substantially similar to that set forth in FIG. 8.

In one aspect, the invention provides polymorph 2-morpholino-N-(3-(4-(5-(pyrrolidine-1-carbonyl)-1H-pyrrol-3-yl)thiazol-2-yl)phenyl)acetamide hydrochloride salt (Form I) characterized by an X-ray diffraction pattern including characteristic peaks at about 26.4, 24.1, 22.8, 20.0, 18.9, and 9.8 degrees 2θ. In one aspect, the polymorph is characterized by an X-ray diffraction pattern including characteristic peaks at about 26.4, 24.1, 22.8, 21.4, 20.0, 19.6, 18.9, 18.0, 16.4, 16.0, 13.7, and 9.8 degrees 2θ. In one aspect, the polymorph is characterized by an X-ray diffraction pattern lacking peaks at about 4.3, 19.2, and 22.1 degrees 2θ.

In one aspect, the invention provides a polymorph, wherein said X-ray diffraction is measured with Copper X-ray source. In one aspect, said X-ray diffraction pattern is measured by a Bruker D8 Advance.

In one aspect, the invention provides a polymorph, wherein said DSC thermogram is measured by a DSC Q2000 V24.4 Build 116.

In one aspect, the invention provides a polymorph, wherein the 2-morpholino-N-(3-(4-(5-(pyrrolidine-1-carbonyl)-1H-pyrrol-3-yl)thiazol-2-yl)phenyl)acetamide hydrochloride salt (Form I) is obtainable by a process comprising the steps of: 1) heating 2-morpholino-N-(3-(4-(5-(pyrrolidine-1-carbonyl)-1H-pyrrol-3-yl)thiazol-2-yl)phenyl)acetamide in toluene, and 2) treating said 2-morpholino-N-(3-(4-(5-(pyrrolidine-1-carbonyl)-1H-pyrrol-3-yl)thiazol-2-yl)phenyl)acetamide in toluene with hydrochloric acid in ethanol. In one aspect, said treating is with a 1.4 M solution of HCl in ethanol.

In one aspect, the invention provides a polymorph, wherein 2-morpholino-N-(3-(4-(5-(pyrrolidine-1-carbonyl)-1H-pyrrol-3-yl)thiazol-2-yl)phenyl)acetamide hydrochloride salt (Form I) is obtainable by recrystallization of the hydrochloride salt of 2-morpholino-N-(3-(4-(5-(pyrrolidine-1-carbonyl)-1H-pyrrol-3-yl)thiazol-2-yl)phenyl)acetamide from an organic solvent. In one aspect, the organic solvent is selected from ethanol and methanol. In one aspect, the organic solvent is ethanol. In one aspect, the organic solvent is methanol.

In one aspect, the invention provides an active ingredient consisting of 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

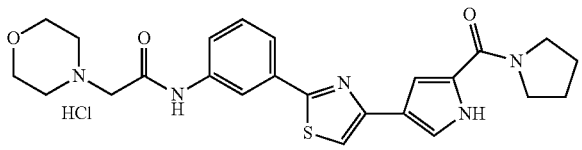

wherein, said active ingredient is characterized by at least one of the following: an X-ray diffraction pattern characterized by an X-ray diffraction peak pattern substantially similar to that set forth in FIG. 8 or a Differential Scanning Calorimetry (DSC) thermogram having a decomposition trace substantially similar to that set forth in FIG. 10.

In one aspect, the invention provides an active ingredient consisting of 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

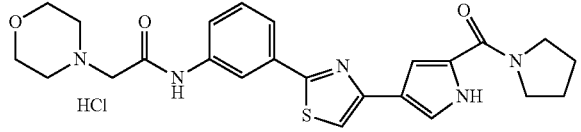

wherein, said active ingredient is characterized by at least one of the following: an X-ray diffraction pattern characterized by an X-ray diffraction peak pattern substantially similar to that set forth in FIG. 8.

In one aspect, the invention provides an active ingredient characterized by an X-ray diffraction pattern including characteristic peaks at about 26.4, 24.1, 22.8, 20.0, 18.9, and 9.8 degrees 2θ. In one aspect, the active ingredient is characterized by an X-ray diffraction pattern including characteristic peaks at about 26.4, 24.1, 22.8, 21.4, 20.0, 19.6, 18.9, 18.0, 16.4, 16.0, 13.7, and 9.8 degrees 2θ. In one aspect, the active ingredient is characterized by an X-ray diffraction pattern lacking peaks at about 4.3, 19.2, and 22.1 degrees 2θ.

In one aspect, the invention provides an active ingredient, wherein said X-ray diffraction is measured with Copper X-ray source. In one aspect, said X-ray diffraction pattern is measured by a Bruker D8 Advance.

In one aspect, the invention provides an active ingredient, wherein said DSC thermogram is measured by a DSC Q2000 V24.4 Build 116.

In one aspect, the invention provides an active ingredient, wherein the 2-morpholino-N-(3-(4-(5-(pyrrolidine-1-carbonyl)-1H-pyrrol-3-yl)thiazol-2-yl)phenyl)acetamide hydrochloride salt (Form I) is obtainable by a process comprising the steps of: 1) heating 2-morpholino-N-(3-(4-(5-(pyrrolidine-1-carbonyl)-1H-pyrrol-3-yl)thiazol-2-yl)phenyl)acetamide in toluene, and 2) treating said 2-morpholino-N-(3-(4-(5-(pyrrolidine-1-carbonyl)-1H-pyrrol-3-yl)phenyl)acetamide in toluene with hydrochloric acid in ethanol. In one aspect, said treating is with a 1.4 M solution of HCl in ethanol.

In one aspect, the invention provides an active ingredient, wherein 2-morpholino-N-(3-(4-(5-(pyrrolidine-1-carbonyl)-1H-pyrrol-3-yl)thiazol-2-yl)phenyl)acetamide hydrochloride salt (Form I) is obtainable by recrystallization of the hydrochloride salt of 2-morpholino-N-(3-(4-(5-(pyrrolidine-1-carbonyl)-1H-pyrrol-3-yl)thiazol-2-yl)phenyl)acetamide from an organic solvent. In one aspect, the organic solvent is selected from ethanol and methanol. In one aspect, the organic solvent is ethanol. In one aspect, the organic solvent is methanol.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

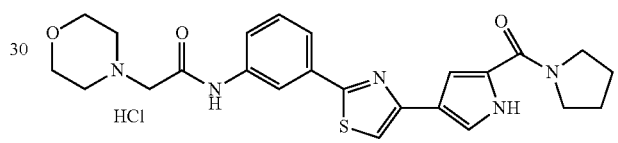

wherein, said active ingredient is characterized by at least one of the following: an X-ray diffraction pattern characterized by an X-ray diffraction peak pattern substantially similar to that set forth in FIG. 8 or a Differential Scanning Calorimetry (DSC) thermogram having a decomposition trace substantially similar to that set forth in FIG. 10, and a pharmaceutically acceptable carrier.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

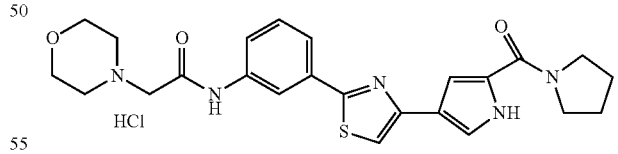

wherein, said active ingredient is characterized by at least one of the following: an X-ray diffraction pattern characterized by an X-ray diffraction peak pattern substantially similar to that set forth in FIG. 8, and a pharmaceutically acceptable carrier.

In one aspect, the invention provides a pharmaceutical composition comprising an active ingredient comprising 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

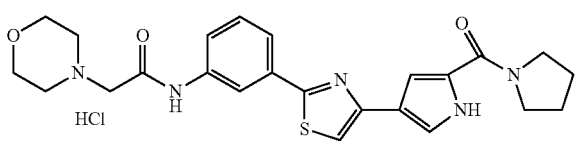

wherein, said active ingredient is characterized by at least one of the following: an X-ray diffraction pattern characterized by an X-ray diffraction peak pattern substantially similar to that set forth in FIG. 8 or a Differential Scanning Calorimetry (DSC) thermogram having a decomposition trace substantially similar to that set forth in FIG. 10, and a pharmaceutically acceptable carrier.

In one aspect, the invention provides a pharmaceutical composition comprising an active ingredient comprising 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

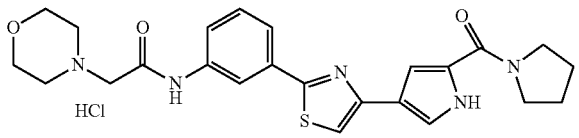

wherein, said active ingredient is characterized by at least one of the following: an X-ray diffraction pattern characterized by an X-ray diffraction peak pattern substantially similar to that set forth in FIG. 8, and a pharmaceutically acceptable carrier.

In one aspect, the invention provides a pharmaceutical composition, wherein the active ingredient is characterized by an X-ray diffraction pattern including characteristic peaks at about 26.4, 24.1, 22.8, 20.0, 18.9, and 9.8 degrees 2θ.

In one aspect, the invention provides a pharmaceutical composition, wherein the active ingredient is characterized by an X-ray diffraction pattern including characteristic peaks at about 26.4, 24.1, 22.8, 21.4, 20.0, 19.6, 18.9, 18.0, 16.4, 16.0, 13.7, and 9.8 degrees 2θ. In one aspect, the active ingredient is characterized by an X-ray diffraction pattern lacking peaks at about 4.3, 19.2, and 22.1 degrees 2θ.

In one aspect, the invention provides a pharmaceutical composition, wherein said X-ray diffraction of the active ingredient is measured with Copper X-ray source. In one aspect, said X-ray diffraction pattern is measured by a Bruker D8 Advance.

In one aspect, the invention provides a pharmaceutical composition, wherein said DSC thermogram of the active ingredient is measured by a DSC Q2000 V24.4 Build 116.

In one aspect, a pharmaceutical composition, wherein the 2-morpholino-N-(3-(4-(5-(pyrrolidine-1-carbonyl)-1H-pyrrol-3-yl)thiazol-2-yl)phenyl)acetamide hydrochloride salt (Form I) is obtainable by a process comprising the steps of: 1) heating 2-morpholino-N-(3-(4-(5-(pyrrolidine-1-carbonyl)-1H-pyrrol-3-yl)thiazol-2-yl)phenyl)acetamide in toluene, and 2) treating said 2-morpholino-N-(3-(4-(5-(pyrrolidine-1-carbonyl)-1H-pyrrol-3-yl)thiazol-2-yl)phenyl)acetamide in toluene with hydrochloric acid in ethanol. In one aspect, said treating is with a 1.4 M solution of HCl in ethanol.

In one aspect, the invention provides a pharmaceutical composition, wherein 2-morpholino-N-(3-(4-(5-(pyrrolidine-1-carbonyl)-1H-pyrrol-3-yl)thiazol-2-yl)phenyl)acetamide hydrochloride salt (Form I) is obtainable by recrystallization of the hydrochloride salt of 2-morpholino-N-(3-(4-(5-(pyrrolidine-1-carbonyl)-1H-pyrrol-3-yl)thiazol-2-yl) phenyl)acetamide from an organic solvent. In one aspect, the organic solvent is selected from ethanol and methanol. In one aspect, the organic solvent is ethanol. In one aspect, the organic solvent is methanol.

Figure 15:
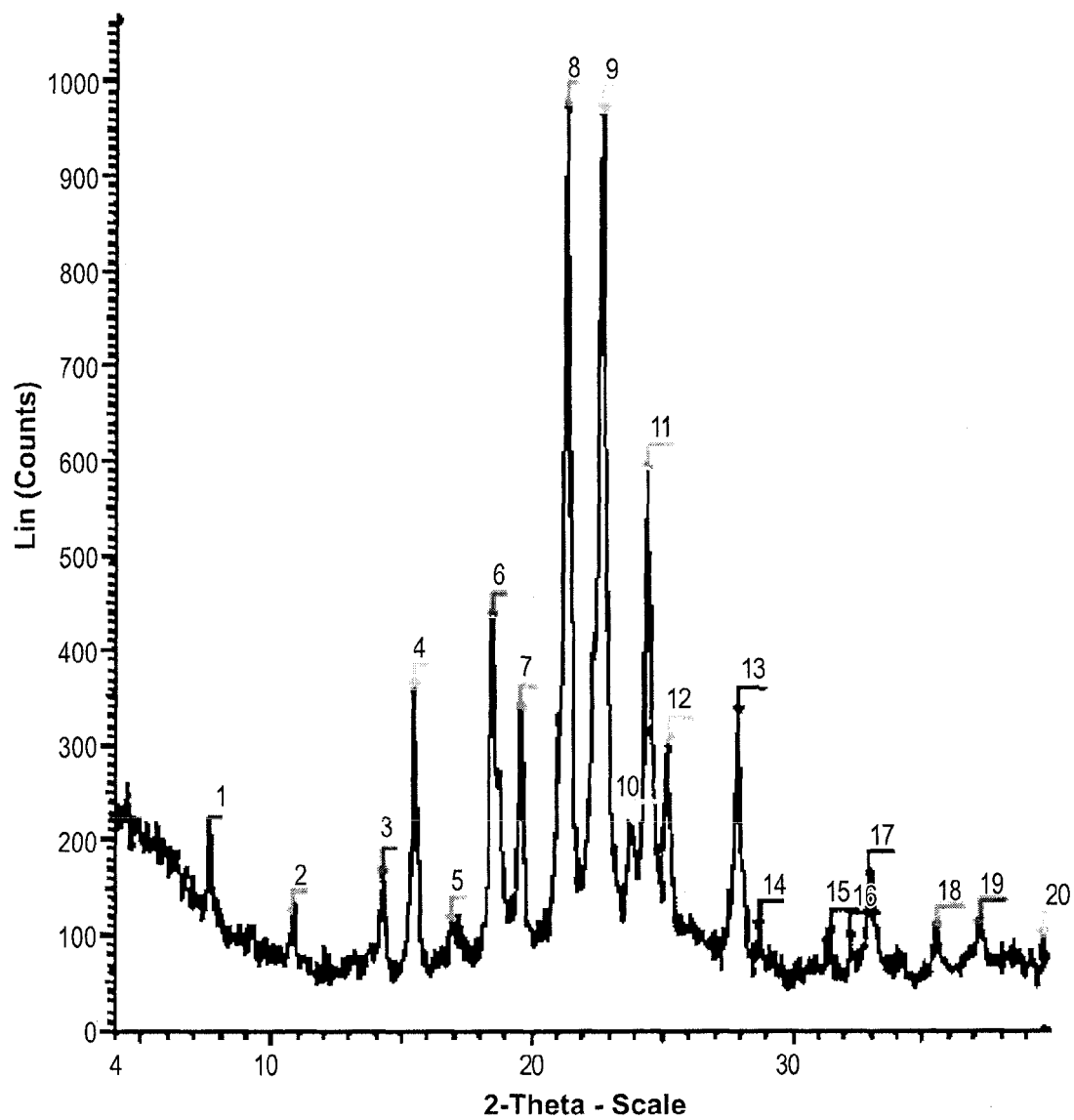
FIG. 15 is a characteristic X-ray diffraction pattern of a crystalline form of 2-morpholino-N-(3-(4-(5-(pyrrolidine-1-carbonyl)-1H-pyrrol-3-yl)thiazol-2-yl)phenyl)acetamide (compound 10X).
Figure 16:
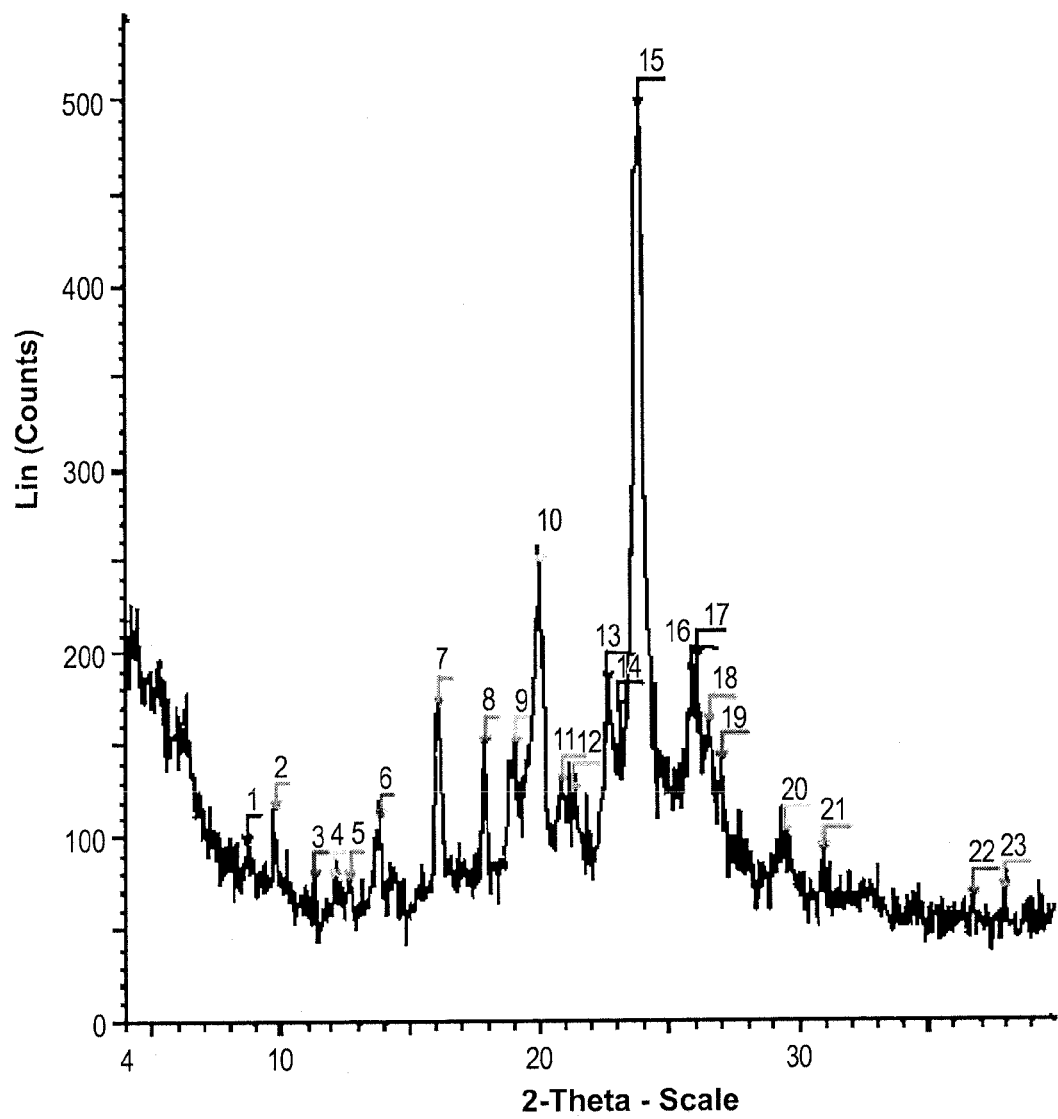
FIG. 16 is a characteristic X-ray diffraction pattern of a crystalline form of 2-morpholino-N-(3-(4-(5-(pyrrolidine-1-carbonyl)-1H-pyrrol-3-yl)thiazol-2-yl)phenyl)acetamide hydrochloride salt (Form I) (compound 9X (sample 3)).
Figure 17:
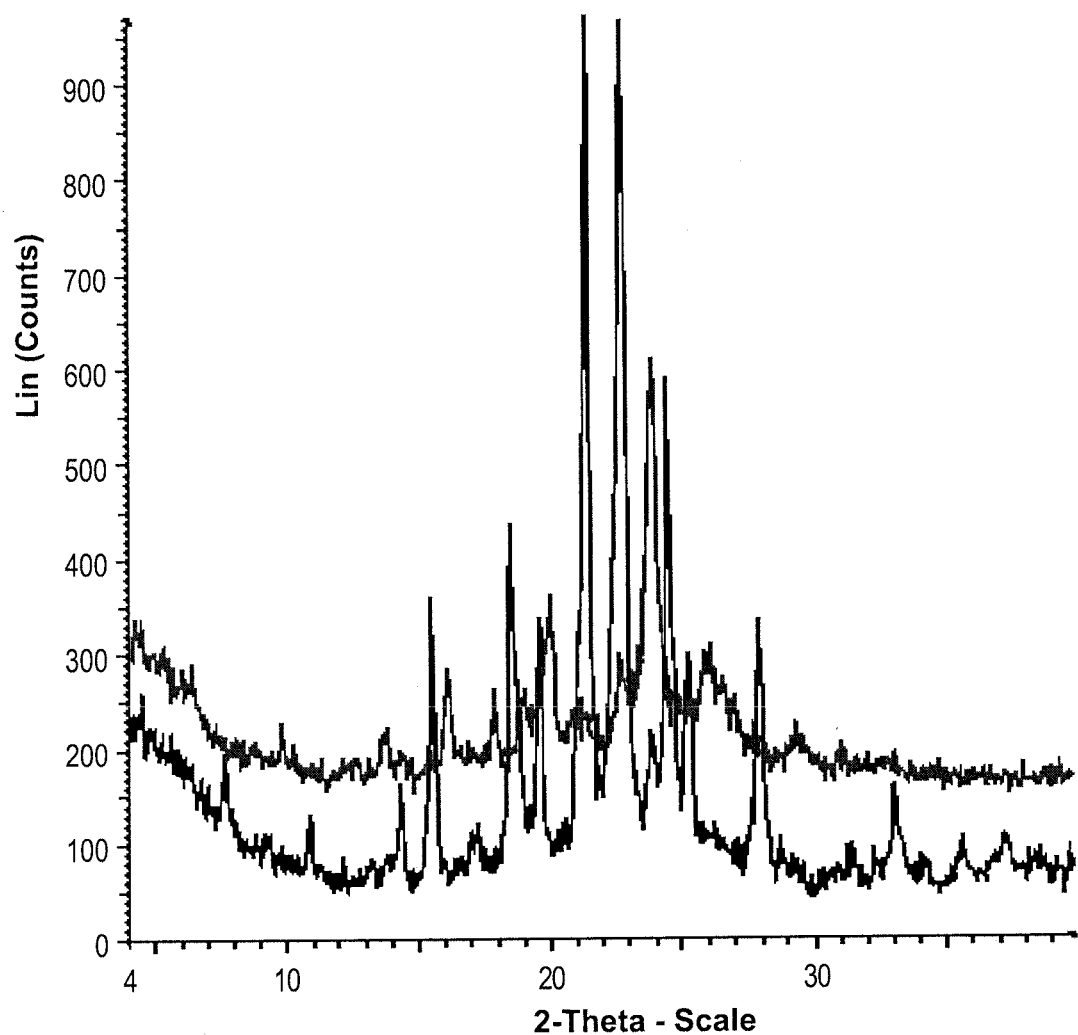
FIG. 17 is an overlay of the X-ray diffraction pattern of compound 10X (on the top) with the X-ray diffraction pattern of compound 9X (sample 3) (on the bottom).
Figure 18:
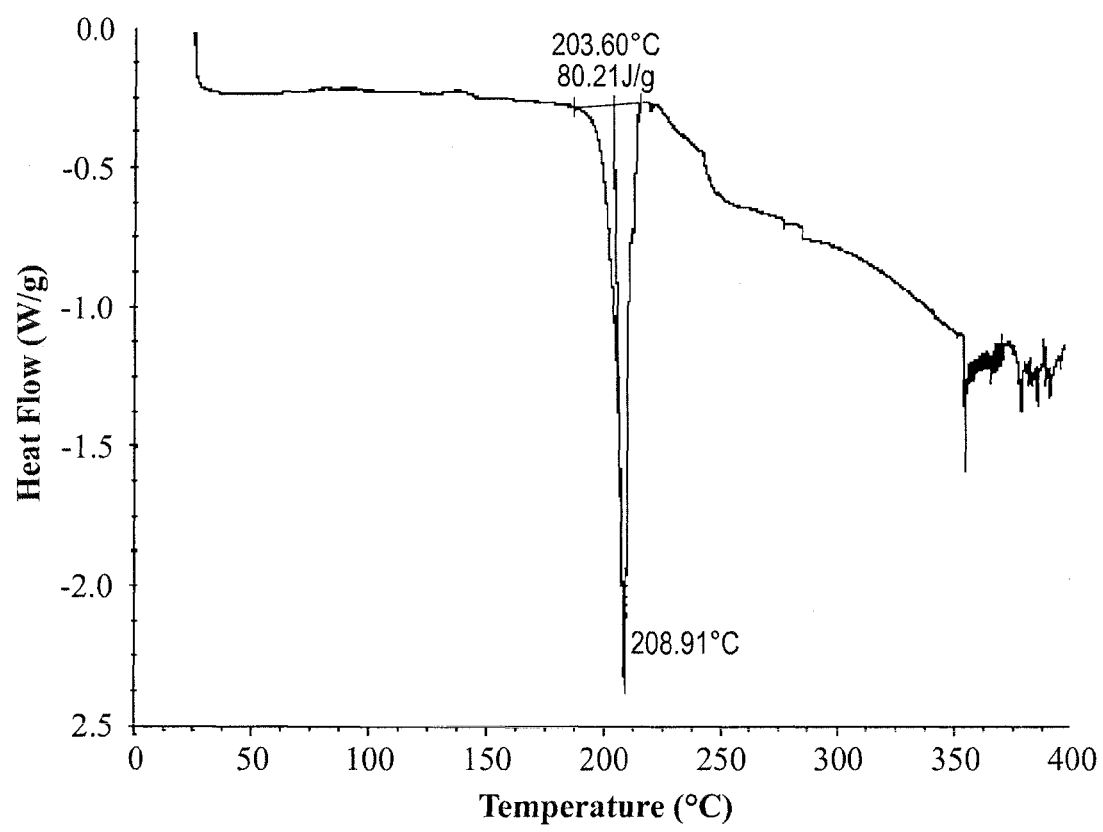
FIG. 18 is a DSC thermogram for 2-morpholino-N-(3-(4-(5-(pyrrolidine-1-carbonyl)-1H-pyrrol-3-yl)thiazol-2-yl)phenyl)acetamide compound 10X (Example 14)

Free Base of 2-morpholino-N-(3-(4-(5-(pyrrolidine-1-carbonyl)-1H-pyrrol-3-yl)thiazol-2-yl)phenyl)acetamide In one aspect, the invention provides a polymorph of 2-morpholino-N-(3-(4-(5-(pyrrolidine-1-carbonyl)-1H-pyrrol-3-yl)thiazol-2-yl)phenyl)acetamide (Form I) represented by the formula:

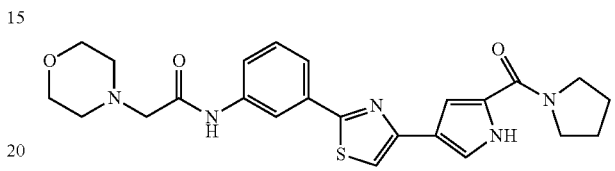

wherein, said polymorph is characterized by at least one of the following: an X-ray diffraction pattern characterized by an X-ray diffraction peak pattern substantially similar to that set forth in FIG. 15 or a Differential Scanning Calorimetry (DSC) thermogram having a decomposition trace substantially similar to that set forth in FIG. 18.

In one aspect, the invention provides a polymorph of 2-morpholino-N-(3-(4-(5-(pyrrolidine-1-carbonyl)-1H-pyrrol-3-yl)thiazol-2-yl)phenyl)acetamide (Form I) represented by the formula:

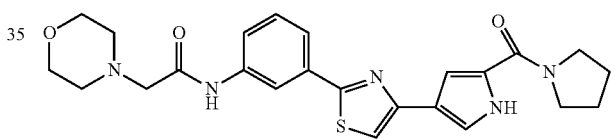

wherein, said polymorph characterized by at least one of the following: an X-ray diffraction pattern characterized by an X-ray diffraction peak pattern substantially similar to that set forth in FIG. 15.

In one aspect, the invention provides a polymorph of 2-morpholino-N-(3-(4-(5-(pyrrolidine-1-carbonyl)-1H-pyrrol-3-yl)thiazol-2-yl)phenyl)acetamide (Form I) characterized by an X-ray diffraction pattern including characteristic peaks at about 21.3, 22.7, and 24.5 degrees 2θ. In one aspect, the polymorph is characterized by an X-ray diffraction pattern including characteristic peaks at about 18.4, 21.3, 22.7, and 24.5 degrees 2θ. In one aspect, the polymorph a polymorph of 2-morpholino-N-(3-(4-(5-(pyrrolidine-1-carbonyl)-1H-pyrrol-3-yl)thiazol-2-yl)phenyl)acetamide (Form I) is characterized by an X-ray diffraction pattern including characteristic peaks at about 15.4, 18.4, 19.5, 21.3, 22.7, 24.5, 25.2, and 28.0 degrees 2θ.

In one aspect, the invention provides a polymorph, wherein the X-ray diffraction is measured with Copper X-ray source. In one aspect, the X-ray diffraction pattern is measured by a Bruker D8 Advance.

In one aspect, the invention provides a polymorph wherein, the DSC thermogram is measured by a DSC Q2000 V24.4 Build 116.

In one aspect, the invention provides a polymorph of 2-morpholino-N-(3-(4-(5-(pyrrolidine-1-carbonyl)-1H-pyrrol-3-yl)thiazol-2-yl)phenyl)acetamide, wherein the 2-morpholino-N-(3-(4-(5-(pyrrolidine-1-carbonyl)-1H-pyrrol-3-yl)thiazol-2-yl)phenyl)acetamide (Form I) is obtainable by recrystallization of 2-morpholino-N-(3-(4-(5-(pyrrolidine-1-carbonyl)-1H-pyrrol-3-yl)thiazol-2-yl)phenyl)acetamide from an organic solvent. In one aspect, the organic solvent is ethanol.

In one aspect, the invention provides an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

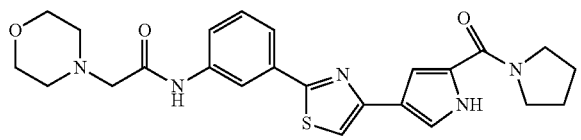

wherein, said active ingredient is characterized by at least one of the following: an X-ray diffraction pattern characterized by an X-ray diffraction peak pattern substantially similar to that set forth in FIG. 15 or a Differential Scanning Calorimetry (DSC) thermogram having a decomposition trace substantially similar to that set forth in FIG. 18.

In one aspect, the invention provides an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

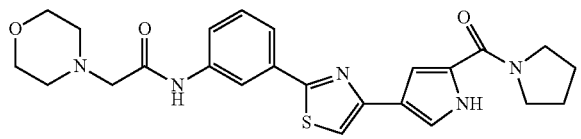

wherein, said active ingredient is characterized by at least one of the following: an X-ray diffraction pattern characterized by an X-ray diffraction peak pattern substantially similar to that set forth in FIG. 15.

In one aspect, the invention provides an active ingredient of 2-morpholino-N-(3-(4-(5-(pyrrolidine-1-carbonyl)-1H-pyrrol-3-yl)thiazol-2-yl)phenyl)acetamide (Form I) characterized by an X-ray diffraction pattern including characteristic peaks at about 21.3, 22.7, and 24.5 degrees 2θ. In one aspect, the active ingredient is characterized by an X-ray diffraction pattern including characteristic peaks at about 18.4, 21.3, 22.7, and 24.5 degrees 2θ. In one aspect, the active ingredient is characterized by an X-ray diffraction including characteristic peaks at about 15.4, 18.4, 19.5, 21.3, 22.7, 24.5, 25.2, and 28.0 degrees 2θ.

In one aspect, the invention provides an active ingredient, wherein the X-ray diffraction of 2-morpholino-N-(3-(4-(5-(pyrrolidine-1-carbonyl)-1H-pyrrol-3-yl)thiazol-2-yl)phenyl)acetamide (Form I) is measured with Copper X-ray source. In one aspect, said X-ray diffraction pattern is measured by a Bruker D8 Advance.

In one aspect, the invention provides an active ingredient, wherein the DSC thermogram of 2-morpholino-N-(3-(4-(5-(pyrrolidine-1-carbonyl)-1H-pyrrol-3-yl)thiazol-2-yl)phenyl)acetamide (Form I) is measured by a DSC Q2000 V24.4 Build 116.

In one aspect, the invention provides an active ingredient, 2-morpholino-N-(3-(4-(5-(pyrrolidine-1-carbonyl)-1H-pyrrol-3-yl)thiazol-2-yl)phenyl)acetamide (Form I) that is obtainable by recrystallization of 2-morpholino-N-(3-(4-(5-(pyrrolidine-1-carbonyl)-1H-pyrrol-3-yl)thiazol-2-yl)phenyl)acetamide from an organic solvent. In one aspect, the organic solvent is ethanol.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

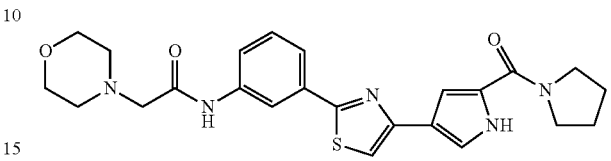

wherein, said active ingredient is characterized by at least one of the following: an X-ray diffraction pattern characterized by an X-ray diffraction peak pattern substantially similar to that set forth in FIG. 15 or a Differential Scanning Calorimetry (DSC) thermogram having a decomposition trace substantially similar to that set forth in FIG. 19, and a pharmaceutically acceptable carrier.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

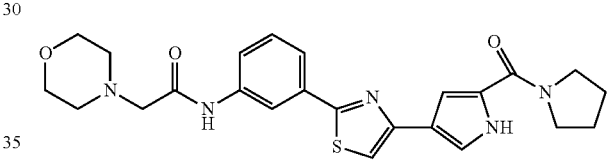

wherein, said active ingredient is characterized by at least one of the following: an X-ray diffraction pattern characterized by an X-ray diffraction peak pattern substantially similar to that set forth in FIG. 15, and a pharmaceutically acceptable carrier.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

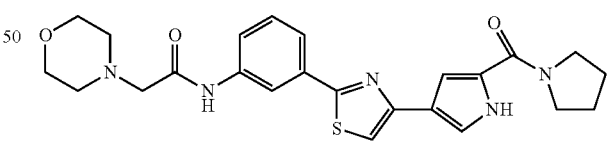

wherein, said active ingredient is characterized by at least one of the following: an X-ray diffraction pattern characterized by an X-ray diffraction peak pattern substantially similar to that set forth in FIG. 15 or a Differential Scanning Calorimetry (DSC) thermogram having a decomposition trace substantially similar to that set forth in FIG. 18, and a pharmaceutically acceptable carrier.

In one aspect, the invention provides a pharmaceutical composition comprising an active ingredient consisting of 2-morpholino-N-(3-(4-(5-(pyrrolidine-1-carbonyl)-1H-pyrrol-3-yl)thiazol-2-yl)phenyl)acetamide (Form I) represented by the formula:

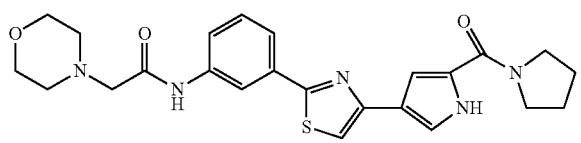

wherein, said active ingredient is characterized by at least one of the following: an X-ray diffraction pattern characterized by an X-ray diffraction peak pattern substantially similar to that set forth in FIG. 15, and a pharmaceutically acceptable carrier.

In one aspect, the invention provides a pharmaceutical composition comprising an active ingredient characterized by an X-ray diffraction pattern including characteristic peaks at about 21.3, 22.7, and 24.5 degrees 2θ. In one aspect, the pharmaceutical composition comprises an active ingredient characterized by an X-ray diffraction pattern including characteristic peaks at about 18.4, 21.3, 22.7, and 24.5 degrees 2θ. In one aspect, the pharmaceutical composition comprises an active ingredient characterized by an X-ray diffraction pattern lacking peaks at about 15.4, 18.4, 19.5, 21.3, 22.7, 24.5, 25.2, and 28.0 degrees 2θ.

In one aspect, the invention provides a pharmaceutical composition, wherein the X-ray diffraction of the active ingredient is measured with Copper X-ray source. In one aspect, the X-ray diffraction pattern is measured by a Bruker D8 Advance.

In one aspect, the invention provides a pharmaceutical composition, wherein the DSC thermogram of the active ingredient is measured by a DSC Q2000 V24.4 Build 116.

In one aspect, the invention provides a pharmaceutical composition, wherein the 2-morpholino-N-(3-(4-(5-(pyrrolidine-1-carbonyl)-1H-pyrrol-3-yl)thiazol-2-yl)phenyl)acetamide (Form I) is obtainable by recrystallization of 2-morpholino-N-(3-(4-(5-(pyrrolidine-1-carbonyl)-1H-pyrrol-3-yl)thiazol-2-yl)phenyl)acetamide from an organic solvent. In one aspect, the organic solvent is ethanol.

In one aspect, the invention provides a pharmaceutical composition, wherein said 2-morpholino-N-(3-(4-(5-(pyrrolidine-1-carbonyl)-1H-pyrrol-3-yl)thiazol-2-yl)phenyl)acetamide (Form I) is substantially free from impurities.

Methods of Use

In one aspect, the invention includes methods of preventing or treating a cell proliferation-related disorder including, cancer; an inflammatory disorder; an immune disorder including, autoimmune disease, immune system dysfunction, and transplant rejection and/or dry eye disease by administering to a subject in need thereof a pharmaceutical composition that includes a compound of the invention and at least one pharmaceutically acceptable excipient to a subject in need thereof. When the pharmaceutical composition includes a compound of the invention that has more than one stereoisomeric form, the pharmaceutical composition may be prepared with a pure or an essentially pure enantiomeric form of the compound, with an enantiopurity of at least 90% enantiomeric excess (EE), at least 95% EE, at least 98% EE, and at least 99% EE. Alternatively, the pharmaceutical composition may be prepared as mixture of enantiomeric forms of the compound (e.g., as a racemic mixture or as a mixture with a ratio of 60:40, 70:30, 80:20 or 90:10 between the enantiomeric forms). The invention also includes use of a compound of the invention in the manufacture of a medicament to prevent or treat a cell proliferation-related disorder including, a cancer; an inflammatory disorder; an immune disorder including, autoimmune disease, immune system dysfunction, and transplant rejection and/or dry eye disease. When the medicament includes a compound of the invention that has more than one stereoisomeric form, the medicament may be prepared with a pure or an essentially pure enantiomeric form of the compound, with an enantiopurity of at least 90% enantiomeric excess (EE), at least 95% EE, more at least 98% EE, and at least 99% EE. Alternatively, the medicament may be prepared as mixture of enantiomeric forms of a compound of the invention (e.g., as a racemic mixture or as a mixture with a ratio of 60:40, 70:30, 80:20 or 90:10 between the enantiomeric forms).

The invention relate to methods of treating or preventing a disease or disorder that is modulated by inhibition of one or more tyrosine kinases (JAK, SYK, and/or BTK), by administering to a subject in need thereof a pharmaceutical composition that includes a compound of the invention and at least one pharmaceutically acceptable excipient. When the pharmaceutical composition includes a compound of the invention that has more than one stereoisomeric form, the pharmaceutical composition may be prepared with a pure or an essentially pure enantiomeric form of the compound, with an enantiopurity of at least 90% enantiomeric excess (EE), at least 95% EE, at least 98% EE, and at least 99% EE. Alternatively, the pharmaceutical composition may be prepared as mixture of enantiomeric forms of a compound of the invention (e.g., as a racemic mixture or as a mixture with a ratio of 60:40, 70:30, 80:20 or 90:10 between the enantiomeric forms). For example, the disease or disorder that is modulated by inhibition of one or more tyrosine kinases is cancer, pre-cancer, or a hyperproliferative disorder.

In some embodiments, the administration of a compound of the invention is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In some embodiments, a compound of the invention is administered with a pharmaceutically acceptable carrier.

One aspect of the invention includes methods of regulating immune system activity in a subject comprising administering a compound of the invention. Embodiments of the invention also include use of a compound of the invention in the manufacture of a medicament to regulate immune system activity. Examples of diseases that may be treated or prevented according to the foregoing methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, psoriatic arthritis, and amyotrophic lateral sclerosis, multiple sclerosis, psoriasis and Sjogren' syndrome, Type II inflammatory disease such as vascular inflammation (including vasculitis, ateritis, atherosclerosis and coronary artery disease), chronic inflammatory diseases such as ankylosing spondylitis (AS) (also known as Bekhterev's disease, Bekhterev syndrome, and Marie-Strumpell diseases), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas. In some embodiments, the compound of the invention inhibits one or more components of a tyrosine kinase signaling cascade. In some embodiments, a compound of the invention inhibits JAK. For example, JAK is JAK3. In some embodiments, a compound of the invention inhibits SYK. In some embodiments, a compound of the invention inhibits BTK. In some embodiments, a compound of the invention inhibits JAK and SYK. In some embodiments, a compound of the invention inhibits JAK and BTK. In some embodiments, a compound of the invention inhibits BTK and SYK. In some embodiments, a compound of the invention inhibits JAK, SYK and BTK. In some embodiments, a compound of the invention inhibits JAK3 and has no activity on JAK2. In some embodiments, regulation of the immune system occurs through the inhibition of lymphocyte proliferation. In certain embodiments, regulation of the immune system occurs through the inhibition of lymphocyte activation. For example, T-cell proliferation and/or activation is inhibited. Additionally or alternatively, B-cell proliferation and/or activation is inhibited. In certain embodiments, the subject is a mammal, e.g., a human.

In some embodiments, the administration of a compound of the invention is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In some embodiments, a compound of the invention is administered with a pharmaceutically acceptable carrier.

Embodiments of the invention are also drawn to methods of treating or preventing cancer or a proliferation disorder in a subject, comprising administering an effective amount of a compound of the invention. The compound of the invention may be a JAK kinase inhibitor (e.g., a JAK3 inhibitor). The compound of the invention may inhibit a JAK kinase directly, or it may affect the JAK kinase pathway. The compound of the invention may be a SYK inhibitor. The compound of the invention may inhibit SYK directly or it may affect the SYK pathway. The compound of the invention may be a BTK inhibitor. The compound of the invention may inhibit BTK directly or it may affect the BTK pathway.

In certain embodiments, the cell proliferation disorder includes any type of cancer including solid tumors and non-solid tumors. In specific embodiments the solid tumors are selected from tumors in the CNS (central nervous system), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas. In other embodiments, non-solid tumors include lymphoproliferative disorders including leukemias and lymphomas. In other embodiments, the disorder is metastatic disease.

A compound of the invention also may be used in the treatment of a cancer or cell proliferation disorder in a combination therapy with one or more of anti-cancer treatments such as surgery, radiation therapy, immunotherapy and/or one or more anti-cancer agents selected from the group consisting of anti-proliferative agents, agents that modulate the cancer cell metabolism, cytotoxic agents, cytostatic agents, and chemotherapeutic agents and salts and derivatives thereof. In one aspect, a compound of the invention may be used in the treatment of a cancer or cell proliferation disorder in combination therapy with any one of the drugs selected from a group consisting of an alkaloid, an alkylating agent, an anti-tumor antibiotic, an antimetabolite, a Bcr-Abl tyrosine kinase inhibitor, a nucleoside analogue, a multidrug resistance reversing agent, a DNA binding agent, microtubule binding drug, a toxin and a DNA antagonist. Those of skill in the art will recognize the chemotherapeutic agents classified into one or more particular classes of chemotherapeutic agents described above.

When use in combination with additional anti-proliferation agents, a compound of the invention may enhance (e.g., synergize) the activity of these agents. Further, such synergism would permit a compound of the invention, additional anti-proliferation agents, or both to be administered at lower dosages, and/or may significantly enhance the anti-proliferation properties of a compound at any given dose.

Definitions

For convenience, certain terms used in the specification, examples and appended claims are collected here.

For the avoidance of doubt, the term "a compound of the invention" refers to a compound of formulae I, II, III, IV, V, VI, VII, VIII, IX, X, XI, XII, XIII, XIV, XV, XVI, XVII, XVIII, or XIX or a compound in Table A, Table B, or Table C. Whenever the is used in the context of the present invention it is to be understood that the reference is being made to both the free base and the corresponding salts, solvates, polymorphs, and prodrugs thereof provided that such is possible and/or appropriate under the circumstances.

The terms "inhibitor," "activator," and "modulator" as used in connection with expression or activity refer to inhibitory, activating, or modulating molecules, respectively. Inhibitors according to the present invention include a compound of the invention or a composition that inhibits expression of one or more components of a tyrosine protein kinase signaling cascade, such as a JAK kinase signaling cascade (e.g., JAK3), a SYK signaling cascade, and/or a BTK signaling cascade or bind to, partially or totally block stimulation, decrease, prevent, delay activation, inactivate, desensitize, or down regulate the activity of one or more components of a protein kinase signaling cascade, such as a JAK kinase signaling cascade (e.g., JAK3), a SYK signaling cascade, and/or a BTK signaling cascade. Samples or assays comprising one or more components of a protein kinase signaling cascade, such as a JAK kinase signaling cascade (e.g., JAK3), SYK signaling cascade, and/or BTK signaling cascade can be treated with a compound of the invention and compared to control samples without a compound of the invention. Control samples (untreated with a compound of the invention) can be assigned a relative activity value of 100%. In certain embodiments, inhibition of one or more components of a protein kinase signaling cascade, such as a JAK kinase (e.g., JAK3), SYK, and/or BTK signaling cascade is achieved when the activity value relative to the control is about 80% or less.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms or (2) relieving the disease state, i.e., causing temporary or permanent regression of the disease state or its clinical symptoms.

"Preventing" means causing the clinical symptoms of the disease state not to develop, i.e., inhibiting the onset of disease, in a subject that may be exposed to or predisposed to the disease state, but does not yet experience or display symptoms of the disease state.

"Disease state" means any disease, disorder, condition, symptom, or indication.

As used herein, the terms "cell proliferative disorder" and "cell proliferation-related disorder" refer to conditions in which the unregulated and/or abnormal growth of cells can lead to the development of an unwanted condition or disease, which can be cancerous or non-cancerous, for example a psoriatic condition.

In some embodiments, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, myelofibrosis, acute myelocytic or chronic myelocytic leukemia, plasma cell neoplasm, lymphoid neoplasm and cancers associated with AIDS.

An "effective amount" of a compound is the quantity which, when administered to a subject having a disease or disorder, results in regression of the disease or disorder in the subject. Thus, for example, for a cell proliferation disorder an effective amount of a compound of the invention is the quantity which, when administered to a subject having a cell proliferation disorder, results in regression of cell growth in the subject. The amount of the compound of the invention to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

"A therapeutically effective amount" means the amount of a compound that, when administered to a mammal, e.g., a human, for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, a compound of the invention or a formulation thereof can be administered, for example, via oral, parenteral, or topical routes, to provide an effective amount of the compound. In on aspect, a compound of the invention can be used to coat or impregnate a medical device, e.g., a stent.

The term "prophylactically effective amount" means an effective amount of a compound of the invention that is administered to prevent or reduce the risk of a disease state.

"Pharmacological effect" as used herein encompasses effects produced in the subject that achieve the intended purpose of a therapy.

The term "crystalline" as used herein, means having a regularly repeating arrangement of molecules or external face planes. The term "crystalline purity" means percentage of a crystalline compound in a sample which may contain an amorphous form of the same compound, at least one other crystalline form of the compound or a mixture thereof. In one aspect, 2-morpholino-N-(3-(4-(5-(pyrrolidine-1-carbonyl)-1H-pyrrol-3-yl)thiazol-2-yl)phenyl)acetamide hydrochloride salt (Form I) has a crystalline purity of about 97.0%, 99.0%, 100% crystalline purity.

Additionally, a polymorph can exist in either a hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

A "polymorph of the invention" as used herein means 2-morpholino-N-(3-(4-(5-(pyrrolidine-1-carbonyl)-1H-pyrrol-3-yl)thiazol-2-yl)phenyl)acetamide hydrochloride salt (Form I) or 2-morpholino-N-(3-(4-(5-(pyrrolidine-1-carbonyl)-1H-pyrrol-3-yl)thiazol-2-yl)phenyl)acetamide (Form I).

"Solvate" means solvent addition forms that contain either stoichiometric or non stoichiometric amounts of solvent. Some polymorphs have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

With respect to the compounds useful in the present invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The invention is intended to include all isotopes of atoms occurring in the compounds of the invention. Isotopes include those atoms having the same atomic number but different mass numbers. By way of general example and without limitation, isotopes of hydrogen include tritium and deuterium, and isotopes of carbon include C-13 and C-14.

The compounds of the invention described herein may have asymmetric centers. Compounds of the invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R_d$) occurs more than one time in any constituent or formula for a compound of the invention, its definition at each occurrence is independent of its definition at every other occurrence. Thus, for example, if a group is shown to be substituted with 0-2 $R_d$ moieties, then the group may optionally be substituted with up to two $R_d$ moieties and $R_d$ at each occurrence is selected independently from the definition of $R_d$. Also, combinations of substituents and/or variables are permissible, but only if such combinations result in stable compounds.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain (linear) saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. In certain embodiments, a straight chain or branched chain alkyl has six or fewer carbon atoms in its backbone (e.g., $C_1$-$C_6$ for straight chain, $C_3$-$C_6$ for branched chain), and in other embodiments, a straight chain (linear) or branched chain alkyl has four or fewer carbon atoms. As used herein "$C_3$-$C_8$ cycloalkyl" has from three to eight carbon atoms in the ring structure, and in other embodiments, "$C_5$-$C_6$ cycloalkyl" has five or six carbons in the ring structure.

Unless the number of carbons is otherwise specified, "lower alkyl" includes an alkyl group, as defined above, but having from one to ten, or in other embodiments from one to six, carbon atoms in its backbone structure. "Lower alkenyl" and "lower alkynyl" have chain lengths of, for example, 2-6 carbon atoms.

The term "substituted alkyl" refers to alkyl moieties having substituents replacing a hydrogen atom on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain (linear) alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has six or fewer carbon atoms in its backbone (e.g., $C_2$-$C_6$ for straight chain (linear), $C_3$-$C_6$ for branched chain). Likewise, cycloalkenyl groups may have from three to eight carbon atoms in their ring structure, and in some embodiments, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "substituted alkenyl" refers to alkenyl moieties having substituents replacing a hydrogen atom on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyl" refers to alkynyl moieties having substituents replacing a hydrogen atom on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes phenyl and napthyl. Aryl rings can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and Spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In some embodiments, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "heterocycloalkyl" is intended to mean any stable monocyclic, bicyclic, or tricyclic ring which is saturated and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" refers to the acyl radical ($CH_3CO$—). "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "thiocarbonyl" or "thiocarboxy" includes compounds and moieties which contain a carbon connected with a double bond to a sulfur atom.

The term "ether" or "alkoxy" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" refers to the group —OH.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In some embodiments, an anionic group is a carboxylate.

In the specification, the structural formula of the compound represents a certain isomer for convenience in some cases, but the invention includes all isomers such as geometrical isomer, optical isomer based on an asymmetrical carbon, stereoisomer, tautomer and the like which occur structurally and an isomer mixture and is not limited to the description of the formula for convenience, and may be any one isomer or a mixture. Therefore, an asymmetrical carbon atom may be present in the molecule and an optically active compound and a racemic compound may be present in the compound, but the invention is not limited to them and includes any one. In addition, a crystal polymorphism may be present but is not limiting, but any crystal form may be single or a crystal form mixture, or an anhydride or hydrate. Further, so-called metabolite which is produced by degradation of the compound in vivo is included in the scope of the invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Calm et al., *Experientia* 1956, 12, 81; Cahn, *J., Chem. Educ.* 1964, 41, 116).

"Geometric Isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, a compound of the invention includes all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography, it has been possible to separate mixtures of two atropic isomers in select cases.

The terms "crystal polymorph" or "polymorph" or "crystal form" means crystal structures in which a compound of the invention can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of a compound of the invention can be prepared by crystallization under different conditions.

Additionally, a compound of the invention, for example, a salt of a compound of the invention, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomer" refers to compounds whose structures differ markedly in arrangement of atoms, but which exist in easy and rapid equilibrium. It is to be understood that the compounds of the invention may be depicted as different tautomers. It should also be understood that when a compound of the invention has tautomeric forms, all tautomeric forms are intended to be within the scope of the invention, and the naming of the compounds does not exclude any tautomer form.

Some compounds of the invention can exist in a tautomeric form which is also intended to be encompassed within the scope of the invention.

In one aspect, a compound of the invention can exist in several tautomeric forms, including the enol and imine form, and the keto and enamine form and geometric isomers and mixtures thereof. All such tautomeric forms are included within the scope of the invention. Tautomers exist as mixtures of a tautomeric set in solution. In solid form, usually one tautomer predominates. Even though one tautomer may be described, the invention includes all tautomers of the compound.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine.

A compound of the invention may include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. A compound of the invention may exist in stereoisomeric form, therefore can be produced as individual stereoisomers or as mixtures.

As used herein, the term "analog" refers to a compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to a compound that has a common core structure and is substituted with various groups as described herein. For example, all of the compounds represented by Formula IV are 4-(thiazol-4-yl)-1H-pyrrole-2-carboxamide derivatives and have 4-(thiazol-4-yl)-1H-pyrrole-2-carboxamide as a common core.

A "pharmaceutical composition" is a formulation containing compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or a salt, solvate, polymorph, or prodrug thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of the invention include powders, sprays, ointments, pastes, creams, lotions, gels, solutions, patches and inhalants.

In some embodiments, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient.

In one aspect, a compound of the invention is capable of further forming salts. All of these forms are also contemplated within the scope of the invention.

"Pharmaceutically acceptable salt" of a compound of the invention means a salt that is pharmaceutically acceptable and that possesses the desired pharmacological activity of the parent compound.

As used herein, "pharmaceutically acceptable salts" refer to derivatives of a compound of the invention, where the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences,* 18th ed. (Mack Publishing Company, 1990).

A compound of the invention can also be prepared as a prodrug, for example pharmaceutically acceptable prodrug. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the invention can be delivered in prodrug form. Thus, the invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs may be prepared by modifying functional groups present in the compound in such a way that the modifications are cleaved, either in routine manipulation or in vivo, to the parent compound. Prodrugs include a compound of the invention wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in a compound of the invention, and the like, See Bundegaard, H. "Design of Prodrugs" pp. 1-92, Elsevier, New York-Oxford (1985).

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

The invention provides methods for the treatment of a cell proliferative disorder in a subject in need thereof by administering to a subject in need of such treatment, a therapeutically effective amount of a compound of the invention, or a pharmaceutically acceptable salt, prodrug, metabolite, polymorph or solvate thereof. The cell proliferative disorder can be cancer or a precancerous condition. The invention further provides the use of a compound of the invention or a pharmaceutically acceptable salt, prodrug, metabolite, polymorph or solvate thereof, for the preparation of a medicament useful for the treatment of a cell proliferative disorder.

The invention also provides methods of protecting against a cell proliferative disorder in a subject in need thereof by administering a therapeutically effective amount of compound of the invention, or a pharmaceutically acceptable salt, prodrug, metabolite, polymorph or solvate thereof, to a subject in need of such treatment. The cell proliferative disorder can be cancer or a precancerous condition. The invention also provides the use of compound of the invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. In one aspect, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. In one aspect, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. The methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; psoriatic arthritis, inflammation; autoimmune disease; dry eye disease, lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease (e.g., ulcerative colitis and Crohn's disease); psoriasis; eczema; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, acute myelogenous leukemia (solid tumors), chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, renal (kidney) cancer, renal cell carcinoma (hypernephroma), laryngeal cancer, acute lymphoblastic leukemia, acute myeloid leukemia (AML) (also known as acute myelogenous leukemia), chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera (erythremia), chronic myelocytic leukemia, agnogenic myeloid metaplasia, and essential thrombocythemia. A cell proliferative disorder of the hematologic system can include hyperplasia, dysplasia, and metaplasia of cells of the hematologic system. In one aspect, a composition of the invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Compositions of the invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. The cell proliferative disorder of the colon is colon cancer. Compositions of the invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed as HER2-negative or HER2-positive. HER2-typing of a breast cancer may be performed by any reproducible means. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. PR-typing of a breast cancer may be performed by any reproducible means. A breast cancer that is to be treated can be typed as receptor positive or receptor negative. A breast cancer that is to be treated can have multiple receptors each independently typed as receptor positive or receptor negative. For example, a breast cancer that can be treated can be "a triple negative breast cancer" (i.e., typed as ER-negative, PR-negative, and HER2-negative). A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the invention or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. In one aspect, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. In one aspect, monotherapy will involve administration of a therapeutically effective amount of an active compound. For example, cancer monotherapy with one of the compound of the invention, or a pharmaceutically acceptable salt, prodrug, metabolite, analog or derivative thereof, to a subject in need of treatment of cancer. Monotherapy may be contrasted with combination therapy, in which a combination of multiple active compounds is administered or with each component of the combination present in a therapeutically effective amount. In one aspect, monotherapy with a compound of the invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the invention, or a pharmaceutically acceptable salt, prodrug, metabolite, polymorph or solvate thereof, to alleviate the symptoms or complications of a disease, condition or disorder, or to eliminate the disease, condition or disorder.

A compound of the invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In one embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". In one aspect, after treatment, tumor size is reduced by about 5% or greater relative to its size prior to treatment; tumor size is reduced by about 10% or greater; reduced by about 20% or greater; reduced by about 30% or greater; reduced by about 40% or greater; reduced by about 50% or greater; and reduced by about greater than 75% or greater. Size of a tumor may be measured by any reproducible means of measurement. The size of a tumor may be measured as a diameter of the tumor.

Treating cancer can result in a reduction in tumor volume. In one aspect, after treatment, tumor volume is reduced by about 5% or greater relative to its size prior to treatment; tumor volume is reduced by about 10% or greater; reduced by about 20% or greater; reduced by about 30% or greater; reduced by about 40% or greater; reduced by about 50% or greater; and reduced by greater than about 75% or greater. Tumor volume may be measured by any reproducible means of measurement.

Treating cancer results in a decrease in number of tumors. In one aspect, after treatment, tumor number is reduced by about 5% or greater relative to number prior to treatment; tumor number is reduced by about 10% or greater; reduced by about 20% or greater;

reduced by about 30% or greater; reduced by about 40% or greater; reduced by about 50% or greater; and reduced by greater than about 75%. Number of tumors may be measured by any reproducible means of measurement. The number of tumors may be measured by counting tumors visible to the naked eye or at a specified magnification. In one aspect, the specified magnification is 2×, 3×, 4×, 5×, 10×, or 50×.

Treating cancer can result in a decrease in number of metastatic lesions in other tissues or organs distant from the primary tumor site. In one aspect, after treatment, the number of metastatic lesions is reduced by about 5% or greater relative to number prior to treatment; the number of metastatic lesions is reduced by about 10% or greater; reduced by about 20% or greater; reduced by about 30% or greater; reduced by about 40% or greater; reduced by about 50% or greater; and reduced by greater than about 75%. The number of metastatic lesions may be measured by any reproducible means of measurement. The number of metastatic lesions may be measured by counting metastatic lesions visible to the naked eye or at a specified magnification. In one aspect, the specified magnification is 2×, 3×, 4×, 5×, 10×, or 50×.

Treating cancer can result in an increase in average survival time of a population of treated subjects in comparison to a population receiving carrier alone. In one aspect, the average survival time is increased by more than 30 days; by more than 60 days; by more than 90 days; and by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. In one aspect, the average survival time is increased by more than 30 days; by more than 60 days; by more than 90 days; and by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the invention, or a pharmaceutically acceptable salt, prodrug, metabolite, analog or derivative thereof. In one aspect, the average survival time is increased by more than 30 days; by more than 60 days; by more than 90 days; and by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the invention, or a pharmaceutically acceptable salt, prodrug, metabolite, analog or derivative thereof. In one aspect, the mortality rate is decreased by more than about 2%; by more than about 5%; by more than about 10%; and by more than about 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. In one aspect, after treatment, tumor growth rate is reduced by at least about 5% relative to number prior to treatment; tumor growth rate is reduced by at least about 10%; reduced by at least about 20%; reduced by at least about 30%; reduced by at least about 40%; reduced by at least about 50%; reduced by at least about 50%; and reduced by at least about 75%. Tumor growth rate may be measured by any reproducible means of measurement. Tumor growth rate can be measured according to a change in tumor diameter per unit time.

Treating cancer can result in a decrease in tumor regrowth. In one aspect, after treatment, tumor regrowth is less than about 5%; tumor regrowth is less than about 10%; less than about 20%; less than about 30%; less than about 40%; less than about 50%; less than about 50%; and less than about 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. In one aspect, after treatment, the rate of cellular proliferation is reduced by at least about 5%; by at least about 10%; by at least about 20%; by at least about 30%; by at least about 40%; by at least about 50%; and by at least about 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. In one aspect, after treatment, the proportion of proliferating cells is reduced by at least about 5%; by at least about 10%; by at least about 20%; by at least about 30%; by at least about 40%; by at least about 50%; and by at least 75%. The proportion of proliferating cells may be measured by any reproducible means of measurement. In one aspect, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. In one aspect, after treatment, size of an area or zone of cellular proliferation is reduced by at least about 5% relative to its size prior to treatment; reduced by at least about 10%; reduced by at least about 20%; reduced by at least about 30%; reduced by at least about 40%; reduced by at least about 50%; and reduced by at least about 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. In one aspect, after treatment, the number of cells having an abnormal morphology is reduced by at least about 5% relative to its size prior to treatment; reduced by at least about 10%; reduced by at least about 20%; reduced by at least about 30%; reduced by at least about 40%; reduced by at least about 50%; and reduced by at least about 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. In one aspect, a compound of the invention, or a pharmaceutically acceptable salt, prodrug, metabolite, polymorph or solvate thereof, acts selectively on a cancer or precancerous cell but not on a normal cell. In one aspect, a compound of the invention, or a pharmaceutically acceptable salt, prodrug, metabolite, polymorph or solvate thereof, acts selectively to modulate one molecular target (e.g., JAK3) but does not significantly modulate another molecular target (e.g., JAK2). The invention also provides a method for selectively inhibiting or activating the activity of an enzyme, such as a kinase (e.g., JAK3). In one aspect, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; greater than fifty times; greater than 100 times; and greater than 1000 times more frequently in population A as compared to population B. For example, cell death would be said to occur selectively in cancer cells if it occurred greater than twice as frequently in cancer cells as compared to normal cells.

A compound of the invention, or a pharmaceutically acceptable salt, prodrug, metabolite, polymorph or solvate thereof, can modulate the activity of a molecular target (e.g., JAK3). Modulating refers to stimulating or inhibiting an activity of a molecular target. In one aspect, a compound of the invention, or a pharmaceutically acceptable salt, prodrug, metabolite, polymorph or solvate thereof, modulates the activity of a molecular target if it stimulates or inhibits the activity of the molecular target by at least 10% relative to the activity of the molecular target under the same conditions but lacking only the presence of said compound. In one aspect, a compound of the invention, or a pharmaceutically acceptable salt, prodrug, metabolite, polymorph or solvate thereof, modulates the activity of a molecular target if it stimulates or inhibits the activity of the molecular target by at least 2-fold, at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro or in vivo by an enzymatic activity assay.

A compound of the invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta).

A change in enzymatic activity caused by a compound of the invention, or a pharmaceutically acceptable salt, prodrug, metabolite, polymorph or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. In one aspect, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of a compound of the invention are described in the examples.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and cell death results in a decrease of at least about 10% in number of cells in a population. In one aspect, cell death means a decrease of at least about 20%; a decrease of at least about 30%; a decrease of at least about 40%; a decrease of at least about 50%; a decrease of at least about 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Prot Natl Acad Sci USA*. 100(5): 2674-8, 2003. In an aspect, cell death occurs by apoptosis.

In one aspect, an effective amount of a compound of the invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the invention, or a pharmaceutically acceptable salt, prodrug, metabolite, polymorph or solvate thereof, can induce or activate cell death selectively in cancer cells. Administering to a subject in need thereof a compound of the invention, or a pharmaceutically acceptable salt, prodrug, metabolite, polymorph or solvate thereof, can induce or activate cell death selectively in cancer cells. Contacting a cell with a compound of the invention, or a pharmaceutically acceptable salt, prodrug, metabolite, polymorph or solvate thereof, can induce cell death selectively in one or more cells affected by a cell proliferative disorder. In one aspect, administering to a subject in need thereof a compound of the invention or a pharmaceutically acceptable salt, prodrug, metabolite, polymorph or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agent(s) as described above in combination with other biologically active ingredients and/or non-drug therapies (e.g., surgery, immunotherapy or radiation treatment). Where the combination therapy comprises a non-drug treatment, the non-drug treatment may be conducted at any suitable time so long as a beneficial effect from the co-action of the combination of the therapeutic agent(s) and non-drug treatment is achieved. For example, in appropriate cases, the beneficial effect is still achieved when the non-drug treatment is temporally removed from the administration of the therapeutic agents, perhaps by days or even weeks.

A compound of the invention, or a pharmaceutically acceptable salt, prodrug, metabolite, analog or derivative thereof, may be administered in combination with a second anti-cancer agent. The second anti-cancer agent (also referred to as an anti-neoplastic agent or anti-proliferative agent) can be an agent that modulates cancer metabolism, an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multikinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemeterxed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In another aspect, the second chemotherapeutic agent can be a cytokine such as G-CSF (granulocyte colony stimulating factor). In another aspect, a compound of the invention, or a pharmaceutically acceptable salt, prodrug, metabolite, analog or derivative thereof, may be administered in combination with radiation therapy. Radiation therapy can also be administered in combination with a compound of the invention and another chemotherapeutic agent described herein as part of a multiple agent therapy. In yet another aspect, a compound of the invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otostat potassium at a molar ratio of 1:0.4:1), Camptothecin-11 (CPT-11, Irinotecan or Camptosar™) or CMFP (cyclophosphamide, methotrexate, 5-fluorouracil and prednisone).

In one aspect, a compound of the invention or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb 1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Throughout the description, where compositions are described as having, including, or comprising specific components, it is contemplated that compositions also consist essentially of or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

In one aspect a compound of the invention or a pharmaceutically acceptable salt thereof, is administered orally, nasally, transdermally, pulmonary, inhalationally, buccally, sublingually, intraperintoneally, subcutaneously, intramuscularly, intravenously, rectally, intrapleurally, intrathecally and parenterally. In some embodiments, a compound of the invention is administered orally. One skilled in the art will recognize the advantages of certain routes of administration.

The dosage regimen utilizing a compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of a compound of the invention can be found in *Remington: the Science and Practice of Pharmacy*, 19$^{th}$ edition, Mack Publishing Co., Easton, Pa. (1995). In one aspect, a compound of the invention or a pharmaceutically acceptable salt thereof is used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In some embodiments, a compound of the invention is prepared for oral administration, wherein a compound of the invention or a salt thereof is combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, a compound of the invention can be combined with sterile aqueous or organic media to form injectable solutions or suspensions. In some embodiments, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of a compound of the invention. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, a compound of the invention is formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the compounds of the invention as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

A compound of the invention is also formulated as "pulsed release" formulations, in which the compound is released from the pharmaceutical compositions in a series of releases (i.e., pulses). A compound of the invention is also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In some embodiments, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex Pharmaceuticals Inc., Lenexa, Kans.). One skilled in the art can evaluate suitable agent/compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the compound; mixing under appropriate conditions, e.g., heating, agitation, sonication, and the like; centrifuging or filtering the resulting mixtures to obtain clear solutions; and analyzing the solutions for concentration of the compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

The compounds of the invention and related derivatives are synthesized by methods known to one skilled in the art.

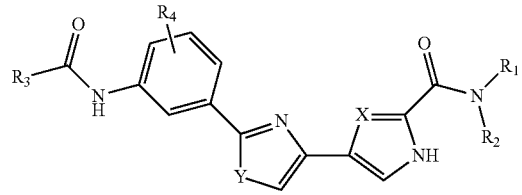

Formula V-1

For example, compounds according to Formula V-1 can be synthesized as described below. In one aspect, the values for formula V-1 shown above: $R_3$, $R^4$, Y, X, $R_1$ and $R_2$ correspond to the values recited for formula VI: $R_3$ is $R^b$, $R^4$ is $R^{a1}$-$R^{a5}$, Y is S, X is CH, $R_1$ and $R_2$ are $R^2$ and $R^3$. The starting material ethyl 4-acetyl-1H-pyrrole-2-carboxylate may be prepared from the commercially available compound ethyl 1H-pyrrole-2-carboxylate according to the published procedure (See, e.g., Journal of the American Chemical Society, 129 (11), 3078-3079; 2007; Chemical & Pharmaceutical Bulletin, 44(1), 48-54; 1996; Heterocycles, 27(8), 1855-60; 1988) using acyl chloride as acylating agent. Alternatively, it may be prepared starting from 4-acetyl-1H-pyrrole-2-carboxylic acid, also a commercially available compound (Scheme 1).

Scheme 1

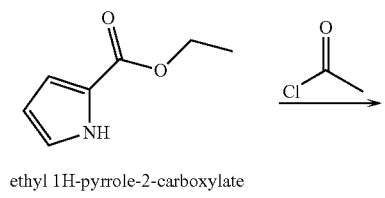

ethyl 1H-pyrrole-2-carboxylate

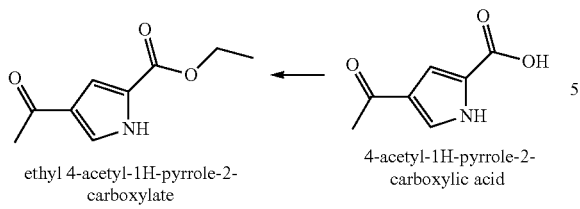

ethyl 4-acetyl-1H-pyrrole-2-carboxylate ← 4-acetyl-1H-pyrrole-2-carboxylic acid

Similarly, the imidazole analog may be prepared starting from commercially available ethyl 1H-imidazole-2-carboxylate (Scheme 2).

Scheme 2

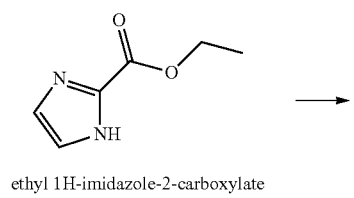

ethyl 1H-imidazole-2-carboxylate

→ ethyl 4-acetyl-1H-imidazole-2-carboxylate

The next step is protecting the pyrrole or imidazole nitrogen and then acetyl bromination (Scheme 3) according to published procedures (See, e.g., Heterocycles, 55(8), 1475-1486; 2001; Journal of Medicinal Chemistry, 33(2), 543-52; 1990; Eur. Pat. Appl., 259085, 9 Mar. 1988).

Scheme 3

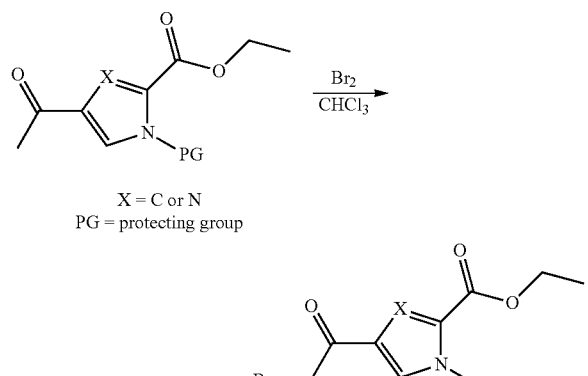

X = C or N
PG = protecting group

Alternatively the above starting materials may undergo acylation reaction with 2-bromoacetylbromide to give directly the desire product (See, e.g., Scheme 4).

Scheme 4

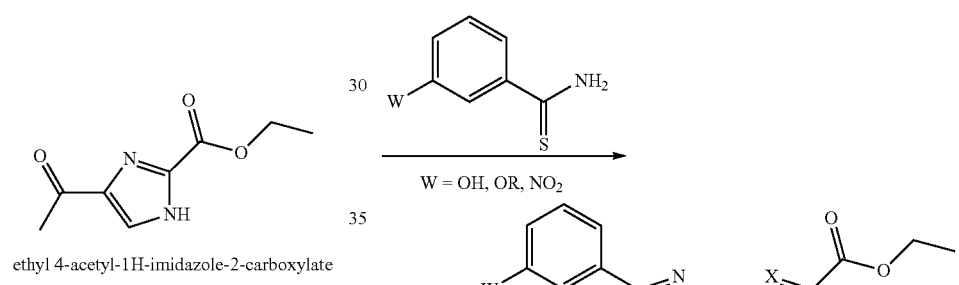

ethyl 1H-pyrrole-2-carboxylate ethyl 4-(2-bromoacetyl)-1H-pyrrole-2-carboxylate
[1]

At the next step, the intermediate ethyl 4-(2-bromoacetyl)-1H-pyrrole-2-carboxylate, or its imidazole analog, undergo a condensation reaction with 3-substitutedbenzothiazole derivatives to give the thiazole compound [2] (Scheme 5).

Scheme 5

W = OH, OR, NO₂

[2]

The thioamides derivatives used in Scheme 5 may be prepared using BF₃-etherate assisted conversion of nitriles into thioamides with Lawesson's reagent (See, e.g., Synthesis, (24), 4012-4018; 2008; Farmaco, 54(8), 533-541; 1999) (Scheme 6).

Scheme 6

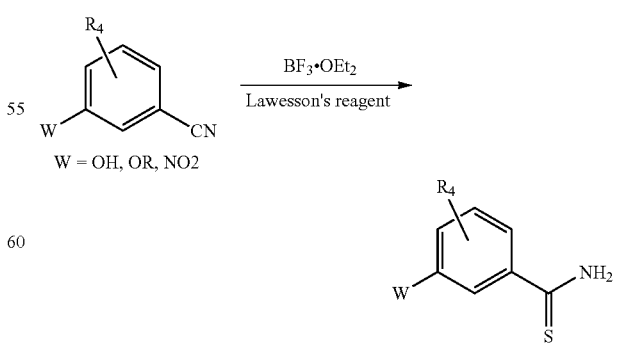

W = OH, OR, NO2

Alternatively condensation of intermediate [1] with 3-substitutedbezamide derivatives will give the oxazole compound

[3] (Scheme 7) (Letters in Drug Design & Discovery, 6(1), 21-28; 2009; Journal of Heterocyclic Chemistry, 18(5), 885-8; 1981).
Scheme 7
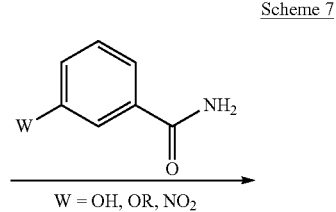
W = OH, OR, NO$_2$
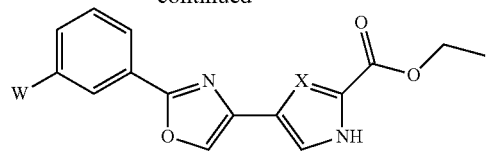
Referring to Scheme 8, the obtained intermediate [3] undergoes amidation reactions on both sides, one on the ethyl ester moiety and the second one on the amine obtained after reduction of the nitro group. When W is hydroxyl, it may undergo an alkylation reaction.
Scheme 8
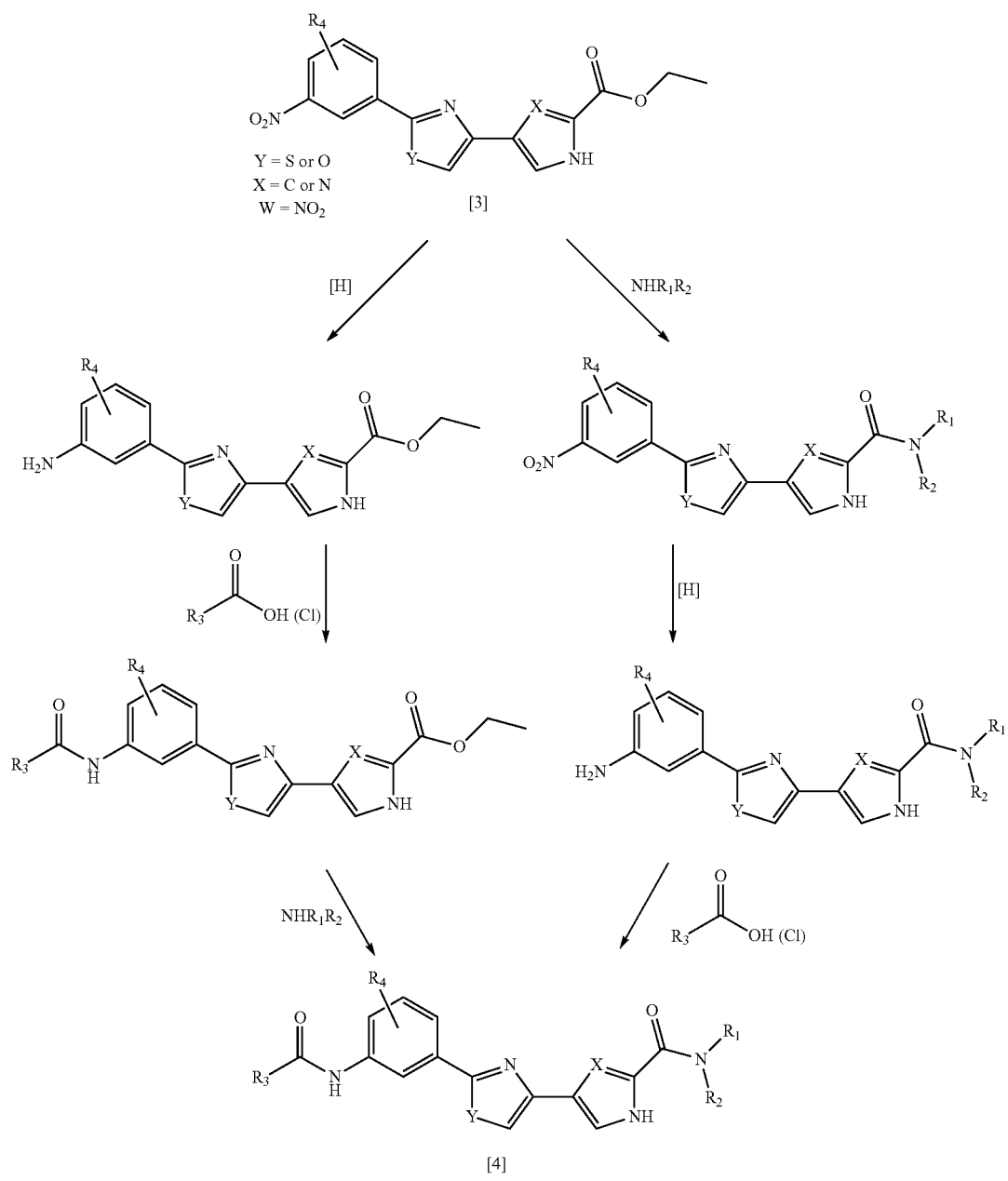

Note that the compound numbers referred to in the synthesis described herein correspond to the numbers shown in the related scheme which proceeds the description of the synthesis.

Example 2

Synthesis of 2-morpholino-N-(3-(4-(5-(pyrrolidine-1-carbonyl)-1H-pyrrol-3-yl)thiazol-2-yl)phenyl)acetamide 2-morpholino-N-(3-(4-(5-(pyrrolidine-1-carbonyl)-1H-pyrrol-3-yl)thiazol-2-yl)phenyl)acetamide (Formula VI-1) was synthesized as follows:

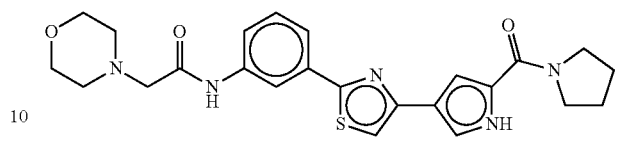

Formula VI-1

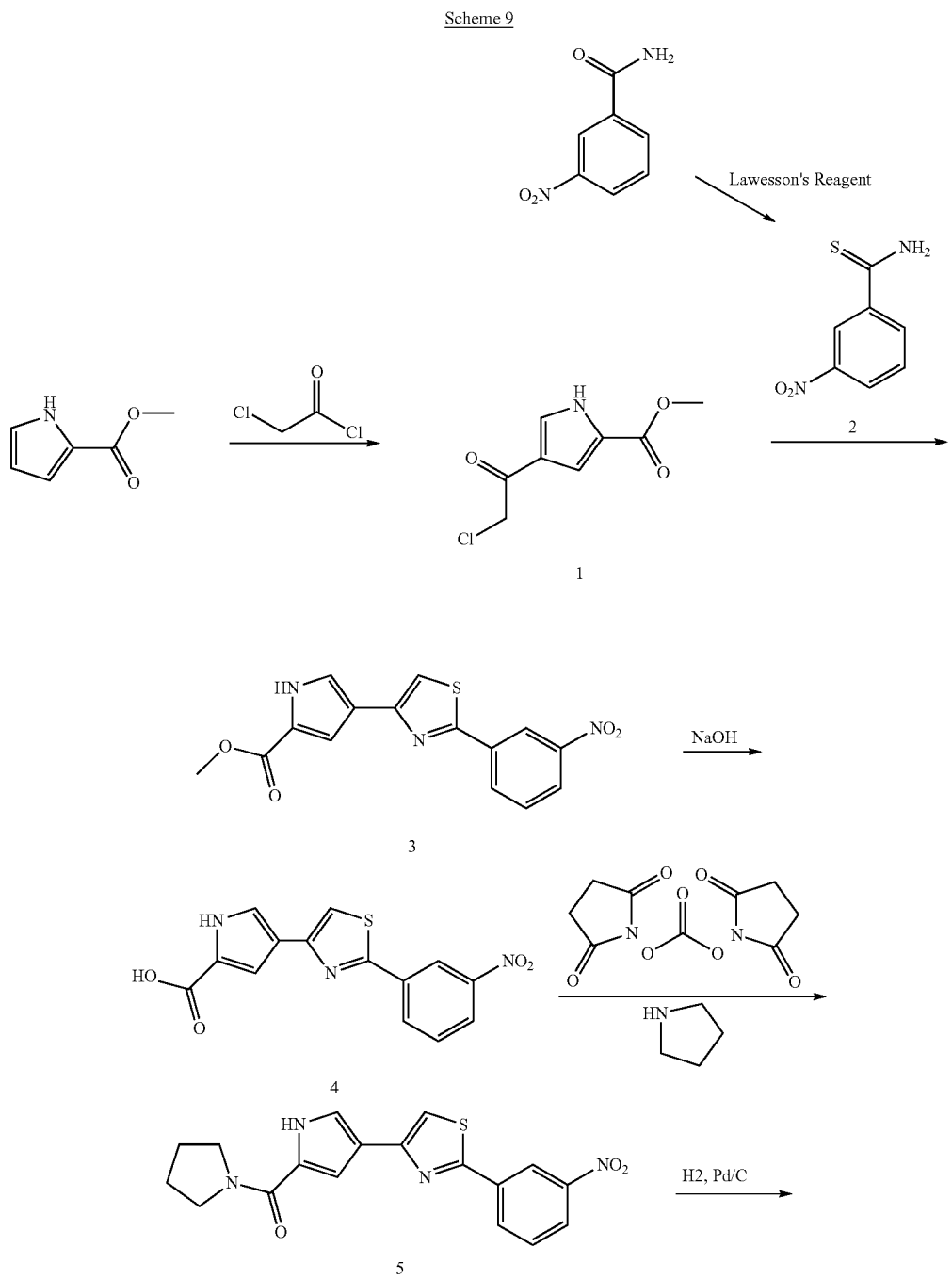

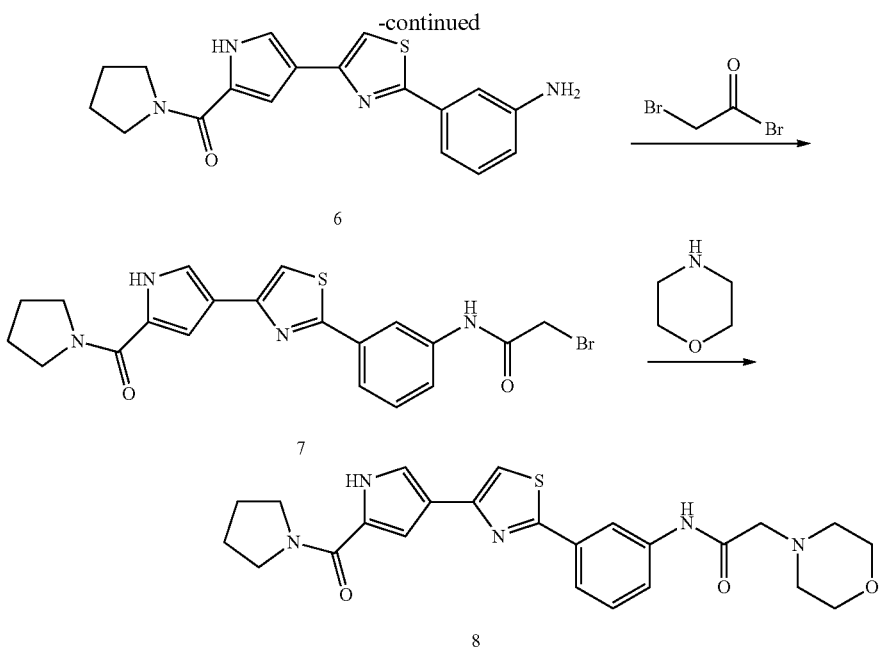

Reagents-Synthesis of 1

| Reagent/raw material | MW (g/mole) | Quantity | mmoles |
|---|---|---|---|
| methyl 1H-pyrrole-2-carboxylate | 125.13 | 6.25 g | 50 |
| AlCl₃ | 133.34 | 13.33 g | 100 |
| Chloroacetyl chloride | 113 | 7.95 mL | 100 |
| DCM | — | 100 mL | — |

Synthesis of 1

A solution of methyl 1H-pyrrole-2-carboxylate in DCM (30 mL) was added dropwise to a stirring mixture of AlCl₃ and chloroacetyl chloride in DCM (70 mL) under cooling on an ice bath resulting in white precipitation formation. When the addition was complete, the mixture was refluxed and monitored by HPLC. After 2 hours, HPLC analysis showed 90% conversion and additional 25 mmoles of the complex were added in order to complete the reaction. When full conversion was observed the reaction was poured into 100 mL of water and crushed ice and stirred for 1 hour. The organic phase was collected and the product (partially as precipitate) was extracted several times to plenty of DCM. The organic fractions were combined, dried over Na₂SO₄ and evaporated, yielding a white solid product (6.85 g, 68% yield).

Reagents-Synthesis of 2

| Reagent/raw material | MW (g/mole) | Quantity | mmoles |
|---|---|---|---|
| 3-nitrobenzamide | 166.13 | 1.66 g | 10 |
| methyl 4-(2-chloroacetyl)-1H-pyrrole-2-carboxylate | 201.6 | 3.02 g | 15 |
| Sodium acetate | 82 | 2.4 g | 30 |
| Acetic acid | | 20 mL | |

Synthesis of 2

Lawesson's reagent was added to a stirring mixture of 3-nitrobenzamide in dimethoxyethane-THF 2:1. The reaction was stirred at 50° C. for 2 hour and when completed sodium bicarbonate was added and the mixture was stirred at room temperature for 1 hour. The solvents were removed under reduced pressure and the oily residue was slowly added to a stirring mixture of water and crushed ice (150 mL). The milky mixture was heated to a boil and then left to cool to room temperature resulting in yellow crystals (1.4 g, 77% yield).

Reagents-Synthesis of 3

| Reagent/raw material | MW (g/mole) | Quantity | mmoles |
|---|---|---|---|
| 3-nitrobenzothioamide | 182.2 | 2.73 g | 15 |
| Lawesson's reagent | 404 | 4.04 g | 10 |
| NaHCO₃ | 84 | 1 g | 12 |
| 1,2 Dimethoxyethane | | 60 mL | |
| THF | — | 30 mL | — |

Synthesis of 3

The reagents were stirred in acetic acid and heated to reflux resulting in a clear solution followed by precipitation formation. The mixture was refluxed for 6-8 hours (conversion of starting materials was monitored by HPLC). The solvent was removed under reduced pressure and the residue was taken in DCM and water. The organic phase was collected and the product was extracted with plenty of DCM (due to poor solubility). The organic phase was evaporated yielding 3.4 g (69%) of green solid.

Reagents-Synthesis of 4

| Reagent/raw material | MW (g/mole) | Quantity | mmoles |
|---|---|---|---|
| methyl 4-(2-(3-nitrophenyl)thiazol-4-yl)-1H-pyrrole-2-carboxylate | 329.33 | 3.3 g | 10 |
| NaOH | 40 | 1.6 g | 40 |
| Dioxane | — | 100 mL | — |
| $H_2O$ | — | 50 mL | — |

Synthesis of 4

NaOH was added to a mixture of the ester in 2:1 Dioxane-$H_2O$. The mixture was heated to 70-80° C. during which a dark solution is formed. When the reaction was complete, the organic solvent was evaporated and the residue was acidified using concentrated hydrochloric acid. The product was extracted to ethyl acetate, dried over $Na_2SO_4$ and evaporated yielding a yellow-green powder (2.9 g, 92% yield).

Reagents-Synthesis of 5

| Reagent/raw material | MW (g/mole) | Quantity | mmoles |
|---|---|---|---|
| 4-(2-(3-nitrophenyl)thiazol-4-yl)-1H-pyrrole-2-carboxylic acid | 315.3 | 2.33 g | 7.4 |
| bis(2,5-dioxopyrrolidin-1-yl) carbonate | 256.17 | 1.9 g | 7.4 |
| Acetonitrile | | 100 mL | |
| Triethylamine | 101 | 3 mL | 22 |
| pyrrolidine | 71.12 | 0.63 mL | 7.5 |

Synthesis of 5:

Triethylamine was added to a mixture of the acid and the activating agent in acetonitrile resulting in clear solution. The components were stirred at room temperature and the active ester formation was monitored by HPLC. Then, pyrrolidine was added and immediate formation of the amide was observed. Additional portions of pyrrolidine were added until full conversion of the active ester was observed. The solvent was then removed under reduced pressure, chloroform was added and the mixture was washed three times with saturated bicarbonate solution. The organic solvent was evaporated yielding a green powder (2 g, 73%).

Reagents-Synthesis of 6

| Reagent/raw material | MW (g/mole) | Quantity | mmoles |
|---|---|---|---|
| (4-(2-(3-nitrophenyl)thiazol-4-yl)-1H-pyrrol-2-yl)(pyrrolidin-1-yl)methanone | 368.41 | 2 g | 5.4 |
| Pd/C | | | |
| THF | — | 50 mL | — |

Synthesis of 6:

The starting nitro compound was dissolved in THF. The catalyst was added and the mixture was subjected to hydrogen atmosphere overnight. The catalyst was removed by filtration over celite and the solvent was evaporated yielding a white foam (1.8 g, quantitative yield).

Reagents-Synthesis of 7 and 8

| Reagent/raw material | MW (g/mole) | Quantity | mmoles |
|---|---|---|---|
| (4-(2-(3-aminophenyl)thiazol-4-yl)-1H-pyrrol-2-yl)(pyrrolidin-1-yl)methanone | 338.43 | 1.8 g | 5.3 |
| Chloroacetylchloride | 113 | 0.46 mL | 5.83 |
| Triethylamine | 101 | 2.2 mL | 16 |
| morpholine | 87.12 | 1.3 mL | 15 |
| Triethylamine* | 101 | 2.1 mL | 15 |
| THF | | 80 mL | |

*Synthesis of 8

Synthesis of 7:

A solution of chloroacetylchloride in THF (30 mL) was added dropwise to a the starting material in a solution of aniline and triethylamine in THF (50 mL) under cooling on an ice bath. The reaction mixture was stirred for 1 hour. The solvent was removed under reduced pressure and the oily residue was used as is in the next step.

Synthesis of 8:

Dioxane was added to the oily residue along with morpholine and triethylamine. The mixture was stirred for 2-3 hours. When the reaction was complete, the solvent was removed under reduced pressure. The residue was taken in boiling EtOAc and washed with saturated bicarbonate solution, the organic phase was evaporated yielding an orange solid (1.5 g, 90% purity), which was further purified by flash chromatograpgy (PE-THF gradient) yielding 280 mg (11.1%) of pure product.

Alternatively, 2-morpholino-N-(3-(4-(5-(pyrrolidine-1-carbonyl)-1H-pyrrol-3-yl)thiazol-2-yl)phenyl)acetamide (Formula VI) was synthesized as follows:

Formula VI-1

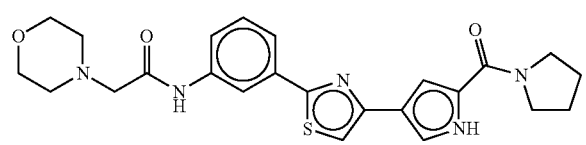

Scheme 9A
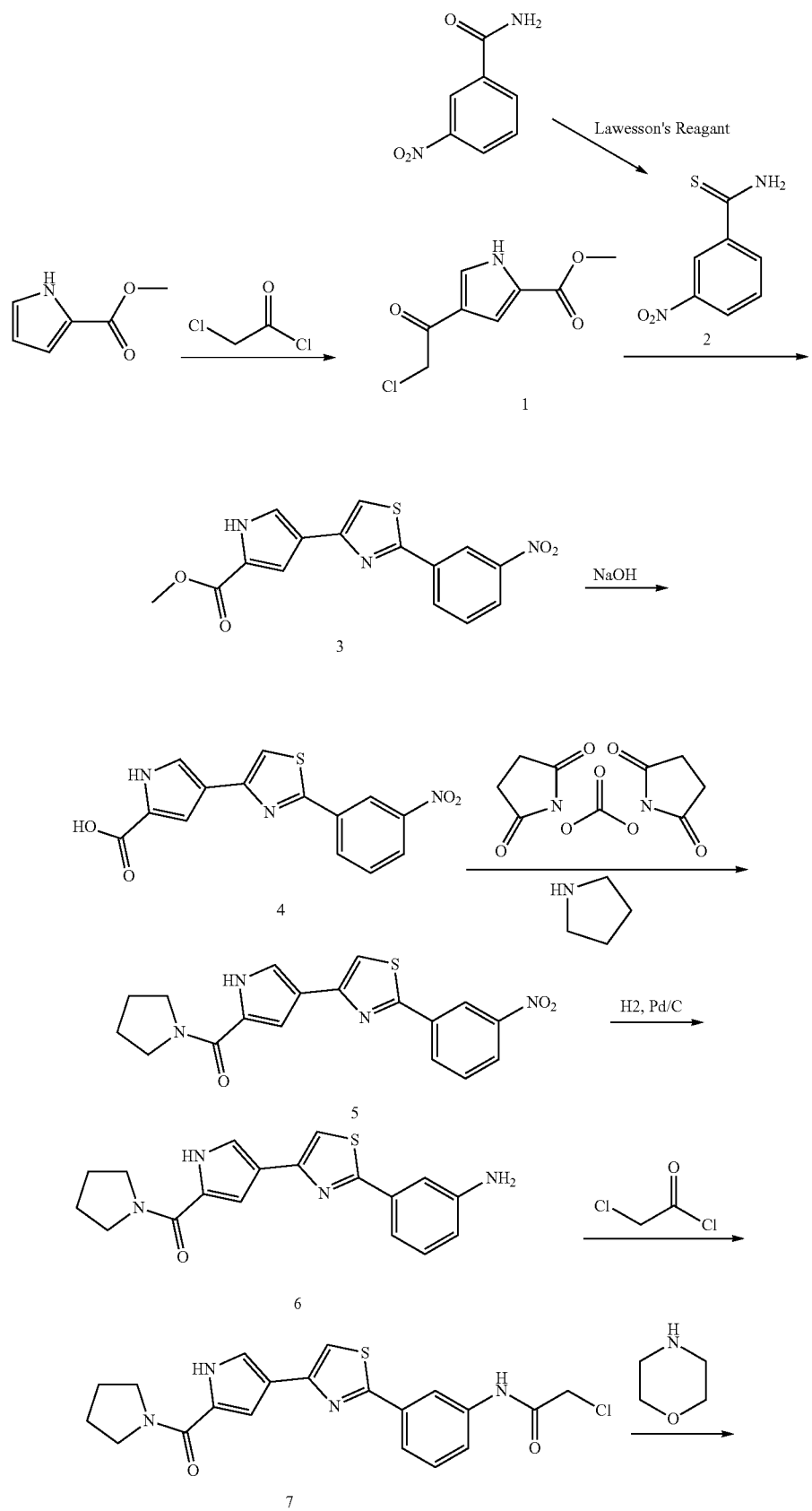

-continued

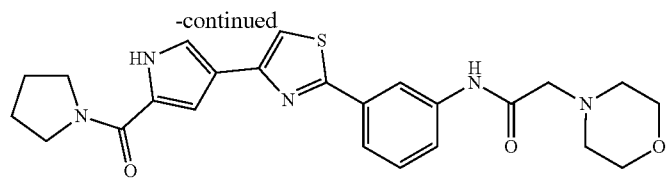

8

Reagents Table-Synthesis of 1

| Reagent/raw material | MW (gr/mole) | Quantity | mmoles |
| --- | --- | --- | --- |
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over Na₂SO₄ and evaporated yielding of gray solid (9 g, 90% yield).

Reagents Table-Synthesis of 2

| Reagent/raw material | MW (gr/mole) | Quantity | mmoles |
| --- | --- | --- | --- |
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF (2:1). The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
| --- | --- | --- | --- |
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
| --- | --- | --- | --- |
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in Dioxane-H₂O (2:1). The reaction mixture was heated to 70-80° C. during which a dark solution is formed. When reaction was completed the organic solvent was evaporated and the residue was acidified using concentrated hydrochloric acid. The product was extracted to ethyl acetate, dried over Na₂SO₄ and evaporated yielding yellow-green powder (5.8 g, 92% yield).

Reagents Table-Synthesis of 5

| Reagent/raw material | MW (gr/mole) | Quantity | mmoles |
| --- | --- | --- | --- |
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl)carbonate | 256.17 | 2.56 g | 10 |
| Acetonitrile-Dioxane 1:1 | — | 200 mL | — |
| Triethylamine | 101 | 4.15 mL | 22 |
| Pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC and small portions of the activating agent were added until a point of 90-95% conversion. Then, pyrrolidine was added and an immediate formation of the amide (precipitate) was observed. Additional portions of pyrrolidine were added until full conversion of the active ester was observed. The solid was collected by filtration, washed with water (70 mL) and dried over vacuum (2 g, 73%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7 and 8

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.43 | 1.8 g | 5.3 |
| Chloroacetylchloride | 113 | 0.46 mL | 5.83 |
| Triethylamine | 101 | 2.2 mL | 16 |
| Morpholine | 87.12 | 1.3 mL | 15 |
| Triethylamine* | 101 | 2.1 mL | 15 |
| THF | | 80 mL | |

*Synthesis of 8

Synthesis of 7

A solution of chloroacetylchloride in DCM (30 mL) was added dropwise to a mixture of aniline and triethylamine in DCM (50 mL) under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with morpholine and triethylamine. The mixture was refluxed vigorously for 2-3 hours (morpholine is added if needed for reaction completion). When the reaction was completed, heating was stopped, norit was added and the mixture was stirred for 30 minutes. The solids were removed by filtration and the solvent was removed under reduced pressure. The oily residue was crystallized from EtOH (2 g, 80%). HPLC—99% purity. LCMS—(ES$^+$) Calcd. 465.58. Found 466.56 (MH$^+$).

Example 3A

JAK3 Enzymatic Activity Assays

The inhibition of JAK3 in 1% DMSO by several compounds was determined using the Z'-LYTE® Biochemical Kinase Assay (Invitrogen, Madison, Wis.). The assays were performed according to manufacturer's protocols, except that prior to the kinase reaction they were pre-incubated for 2 hours at 4° C., in order to be able to assay for time-dependent inhibition.

In addition to the compound, each 10 µL JAK3 kinase reaction contained 0.43-1.89 ng JAK3 and 2 µM peptide substrate in 50 mM HEPES (pH 7.5), 0.01% BRIJ-35, 10 mM MgCl$_2$ and 1 mM EGTA. The kinase reaction was allowed to proceed for 1 hour. The K$_i$ for the JAK3 activity cell free (2 hr preincubation at 4° C.) compounds of the invention is presented below in Table 1 (3$^{rd}$ column). The data is presented whereby the letter "A" means the compound has K$_i$ between 0.0000001 µM≤1 µM, the letter "B" means the compound has a K$_i$ between 1.1 µM≤10 µM, the letter "C" means the compound has a K$_i$>10 µM.

The IC$_{50}$ for cell based JAK3 pathway inhibition for compounds of the invention is also presented below in Table 1 (4th column). The IC$_{50}$ for cell based JAK3 pathway inhibition for compounds of the invention was determined as follows: STAT6-bla RA1 cells were thawed and resuspended in Assay Media (OPTI-MEM, 0.5% dialyzed FBS, 0.1 mM NEAA, 1 mM sodium pyruvate, 100 U/mL/100 µg/mL Pen/Strep, and 550 ng/mL CD40L) to a concentration of 781,250 cells/mL. 32 µL of the cell suspension (25,000 cells) was added to each well of a 384-well TC-Treated assay plate. Cells in Assay Media were incubated for 16-24 hours in the plate at 37° C./5% CO$_2$ in a humidified incubator. 4 µL of a 10× serial dilution of a compound of the invention was added to appropriate wells of the plate and pre-incubated at 37° C./5% CO$_2$ in a humidified incubator with cells for 30 minutes. 4 µL of 10× control activator IL-4 at the predetermined EC$_{80}$ concentration was added to wells containing the compound of the invention. The plate was incubated for 5 hours at 37° C./5% CO$_2$ in a humidified incubator. 8 µL of 1 µM Substrate Loading Solution was added to each well and the plate was incubated for 2 hours at room temperature. The plate was read on a fluorescence plate reader.

The data is presented whereby the letter "E" means the compound has an IC$_{50}$ between 0.0000001 µM≤0.1 µM, the letter "F" means the compound has an IC$_{50}$ between 0.11 µM≤1.0 µM, the letter "G" means the compound has an IC$_{50}$ between 1.1 µM≤10 µM, and the letter "H" means the compound has an IC$_{50}$ of >10 µM.

It will be recognized by one skilled in the art that the compounds can be assessed against other tyrosine kinases and that the presentation of data is illustrative and in no way intended to limit the scope of the present invention. The compounds of the invention can be assayed against a range of tyrosine kinases depending upon the performance activity desired to be gathered. Furthermore, the letters "A", "B", "C", "E", "F", "G", and "H" are also illustrative and in no way is intended to limit the scope of the present invention. For example, the symbol "C" is not meant to indicate that a compound necessarily lacks activity or utility but rather that its K$_i$ value against the indicated tyrosine kinase is greater than 10 µM.

Example 3B

B Cell Receptor NFAT-bla RA1 Inhibition Activity Assays

The inhibition of B cell receptor NFAT-bla RA 1 (activated by goat anti-human IgM, which stimulates the SYK signaling pathway) by several compounds was determined using the Screening Protocol and Assay Conditions (Invitrogen, Madison, Wis.). The assays were performed according to manufacturer's protocols. See Example 4, Cell-line Specific Protocols B cell receptor activity in Ramos cells for details.

The IC$_{50}$ for B cell receptor NFAT-bla RA1 inhibition for compounds of the invention is presented below in Table 1 (6th column).

The data is presented whereby the letter "I" means the compound has an IC$_{50}$ between 0.0000001 μM≤0.1 μM, the letter "J" means the compound has an IC$_{50}$ between 0.11 μM≤1.0 μM, the letter "K" means the compound has an IC$_{50}$ between 1.1 μM≤10 μM, and the letter "L" means the compound has an IC$_{50}$ of >10 μM. The letters "I", "J", "K", and "L" are also illustrative and in no way is intended to limit the scope of the present invention.

Example 3C

Interleukin 4/STAT6-STAT6-bla RA1 Inhibition Activity Assays

The inhibition of Interleukin 4/STAT6-STAT6-bla RA1 (activated by IL-4) by several compounds was determined using the Screening Protocol and Assay Conditions (Invitrogen, Madison, Wis.). The assays were performed according to manufacturer's protocols. Example 4, Cell-line Specific Protocols IL-4-stimulated STAT6 activity in Ramos cells for details. The IC$_{50}$ for Interleukin 4/STAT6-STAT6-bla RA1 inhibition for compounds of the invention is presented below in Table 1 (7th column).

The data is presented whereby the letter "M" means the compound has an IC$_{50}$ between 0.0000001 μM≤0.1 μM, the letter "N" means the compound has an IC$_{50}$ between 0.11 μM≤1.0 μM, the letter "O" means the compound has an IC$_{50}$ between 1.1 μM≤10 μM, and the letter "P" means the compound has an IC$_{50}$ of >10 μM. The letters "M", "N", "O", and "P" are also illustrative and in no way is intended to limit the scope of the present invention.

TABLE 1

| Cmpd Name | Structure | JAK3 activity cell free (2 hr preincubation at (4° C.) K$_j$ | Cell based JAK3 pathway inhibition IC$_{50}$ | Max % Inh | Cell based IL4 stimulation IC$_{50}$ | Cell based IGM stimulation IC$_{50}$ |
|---|---|---|---|---|---|---|
| 7A | 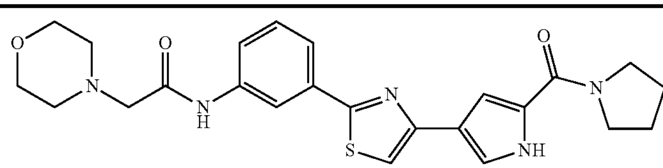 | B | F | 75 | I | M |
| 12A | 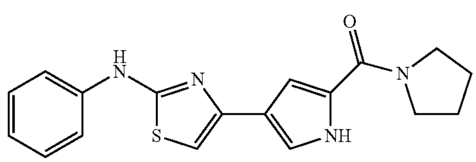 [SMILES: O=C(c1cc(-c2csc(Nc3ccccc3)n2)c[nH]1)N1CCCC1] | A | F | 81 | | |
| 16A | 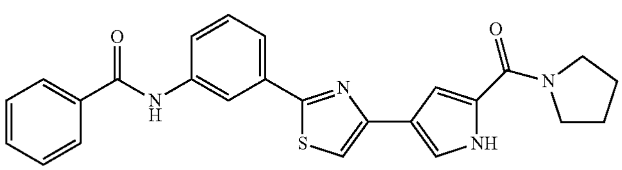 [SMILES: O=C(Nc1cccc(-c2nc(-c3c[nH]c(C(=O)N4CCCC4)c3)cs2)c1)c1ccccc1] | C | | | | |
| 17A | 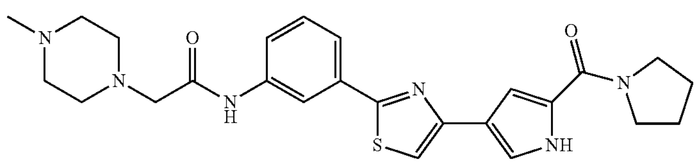 [SMILES: CN1CCN(CC(=O)Nc2cccc(-c3nc(-c4c[nH]c(C(=O)N5CCCC5)c4)cs3)c2)CC1] | C | F | | | |
| 13A | 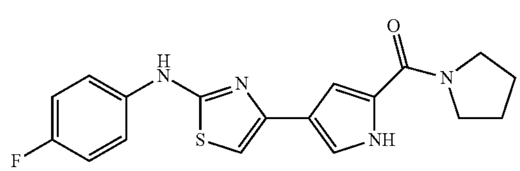 [SMILES: O=C(c1cc(-c2csc(Nc3ccc(F)cc3)n2)c[nH]1)N1CCCC1] | A | F | 78 | | |
| 15A | 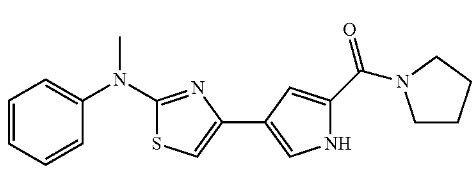 [SMILES: CN(c1ccccc1)c1nc(-c2c[nH]c(C(=O)N3CCCC3)c2)cs1] | C | | | | |

TABLE 1-continued

| Cmpd Name | Structure | JAK3 activity cell free (2 hr preincubation at (4° C.) $K_j$ | Cell based JAK3 pathway inhibition $IC_{50}$ | Max % Inh | Cell based IL4 stimulation $IC_{50}$ | Cell based IGM stimulation $IC_{50}$ |
|---|---|---|---|---|---|---|
| 14A | 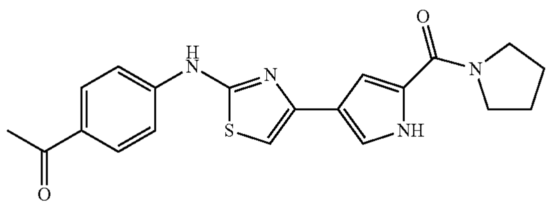 [SMILES: CC(=O)c1ccc(Nc2nc(-c3c[nH]c(C(=O)N4CCCC4)c3)cs2)cc1] | B | | | | |
| 18A | 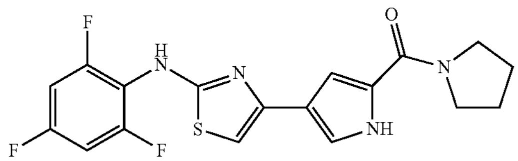 [SMILES: O=C(c1cc(-c2csc(Nc3c(F)cc(F)cc3F)n2)c[nH]1)N1CCCC1] | B | | | | |
| 19A | 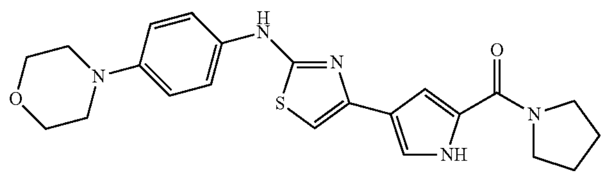 [SMILES: O=C(c1cc(-c2csc(Nc3ccc(N4CCOCC4)cc3)n2)c[nH]1)N1CCCC1] | B | | | | |
| 20A | 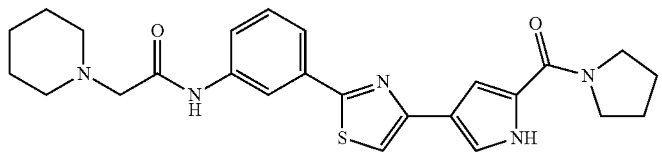 [SMILES: O=C(CN1CCCCC1)Nc1cccc(-c2nc(-c3c[nH]c(C(=O)N4CCCC4)c3)cs2)c1] | | F | 80.22 | | |
| 21A | 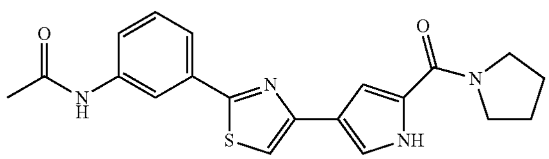 [SMILES: CC(=O)Nc1cccc(-c2nc(-c3c[nH]c(C(=O)N4CCCC4)c3)cs2)c1] | | F | 84.41 | | |
| 22A | 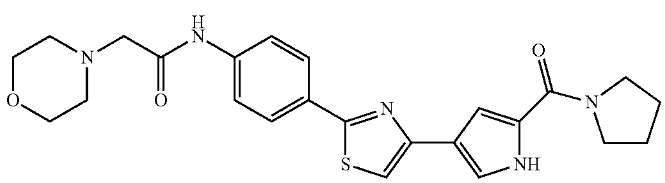 [SMILES: O=C(CN1CCOCC1)Nc1ccc(-c2nc(-c3c[nH]c(C(=O)N4CCCC4)c3)cs2)cc1] | | F | 100 | | |
| 23A | 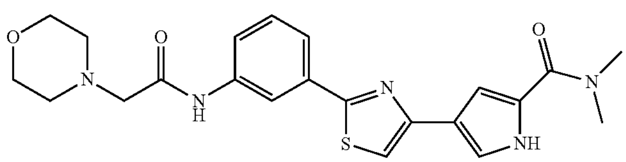 [SMILES: CN(C)C(=O)c1cc(-c2csc(-c3cccc(NC(=O)CN4CCOCC4)c3)n2)c[nH]1] | | G | 75.10 | | |
| 24A | 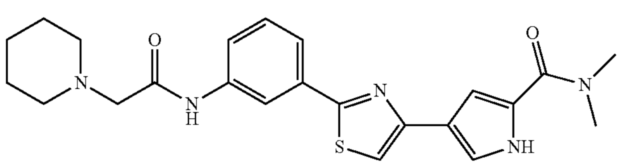 [SMILES: CN(C)C(=O)c1cc(-c2csc(-c3cccc(NC(=O)CN4CCCCC4)c3)n2)c[nH]1] | | G | 74.68 | | |

TABLE 1-continued

| Cmpd Name | Structure | JAK3 activity cell free (2 hr preincubation at (4° C.) $K_j$ | Cell based JAK3 pathway inhibition $IC_{50}$ | Max % Inh | Cell based IL4 stimulation $IC_{50}$ | Cell based IGM stimulation $IC_{50}$ |
|---|---|---|---|---|---|---|
| 25A | 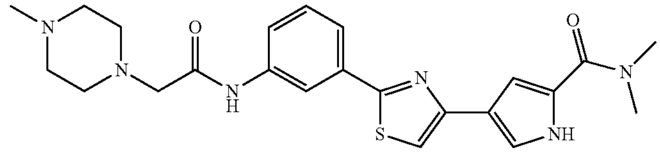 | | H | #N/A | | |
| 26A | 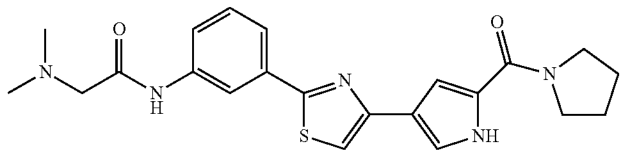 [SMILES: CN(C)CC(=O)Nc1cccc(-c2nc(-c3c[nH]c(C(=O)N4CCCC4)c3)cs2)c1] | | F | 74.58 | | |
| 27A | 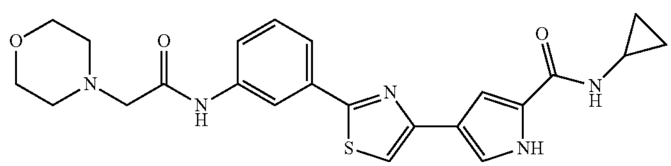 [SMILES: O=C(CN1CCOCC1)Nc1cccc(-c2nc(-c3c[nH]c(C(=O)NC4CC4)c3)cs2)c1] | | G | 100 | | |
| 28A | 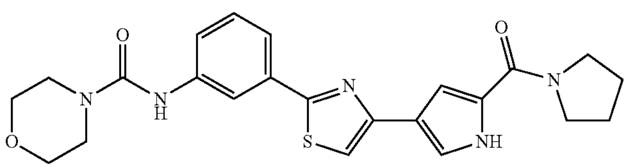 [SMILES: O=C(Nc1cccc(-c2nc(-c3c[nH]c(C(=O)N4CCCC4)c3)cs2)c1)N1CCOCC1] | | F | 82.29 | | |
| 29A | 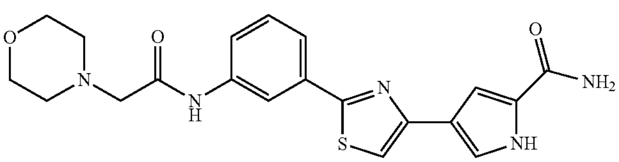 [SMILES: NC(=O)c1cc(-c2csc(-c3cccc(NC(=O)CN4CCOCC4)c3)n2)c[nH]1] | | H | #N/A | | |
| 30A | 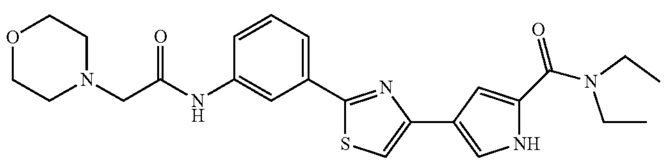 [SMILES: CCN(CC)C(=O)c1cc(-c2csc(-c3cccc(NC(=O)CN4CCOCC4)c3)n2)c[nH]1] | | G | 98.15 | | |
| 31A | 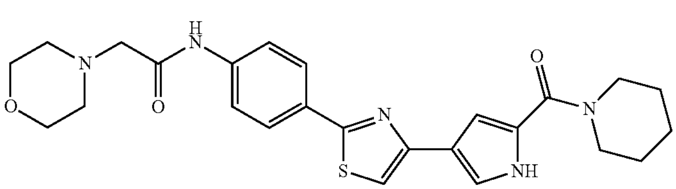 [SMILES: O=C(CN1CCOCC1)Nc1ccc(-c2nc(-c3c[nH]c(C(=O)N4CCCCC4)c3)cs2)cc1] | | G | 76.84 | | |
| 32A | 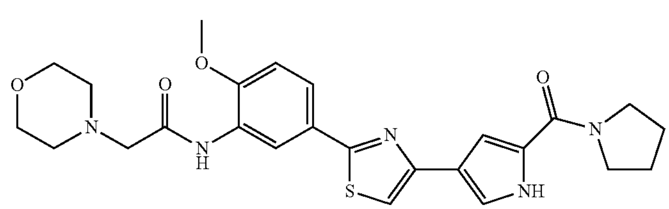 [SMILES: COc1ccc(-c2nc(-c3c[nH]c(C(=O)N4CCCC4)c3)cs2)cc1NC(=O)CN1CCOCC1] | | F | 71.7; 63 | | |

TABLE 1-continued

| Cmpd Name | Structure | JAK3 activity cell free (2 hr preincubation at (4° C.) K<sub>j</sub> | Cell based JAK3 pathway inhibition IC<sub>50</sub> | Max % Inh | Cell based IL4 stimulation IC<sub>50</sub> | Cell based IGM stimulation IC<sub>50</sub> |
|---|---|---|---|---|---|---|
| 33A | 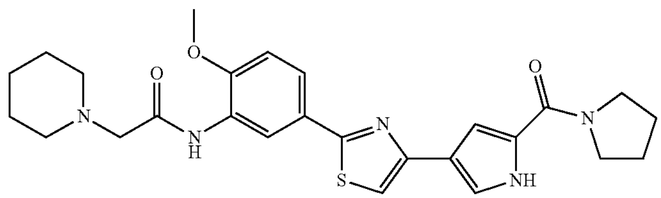 [SMILES: COc1ccc(-c2nc(-c3c[nH]c(C(=O)N4CCCC4)c3)cs2)cc1NC(=O)CN1CCCCC1] | | F | 69.83; 59.2 | | |
| 34A | 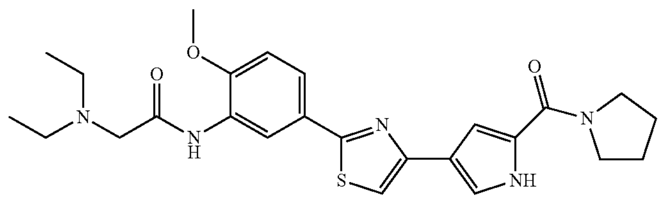 [SMILES: CCN(CC)CC(=O)Nc1cc(-c2nc(-c3c[nH]c(C(=O)N4CCCC4)c3)cs2)ccc1OC] | | F | 79.67 | | |
| 35A | 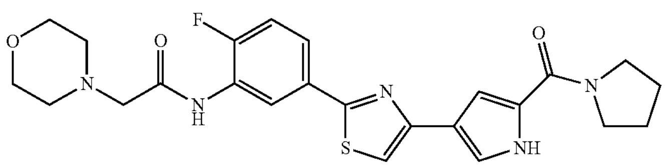 [SMILES: O=C(CN1CCOCC1)Nc1cc(-c2nc(-c3c[nH]c(C(=O)N4CCCC4)c3)cs2)ccc1F] | | F | 78.89 | | |
| 8A | 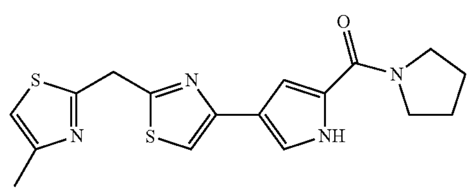 [SMILES: Cc1csc(Cc2nc(-c3c[nH]c(C(=O)N4CCCC4)c3)cs2)n1] | | B | | | |
| 5A | 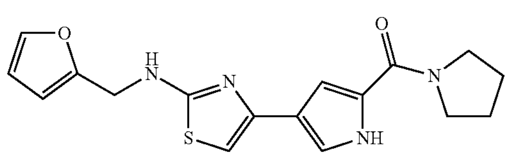 [SMILES: O=C(c1cc(-c2csc(NCc3ccco3)n2)c[nH]1)N1CCCC1] | | B | G | 68 | |
| 10A | 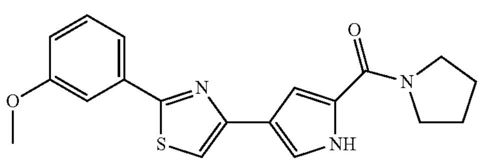 [SMILES: COc1cccc(-c2nc(-c3c[nH]c(C(=O)N4CCCC4)c3)cs2)c1] | | B | | | |
| 9A | 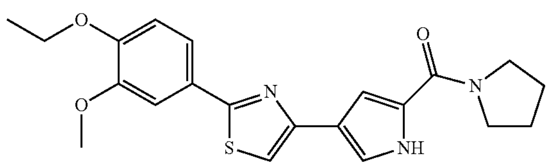 [SMILES: CCOc1ccc(-c2nc(-c3c[nH]c(C(=O)N4CCCC4)c3)cs2)cc1OC] | | B | | | |
| 3A | 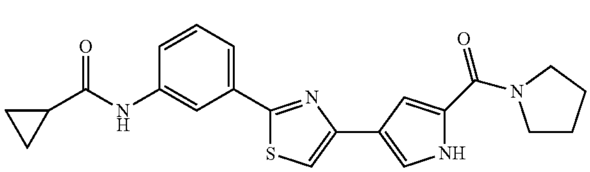 [SMILES: O=C(Nc1cccc(-c2nc(-c3c[nH]c(C(=O)N4CCCC4)c3)cs2)c1)C1CC1] | | A | | | I |

TABLE 1-continued

| Cmpd Name | Structure | JAK3 activity cell free (2 hr preincubation at (4° C.) K_j | Cell based JAK3 pathway inhibition IC_50 | Max % Inh | Cell based IL4 stimulation IC_50 | Cell based IGM stimulation IC_50 |
|---|---|---|---|---|---|---|
| 2A | 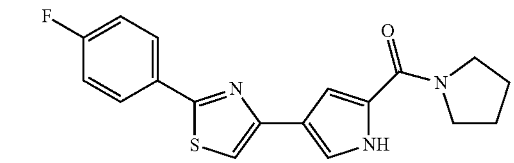 [SMILES: O=C(c1cc(-c2csc(-c3ccc(F)cc3)n2)c[nH]1)N1CCCC1] | A | | | | I |
| 4A | 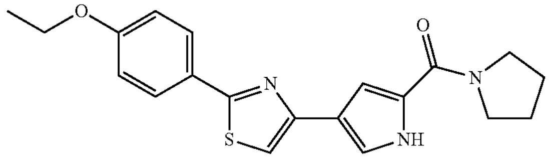 [SMILES: CCOc1ccc(-c2nc(-c3c[nH]c(C(=O)N4CCCC4)c3)cs2)cc1] | A | | | | |
| 11A | 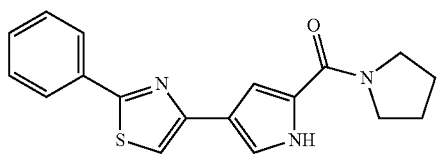 [SMILES: O=C(c1cc(-c2csc(-c3ccccc3)n2)c[nH]1)N1CCCC1] | B | | | | J |
| 39A | 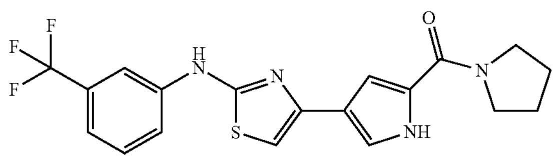 [SMILES: O=C(c1cc(-c2csc(Nc3cccc(C(F)(F)F)c3)n2)c[nH]1)N1CCCC1] | B | | | | |
| 40A | 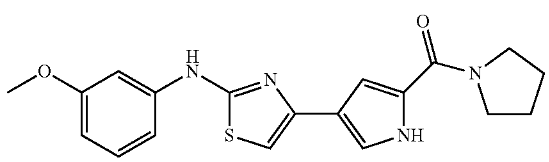 [SMILES: COc1cccc(Nc2nc(-c3c[nH]c(C(=O)N4CCCC4)c3)cs2)c1] | A | | | | |
| 41A | 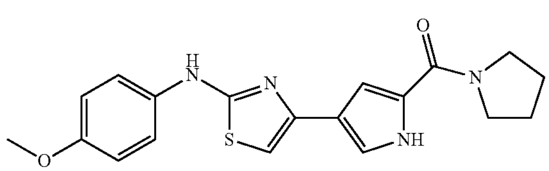 [SMILES: COc1ccc(Nc2nc(-c3c[nH]c(C(=O)N4CCCC4)c3)cs2)cc1] | A | | | | |
| 42A | 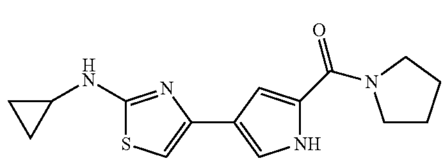 [SMILES: O=C(c1cc(-c2csc(NC3CC3)n2)c[nH]1)N1CCCC1] | A | | | | |
| 43A | 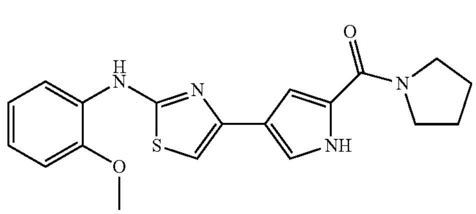 [SMILES: COc1ccccc1Nc1nc(-c2c[nH]c(C(=O)N3CCCC3)c2)cs1] | A | | | | |

TABLE 1-continued

| Cmpd Name | Structure | JAK3 activity cell free (2 hr preincubation at (4° C.) $K_j$ | Cell based JAK3 pathway inhibition $IC_{50}$ | Max % Inh | Cell based IL4 stimulation $IC_{50}$ | Cell based IGM stimulation $IC_{50}$ |
|---|---|---|---|---|---|---|
| 44A | 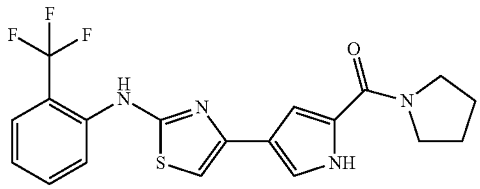 [SMILES: O=C(c1cc(-c2csc(Nc3ccccc3C(F)(F)F)n2)c[nH]1)N1CCCC1] | A | | | | |
| 45A | 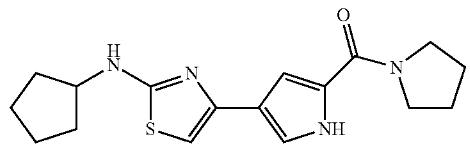 [SMILES: O=C(c1cc(-c2csc(NC3CCCC3)n2)c[nH]1)N1CCCC1] | B | | | | |
| 46A | 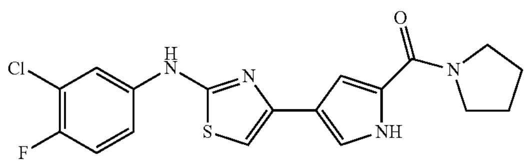 [SMILES: O=C(c1cc(-c2csc(Nc3ccc(F)c(Cl)c3)n2)c[nH]1)N1CCCC1] | A | | | | |
| 47A | 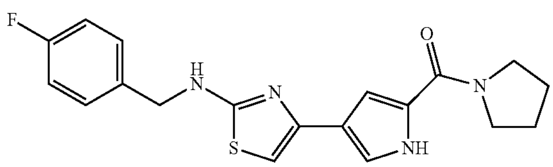 [SMILES: O=C(c1cc(-c2csc(NCc3ccc(F)cc3)n2)c[nH]1)N1CCCC1] | B | | | | |
| 48A | 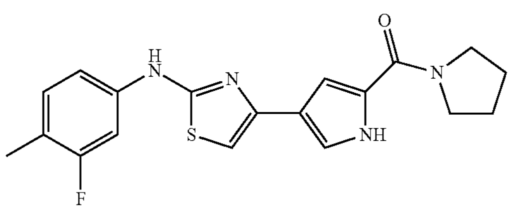 [SMILES: Cc1ccc(Nc2nc(-c3c[nH]c(C(=O)N4CCCC4)c3)cs2)cc1F] | A | | | | |
| 49A | 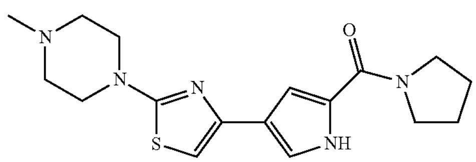 [SMILES: CN1CCN(c2nc(-c3c[nH]c(C(=O)N4CCCC4)c3)cs2)CC1] | A | | | | |
| 50A | 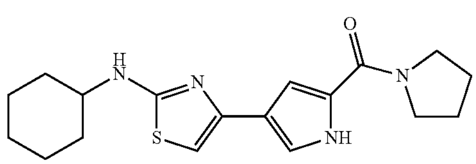 [SMILES: O=C(c1cc(-c2csc(NC3CCCCC3)n2)c[nH]1)N1CCCC1] | A | | | | |
| 51A | 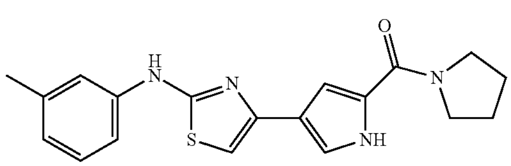 [SMILES: Cc1cccc(Nc2nc(-c3c[nH]c(C(=O)N4CCCC4)c3)cs2)c1] | A | | | | |

TABLE 1-continued

| Cmpd Name | Structure | JAK3 activity cell free (2 hr preincubation at (4° C.) $K_j$ | Cell based JAK3 pathway inhibition $IC_{50}$ | Max % Inh | Cell based IL4 stimulation $IC_{50}$ | Cell based IGM stimulation $IC_{50}$ |
|---|---|---|---|---|---|---|
| 52A | 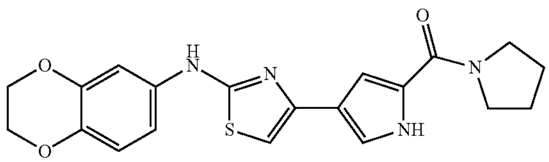 [SMILES: O=C(c1cc(-c2csc(Nc3ccc4c(c3)OCCO4)n2)c[nH]1)N1CCCC1] | A | | | | |
| 53A | 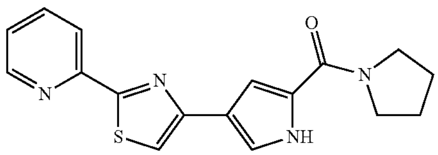 [SMILES: O=C(c1cc(-c2csc(-c3ccccn3)n2)c[nH]1)N1CCCC1] | A | F | 72 | | |
| 54A | 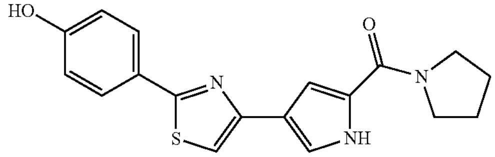 [SMILES: O=C(c1cc(-c2csc(-c3ccc(O)cc3)n2)c[nH]1)N1CCCC1] | A | | | | |
| 55A | 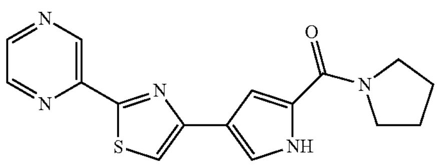 [SMILES: O=C(c1cc(-c2csc(-c3cnccn3)n2)c[nH]1)N1CCCC1] | A | | | | |
| 56A | 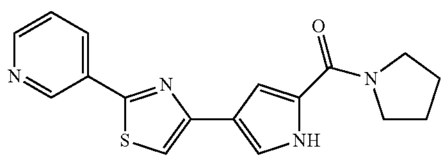 | A | | | | |
| 57A | 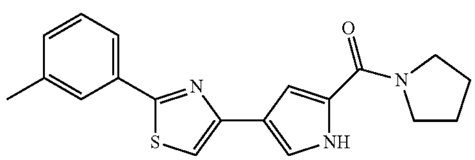 [SMILES: Cc1cccc(-c2nc(-c3c[nH]c(C(=O)N4CCCC4)c3)cs2)c1] | A | | | | |
| 58A | 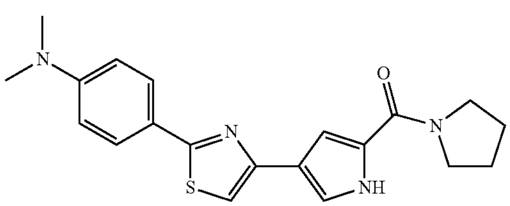 [SMILES: CN(C)c1ccc(-c2nc(-c3c[nH]c(C(=O)N4CCCC4)c3)cs2)cc1] | A | | | | |
| 59A | 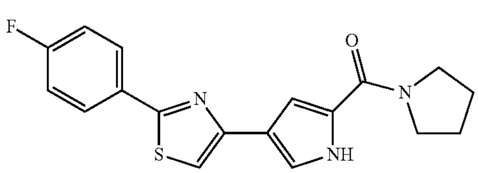 [SMILES: O=C(c1cc(-c2csc(-c3ccc(F)cc3)n2)c[nH]1)N1CCCC1] | A | | | | |

TABLE 1-continued

| Cmpd Name | Structure | JAK3 activity cell free (2 hr preincubation at (4° C.) $K_j$ | Cell based JAK3 pathway inhibition $IC_{50}$ | Max % Inh | Cell based IL4 stimulation $IC_{50}$ | Cell based IGM stimulation $IC_{50}$ |
|---|---|---|---|---|---|---|
| 60A | 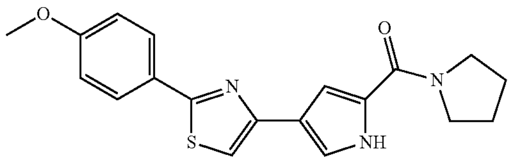 [SMILES: COc1ccc(-c2nc(-c3c[nH]c(C(=O)N4CCCC4)c3)cs2)cc1] | A | | | | |
| 61A | 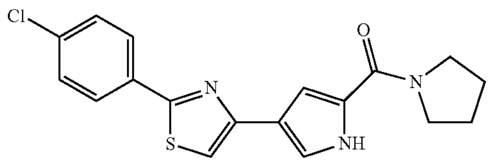 [SMILES: O=C(c1cc(-c2csc(-c3ccc(Cl)cc3)n2)c[nH]1)N1CCCC1] | A | | | F | 60 |
| 62A | 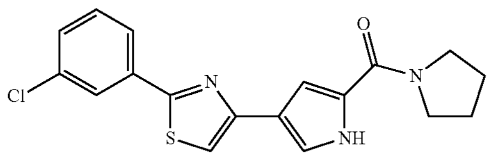 [SMILES: O=C(c1cc(-c2csc(-c3cccc(Cl)c3)n2)c[nH]1)N1CCCC1] | A | | | | |
| 63A | 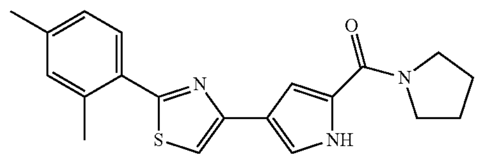 [SMILES: Cc1ccc(-c2nc(-c3c[nH]c(C(=O)N4CCCC4)c3)cs2)c(C)c1] | A | | | F | 63 |
| 64A | 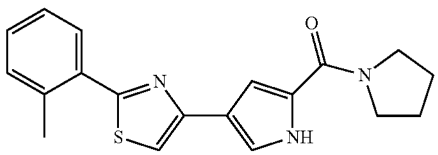 [SMILES: Cc1ccccc1-c1nc(-c2c[nH]c(C(=O)N3CCCC3)c2)cs1] | B | | | | |
| 6A | | B | | G | | | empty cells = not tested
N/A = number not available

Example 4

In Vitro Cellular Assays

This example describes assays for measuring the ability compounds of the invention to inhibit cell proliferation of a variety of cell lines and to inhibit several signal transduction pathways.
Mechanism Based Assay Protocols
General Protocol
Mechanism-based inhibition assays using compound 7A (Table 1) were performed using GeneBLAzer® Technology (Invitrogen Corporation), according to manufacturer specifications. Briefly, GeneBLAzer® Technology uses a mammalian-optimized Beta-lactamase reporter gene (bla) combined with a FRET-enabled substrate to provide reliable and sensitive detection in intact cells. Cells were loaded with an engineered fluorescent substrate containing two fluorophores, coumarin and fluorescein. Without bla expression, the substrate molecule remains intact. In this state, excitation of the coumarin results in fluorescence resonance energy transfer to the fluorescein moiety and emission of green light. But when bla is expressed, the substrate is cleaved, the fluorophores are separated, and energy transfer is disrupted. Excitation of the coumarin in the presence of Beta-lactamase activity results in a blue fluorescence signal. The resulting coumarin:fluorescein ratio provides a normalized reporter response, which can minimize experimental noise that can mask the underlying biological response of interest. More specific details are provided below.

General Activator Assay Protocol
1. 32 µL of cells diluted in Assay Media to appropriate cell density were added to an assay plate. If needed, cells were incubated at 37° C./5% $CO_2$ for 6 or 16-24 hours (depending upon cell line specifics) before compound was added.
2. 40 nL of 1000× compound or known activator titration plus 4 µL of assay media was added to the cells in the assay plate.
3. 4 µL of Assay Media was added to all wells to bring the final assay volume to 40
4. The assay plate was incubated for 5 or 16 hours (depending upon cell line specifics) at 37° C./5% $CO_2$ in a humidified incubator.
5. 8 µL of the Substrate Loading Solution was added to the assay plate.
6. The assay plate was incubated for 2 hours at room temperature, in the dark.
7. The assay, plate was read on a fluorescence plate reader (Tecan Safire$^2$) and the data is analyzed.

General Inhibitor Assay Protocol
An activator assay screen was run to obtain the $EC_{80}$ concentration of the known activator to add in step 3.
1. 32 µL of cells diluted in Assay Media to appropriate cell density were added to an assay plate. If needed, cells were incubated at 37° C./5% $CO_2$ for 6 or 16-24 hours (depending upon cell line specifics) before compound was added.
2. 40 nL of 1000× compound or known inhibitor titration plus 4 µL of assay media was added to the cells in the assay plate and incubated for 30 minutes at 37° C./5% $CO_2$ in a humidified incubator.
3. 4 µL of the $EC_{80}$ concentration of activator, as determined in an Activator assay, was added to all wells containing compound and known inhibitor to bring the final assay volume to 40 µL.
4. 4 µL of Assay Medium was added to remaining control wells to bring the volume up to 40 µL.
5. The assay plate was incubated for 5 or 16 hours (depending upon cell line specifics) at 37° C./5% $CO_2$ in a humidified incubator.
6. 8 µL of the Substrate Loading Solution was added to the assay plate.
7. The assay plate was incubated for 2 hours at room temperature, in the dark.
8. The assay plate was read on a fluorescence plate reader (Tecan Safire) and the data is analyzed.

Cell-line Specific Protocols
IL-4-Stimulated STAT6 Activity in Ramos Cells
STAT6-bla RA1 cells were thawed. 32 µL of cell suspension were added to each well of a 384-well TC-Treated assay plate. Cells in Assay Media were incubated for 16-24 hours in the plate at 37° C./5% $CO_2$ in a humidified incubator. 4 µL of a 10× serial dilution of JAK Inhibitor I (control inhibitor starting concentration, 10,000 nM) or compound were added to appropriate wells of the plate and pre-incubated at 37° C./5% $CO_2$ in a humidified incubator with cells for 30 minutes. 4 µL of 10× control activator IL-4 at the predetermined $EC_{80}$ concentration was added to wells containing the control inhibitor or compound. The plate was incubated for 5 hours at 37° C./5% $CO_2$ in a humidified incubator. 8 µL of 1 µM Substrate Loading Solution was added to each well and the plate was incubated for 2 hours at room temperature. The plate was read on a fluorescence plate reader.

B Cell Receptor Activity in Ramos Cells
NFAT-bla RA1 cells were thawed. 4 µL of a 10× serial dilution of Syk Inhibitor II (control inhibitor starting concentration, 10,000 nM) or compound was added to appropriate wells of a Poly-D-Lysine assay plate. 32 µL of cell suspension was added to the wells and pre-incubated at 37° C./5% $CO_2$ in a humidified incubator with compound and control inhibitor titration for 30 minutes. 4 µL of 10× control activator Goat anti-Human IgM at the pre-determined $EC_{80}$ concentration was added to wells containing the control inhibitor or compound. The plate was incubated for 5 hours at 37° C./5% $CO_2$ in a humidified incubator. 8 µL of 1 µM Substrate Loading Solution was added to each well and the plate was incubated for 2 hours at room temperature. The plate was read on a fluorescence plate reader.

IL-2-Stimulated STAT5 Activity in CTLL-2 Cells
Irf1-bla CTLL-2 cells were thawed and prepared as described above for the Activator Screen. 32 µL of cell suspension was added to each well of a 384-well TC-Treated assay plate. Cells in Assay Media were incubated for 16-24 hours in the plate at 37° C./5% CO2 in a humidified incubator. 4 µL of a 10× serial dilution of JAK Inhibitor I (control inhibitor starting concentration, 1,000 nM) or compound was added to appropriate wells of the plate and pre-incubated at 37° C./5% CO2 in a humidified incubator with cells for 30 minutes. 4 µL of 10× control activator EPO at the predetermined EC80 concentration was added to wells containing the control inhibitor or compound. The plate was incubated for 5 hours at 37° C./5% CO2 in a humidified incubator. 8 µL of 1 µM Substrate Loading Solution was added to each well and the plate was incubated for 2 hours at room temperature. The plate was read on a fluorescence plate reader.

NFkB-NFkB-bla THP-1-Activator Screen
NFkB-bla THP-1 cells were thawed and resuspended in Assay Media (RPMI, 10% dialyzed FBS, 0.1 mM NEAA, 1 mM Sodium Pyruvate, 100 U/mL/100 µg/mL Pen/Strep) to a concentration of 625,000 cells/mL. 32 µL of cell suspension (20,000 cells) were added to each well of a 384-well TC-Treated assay plate. Cells in Assay Media were incubated for 16-24 hours in the plate at 37° C./5% CO2 in a humidified incubator. 4 µL of a 10× serial dilution of TNF-alpha (control activator starting concentration, 1 nM) or compounds were added to appropriate wells of the plate. 4 µL of Assay Media is added to all wells to bring the final assay volume to 40 µL. The plate was incubated for 5 hours at 37° C./5% $CO_2$ in a humidified incubator. 8 µL of 1 µM Substrate Loading Solution was added to each well and the plate was incubated for 2 hours at room temperature. The plate was read on a fluorescence plate reader.

NFkB/Ramos
Cells were plated on the day prior to the assay. Media required included:

| Component | Growth Medium | Assay Medium | Freezing Medium |
|---|---|---|---|
| RPMI 1640 | 90% | 90% | 85% |
| Heat inactivated FBS | 10% | 10% | 10% |
| Sodium pyruvate | 1 mM | 1 mM | 1 mM |
| Penicillin | 100 U/ml | 100 U/ml | 100 U/ml |
| Streptomycin | 100 µg/ml | 100 µg/ml | 100 µg/ml |
| Blasticidin antibiotic | 5 µg/ml | — | — |
| DMSO | — | — | 5% |
| Non-Essential Amino Acids | 0.1 mM | 0.1 mM | 0.1 mM |

Note:
Unless otherwise stated, have all media and solutions at least at room temperature (we recommend 37° C. for optimal performance) before adding them to the cells.

1. Cells were harvest from culture in Growth Medium and resuspend in Assay Medium at a density of $1.6 \times 10^6$ cells/ml.

2. 32 µl per well of Assay medium were added to the cell-free control wells. 32 µl per well of a cell suspension were added to Unstimulated and Stimulated wells
3. After plating, the plates were incubated in a 37° C./5% $CO_2$ incubator for 16-20 hours.

Preparation of DMSO Solution:

A solution was prepared of 5% DMSO solution (10×) in Assay Media.

Preparation of Stock Solution:

A solution was prepared of 10×TNFα solution in Assay Medium. It is recommended to run a dose response curve to determine the $EC_{80}$ for the Stimulation Solution.

Cell Stimulation 1. 4 µl of 10×DMSO solution was added to each well.
2. 4 µl of Assay Medium was added to the Unstimulated wells and to the Cell-Free wells.
3. 4 µl of the 10×TNFα was added to the Stimulated wells.
4. The assay plate was incubated in a humidified 37° C./5% $CO_2$ incubator for 5 hours.

Substrate Loading and Incubation

This protocol is designed for loading cells with Live-BLAzer™-FRET B/G Substrate (CCF4-AM) or CCF2-AM. If alternative substrates are used it is recommended to follow the loading protocol provided with the substrate. 6× Live-BLAzer™-FRET B/G Substrate (CCF4-AM) or CCF2-AM Mixture was prepared and cell loading was done in the absence of direct strong lighting.

1. Solution A was prepared: 1 mM LiveBLAzer™-FRET B/G Substrate (CCF2-AM, MW=1096) stock solution in a dry DMSO. Aliquots of the stock solution were stored at −20° C. until use.
2. The preparation of 6× Live BLAzer™-FRET B/G (CCF4-AM) Substrate Mixture was carried out as follows:

Added 6 µl of Solution A to 60 µl of Solution B and vortexed.

Added 934 µl Solution C to the combined solutions from above step and vortexed.

3. Removed assay plate from the humidified 37° C./5% $CO_2$ incubator.
4. Added 8 µl of 6× Substrate Mixture from Step 2 to each well.
5. Covered the plate to protect it from light and evaporation.
6. Incubated at room temperature for 2.5 hours.

Detailed Growth Conditions for Cells Used in the Protocol Above

Thawing Method 1. 14 ml of Growth Medium without Blasticidin was placed into a T75 flask.
2. The flask was placed in a humidified 37° C./5% $CO_2$ incubator for 15 minutes and the medium was allowed to equilibrate to the proper pH and temperature.
3. The vial of cells to be thawed was removed from liquid nitrogen and thawed rapidly by placing at 37° C. in a water bath with gentle agitation for 1-2 minutes.
4. The vial was decontaminated by wiping with 70% ethanol before opening in a Class II biological safety cabinet.
5. The vial contents were transferred drop-wise into 10 ml of Growth Medium without Blasticidin in a sterile 15-ml conical tube.
6. Cells were centrifuged at 200×g for 5 minutes.
7. The supernatant was aspirated and the cell pellet resuspended in 1 ml of fresh Growth Medium without Blasticidin.
8. The contents were transferred to the T75 tissue culture flask containing pre-equilibrated Growth Medium without Blasticidin and the flask was placed in a humidified 37° C./5% $CO_2$ incubator.
9. At first passage, a switch was made to Growth Medium with Blasticidin.

Propagation Method

1. Cells were passaged or fed at least twice a week. Cells were maintained at a cell density between $2\times10^5$ and $1\times10^6$ cell/ml.
2. To passage cells, the desired amount of cell suspension were centrifuged and resuspended at 200,000 cells/ml in fresh Growth Media.

Freezing Method

1. The cells were harvested as described in Section 7.2. The cells were counted and then spun cells down and resuspended in 4° C. Freezing Medium at $5\times10^6$ cells/ml.
2. 1.0-ml aliquots were dispensed into cryogenic vials.
3. Aliquots were placed in an insulated container for slow cooling and stored overnight at −80° C.
4. Transferred to liquid nitrogen the next day for storage.

JAK2/STAT5-irf1-bla TF1-Activator Screen irf1-bla TF1 cells were thawed and resuspended in Assay Media (OPTI-MEM, 0.5% dialyzed FBS, 0.1 mM NEAA, 1 mM Sodium Pyruvate, 100 U/mL/100 µg/mL Pen/Strep) to a concentration of 1,562,500 cells/mL. 32 µL of cell suspension (50,000 cells) were added to each well of a 384-well TC-Treated assay plate. Cells in Assay Media were incubated for 16-24 hours in the plate at 37° C./5% $CO_2$ in a humidified incubator. 4 µL of a 10× serial dilution of EPO (control activator starting concentration, 10 nM) or compounds were added to appropriate wells of the plate. 4 µL of Assay Media was added to all wells to bring the final assay volume to 40 µL. The plate was incubated for 5 hours at 37° C./5%/$CO_2$ in a humidified incubator. 8 µL of 1 µM Substrate Loading Solution is added to each well and the plate is incubated for 2 hours at room temperature. The plate is read on a fluorescence plate reader.

IL-2-Stimulated Proliferation of PBMC

Fresh blood collection and PBMC separation assay

1. Three donors were used to collect enough blood samples. The fresh blood was stored in Heparin Sodium tubes.
2. Transferred blood to 50 ml centrifugal tube. 15 ml of blood was put into a tube.
3. Added same volume of DPBS into the blood tube and mixed gently.
4. Slowly underlayed 10 ml Ficoll using pipette (being careful to not disturb the 2 phases).
5. Centrifuged 30 min at 800 g at RT without break.
6. Aspirated the buffy coat (containing PBMC) at the interface between serum and ficoll. The PBMC was washed by enough DPBS and centrifuged at 900 g to remove the Ficoll.
7. Added RPMI-1640 Medium to the collected PBMC and counted the concentration of PBMC. At least 1 million of PBMC were separated from 1 ml of blood.

IL-2-induced proliferation of PBMC by Cell Titer Glow assay

1. Counted the PBMC numbers and adjusted cell density to 1.0*10^6/ml.
2. Seeded cells in complete RPMI in the presence of PHA (phytohemagglutinin, 10 ug/ml).
3. Added 100 µl of cell suspension to the 96-well plate (white) according to the planned plate map. So there were 1.0*10^5 cells in each well. Cultured for 3 days.
4. Replaced media with complete RPMI plus IL-2, 100 units/ml and compounds, e.g compounds were added only at IL-2 incubation step. Cultured for 2 days.
5. Carried out plus/minus stimulation by adding IL-2 to the wells according to the planned plate map.

6. Incubated the plate at 37° C. in the CO2 cell incubator for 2 days. The outer wells of 96-well plates often dried out with >5 days of culture. It is preferable to set up the plates so that the outer wells may be filled with sterile water or PBS.
7. On endpoint, equilibrated the plate to room temperature for approximately 30 minutes.
8. Added 100 µA of CellTiter-Glo Reagent in each well of the plate
9. Mixed contents for 2 minutes on an orbital shaker to induce cell lysis.
10. Allowed the plate to incubate at room temperature for 10 minutes to stabilize luminescent signal.
11. Recorded luminescence with Flexstation 3 and export the data.

Proliferation of RS4; 11, Ramos, Namalwa, RL, Molt-4 and Daudi Cells

Growth inhibitory activity against the human tumor cell lines, RS4; 11 and Daudi was determined using Promega's Cell Titer-Glo® assay. The human tumor cells were placed in a 96-well microculture plate (Costar white, flat bottom #3917) in a total volume of 90 µL/well. After 24 hours of incubation in a humidified incubator at 37° C. with 5% $CO_2$ and 95% air, 10 of serially diluted test agents in growth medium were added to each well. After 96 total hours of culture in a $CO_2$ incubator, the plated cells and Cell Titer-Glo® (Promega # G7571) reagents were brought to room temperature to equilibrate for 30 minutes. 100 µL of Cell Titer-Glo® reagent was added to each well. The plate was shaken for 2 minutes and then left to equilibrate for 10 minutes before reading luminescence on the Tecan GENios microplate reader.

Percent inhibition of cell growth was calculated relative to untreated control wells. All tests were performed in duplicate at each concentration level. The $IC_{50}$ value for the test agents was estimated using Prism 3.03 by curve-fitting the data using the following four parameter-logistic equation:

$$Y = \frac{Top - Bottom}{1 + \left(\frac{X}{IC_{50}}\right)^n} + Bottom$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve.

Proliferation of NALM-6 Cells

Cell proliferation of the human B cell precursor leukemia tumor cell line NALM-6 was measured by a cell proliferation index assay. This assay was based on the dilution rate of a fluorescent membrane marker which is directly linked to the cell division. Briefly, the assay was performed by loading the cells with a non-toxic fluorescent phospholipid analog before the seeding. The probe inserts stably into the plasmic membrane and was distributed between daughter cells after division. Flow cytometry analysis of the fluorescent probe was performed directly after the loading of the cells and after 96 hours of culture. The dilution rate of the fluorescent probe at the single cell level was directly correlated to the number of cell divisions. All experiments were performed in triplicate.

Detection of cellular events was performed in triplicate in 96 well-plates after 72 hours of treatment by automated flow cytometry. Non-linear regressions were performed with GraphPad Prism 4.01 software.

The time course of the experiment was as follows:

Cells were previously thawed and amplified in standard culture conditions (37° C., 5% $CO_2$). NALM-6 cells were cultivated in RPMI 1640+10% inactivated Fetal Bovine Serum.

Day 0: Cells were labeled for subsequent proliferation measurement and seeded at 8000 cells/well in 96-well culture plates following standard culture conditions.

Day 1: After 24 hours of culture, cells were treated with Staurosporine (antiproliferative reference compound) in dose response (8 concentrations including the zero); and with six compounds in dose response (8 concentrations including the zero).

Day 4: After 72 hours of treatment, the cells were analyzed by automated flow cytometry.

Results

The results of mechanism-based and cell proliferation based assays using compound 7A are summarized in the following Tables. In Table 2, * the lower cell-free potency is due to "non-Type I" inhibition.

TABLE 2

| JAK3 Ki | | | T cells | | Cell-based selectivity | | |
|---|---|---|---|---|---|---|---|
| | | | | | IC50 µM | | |
| (uM, cell-free) * | B cells mechanism-based | | mechanism-based | outcome-based | NF-kB pathway | | JAK2 pathway |
| | Ramos cells | Ramos cells | mCTLL-2 | IL-2 stimulated PBMCs | THP-1 cells | Ramos cells | TF-1 cells |
| | IL4 stimulated STAT6 activity | IgM stimulated NFAT activity | IL-2 Stimulated STAT5 activity | Proliferation | | | |
| 0.795 | 0.032 | 0.124 | 6.2 | 3-6 | 40.8 | >100 | 49.5 |

TABLE 3

| | | | | IC50 (uM) | | | |
|---|---|---|---|---|---|---|---|
| | | | B cells | | | | T cells |
| | | | Outcome-Based: Proliferation | | | | |
| Daudi cells | Ramos cells | RS4; 11 cells | NALM-6 cells | Namalwa cells | | RL cells | Molt-4 cells |
| Burkitt's Lymphoma | Burkitt's lymphoma | ALL | ALL | Burkitt's Lymphoma | | Non-Hodjkin lymphoma | ALL |
| 0.159 | 0.534 | 0.500 | 0.480 | 28 | | 26 | 35 |

Example 5

Pharmacological Profile

In one aspect, compounds of the invention are administered orally. For example, the pharmacological profile of compound 7A is shown below in Table 5. It meets the criteria for an oral clinical development candidate.

TABLE 5

| | | | Caco-2 | | | | | | Mouse PK (PO) | |
|---|---|---|---|---|---|---|---|---|---|---|
| | cLogP | hLM T½ (min) | Papp A-B (×10$^6$/cm·s$^{-1}$) | Eflux | hERG IC50 (uM) | Protein Binding | CYP inhibition | Solubility Turbidity (uM) | T½ (hr) | % F |
| Criteria | 2-5 | >30 | >17 | no | >5 | <99% | >10 | >50 uM | >1 hr | >30% |
| Compound 7A | 2.2 | 36 | 24 | no | >10 | 98% | >10 | 60-80 | 3.2 hr | 88% |

Example 6

Safety

Compounds of the invention are safe for administration. For example, excellent safety data was obtained in a 6-day maximum tolerated dose study at 100 mg/kg and 300 mg/kg of compound 7A, PO administered to six to eight-week old female ICR nude mice. Animals administered compound 7 showed no mortality, no weight loss, no change in food consumption, no abnormalities in clinical observation, and necropsy was normal (internal and external).

FIG. 1 shows changes in body weight for the study and Table 6 below shows individual food consumption in grams on day 1 and day 6 of the study.

TABLE 6

| | Individual food consumption (g) | |
|---|---|---|
| Group No. | Day 1 | Day 6 |
| PO-Control 0 mg/kg | 5.37 | 5.34 |
| PO-Low 100 mg/kg | 4.61 | 5.44 |
| PO-High 300 mg/kg | 4.45 | 5.13 |

Example 7

In Vivo Xenograft Study with B-Cell Lymphoma

The anti-tumor effect of compounds of the invention can be evaluated in vivo. For example, the anti-tumor effect of compound 7A was determined using a mouse xenograft study with B-cell lymphoma (Daudi cell line). Mice (n=8 all) were administered compound 7A over a period of 28 days. The compound was dosed at 100 mg/kg IP QD and 300 mg/kg PO QD. Tumor volume was measured over time.

The Daudi cell line culture was prepared using Daudi cell line (ATCC, USA), RPMI 1640 medium (Invitrogen, USA), and FBS (Invitrogen, Australia). The female Balb/c nude mice (Slac Laboratory Animal Co., Ltd., Shanghai, China) were allowed a 3-day acclimatization period before the mice were implanted subcutaneously (s.c.) with 200 μl of 10×10$^6$ Daudi cells in 50% Matrigel in the right flank. When tumors reached an average volume of 100-200 mm$^3$, the tumor-bearing mice were randomly assigned to groups of eight prior to dosing in 10 ml/kg of vehicle or compound 7A for 28 days. During the treatment, the suspension of compound 7A was made fresh daily in 0.5% CMC (Sigma, USA) and 1% Tween 80 (Sigma, USA).

The mice were weighed at each dosing and recorded every day. Tumor size was measured every other day in two dimensions using a caliper, and the volume was expressed in mm$^3$ using the formula: $V=0.5\ a \times b^2$ where a and b were the long and short diameters of the tumor, respectively. At the experiment endpoint, mice were euthanized by $CO_2$ exposure on the next day after the last dose. Tumor volume, weight of dissected tumors, and mouse body weight were measured and recorded. Tumors were photographed and then saved in −80° C. for future assays.

The difference between the mean values of tumor volume in treated and vehicle groups was analyzed for significance using one way ANOVA test at each time point after log transformation. The difference between the mean values of tumor weight in treated and vehicle groups was analyzed for significance using t-test. In both analyses, P<0.05 was considered to be statistically significant.

Figure 2:
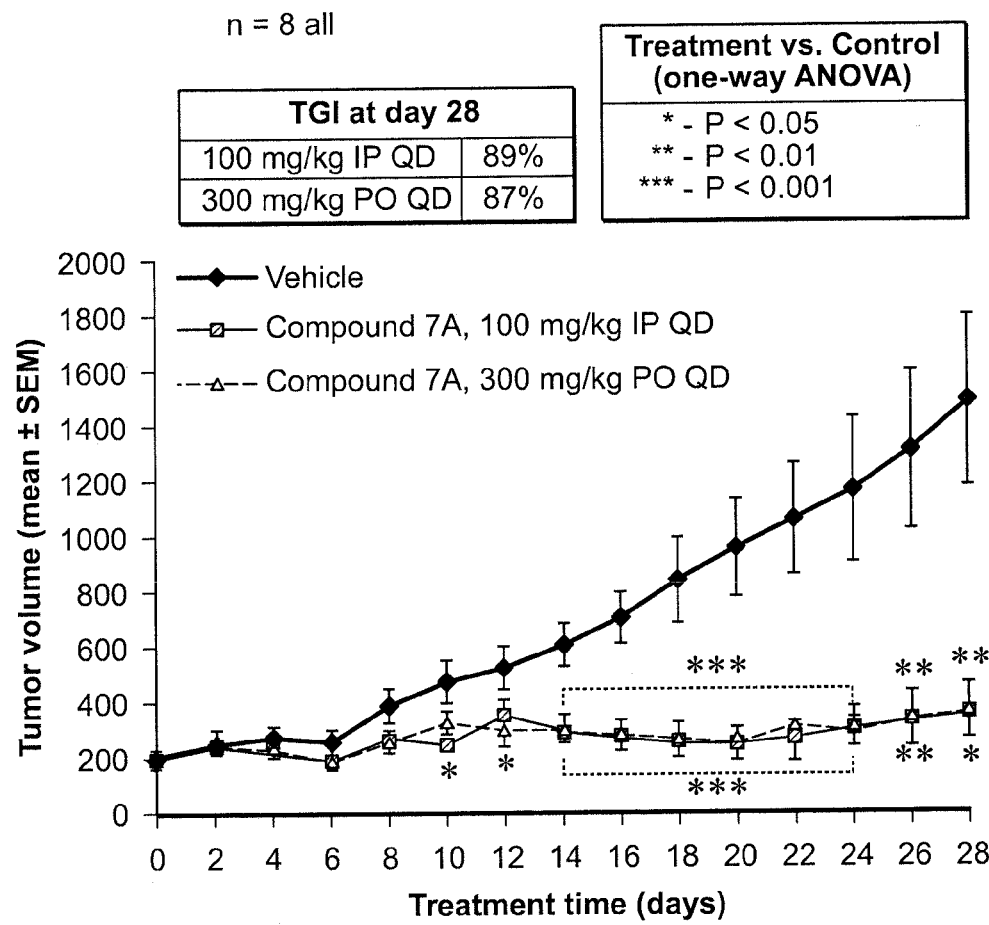
FIG. 2 is a line graph which shows changes in tumor volume in a mouse xenograft study with B-cell lymphoma (Daudi cell line) over 28 days when the mice were treated with vehicle or compound 7A (100 mg/kg and 300 mg/kg).
Figure 3A:
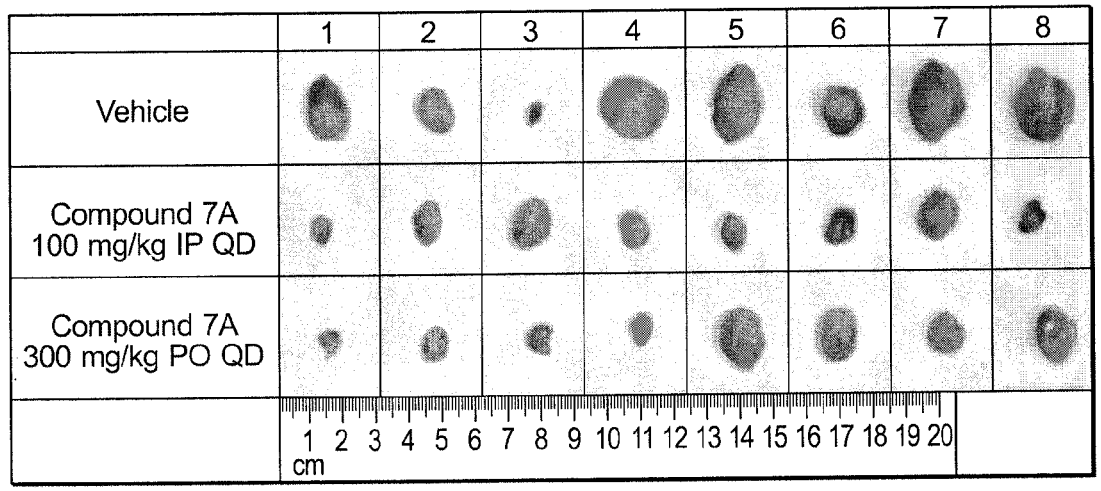
FIG. 3A is a chart which shows changes in tumor size in a mouse xenograft study with B-cell lymphoma (Daudi cell line) when mice were treated with vehicle or compound 7A (100 mg/kg and 300 mg/kg).
Figure 3B:
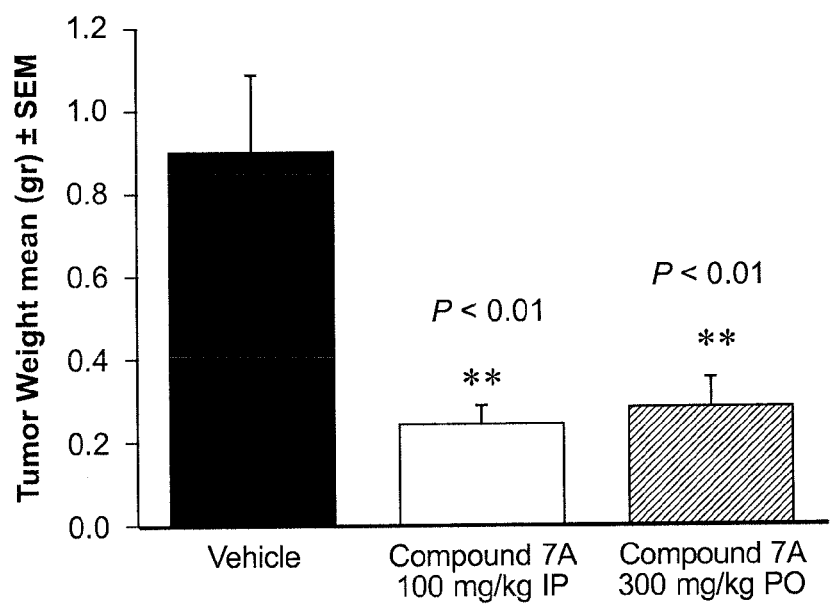
FIG. 3B is a bar graph which compares tumor weight of mice treated with vehicle or compound 7A (100 mg/kg and 300 mg/kg) in a mouse xenograft study with B-cell lymphoma (Daudi cell line) over 28 days.
Figure 3C:
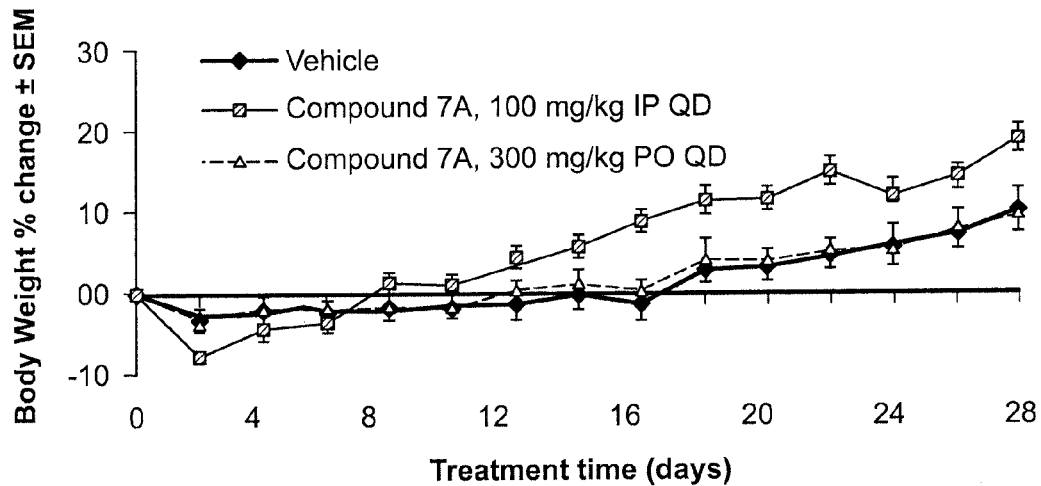
FIG. 3C is a line graph which shows changes in body weight of mice treated with vehicle or compound 7A (100 mg/kg and 300 mg/kg) in a mouse xenograft study with B-cell lymphoma (Daudi cell line) over 28 days.

Mice treated with 100 mg/kg IP QD showed 89% tumor growth inhibition and mice treated with 300 mg/kg PO QD showed 87% tumor growth inhibition. The results of this study are shown in FIGS. 2 and 3. FIG. 2 is shows the changes in tumor volume. FIGS. 3A and 3B compare tumor size and weight and FIG. 3C compares changes in body weight.

Example 8

In Vivo CIA Model

Compounds of the invention were evaluated in mouse collagen induced arthritis (CIA) models. There are several known CIA models as outlined in the table below:

|  | Mild Disease | | Severe Disease Acute disease model |
|---|---|---|---|
|  | Slow-progressing disease model | Semi-therapeutic model |  |
| Immunization | Day −21 type II collagen + complete Freund's Adjuvant | Day −21 type II collagen + complete Freund's Adjuvant | Day −21 type II collagen + complete Freund's Adjuvant |
| Booster | Day −1 type II collagen + incomplete Freund's Adjuvant | Day −1 type II collagen + incomplete Freund's Adjuvant | Day −1 type II collagen + complete Freund's Adjuvant |
| Treatment time | 20 days | 22 days | 11 days |
| Severe disease starts at | ~Day 12 | ~Day 12 | Day 4 |

The CIA studies utilized a mild (slow-progressing) disease model. The DBA/1 mice developed collagen induced arthritis (CIA) after immunization with Hooke Kit™ chicken collagen/Complete Freund's Adjuvant (CFA) emulsion (EK-0210), followed by a booster dose of Hooke Kit™ chicken collagen/Incomplete Freund's Adjuvant (IFA) emulsion (EK-0211). Each study used 54 female DBA/1 mice (Taconic Farms model DBA1BO, 9 weeks old) later assigned to 4 experimental groups with 10 mice per group. 4 mice were not immunized nor treated, and they were left as naïve controls group for possible histological analysis. The other 50 mice were treated therapeutically.

One study comprises group 1—Vehicle, group 2—CP-690550, 30 mg/kg PO QD, group 3—R-788, 60 mg/kg PO QD and group 4—compound 7, 100 mg/kg, IP QD. The other study comprises group 1—Vehicle, group 2—compound 7, 15 mg/kg PO QD, group 3—compound 7, 30 mg/kg PO QD and group 4—compound 7, 100 mg/kg, IP QD.

Mice were first immunized with collagen/CFA emulsion on Day 0 after being acclimated for at least 7 days. The procedure of immunization was as follows: A mouse was immobilized using a restrainer. The tail was cleaned with 70% ethanol and the area was wiped dry with sterile gauze. The syringe containing collagen/CFA emulsion was positioned parallel to the tail and the tip of the needle was pointed toward the body of the mouse, over the space between the dorsal and lateral vein of the tail. The needle was inserted 7 to 10 mm into the subcutaneous space to ensure the needle visible under the skin. The site of needle entry was pressed firmly to prevent any back-leakage of emulsion during the injection. 0.05 ml of the emulsion was injected as the white emulsion was seen entering the subcutaneous space. The needle was kept inserted for 10 to 15 seconds after the injection to avoid leakage of the emulsion. Then the mouse was released back to the cage. The procedure was repeated with all the mice.

The procedure of booster with chicken collagen/IFA on Day 21 was as follows: An immunized mouse was immobilized using a restrainer. The tail was cleaned with 70% ethanol and the area was wiped dry with sterile gauze. The syringe/needle containing type II collagen/IFA emulsion was positioned parallel to the tail and the tip of the needle was pointed toward the body of the mouse. The emulsion was injected at the side of the tail which had not received the initial immunization injection. And the pale area was chosen for injection to avoid puncturing a dilated blood vessel or its close area. The needle was inserted 7 to 10 mm into the subcutaneous space to ensure the needle visible under the skin. The needle and the tail were pressed very tightly at the site of needle entry to prevent any back-leakage of emulsion during the injection. 0.05 ml of the emulsion (or 0.025 ml of emulsion at two sites) was injected very slowly. The needle was kept inserted for 10 to 15 seconds after the injection to avoid leakage of the emulsion. Then the mouse was released back to the cage. The procedure was repeated with all the immunized mice.

Mice were checked for signs of CIA every 2 to 3 days, starting on day 14 after the immunization. As soon as the first signs of joint inflammation occur, the mice were provided with food pellets and wet food on the floor of the cage, and easily accessible water. Transgel (Charles River Laboratories) was used as a source of water.

The immunized mice were initially considered a single group until booster with chicken collagen/IFA on Day 21. Mice with any signs of arthritis on Day 21 were excluded from the study. Each mouse with newly developed clinical signs of CIA was assigned to 1 of the 5 experimental groups in a balanced manner and treatment of those mice was initiated on the same day.

Mice were orally dosed at the same time every day (+/−1 hour) until the end of the study. The compounds of the invention were formulated weekly (3 preparations in total).

All readouts including CIA scores, ankylosis scores, body weight and hind paw thickness, were taken until the end of the study which was 20 days after enrollment of each mouse. The last day of study was different for different mice.

CIA scores: Daily CIA scoring started on Day 21 and continued until 40 mice were enrolled into the study. After enrollment, mice were scored every other day. CIA scoring was performed blind, by a person unaware of both treatment and of previous scores for each mouse. Mice were scored on the scale of 0 to 16 (0 to 4 for each paw, adding the scores for all 4 paws), using the following criteria:

| Paw Score | Clinical Observations |
|---|---|
| 0 | Normal paw. |
| 1 | One toe inflamed and swollen. |
| 2 | More than one toe, but not entire paw, inflamed and swollen, OR Mild swelling of entire paw. |
| 3 | Entire paw inflamed and swollen. |
| 4 | Very inflamed and swollen paw or ankylosed paw. If the paw is ankylosed, the mouse cannot grip the wire top of the cage. |

Ankylosis scores: Ankylosis scoring was performed blind, by a person unaware of both treatment and of previous scores for each mouse. At the same time CIA scoring was performed (both during and after enrollment), ankylosis was scored as the sum of scores from 0-3 for each paw using the following criteria:

| Paw Score | Clinical Observations |
|---|---|
| 0 | No ankylosis |
| 1 | Mild ankylosis |
| 2 | Moderate ankylosis |
| 3 | Severe ankylosis |

Body weight: Body weight was measured on Day −1 (one day before immunization) and then again on the day of enrollment. After enrollment, body weight was measured every other day.

Hind paw thickness: Twice between Days 1 and 14 after immunization (before enrollment begins), both hind paws of all the mice were measured using calipers to establish baseline values for paw thickness. Upon enrollment into one of the experimental groups, each mouse was examined for hind paw swelling. Those mice with a swollen hind paw at that time had that paw measured with calipers. If both hind paws were swollen, the more swollen paw was measured. Those mice thereafter had the same hind paw measured with calipers at the same time as CIA scoring. Mice which first developed paw swelling in a front paw did not have thickness of any of their paws measured after enrollment.

Figure 4A:
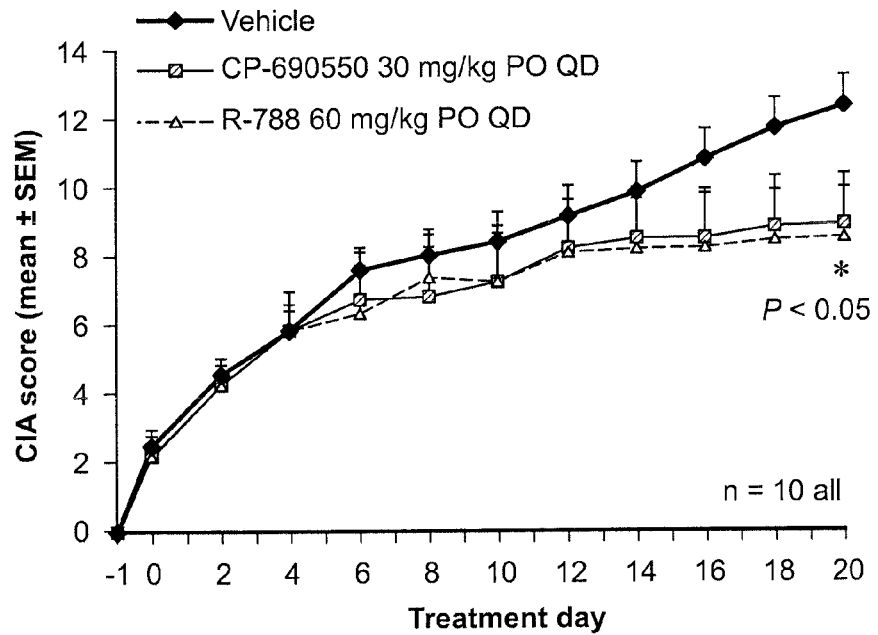
FIG. 4A is a line graph which shows changes in CIA (collagen-induced arthritis) scores in a 20-day study of mice treated with vehicle or CP-690550 (30 mg/kg) or R-788 (60 mg/kg) using a slow-progressing CIA disease model.
Figure 4B:
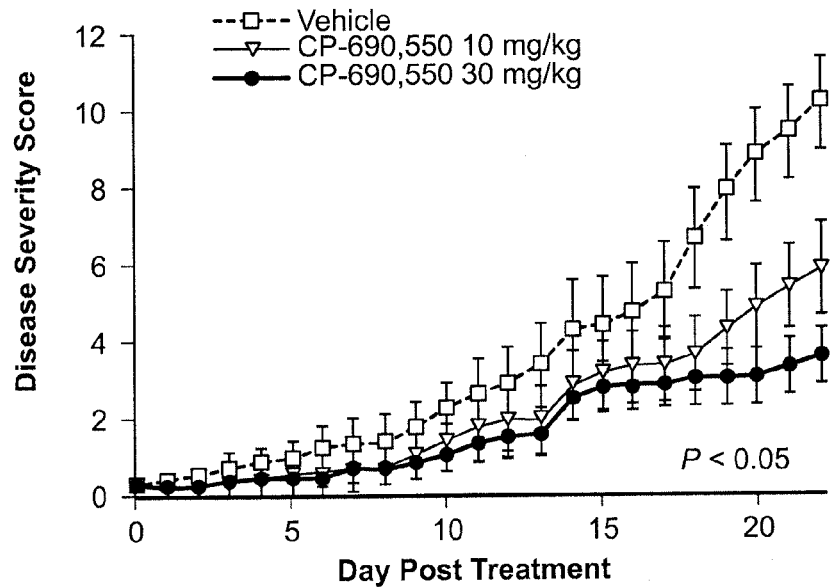
FIG. 4B is a line graph which shows changes in disease severity scores in a 20-day study of collagen-induced arthritis in mice treated with vehicle or CP-690550 (10 and 30 mg/kg) using a semi-therapeutic model.
Figure 4C:
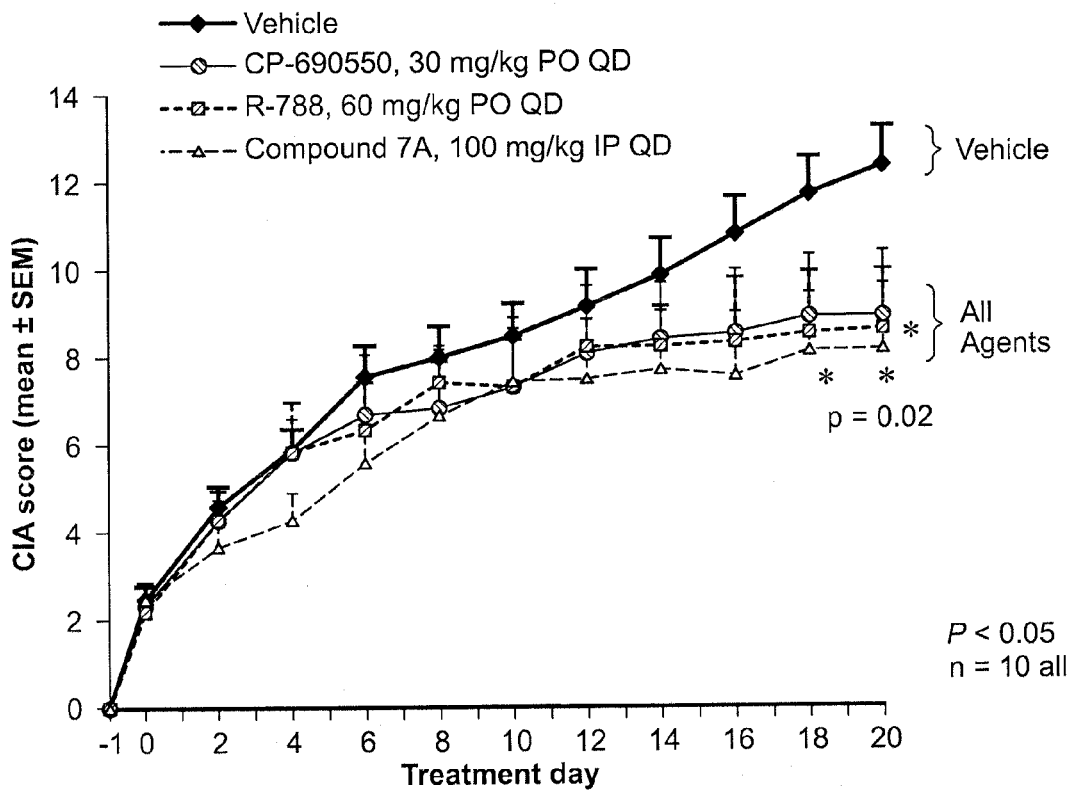
FIG. 4C is a line graph which shows changes in CIA scores in a 20-day study of mice treated with vehicle, CP-690550 (30 mg/kg), R-788 (60 mg/kg), or compound 7A (100 mg/kg) using a slow-progressing CIA disease model.
Figure 4D:
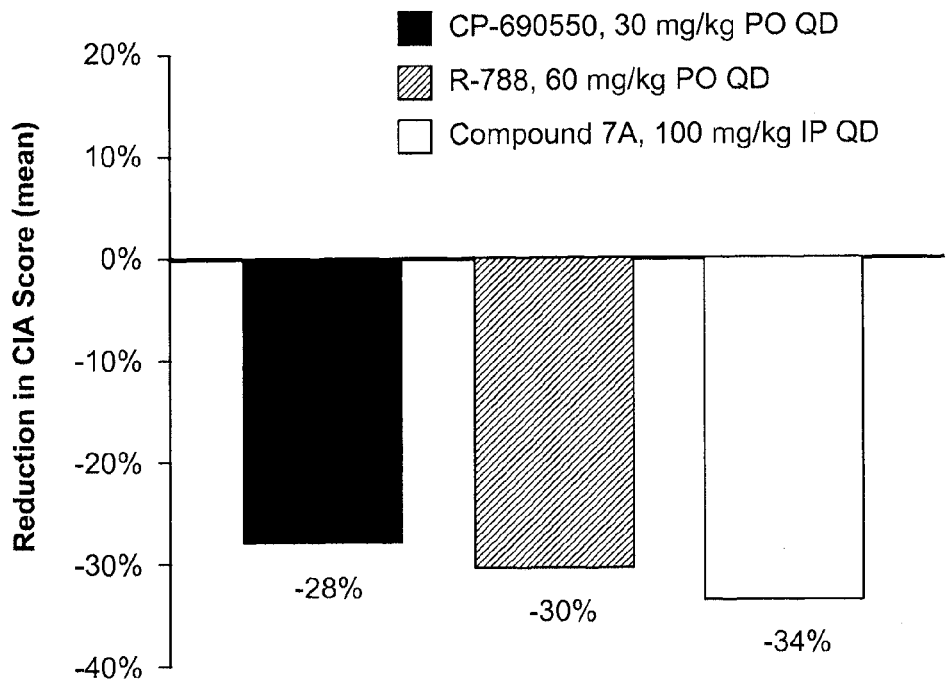
FIG. 4D is a bar graph which compares reduction in CIA score on the last day of a 20-day study of mice treated with CP-690550 (30 mg/kg), R-788 (60 mg/kg), or compound 7A (100 mg/kg) versus mice treated with combined vehicle using a slow-progressing CIA disease model.
Figure 4E:
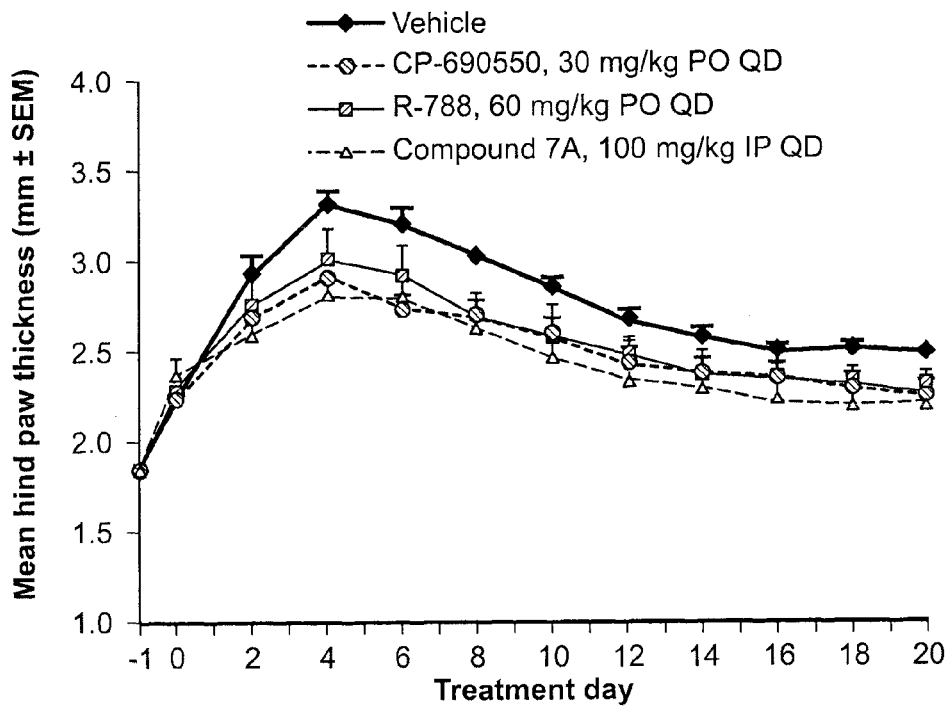
FIG. 4E is a line graph which shows changes in mean hind paw thickness in mm during a 20-day CIA study of mice treated with vehicle, CP-690550 (30 mg/kg), R-788 (60 mg/kg), or compound 7A (100 mg/kg).
Figure 4F:
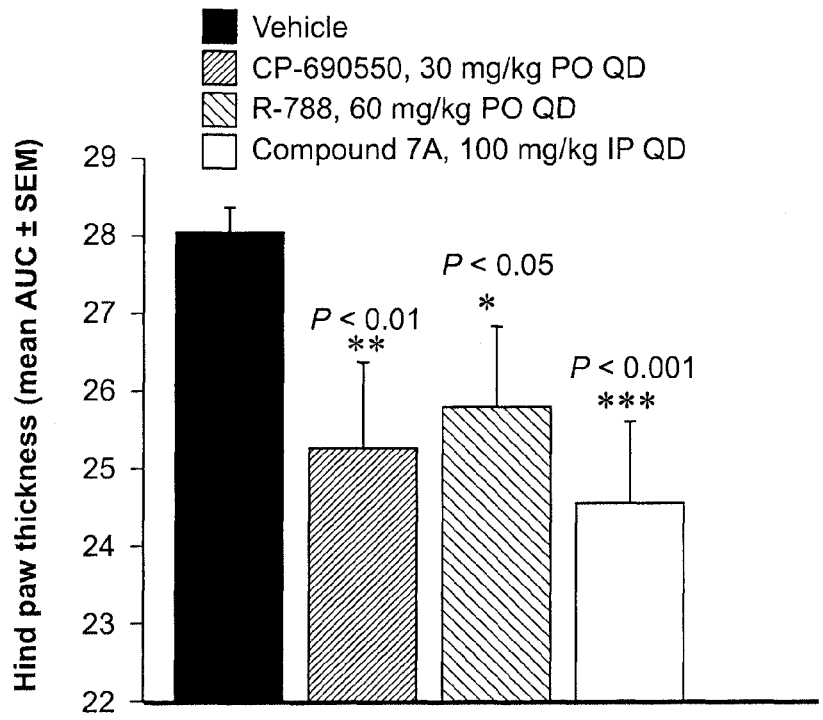
FIG. 4F is a bar graph which compares AUC of hind paw thickness curves during a 20-day CIA study of mice treated with vehicle, CP-690550 (30 mg/kg), R-788 (60 mg/kg), or compound 7A (100 mg/kg).
Figure 4G:
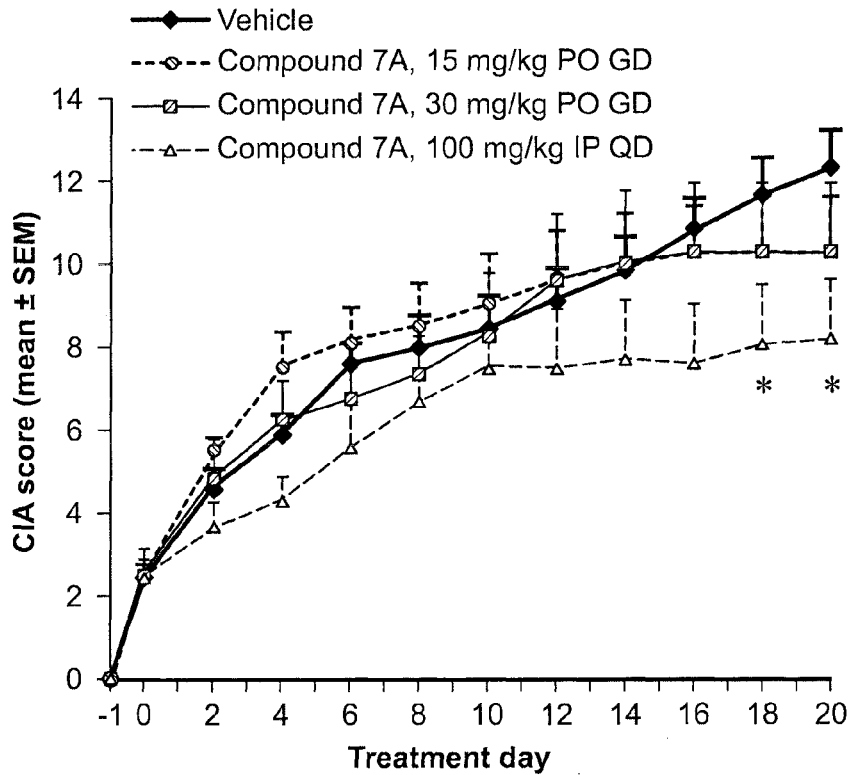
FIG. 4G is a line graph which shows changes in mean CIA scores during a 20-day CIA study of mice treated with vehicle or compound 7A (at 15, 30, and 100 mg/kg) using a slow-progressing CIA disease model.
Figure 4H:
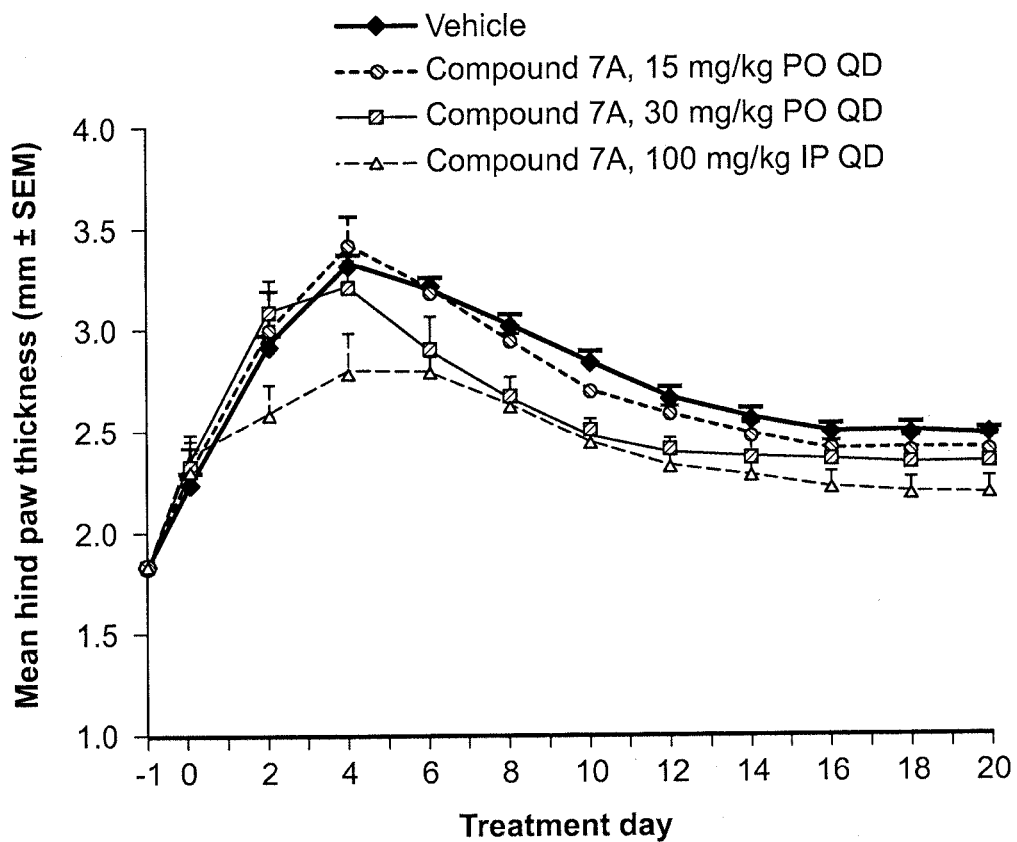
FIG. 4H is a line graph which shows changes in mean hind paw thickness in mm during a 20-day CIA study of mice treated with vehicle or compound 7A (at 15, 30, and 100 mg/kg) using a slow-progressing CIA disease model.
Figure 4I:
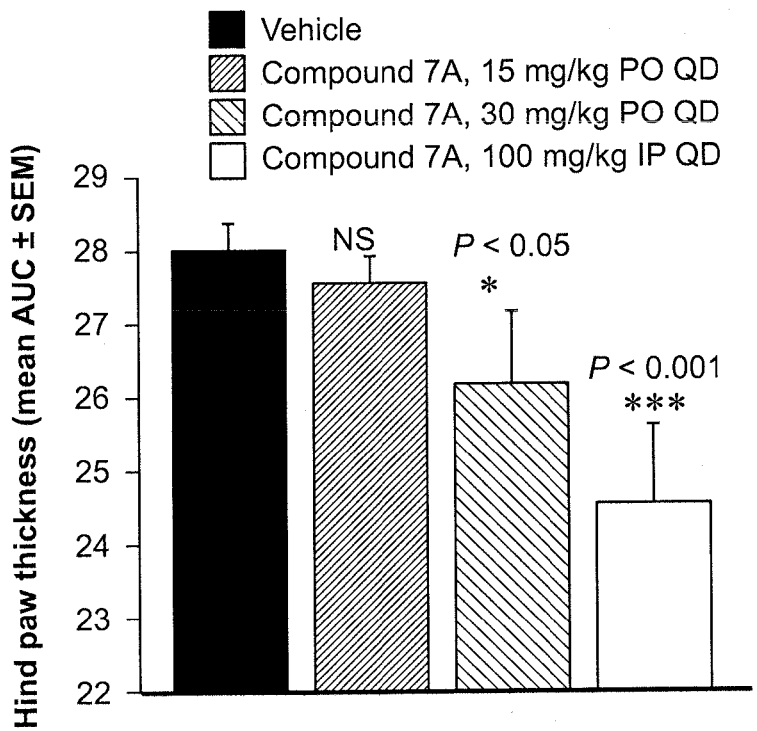
FIG. 4I is a bar graph which compares mean AUC of hind paw thickness curves during a 20-day CIA study of mice treated with vehicle or compound 7A (15, 30, and 100 mg/kg) using a slow-progressing CIA disease model.

FIGS. 4A and 4B show the results of positive controls in mild disease models. The control compounds are CP-690,550 (tofacitinib), a pan-JAK inhibitor in Phase III clinical trials for Pfizer and R-788 (fostamatinib), a non-selective SYK inhibitor in Phase III clinical trials for Rigel/AstraZeneca. FIG. 4A shows the CIA score over 20 treatment days with the positive controls in the known mild disease model. CP-690, 550 was administered at 30 mg/kg PO QD and R-788 was administered at 60 mg/kg PO QD. FIG. 4B shows the disease severity score for 20 days post treatment with positive controls in the known semi-therapeutic CIA model (Pfizer 2010) (H. T. Lin et al., Arthritis Rheum. (2010), 62:2283-93). CP-690,550 was administered at 10 mg/kg and 30 mg/kg. FIG. 4C shows the results of compound 7A in the mild CIA model in comparison to controls. Compound 7A was administered at 100 mg/kg IP QD, n=10 all; P<0.05. Compound 7A showed a reduction in CIA score on the last day vs. combined vehicle (FIG. 4D). An increase in hind paw thickness is a sign of arthritis. FIGS. 4E and 4F show the results of hind paw thickness following treatment over 20 days administering compound 7A at 100 mg/kg IP QD in comparison to positive controls. FIG. 4G shows CIA scores for compound 7A administered at 3 different dosage amounts (15 mg/kg PO QD, 30 mg/kg PO QD, and 100 mg/kg IP QD) over 20 days.

Example 9

Synthesis of Compounds of the Invention

Provided below are illustrative synthetic examples of the compounds of the invention. Note that the compound numbers referred to in the synthesis described herein correspond to the numbers shown in the related scheme which proceeds the description of the synthesis.

Synthesis of Compound:

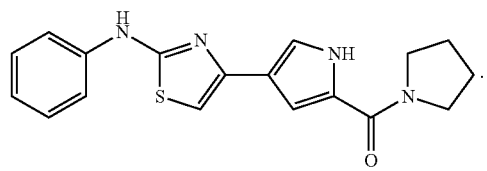 [SMILES: O=C(c1cc(-c2csc(Nc3ccccc3)n2)c[nH]1)N1CCCC1]

Scheme 10

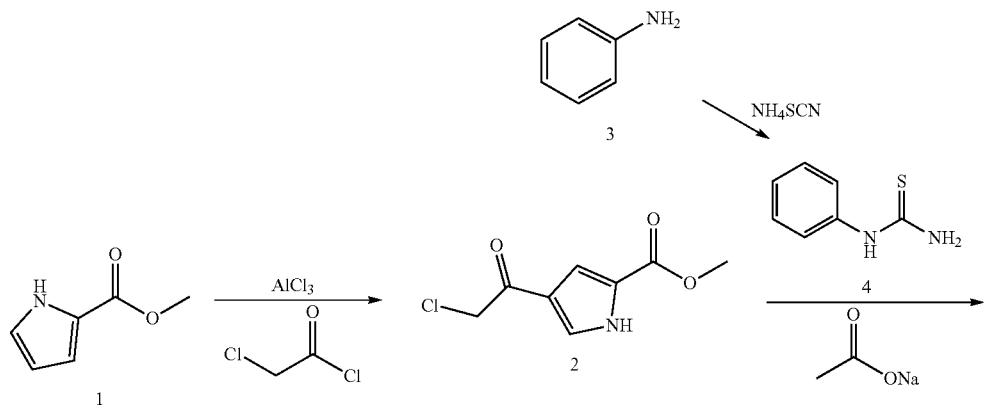

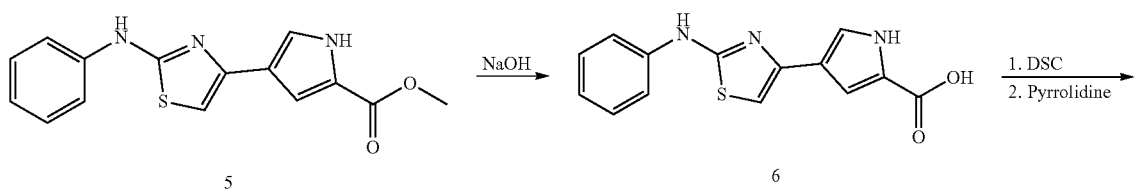

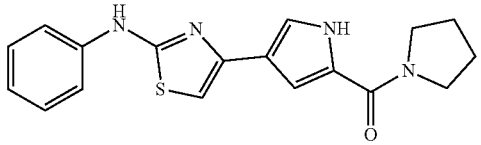

7

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (Quantitative, yellow powder).

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over $Na_2SO_4$ and evaporated yielding of gray solid (9 g, 90% yield).

Reagents Table-Synthesis of 4

| Reagent/raw material | MW (gr/mole) | Quantity | mmoles |
|---|---|---|---|
| Aniline | 93 | 9.11 mL | 100 |
| Ammonium isothiocyanate | 76 | 11.4 g | 150 |
| HCl 1N | — | 100 mL | — |

Procedure

Both reagents were refluxed overnight in HCl 1N. When full conversion was observed, reaction was stopped and the mixture was cooled on ice bath. The precipitate formed was collected by filtration and washed with water (30 mL). Yield 4.5 g (30%).

Reagents Table-Synthesis of 5

| Reagent/raw material | MW (gr/mole) | Quantity | mmoles |
|---|---|---|---|
| Phenyl thiourea | 152.22 | 3.04 g | 20 |
| Methyl 4-(2-chloroacetyl)-1H-pyrrole-2-carboxylate | 201.6 | 4.03 g | 20 |
| Sodium acetate | 82 | 3.28 g | 40 |
| Acetic acid | — | 20 mL | — |

Reagents Table-Synthesis of 6

| Reagent/raw material | MW (gr/mole) | Quantity | mmoles |
|---|---|---|---|
| Methyl 4-(2-(phenylamino)thiazol-4-yl)-1H-pyrrole-2-carboxylate | 299 | 5.98 g | 20 |
| NaOH | 40 | 3.2 g | 80 |
| Dioxane | — | 100 mL | — |
| $H_2O$ | — | 50 mL | — |

Procedure

NaOH was added to a mixture of the ester in Dioxane-$H_2O$ 2:1 (150 mL). The mixture was heated to 70-80° C. during which a dark solution is formed. When reaction was completed the organic solvent was evaporated and the residue was acidified to pH −5 using concentrated hydrochloric acid. The product was extracted to ethyl acetate (if extraction fails additional HCl 1N should be added), dried over $Na_2SO_4$ and evaporated yielding green powder (quantitative yield).

Reagents Table-Synthesis of 7

| Reagent/raw material | MW (gr/mole) | Quantity | mmoles |
|---|---|---|---|
| 4-(2-(Phenylamino)thiazol-4-yl)-1H-pyrrole-2-carboxylic acid | 285 | 2.85 g | 10 |
| bis(2,5-Dioxopyrrolidin-1-yl)carbonate | 256.17 | 2.56 g | 10 |
| Acetonitrile | — | 200 mL | — |
| Triethylamine | 101 | 4.15 mL | 30 |
| Pyrrolidine | 71.12 | 1.25 mL | 15 |

Procedure

Triethylamine was added to a mixture of the acid in acetonitrile resulting in clear solution. The activating agent was then added and the components were stirred at rt. Active ester formation was monitored by HPLC and small portions of the activating agent were added until a point of 90-95% conversion. Then, pyrrolidine was added and an immediate formation of the amide (precipitate) was observed. Additional portions of pyrrolidine were added until full conversion of the active ester was observed. The organic solvent was removed under reduced pressure. DCM was added along with saturated bicarbonate solution. The precipitate formed upon shaking in the separatory funnel was collected by filtration and washed with boiling MeOH. (1.3 g, 38%). HPLC—98% purity. LCMS—(ES$^+$) Calcd. 338.43. Found 339.25 (MH$^+$).

Synthesis of Compound:

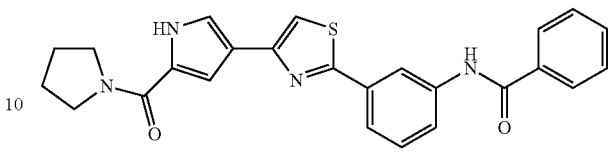

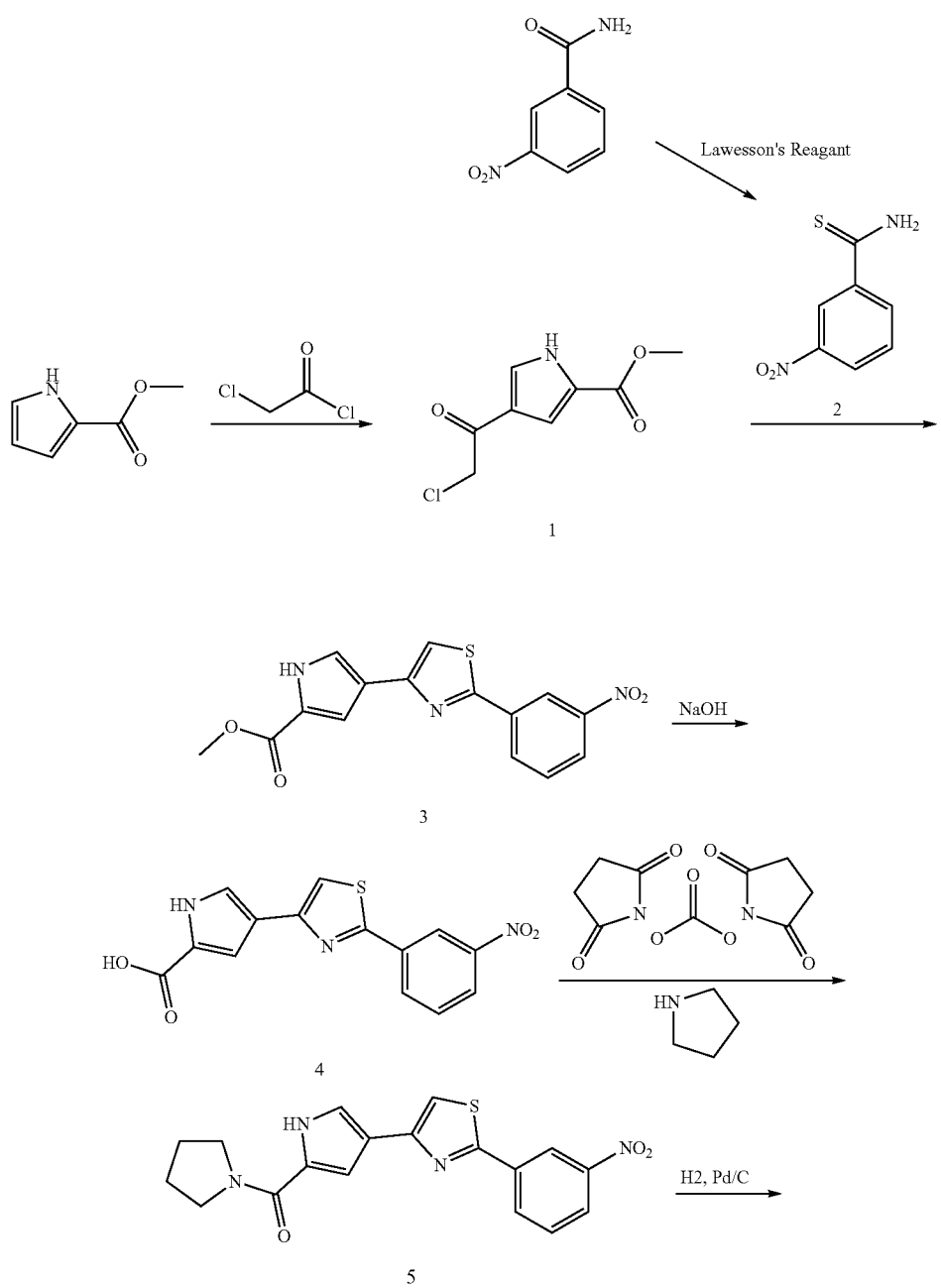

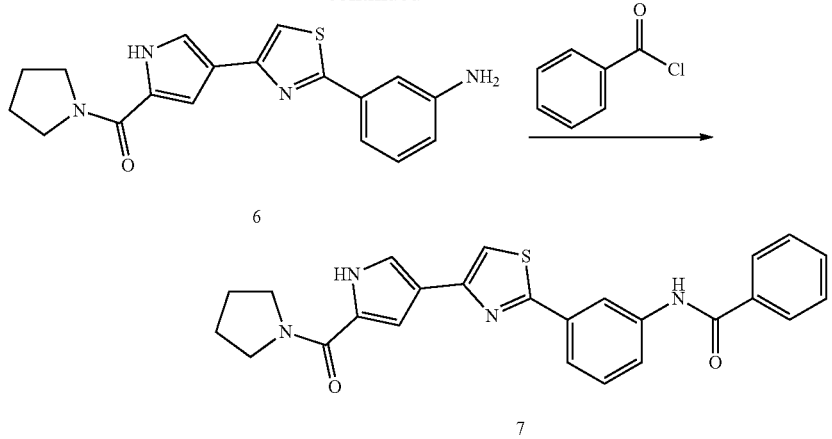

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over Na₂SO₄ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF (2:1). The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in Dioxane-H₂O (2:1). The reaction mixture was heated to 70-80° C. during which a dark solution is formed. When reaction was completed the organic solvent was evaporated and the residue was acidified using concentrated hydrochloric acid. The product was extracted to ethyl acetate, dried over Na$_2$SO$_4$ and evaporated yielding yellow-green powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl)carbonate | 256.17 | 2.56 g | 10 |
| Acetonitrile | — | 200 mL | — |
| Triethylamine | 101 | 4.15 mL | 22 |
| pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC and small portions of the activating agent were added until a point of 90-95% conversion. Then, pyrrolidine was added and an immediate formation of the amide (precipitate) was observed. Additional portions of pyrrolidine were added until full conversion of the active ester was observed. The Organic solvent was removed under reduced pressure. Saturated solution of bicarbonate was added and the product was taken to DCM (~1000 mL, washed with additional portion of bicarbonate, dried over Na$_2$SO$_4$ and evaporated yielding yellow powder (quantitative yield).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1- | 368.41 | 2 g | 5.4 |

| Reagent/raw material | MW (gr/mole) | Quantity | mmoles |
|---|---|---|---|
| yl)methanone | | | |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.43 | 0.507 g | 1.5 |
| Benzoyl chloride | 140.57 | 0.174 mL | 1.5 |
| Triethylamine | 101 | 0.62 mL | 4.5 |

Synthesis of 7

The components were stirred in a mixture of DCM-THF 3:1. The solvents were removed under reduced pressure and the product was crystallized from MeOH. (170 mg, 25%), HPLC—98% purity. LCMS—(ES$^+$) Calcd. 442.53. Found 443.46 (MH$^+$).

Synthesis of Compound:

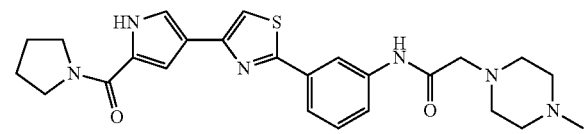 [SMILES: CN1CCN(CC(=O)Nc2cccc(-c3nc(-c4c[nH]c(C(=O)N5CCCC5)c4)cs3)c2)CC1]

Scheme 12

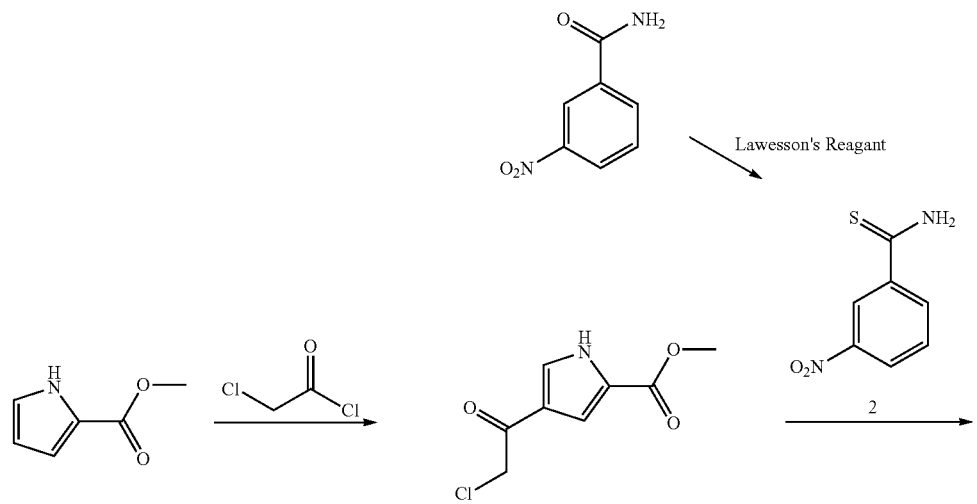

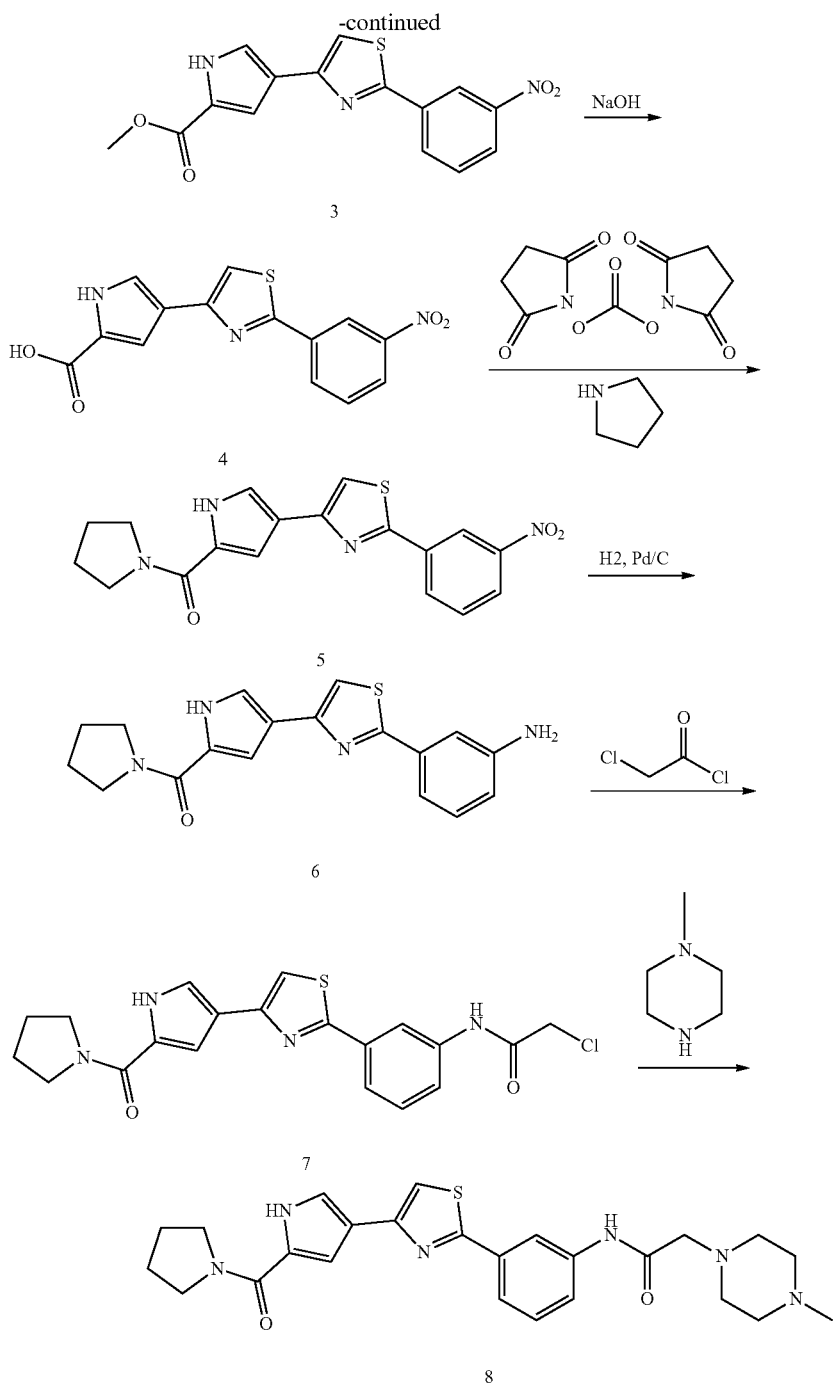

Reagents Table-Synthesis of 1

| Reagent/raw material | MW (gr/mole) | Quantity | mmoles |
| --- | --- | --- | --- |
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO$_3$ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in Dioxane-H$_2$O 2:1. The mixture was heated to 70-80° C. during which a dark solution is formed. When reaction was completed the organic solvent was evaporated and the residue was acidified using concentrated hydrochloric acid. The product was extracted to ethyl acetate, dried over Na$_2$SO$_4$ and evaporated yielding yellow-green powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl)carbonate | 256.17 | 2.56 g | 10 |
| Acetonitrile | — | 200 mL | — |
| Triethylamine | 101 | 4.15 mL | 22 |
| Pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC and small portions of the activating agent were added until a point of 90-95% conversion. Then, pyrrolidine was added and an immediate formation of the amide (precipitate) was observed. Additional portions of pyrrolidine were added until full conversion of the active ester was observed. The Organic solvent was removed under reduced pressure. Saturated solution of bicarbonate was added and the product was taken to DCM (~1000 mL, washed with additional portion of bicarbonate, dried over Na$_2$SO$_4$ and evaporated yielding yellow powder (quantitative yield).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7 and 8

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.43 | 0.507 g | 1.5 |
| Chloroacetylchloride | 113 | 0.13 mL | 1.65 |
| Triethylamine | 101 | 0.62 mL | 4.5 |
| 1-Methyl piperazine* | 100 | 0.33 mL | 3 |
| Triethylamine* | 101 | 0.62 mL | 4.5 |

*Synthesis of 8

Synthesis of 7

A solution of chloroacetylchloride in DCM (30 mL) was added dropwise to a mixture of aniline and triethylamine in DCM (50 mL) under cooling on ice bath (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with 1-methylpiperazine and triethylamine. The mixture was refluxed vigorously for 2 hours (1-methylpiperazine is added if needed for reaction completion). When the reaction was completed, heating was stopped, and the solvent was removed under reduced pressure. The oily residue was triturated in boiling acetone. (Yield—150 mg, 20%). HPLC—100% purity. LCMS—(ES$^+$) Calcd. 478.61. Found 479.56 (MH$^+$).

Synthesis of Compound:

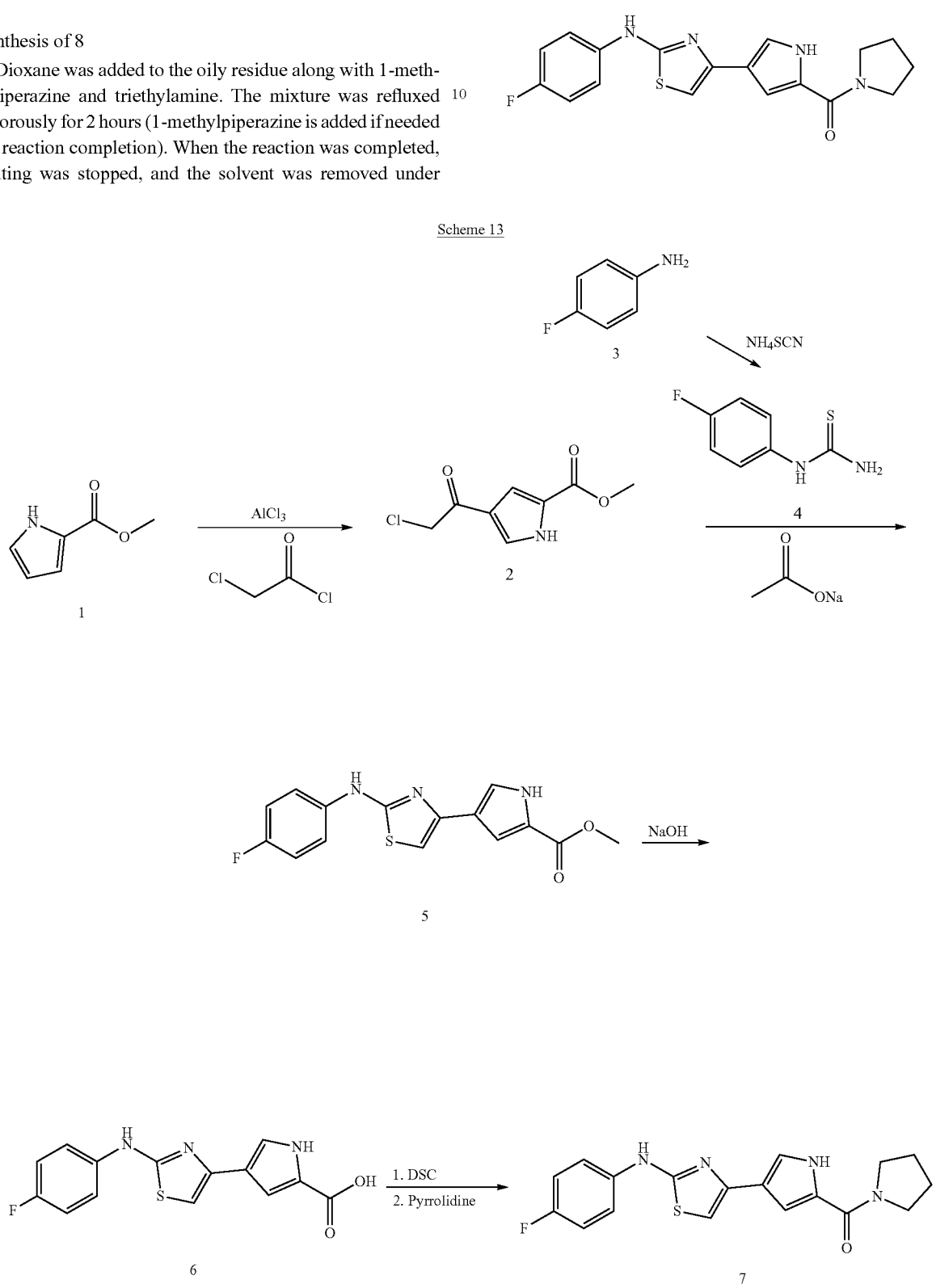

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; The organic phase was dried over Na₂SO₄ and evaporated yielding of gray solid (9 g, 90% yield).

Reagents Table-Synthesis of 4

| Reagent/raw material | MW (gr/mole) | Quantity | mmoles |
|---|---|---|---|
| 4-Fluoroaniline | 111.12 | 5.55 g | 50 |
| Ammonium isothiocyanate | 76 | 5.7 g | 75 |
| HCl 1N | — | 50 mL | — |

Procedure

Both reagents were refluxed overnight in HCl 1N. The orange color of the aniline disappeared after 1 h. The mixture was cooled and the precipitate formed was collected by filtration and washed with water (30 mL). Yield 3 g (35%).

Reagents Table-Synthesis of 5

| Reagent/raw material | MW (gr/mole) | Quantity | mmoles |
|---|---|---|---|
| 4-Fluorophenyl thiourea | 170.2 | 1.70 g | 10 |
| Methyl 4-(2-chloroacetyl)-1H-pyrrole-2-carboxylate | 201.6 | 2.01 g | 10 |
| Sodium acetate | 82 | 1.64 g | 20 |
| Acetic acid | — | 10 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. White powder, quantitative yield.

Reagents Table-Synthesis of 6

| Reagent/raw material | MW (gr/mole) | Quantity | mmoles |
|---|---|---|---|
| Methyl 4-(2-((4-fluorophenyl)amino)thiazol-4-yl)-1H-pyrrole-2-carboxylate | 317 | 3.11 g | 9.8 |
| NaOH | 40 | 1.57 g | 40 |
| Dioxane | — | 100 mL | — |
| H₂O | — | 50 mL | — |

Procedure

NaOH was added to a mixture of the ester in Dioxane-H₂O 2:1 (150 mL). The mixture was heated to 70-80° C. during which a dark solution is formed. When reaction was completed the organic solvent was evaporated and the residue was acidified to pH ~1-2 using hydrochloric acid (1N). The product was extracted to ethyl acetate, dried over Na₂SO₄ and evaporated yielding green powder (2.5 g, 84%).

Reagents Table-Synthesis of 7

| Reagent/raw material | MW (gr/mole) | Quantity | mmoles |
|---|---|---|---|
| 4-(2-((4-Fluorophenyl)amino)thiazol-4-yl)-1H-pyrrole-2-carboxylic acid | 303 | 0.61 g | 2 |
| bis(2,5-Dioxopyrrolidin-1-yl)carbonate | 256.17 | 0.51 g | 2 |
| Acetonitrile | — | 60 mL | — |
| Dioxane | — | 20 mL | — |
| Triethylamine | 101 | 0.83 mL | 6 |
| pyrrolidine | 71.12 | 0.33 mL | 4 |

Procedure

Triethylamine was added to a mixture of the acid and activating agent in acetonitrile. No solubility was observed, dioxane was added resulting in clear solution. Active ester formation was monitored by HPLC and small portions of the activating agent were added until a point of 90-95% conversion. Then, pyrrolidine was added and an immediate formation of the amide (precipitate) was observed. Additional portions of pyrrolidine were added until full conversion of the active ester was observed. The organic solvent was removed under reduced pressure. Ethyl acetate was added along with saturated bicarbonate solution. The precipitate formed upon shaking in the separatory funnel was collected by filtration. The organic phase was dried over Na₂SO₄, filtrated and evaporated yielding brown oil which was triturated using EtOH (Yield 25 mg, 3.5%). HPLC—100% purity. LCMS—(ES⁺) Calcd. 356.42. Found 357.33 (MH⁺).

Synthesis of Compound:

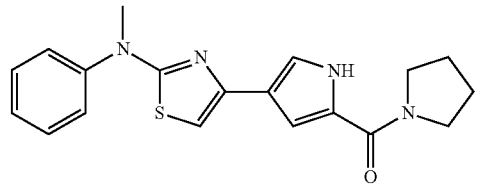 [SMILES: CN(c1ccccc1)c1nc(-c2c[nH]c(C(=O)N3CCCC3)c2)cs1]

Scheme 14
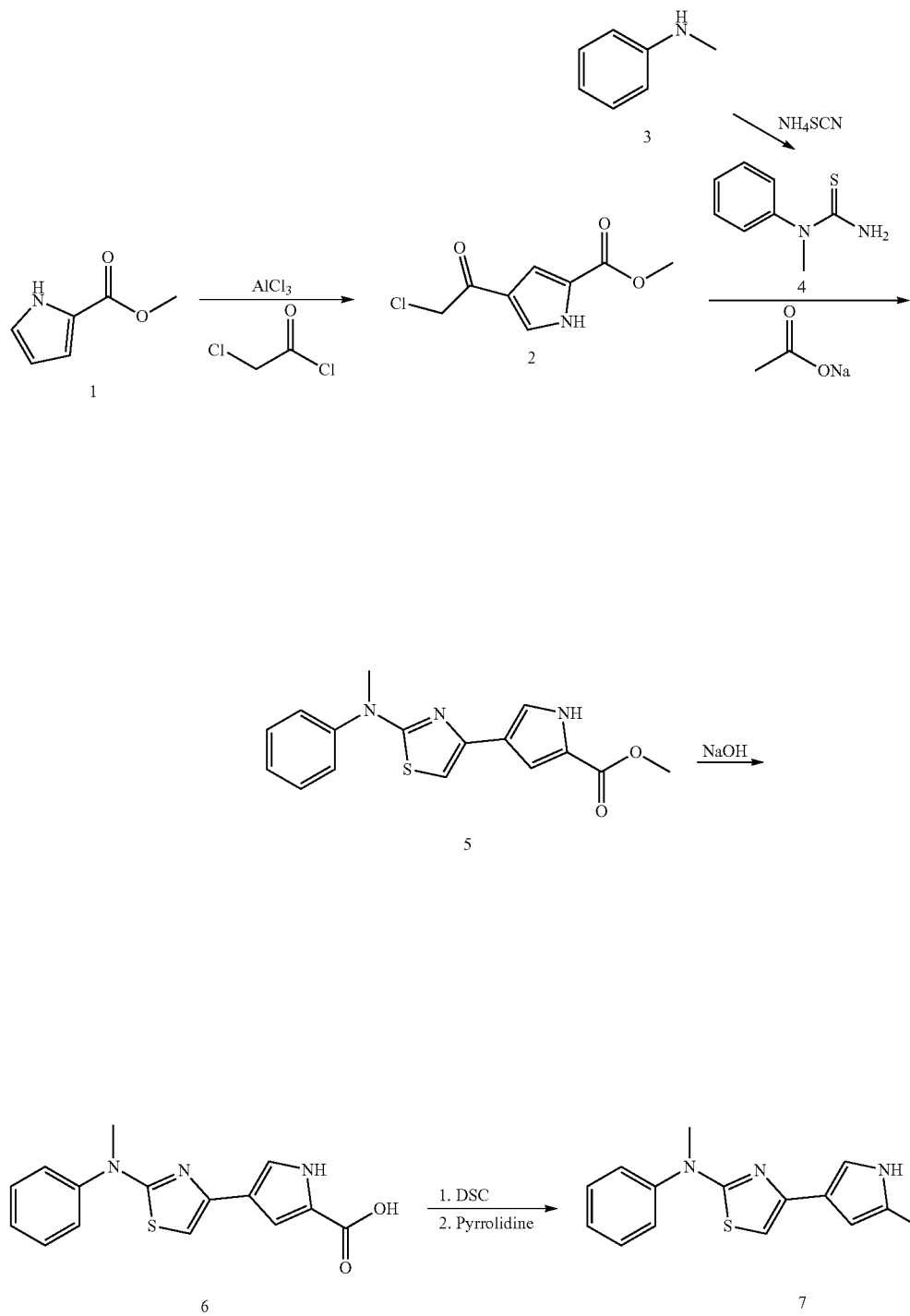

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over Na₂SO₄ and evaporated yielding of gray solid (9 g, 90% yield).

Reagents Table-Synthesis of 4

| Reagent/raw material | MW (gr/mole) | Quantity | mmoles |
|---|---|---|---|
| N-Methylaniline | 166 | 8.3 g | 50 |
| Ammonium isothiocyanate | 76 | 5.7 g | 75 |
| HCl 1N | — | 50 mL | — |

Procedure

Both reagents were refluxed overnight in HCl 1N. The product was extracted to ethyl acetate (100 mL). The organic phase was dried over Na₂SO₄ and evaporated yielding oily residue.

Reagents Table-Synthesis of 5

| Reagent/raw material | MW (gr/mole) | Quantity | mmoles |
|---|---|---|---|
| 1-Methyl-1-phenylthiourea | 166.2 | 1.16 g | 7 |
| Methyl 4-(2-chloroacetyl)-1H-pyrrole-2-carboxylate | 201.6 | 1.41 g | 7 |
| Sodium acetate | 82 | 1.15 g | 14 |
| Acetic acid | — | 7 mL | — |

Procedure

The reagents were stirred in acetic acid and heated to reflux resulting in a clear solution. When full conversion was observed the organic phase was taken in ethyl acetate and washed with water. The organic phase was dried over Na₂SO₄ and evaporated yielding brown oily product (2.1 g, 95%).

Reagents Table-Synthesis of 6

| Reagent/raw material | MW (gr/mole) | Quantity | mmoles |
|---|---|---|---|
| Methyl 4-(2-(methyl(phenyl)amino)thiazol-4-yl)-1H-pyrrole-2-carboxylate | 313.37 | 2 g | 6.4 |
| NaOH | 40 | 1.02 g | 25.5 |
| Dioxane | — | 100 mL | — |
| H₂O | — | 50 mL | — |

Procedure

NaOH was added to a mixture of the ester in Dioxane-H₂O 2:1 (150 mL). The mixture was heated to 70-80° C. during which a dark solution is formed. When reaction was completed the organic solvent was evaporated and the residue was acidified to pH −1-2 using hydrochloric acid (1N). The product was extracted to ethyl acetate, dried over Na₂SO₄ and evaporated yielding brown foam (1.6 g, 84%).

Reagents Table-Synthesis of 7

| Reagent/raw material | MW (gr/mole) | Quantity | mmoles |
|---|---|---|---|
| 4-(2-(Methyl(phenyl)amino)thiazol-4-yl)-1H-pyrrole-2-carboxylic acid | 299.35 | 1.67 g | 5.6 |
| bis(2,5-Dioxopyrrolidin-1-yl)carbonate | 256.17 | 1.43 g | 5.6 |
| Acetonitrile | — | 60 mL | — |
| Dioxane | — | 20 mL | — |
| Triethylamine | 101 | 2.3 mL | 16.7 |
| Pyrrolidine | 71.12 | 0.93 mL | 11.2 |

Procedure

The acid, Et₃N and the activating agent were taken in a mixture of acetonitrile-dioxane 1:1 (100 mL). Active ester formation was monitored by HPLC and small portions of the activating agent were added until a point of full conversion. Then, pyrrolidine was added and the mixture was stirred at rt. The organic solvents were removed under reduced pressure. Ethyl acetate was added and the organic phase was washed with saturated bicarbonate solution, dried over Na₂SO₄, filtrated and evaporated yielding brown foam which was triturated using boiling EtOH (brown powder, 160 mg, 8%). HPLC—100% purity. LCMS—(ES⁺) Calcd. 352.45. Found 353.32 (MH⁺).

Synthesis of Compound:

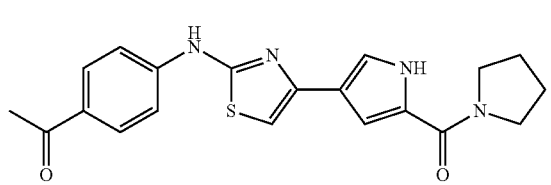 [SMILES: CC(=O)c1ccc(Nc2nc(-c3c[nH]c(C(=O)N4CCCC4)c3)cs2)cc1]

Scheme 15

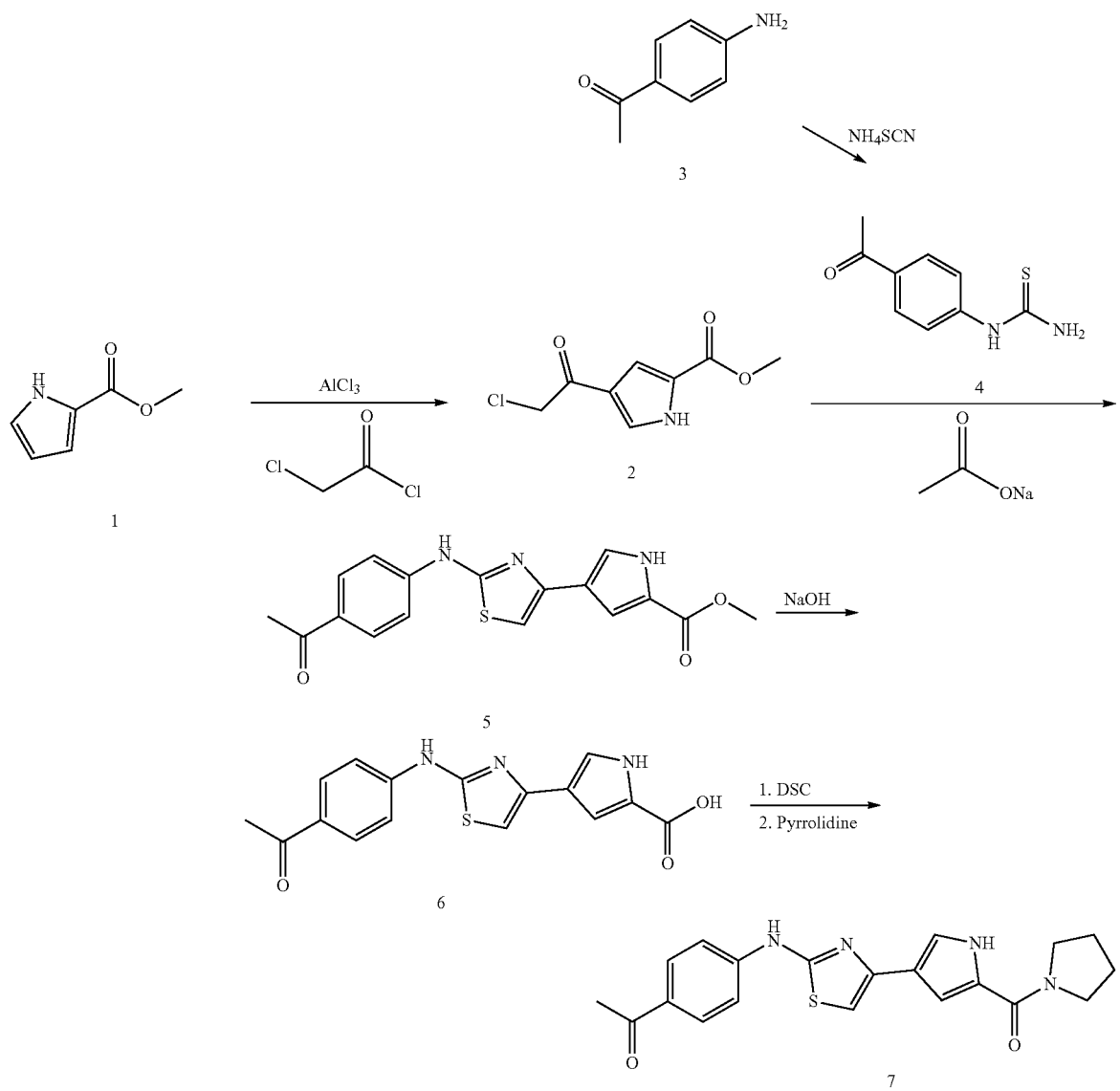

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution. The organic phase was dried over Na₂SO₄ and evaporated yielding of gray solid (9 g, 90% yield).

Reagents Table-Synthesis of 4

| Reagent/raw material | MW (gr/mole) | Quantity | mmoles |
|---|---|---|---|
| 1-(4-Aminophenyl)ethanone | 135 | 2.5 g | 18.5 |
| Ammonium isothiocyanate | 76 | 2.11 g | 27.7 |
| HCl 1N | | 15 mL | |

Procedure

Both reagents were refluxed overnight in HCl 1N. Precipitate was formed, HCl 1N (10 mL) was added and the mixture was cooled on ice bath. The yellow solid was collected by filtration (2.5 g, 70%).

Reagents Table-Synthesis of 5

| Reagent/raw material | MW (gr/mole) | Quantity | mmoles |
|---|---|---|---|
| 1-(4-Acetylphenyl)thiourea | 194.25 | 1.36 g | 7 |
| Methyl 4-(2-chloroacetyl)-1H-pyrrole-2-carboxylate | 201.6 | 1.41 g | 7 |
| Sodium acetate | 82 | 1.15 g | 14 |
| Acetic acid | — | 7 mL | — |

Procedure

The reagents were stirred in acetic acid and heated to reflux. When full conversion was observed the mixture was cooled to rt. The solid was collected by filtration, washed with ice water (80 mL) Yielding yellow powder (quantitative yield).

Reagents Table-Synthesis of 6

| Reagent/raw material | MW (gr/mole) | Quantity | mmoles |
|---|---|---|---|
| Methyl 4-(2-((4-acetylphenyl)amino)thiazol-4-yl)-1H-pyrrole-2-carboxylate | 341.38 | 2.38 g | 7 |
| NaOH | 40 | 1.12 g | 28 |
| Dioxane | — | 100 mL | — |
| H$_2$O | — | 50 mL | — |

Procedure

NaOH was added to a mixture of the ester in Dioxane-H$_2$O 2:1 (150 mL). The mixture was heated to 70-80° C. during which a dark solution is formed. When reaction was completed the organic solvent was evaporated and the residue was acidified to pH −1-2 using hydrochloric acid (1N). The product was collected by filtration (1.34 g, 58%).

Reagents Table-Synthesis of 7

| Reagent/raw material | MW (gr/mole) | Quantity | mmoles |
|---|---|---|---|
| 4-(2-((4-Acetylphenyl)amino)thiazol-4-yl)-1H-pyrrole-2-carboxylic acid | 327.36 | 0.98 g | 3 |
| bis(2,5-Dioxopyrrolidin-1-yl)carbonate | 256.17 | 0.768 g | 3 |
| Acetonitrile | — | 75 mL | — |
| Dioxane | — | 75 mL | — |
| Triethylamine | 101 | 1.25 mL | 9 |
| Pyrrolidine | 71.12 | 0.50 mL | 6 |

Procedure

The acid, Et$_3$N and the activating agent were taken in a mixture of acetonitrile-dioxane 1:1 (100 mL). DMF was added in order to achieve solubility. Active ester formation was monitored by HPLC and small portions of the activating agent were added until a point of full conversion. Then, pyrrolidine was added and the mixture was stirred at rt. The organic solvents were removed under reduced pressure and the residue was triturated using water and ethanol. The mixture was boiled and the solid was collected by filtration. Yield 60 mg (5%). HPLC—100% purity. LCMS—(ES$^+$) Calcd. 380.46. Found 381.38 (MH$^+$).

Synthesis of Compound:

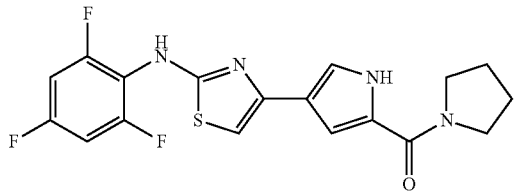 [SMILES: O=C(c1cc(-c2csc(Nc3c(F)cc(F)cc3F)n2)c[nH]1)N1CCCC1]

Scheme 16

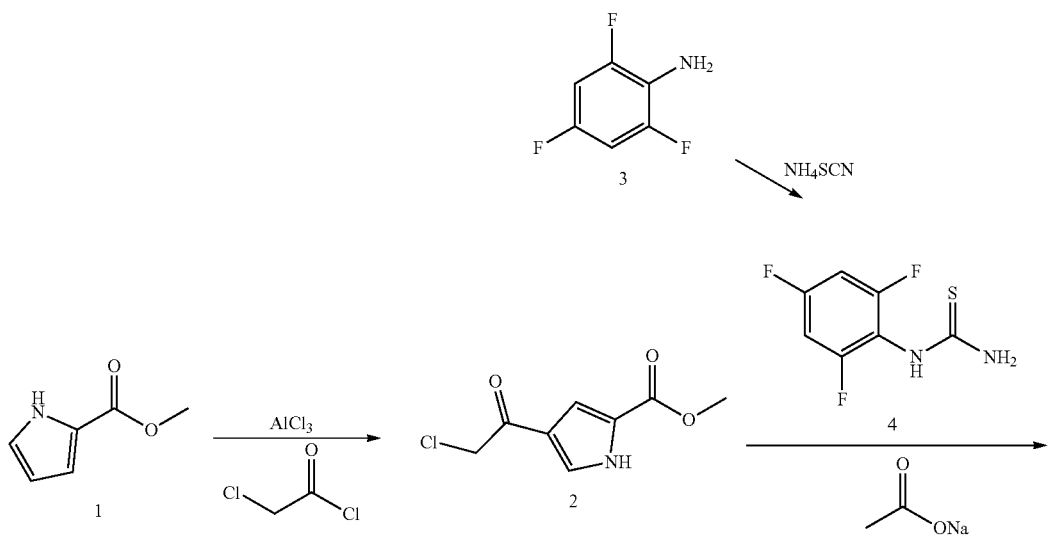

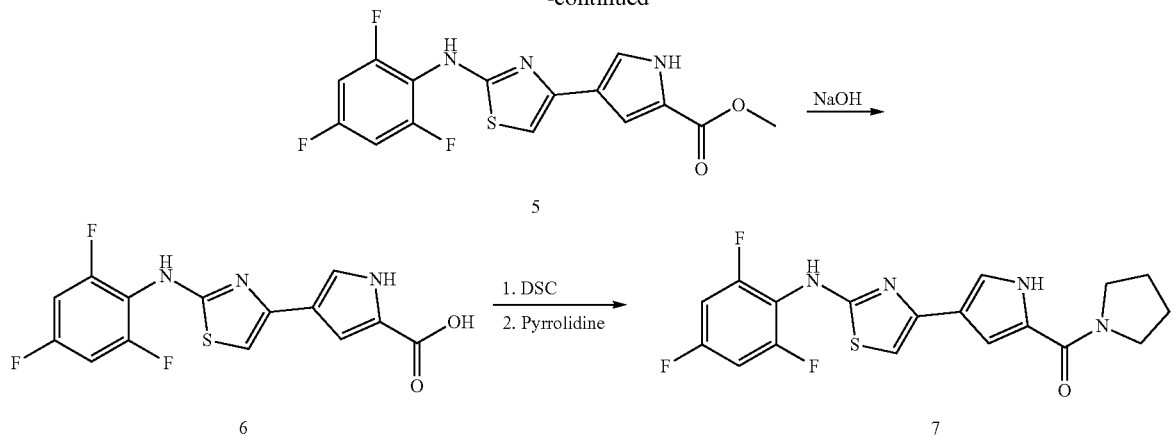

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; The organic phase was dried over Na$_2$SO$_4$ and evaporated yielding of gray solid (9 g, 90% yield).

Reagents Table-Synthesis of 4

| Reagent/raw material | MW (gr/mole) | Quantity | mmoles |
|---|---|---|---|
| 2,4,6 Trifluoroaniline | 147 | 2.2 g | 15 |
| Ammonium isothiocyanate | 76 | 1.37 g | 18 |
| HCl 1N | | 15 mL | |

Procedure

Both reagents were refluxed overnight in HCl 1N, when full conversion was observed; the mixture was cooled on ice bath. The product was collected by filtration (2.1 g, 68%).

Reagents Table-Synthesis of 5

| Reagent/raw material | MW (gr/mole) | Quantity | mmoles |
|---|---|---|---|
| 1-(2,4,6-Trifluorophenyl)thiourea | 206 | 1.03 g | 5 |
| Methyl 4-(2-chloroacetyl)-1H-pyrrole-2-carboxylate | 201.6 | 1.008 g | 5 |
| Sodium acetate | 82 | 0.82 g | 10 |
| Acetic acid | — | 5 mL | — |

Procedure

The reagents were stirred in acetic acid and heated to reflux. When full conversion was observed the mixture was cooled to rt. The solid was collected by filtration, washed with ice water (80 mL) yielding yellow powder (quantitative yield).

Reagents Table-Synthesis of 6

| Reagent/raw material | MW (gr/mole) | Quantity | mmoles |
|---|---|---|---|
| Methyl 4-(2-((2,4,6-trifluorophenyl)amino)thiazol-4-yl)-1H-pyrrole-2-carboxylate | 353 | 1.76 g | 5 |
| NaOH | 40 | 0.8 g | 20 |
| Dioxane | — | 100 mL | — |
| H$_2$O | — | 50 mL | — |

Procedure

NaOH was added to a mixture of the ester in Dioxane-H$_2$O 2:1 (60 mL). The mixture was heated to 70-80° C. during which a dark solution is formed. When reaction was completed the organic solvent was evaporated and the residue was acidified to pH ~1-2 using hydrochloric acid (1N). The product was collected by filtration (1.45 g, 85%).

Reagents Table-Synthesis of 7

| Reagent/raw material | MW (gr/mole) | Quantity | mmoles |
|---|---|---|---|
| 4-(2-((2,4,6-Trifluorophenyl)amino)thiazol-4-yl)-1H-pyrrole-2-carboxylic acid | 339.29 | 0.68 g | 2 |
| bis(2,5-Dioxopyrrolidin-1-yl)carbonate | 256.17 | 0.512 g | 2 |
| Acetonitrile | — | 25 mL | — |
| Dioxane | — | 25 mL | — |
| Triethylamine | 101 | 0.83 mL | 6 |
| Pyrrolidine | 71.12 | 0.25 mL | 3 |

Procedure

The acid, Et$_3$N and the activating agent were taken in a mixture of acetonitrile-dioxane 1:1. Active ester formation was monitored by HPLC and small portions of the activating agent were added until a point of full conversion. Then, pyrrolidine was added and the mixture was stirred at rt. The organic solvents were removed under reduced pressure and the residue was boiled in acetone. The white precipitation was removed by filtration. The filtrate was evaporated and crystallized from EtOH-water. The mixture was boiled and the solid was collected by filtration. Yield 300 mg (38%). HPLC—100% purity. LCMS—(ES$^+$) Calcd. 392.40. Found 393.36 (MH$^+$).

Synthesis of Compound:

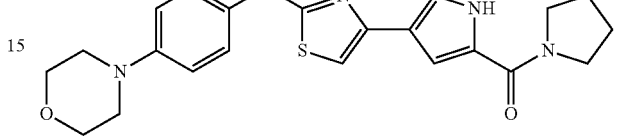

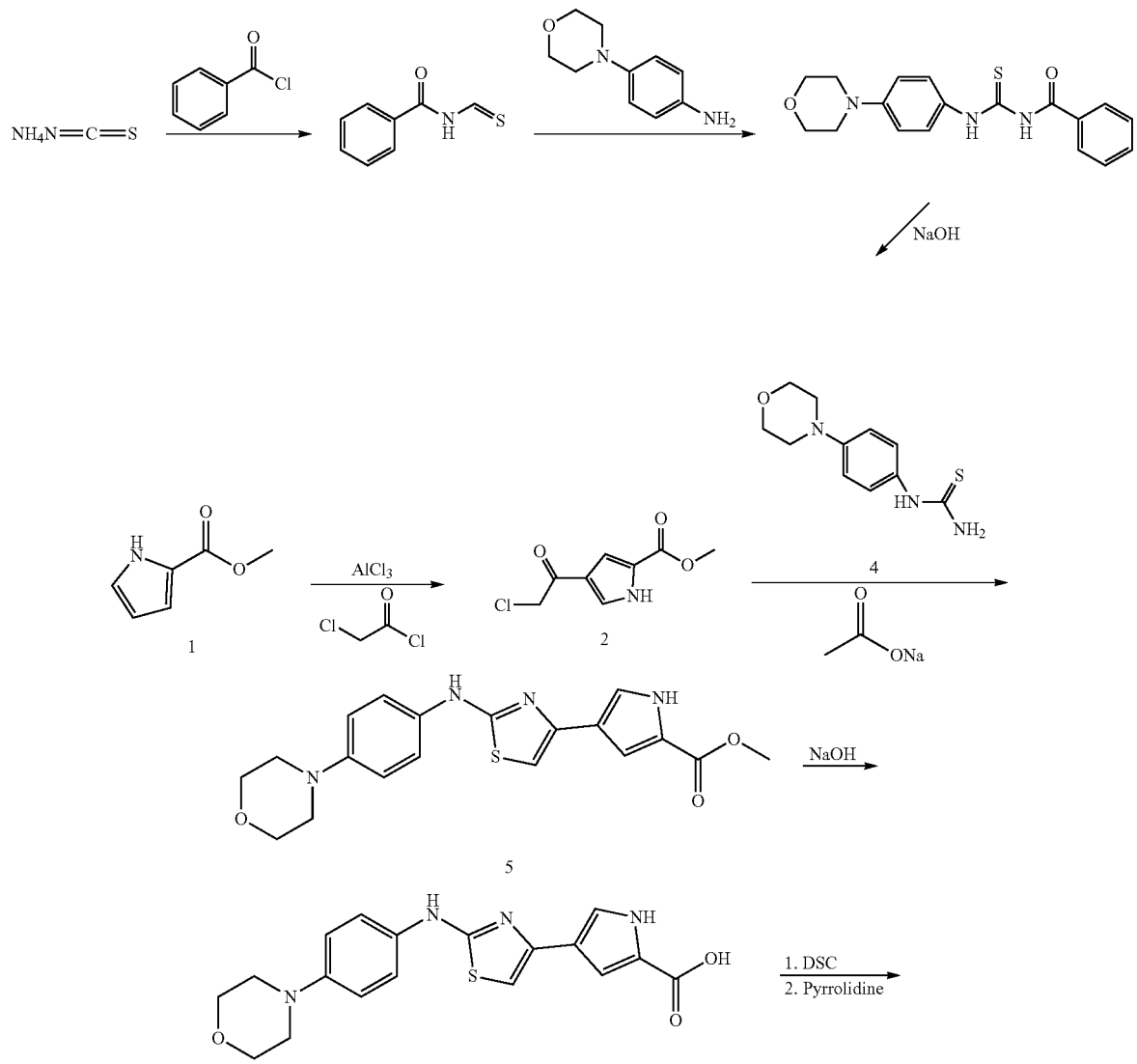

Scheme 17

-continued

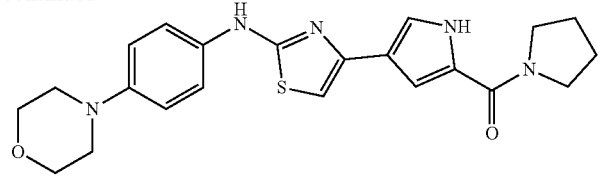

7

Reagents Table-Synthesis of 2

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; The organic phase was dried over $Na_2SO_4$ and evaporated yielding of gray solid (9 g, 90% yield).

Reagents Table-Synthesis of 4

| Reagent/raw material | MW (gr/mole) | Quantity | mmoles |
|---|---|---|---|
| Benzoyl chloride | 140.57 | 1.74 mL | 15 |
| Ammonium isothiocyanate | 76 | 1.29 g | 17 |
| 4-Morpholinoaniline | 178 | 2.67 g | 15 |
| Acetone | — | 15 mL | — |
| NaOH | 5% NaOH | 100 mL | — |

Procedure

A solution of benzoyl chloride in acetone was added dropwise to a solution of ammonium isothiocyanate in acetone. The resulting mixture was refluxed for 30 minutes followed by the addition of aniline and reflux for additional 30 minutes. The components were poured into crushed ice (100 mL) resulting in dark solid which was collected by filtration and added to NaOH (5%, 100 mL) solution. The mixture was stirred at 80° C. The hydrolyzed product was collected by filtration (1.5 g, 42%).

Reagents Table-Synthesis of 5

| Reagent/raw material | MW (gr/mole) | Quantity | mmoles |
|---|---|---|---|
| 1-(4-Morpholinophenyl)thiourea | 237 | 1.19 g | 5 |
| Methyl 4-(2-chloroacetyl)-1H-pyrrole-2-carboxylate | 201.6 | 1.01 g | 5 |
| Sodium acetate | 82 | 0.82 g | 10 |
| Acetic acid | — | 5 mL | — |

Procedure

The reagents were stirred in acetic acid and heated to reflux. When full conversion was observed the mixture was cooled to rt. Upon which precipitate was formed. The solid was collected by filtration, washed with plenty of ice water yielding 1.56 g (80%) of green solid.

Reagents Table-Synthesis of 6

| Reagent/raw material | MW (gr/mole) | Quantity | mmoles |
|---|---|---|---|
| Methyl 4-(2-((4-morpholinophenyl)amino)thiazol-4-yl)-1H-pyrrole-2-carboxylate | 384 | 1.56 g | 4 |
| NaOH | 40 | 0.64 g | 16 |
| Dioxane | — | 60 mL | — |
| $H_2O$ | — | 30 mL | — |

Procedure

NaOH was added to a mixture of the ester in Dioxane-$H_2O$ 2:1 (60 mL). The mixture was heated to 70-80° C. during which a dark solution is formed. When reaction was completed the organic solvent was evaporated and the residue was acidified to pH −1-2 using hydrochloric acid (1N). The product was collected by filtration (0.9 g, 60%).

Reagents Table-Synthesis of 7

| Reagent/raw material | MW (gr/mole) | Quantity | mmoles |
|---|---|---|---|
| 4-(2-((4-Morpholinophenyl)amino)thiazol-4-yl)-1H-pyrrole-2-carboxylic acid | 370.43 | 0.74 g | 2 |
| bis(2,5-Dioxopyrrolidin-1-yl)carbonate | 256.17 | 0.51 g | 2 |
| Acetonitrile | — | 75 mL | — |
| Dioxane | — | 75 mL | — |
| DMF | — | 30 mL | — |
| Triethylamine | 101 | 0.83 mL | 6 |
| Pyrrolidine | 71.12 | 0.5 mL | 6 |

Procedure

The acid, $Et_3N$ and the activating agent were stirred in a mixture of acetonitrile-dioxane 1:1 (150 mL). In order to achieve solubility DMF (30 mL) was added. Active ester formation was monitored by HPLC and small portions of the activating agent were added until a point of full conversion. Then, pyrrolidine was added and the mixture was stirred at rt. The organic solvents were removed under reduced pressure and the residue was triturated with water and the residue washed with additional amount of water and collected by filtration. The solid obtained was washed with boiling EtOH and collected by filtration yielding green solid (60 mg, 7%). HPLC—95% purity. LCMS—(ES$^+$) Calcd. 423.53. Found 424.43 (MH$^+$).

Synthesis of Compound:

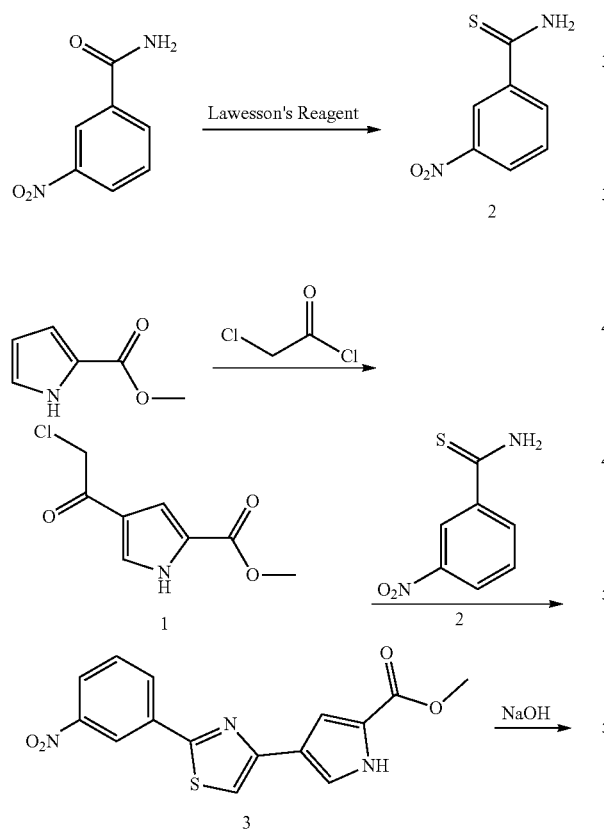

Scheme 18

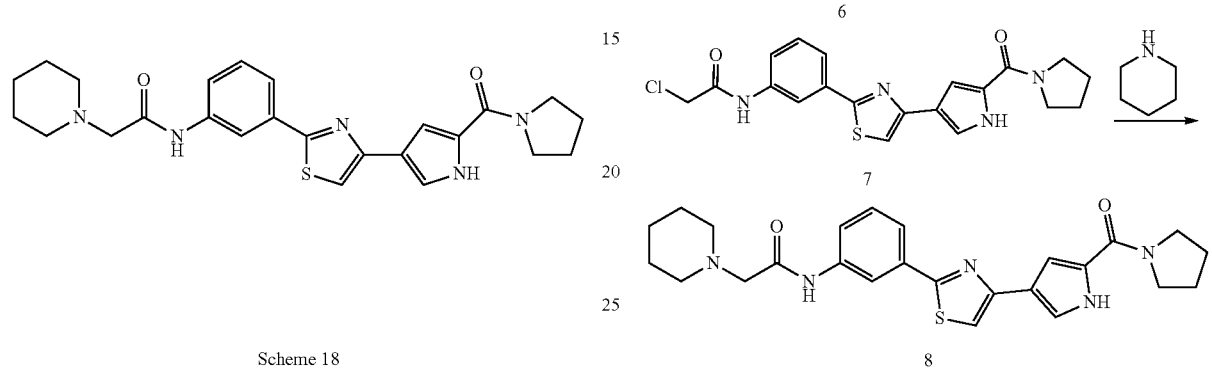

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO$_3$ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in dioxane-H$_2$O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxypyrrolidin-1-yl)carbonate | 256.17 | 2.56 g | 10 |
| Acetonitrile-Dioxane 1:1 | — | 200 mL | — |
| Triethylamine | 101 | 4.15 mL | 22 |
| pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was collected by filtration, washed with water (70 mL) and dried over vacuum (2 g, 73%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7 and 8

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.4 | 1.8 g | 5.3 |
| Chloroacetylchloride | 113 | ~0.1 mL | 1.2 |
| Triethylamine | 101 | 0.41 mL | 3 |
| Piperidine | 85 | 0.3 mL | 3 |
| Triethylamine* | 101 | 0.41 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with piperidine and triethylamine. The mixture was refluxed vigorously for 2-3 hours (morpholine is added if needed for reaction completion). When the reaction was completed, heating was stopped, The product was recrystallized from MeOH (159 mg, 34%). HPLC—99% purity. MS—(ES$^+$) Calcd. 463.2. Found 464.2 (MH$^+$).

Synthesis of Compound:

Scheme 19

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |

-continued

| Reagent/raw material | MW (gr/mole) | Quantity | mmoles |
|---|---|---|---|
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in dioxane-H$_2$O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl)carbonate | 256.17 | 2.56 g | 10 |
| Acetonitrile-Dioxane 1:1 | — | 200 mL | — |
| Triethylamine | 101 | 4.15 mL | 22 |
| pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was collected by filtration, washed with water (70 mL) and dried over vacuum (2 g, 73%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.4 | 0.507 g | 1.5 |
| Acetylchloride | 78.5 | ~0.13 mL | 1.8 |
| Triethylamine | 101 | 0.62 mL | 4.5 |
| DCM | — | 20 mL | — |

Procedure

A solution of acetyl chloride in DCM was added dropwise to a mixture of aniline and triethylamine in DCM under cooling on ice bath. Partial dissolution was observed followed by white precipitation. The solid was collected by filtration, washed with water and dried over vacuum yielding white powder (0.128 g 22%). HPLC—100% purity. LCMS—(ES$^+$) Calcd. 380.13. Found 381.1 (MH$^+$).

Synthesis of Compound:

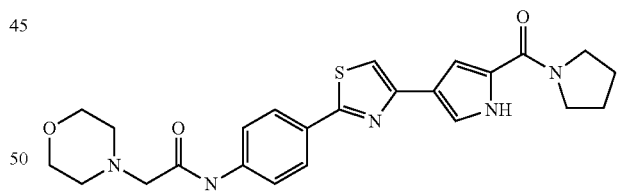

Scheme 20

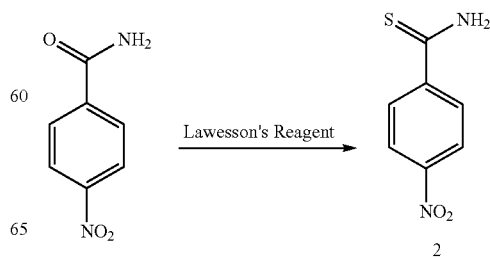

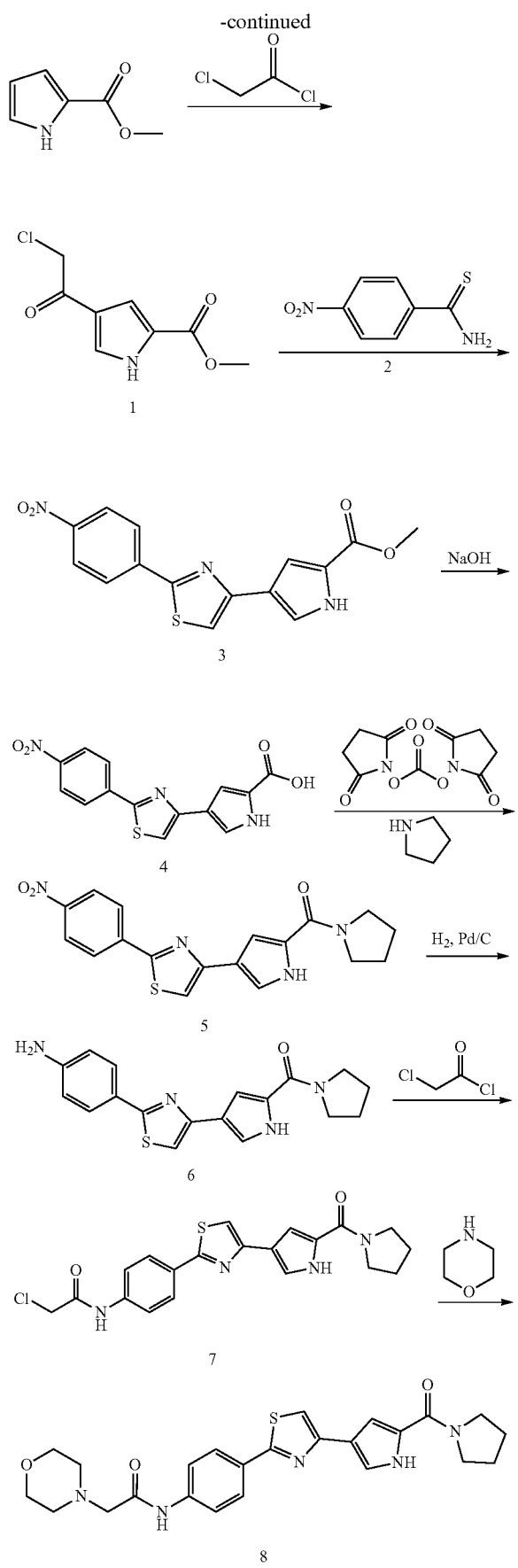

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 4-Nitrobenzamide | 182.2 | 6.64 g | 40 |
| Lawesson's reagent | 404 | 12.12 g | 30 |
| $NaHCO_3$ | 84 | 2.52 g | 30 |
| 1,2 Dimethoxyethane | — | 100 mL | — |
| THF | — | 50 mL | — |

Procedure

Lwesson's reagent was added to a stirring mixture of 4-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (600 mL). The milky mixture was heated to boil and then left to cool to 30° C. resulting in orange crystals. (4.5 g, 61% yield).

Reagents Table-Synthesis of 3

| Reagent/raw material | MW (gr/mole) | Quantity | mmoles |
|---|---|---|---|
| 4-Nitrobrhioenzamide | 182 | 2.00 g | 11 |
| Methyl 4-(2-chloroacetyl)-1H-pyrrole-2-carboxylate | 201.6 | 2.22 g | 11 |
| Sodium acetate | 82 | 1.80 g | 22 |
| Acetic acid | — | 8 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (2.86 g 79% mustard yellow powder).

Reagents Table-Synthesis of 4

| Reagent/raw material | MW (gr/mole) | Quantity | mmoles |
|---|---|---|---|
| Methyl 4-(2-(4-nitrophenyl)thiazol-4-yl)-1H-pyrrole-2-carboxylate | 329.33 | 2.86 g | 8.7 |
| NaOH | 40 | 1.39 g | 34.8 |
| Dioxane | — | 100 mL | — |
| $H_2O$ | — | 50 mL | — |

Procedure

NaOH was added to a mixture of the ester in dioxane-$H_2O$ 2:1. The mixture was heated to 70-80° C. during which a dark solution is formed. When reaction was completed the organic solvent was evaporated and the residue was acidified using concentrated hydrochloric acid. The product was collected by filtration. Yellow powder (quantitative yield).

Reagents Table-Synthesis of 5

| Reagent/raw material | MW (gr/mole) | Quantity | mmoles |
|---|---|---|---|
| 4-(2-(4-Nitrophenyl)thiazol-4-yl)-1H-pyrrole-2-carboxylic acid | 315.3 | 2.71 g | 8.6 |
| bis(2,5-Dioxopyrrolidin-1-yl)carbonate | 256.17 | 2.20 g + 1.3 g | 8.6 + 5 |
| Acetonitrile-Dioxane 1:1 | — | 90 mL | — |
| Triethylamine | 101 | 3.6 mL | 26 |
| pyrrolidine | 71.12 | 2.17 mL | 26 |

Procedure

Triethylamine was added to a mixture of the acid in acetonitrile-dioxane mixture resulting in clear solution. The activating agent was then added and the components were stirred at rt. Active ester formation was monitored by HPLC. Extra portions of the activating agent were added (1.28 g, 5 mmole total) until a point of 95% conversion. Then, pyrrolidine was added and an immediate formation of the amide (precipitate) was observed. Additional portions of pyrrolidine were introduced until full conversion of the active ester was observed. The solid obtained was collected by filtration, washed with water (100 mL) and dried over vacuum (1.6 g, 50%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 1.6 g | 4.3 |
| Pd/C | — | 150 mg | — |
| THF | — | 300 mL | — |

Procedure

The nitro compound was dissolved in boiling THF. The catalyst was added and the mixture was subjected to hydrogen atmosphere overnight. The catalyst was removed by filtration over celite and the solvent was evaporated yielding yellow powder (0.8 g, 55%).

Reagents Table-Synthesis of 7 and 8

| Reagent/raw material | MW (gr/mole) | Quantity | mmoles |
|---|---|---|---|
| (4-(2-(4-Aminophenyl)thiazol-4-yl)-1H-pyrrol-2-yl)(pyrrolidin-1-yl)methanone | 338.4 | 0.338 g | 1 |
| Chloroacetylchloride | 113 | ~0.1 mL | 1.2 |
| Triethylamine | 101 | 0.41 mL | 3 |
| morpholine | 87.12 | 0.35 mL | 4 |
| Triethylamine* | 101 | 0.41 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with morpholine and triethylamine. The mixture was refluxed vigorously for 2-3 hours (morpholine is added if needed for reaction completion). When the reaction was completed, heating was stopped. The product was recrystallized from MeOH, collected by filtration and washed with water (109 mg, 23%). HPLC—96% purity. MS—($ES^+$) Calcd. 465.18. Found 466.3 ($MH^+$).

Synthesis of Compound:

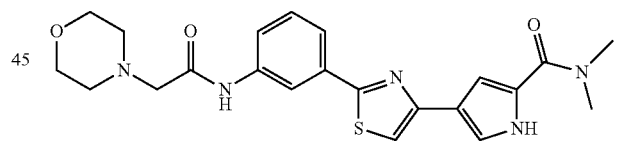

Scheme 21

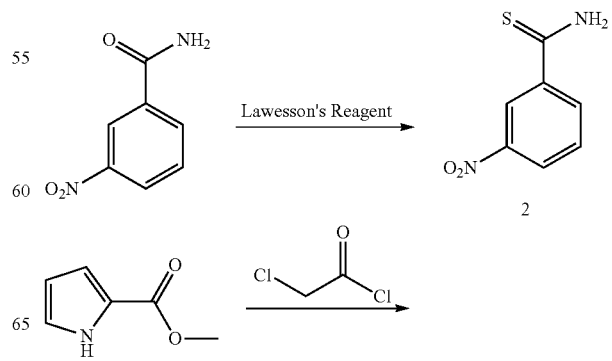

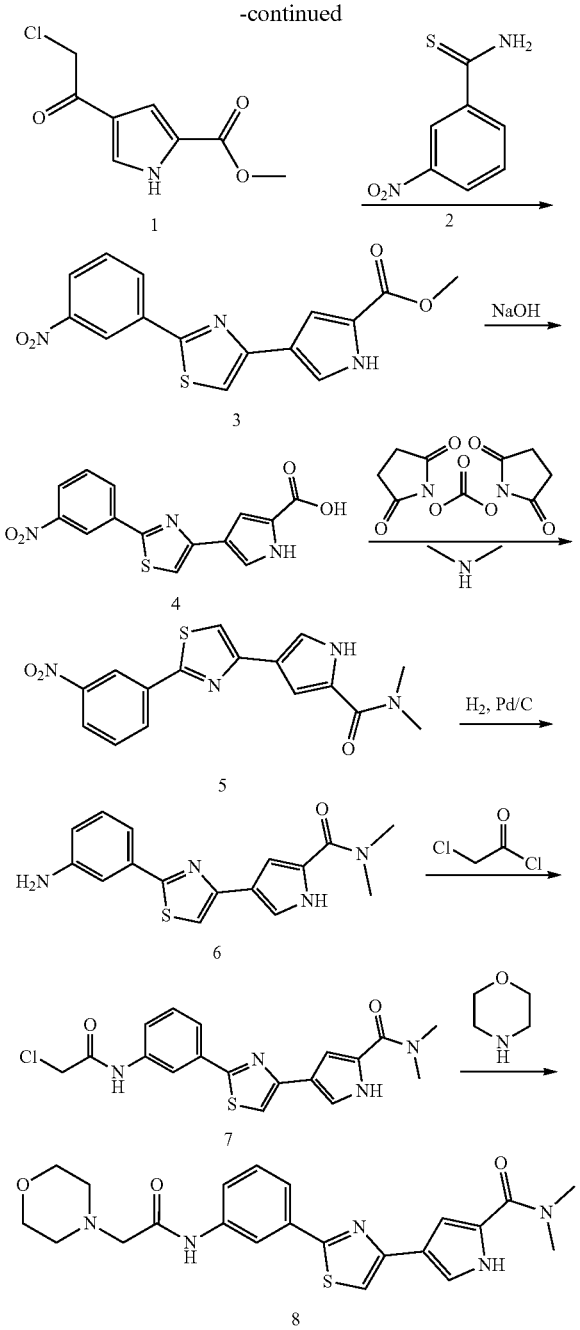

Reagents Table-Synthesis of 1

| Reagent/raw material | MW (gr/mole) | Quantity | mmoles |
| --- | --- | --- | --- |
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
| --- | --- | --- | --- |
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
| --- | --- | --- | --- |
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
| --- | --- | --- | --- |
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in dioxane-$H_2O$ 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 630.6 mg | 2.0 |
| bis(2,5-Dioxopyrrolidin-1-yl)carbonate (DSC) | 256.17 | 769 mg | 3.0 |
| Acetonitrile-Dioxane 1:1 | — | 40 mL | — |
| Triethylamine | 101 | 0.84 mL | 6.0 |
| Dimethylamine | 45.1 | 3 mL | 5.0 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, dimethylamine was added and an immediate formation of the amide was observed (the color of the reaction changed). Additional portions of dimethylamine were introduced until full conversion of the active ester was observed. The solid obtained was removed by filtration, washed with water and dried under high vacuum to afford the desired product as a brownish solid: 580 mg, 84.7% yield.

Reagents Table-Synthesis of 6

| Reagent/raw material | MW (gr/mole) | Quantity | mmoles |
|---|---|---|---|
| N,N-Dimethyl-4-(2-(3-nitrophenyl)thiazol-4-yl)-1H-pyrrole-2-carboxamide | 342.4 | 580 mg | 1.69 |
| Pd/C | — | 100 mg | cat. |
| THF | — | 50 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 470 mg, 89% yield.

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-N,N-dimethyl-1H-pyrrole-2-carboxamide | 312.4 | 470 mg | 1.5 |
| Chloroacetylchloride | 113 | 0.13 mL | 1.65 |
| Triethylamine | 101 | 0.63 mL | 4.5 |
| Morpholine | 87.12 | 0.12 mL | 1.5 |
| Triethylamine* | 101 | 0.21 mL | 1.5 |
| DCM | — | 25 mL | — |
| Dioxane | — | 8 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with morpholine and triethylamine. The mixture was refluxed vigorously for 2 hours (morpholine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:THF gradient) to afford the pure product as a white solid: 35 mg, 15.9% yield, 100% purity. HPLC—100% purity. MS—($ES^+$) Calcd. 439.5. Found 440.1 ($MH^+$).

Synthesis of Compound:

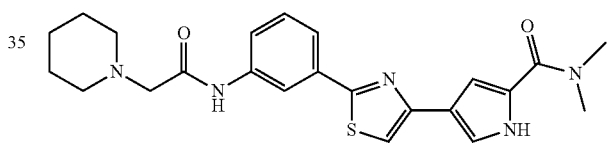

Scheme 22

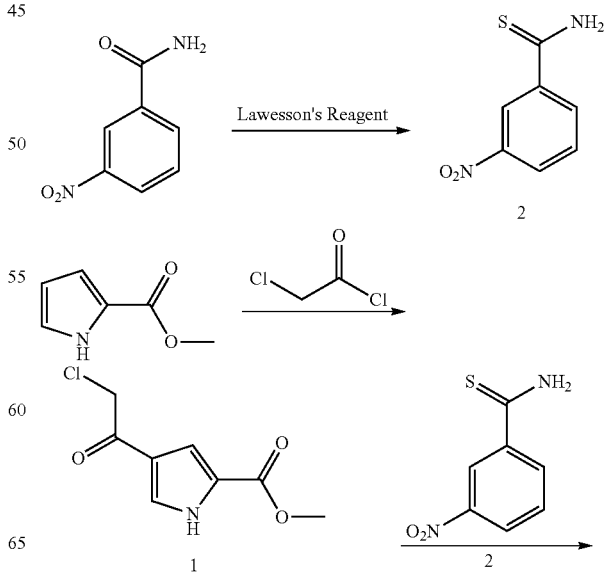

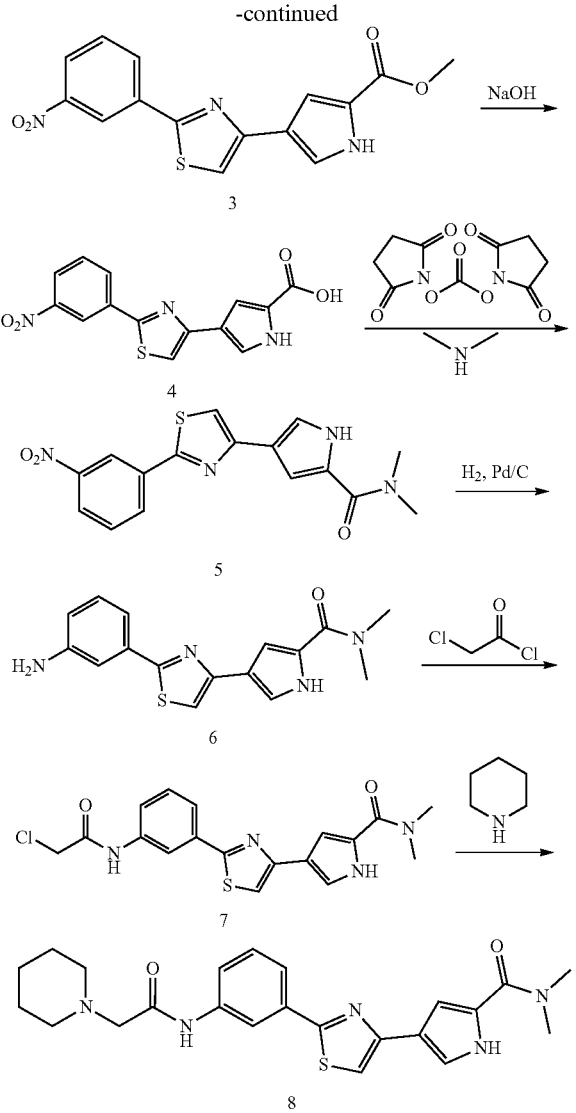

Reagents Table-Synthesis of 1

| Reagent/raw material | MW (gr/mole) | Quantity | mmoles |
| --- | --- | --- | --- |
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
| --- | --- | --- | --- |
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
| --- | --- | --- | --- |
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
| --- | --- | --- | --- |
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in dioxane-H₂O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 630.6 mg | 2.0 |
| bis(2,5-Dioxopyrrolidin-1-yl) carbonate (DSC) | 256.17 | 769 mg | 3.0 |
| Acetonitrile-Dioxane 1:1 | — | 40 mL | — |
| Triethylamine | 101 | 0.84 mL | 6.0 |
| Dimethylamine | 45.1 | 3 mL | 5.0 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, dimethylamine was added and an immediate formation of the amide was observed (the color of the reaction changed). Additional portions of dimethylamine were introduced until full conversion of the active ester was observed. The solid obtained was removed by filtration, washed with water and dried under high vacuum to afford the desired product as a brownish solid: 580 mg, 84.7% yield.

Reagents Table-Synthesis of 6

| Reagent/raw material | MW (gr/mole) | Quantity | mmoles |
|---|---|---|---|
| N,N-dimethyl-4-(2-(3-nitrophenyl)thiazol-4-yl)-1H-pyrrole-2-carboxamide | 342.4 | 580 mg | 1.69 |
| Pd/C | — | 100 mg | cat. |
| THF | — | 50 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 470 mg, 89% yield.

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-N,N-dimethyl-1H-pyrrole-2-carboxamide | 312.4 | 470 mg | 1.5 |
| Chloroacetylchloride | 113 | 0.13 mL | 1.65 |
| Triethylamine | 101 | 0.63 mL | 4.5 |
| Piperidine | 85.2 | 128 mg | 1.5 |
| Triethylamine* | 101 | 0.21 mL | 1.5 |
| DCM | — | 25 mL | — |
| Dioxane | — | 8 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with piperidine and triethylamine. The mixture was refluxed vigorously for 1 hour (piperidine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:THF gradient) to afford the pure product as a yellow solid: 15 mg, 6.9% yield, 96% purity. HPLC—96% purity. MS—(ES$^+$) Calcd. 437.5. Found 438.1 (MH$^+$).

Synthesis of Compound:

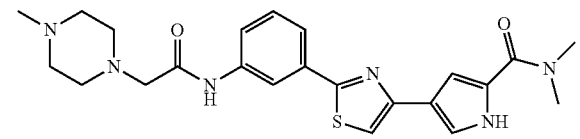

Scheme 23

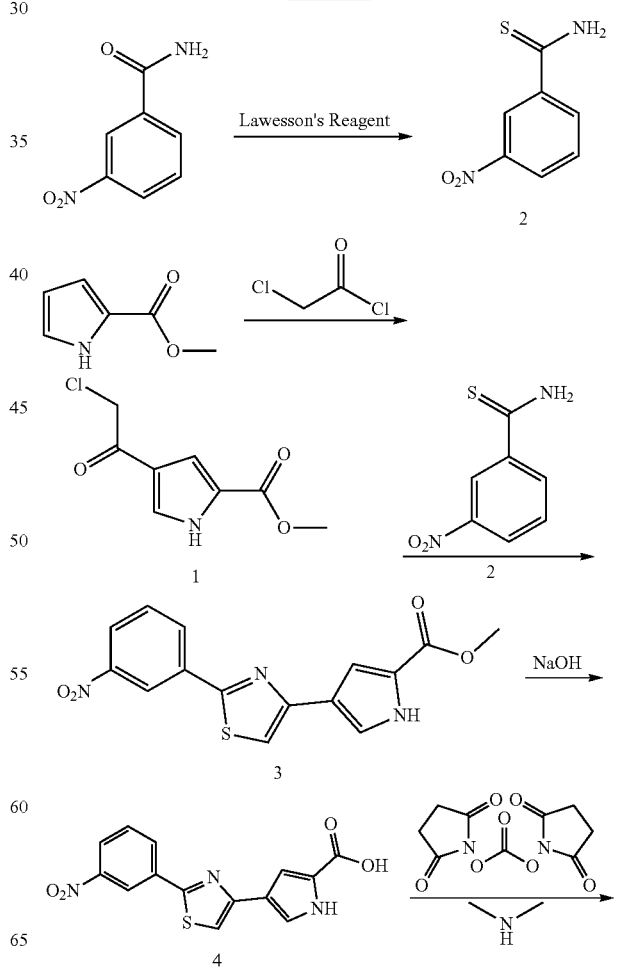

-continued

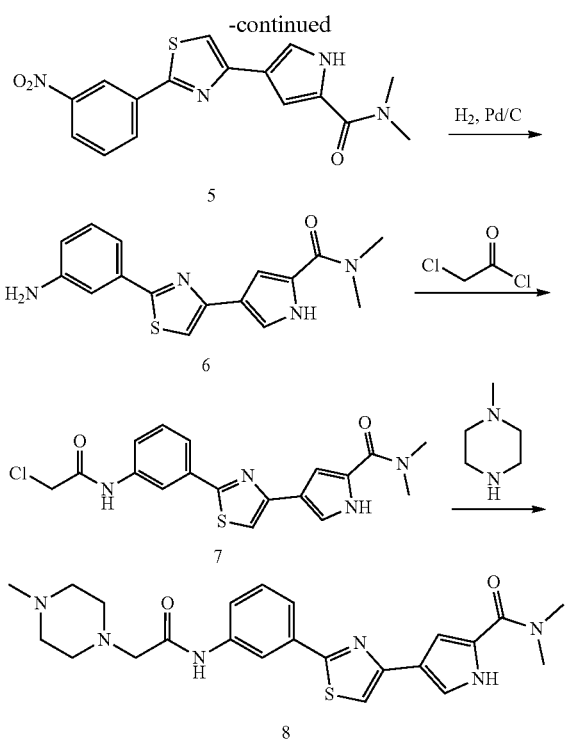

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in dioxane-H₂O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 630.6 mg | 2.0 |
| bis(2,5-Dioxopyrrolidin-1-yl) carbonate (DSC) | 256.17 | 769 mg | 3.0 |
| Acetonitrile-Dioxane 1:1 | — | 40 mL | — |
| Triethylamine | 101 | 0.84 mL | 6.0 |
| Dimethylamine | 45.1 | 3 mL | 5.0 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, dimethylamine was added and an immediate formation of the amide was observed (the color of the reaction changed). Additional portions of dimethylamine were introduced until full conversion of the active ester was observed. The solid obtained was removed by filtration, washed with water and dried under high vacuum to afford the desired product as a brownish solid: 580 mg, 84.7% yield.

Reagents Table-Synthesis of 6

| Reagent/raw material | MW (gr/mole) | Quantity | mmoles |
|---|---|---|---|
| N,N-Dimethyl-4-(2-(3-nitrophenyl)thiazol-4-yl)-1H-pyrrole-2-carboxamide | 342.4 | 580 mg | 1.69 |
| Pd/C | — | 100 mg | cat. |
| THF | — | 50 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 470 mg, 89% yield.

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-N,N-dimethyl-1H-pyrrole-2-carboxamide | 312.4 | 470 mg | 1.5 |
| Chloroacetylchloride | 113 | 0.13 mL | 1.65 |
| Triethylamine | 101 | 0.63 mL | 4.5 |
| 1-Methylpiperazine | 100.2 | 150.3 mg | 1.5 |
| Triethylamine* | 101 | 0.21 mL | 1.5 |
| DCM | — | 25 mL | — |
| Dioxane | — | 8 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with 1-methylpiperazine and triethylamine. The mixture was refluxed vigorously for 1 hour (1-methylpiperazine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:THF gradient) to afford the pure product as a yellow solid: 156 mg, 69% yield, 100% purity. HPLC—100% purity. MS—(ES$^+$) Calcd. 452.6. Found 453.1 (MH$^+$).

Synthesis of Compound:

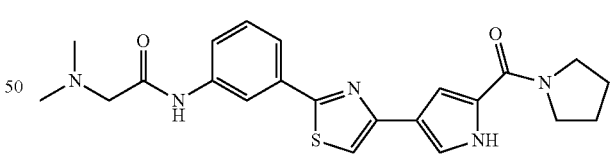

Scheme 24

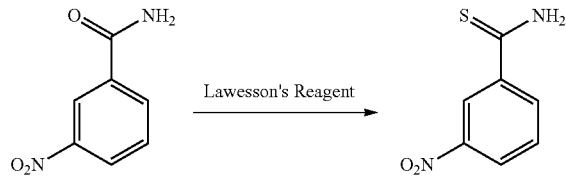

-continued
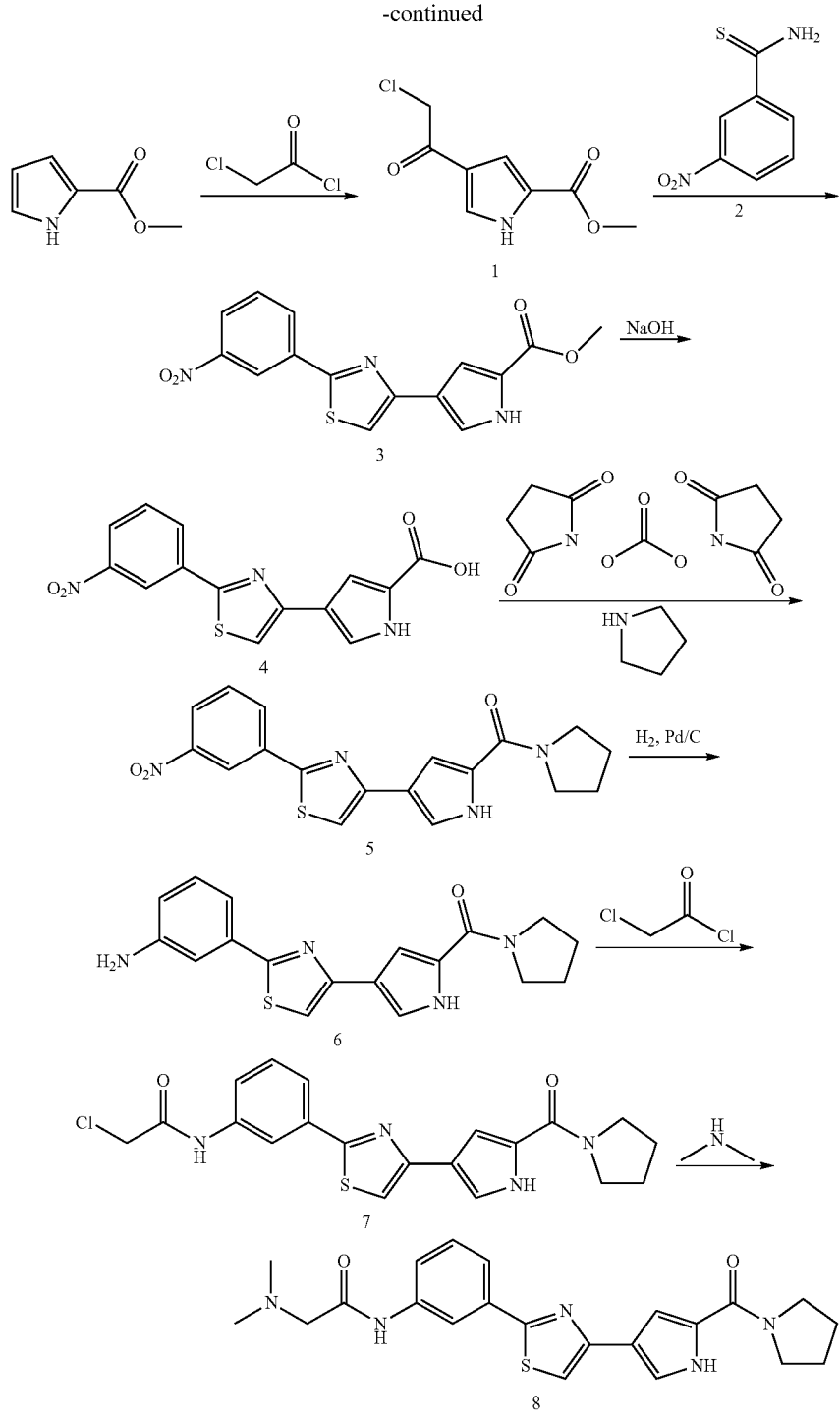
Reagents Table-Synthesis of 1
| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |
Procedure
A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in dioxane-H₂O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl)-carbonate | 256.17 | 2.56 g | 10 |
| Acetonitrile-Dioxane 1:1 | — | 200 mL | — |
| Triethylamine | 101 | 4.15 mL | 22 |
| pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was collected by filtration, washed with water (70 mL) and dried over vacuum (2 g, 73%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table

Synthesis of 7 and 8

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.4 | 0.338 g | 1 |
| Chloroacetylchloride | 113 | ~0.1 mL | 1.2 |
| Triethylamine | 101 | 0.41 mL | 3 |
| Dimethylamine (2M in MeOH) | 85 | 2 mL | 4 |

-continued

| Reagent/raw material | MW (gr/mole) | Quantity | mmoles |
|---|---|---|---|
| Triethylamine* | 101 | 0.41 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with dimethylamine and triethylamine. The mixture was refluxed vigorously for 2-3 hours (dimethylamine is added if needed for reaction completion). When the reaction was completed, heating was stopped. The solvent was removed under reduced pressure. The residue was triturated using isopropanol, collected by filtration and washed with water. Drying on high vacuum afforded 55 mg (13%). HPLC—96% purity. MS—(ES+) Calcd. 423.17. found 424.2 (MH+).

Synthesis of Compound:

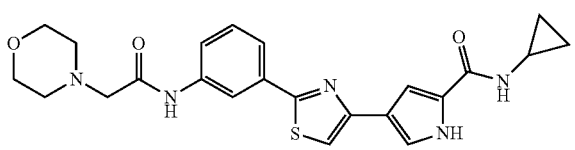 [SMILES: O=C(CN1CCOCC1)Nc1cccc(-c2nc(-c3c[nH]c(C(=O)NC4CC4)c3)cs2)c1]

Scheme 25

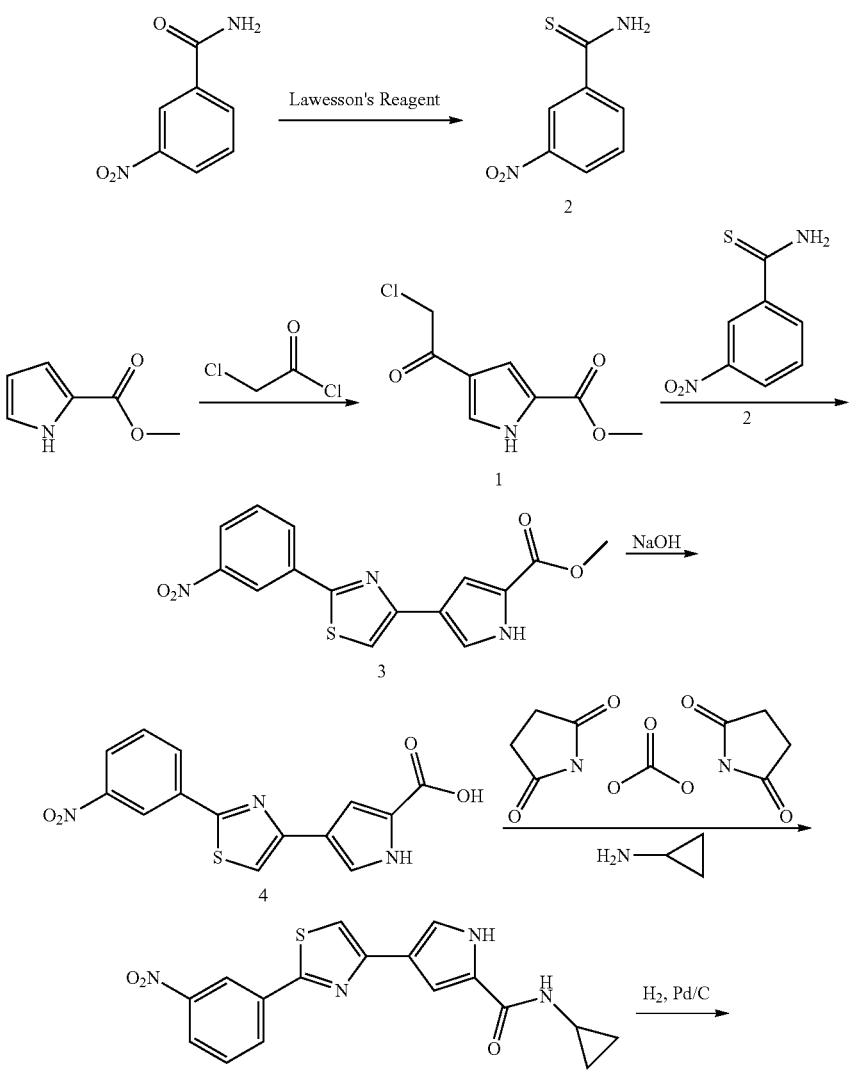

-continued

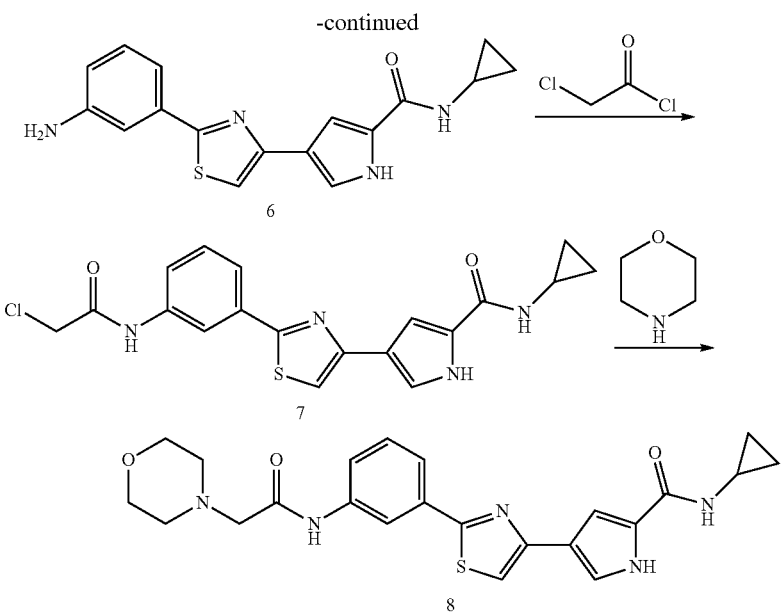

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO$_3$ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in dioxane-H$_2$O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 0.945 g | 3 |
| bis(2,5-Dioxopyrrolidin-1-yl) carbonate (DSC) | 256.17 | 0.768 + 0.384 g | 3 + 1.5 |
| Acetonitrile-Dioxane 1:1 | — | 50 mL | — |
| Triethylamine | 101 | 1.25 mL | 9 |
| Cyclopropylamine | 57.1 | 0.7 mL | 10 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, cyclopropylamine was added and an immediate formation of the amide (precipitate) was observed. Additional portions of pyrrolidine were introduced until full conversion of the active ester was observed. The solid obtained was removed by filtration, and the filtrate (90% purity) was evaporated and the resulting solid was stirred in water (30 mL). Vacuum drying afforded 0.46 g (43%) of yellow solid.

Reagents Table-Synthesis of 6

| Reagent/raw material | MW (gr/mole) | Quantity | mmoles |
|---|---|---|---|
| N-Cyclopropyl-4-(2-(3-nitrophenyl)thiazol-4-yl)-1H-pyrrole-2-carboxamide | 354.38 | 0.46 g | 1.3 |
| Pd/C | — | 150 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (0.32 g, 76%).

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-N-cyclopropyl-1H-pyrrole-2-carboxamide | 324 | 0.320 g | 0.99 |
| Chloroacetylchloride | 113 | ~0.1 mL | 1.2 |
| Triethylamine | 101 | 0.41 mL | 3 |
| Morpholine | 87.12 | 0.35 mL | 4 |
| Triethylamine* | 101 | 0.41 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with morpholine and triethylamine. The mixture was refluxed vigorously for 2 hours (morpholine is added if needed for reaction completion). When the reaction was completed, heating was stopped, The solvent was removed under reduced pressure. The residue was taken in EtOH and norit was added. The mixture was stirred for 30 minutes and charcoal was removed by filtration. The filtrate was evaporated and the oily product was purified on normal phase silica (eluted by PE:THF gradient). 20 mg (4.46%). HPLC—98% purity. MS—(ES$^+$) Calcd. 451.17. Found 451.6 (MH$^+$).

Synthesis of Compound:

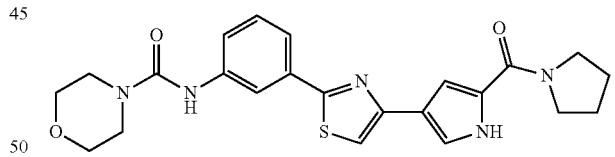

Scheme 26

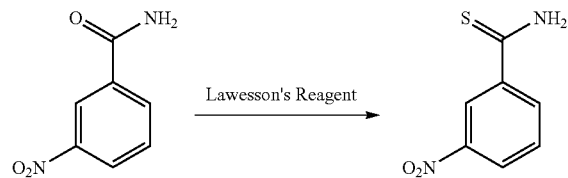

Lawesson's Reagent

-continued
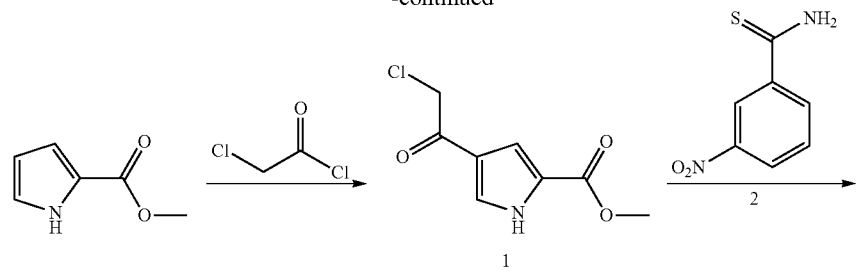
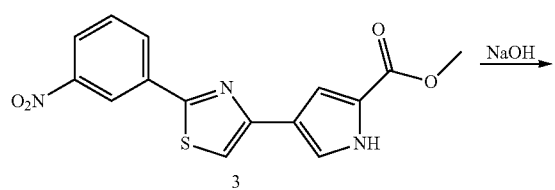
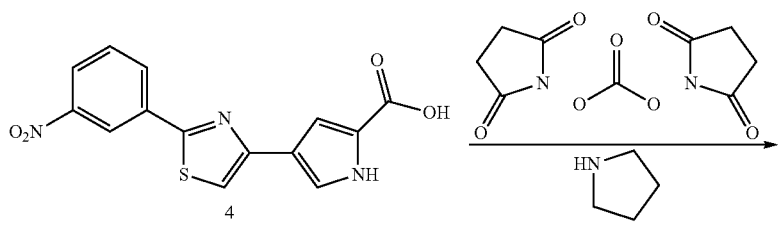
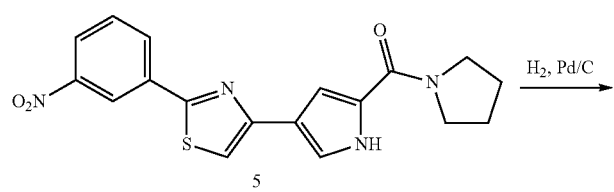
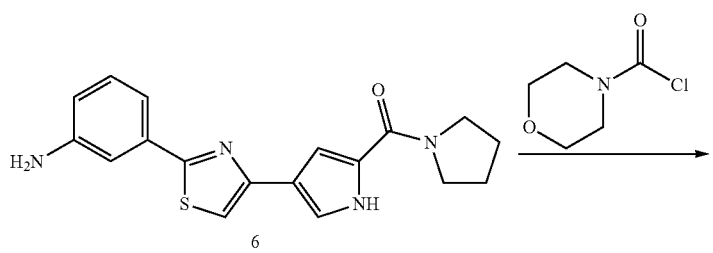
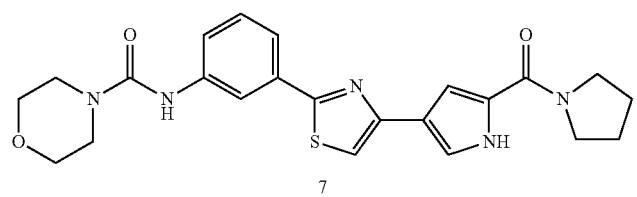

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl₃ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl₃ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na₂SO₄ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO₃ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H₂O | — | 50 mL | — |

Procedure

NaOH was added to a mixture of the ester in dioxane-H₂O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmloes |
|---|---|---|---|
| 4-(2-(3-Nitrophenyl)thiazol-4-yl)-1H-pyrrole-2-carboxylic acid | 315.3 | 3.15 g | 10 |
| bis(2,5-Dioxopyrrolidin-1-yl) carbonate | 256.17 | 2.56 g | 10 |
| Acetonitrile-Dioxane 1:1 | — | 200 mL | — |
| Triethylamine | 101 | 4.15 mL | 22 |
| pyrrolidine | 71.12 | 1.25 mL | 15 |

Procedure

Triethylamine was added to a mixture of the acid in acetonitrile-dioxane mixture resulting in clear solution. The activating agent was then added and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was collected by filtration, washed with water (70 mL) and dried over vacuum (2 g, 73%).

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 2 g | 5.4 |
| Pd/C | — | 150 mg | — |
| THF | — | 50 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.8 g, quantitative yield).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338.4 | 0.338 g | 1 |
| N-carbonyl chloride Morpholine | 149.5 | ~0.23 mL | 2 |
| Triethylamine | 101 | 0.41 mL | 3 |
| Acetonitrile-THF 1:1 | — | 60 mL | — |

Synthesis of 7

The components were stirred at 70° C. in a mixture of Acetonitrile-THF 1:1. Reaction progress was monitored by HPLC. Full conversion was observed following overnight stirring and the solvents were removed under reduced pressure. The product was purified on normal phase silica (elusion using PE-THF) gradient. (32 mg, 7%). HPLC—98% purity. MS—(ES$^+$) Calcd. 451.17. Found 451.7 (MH$^+$).

Synthesis of Compound:

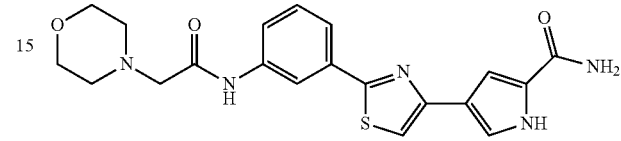

Scheme 27

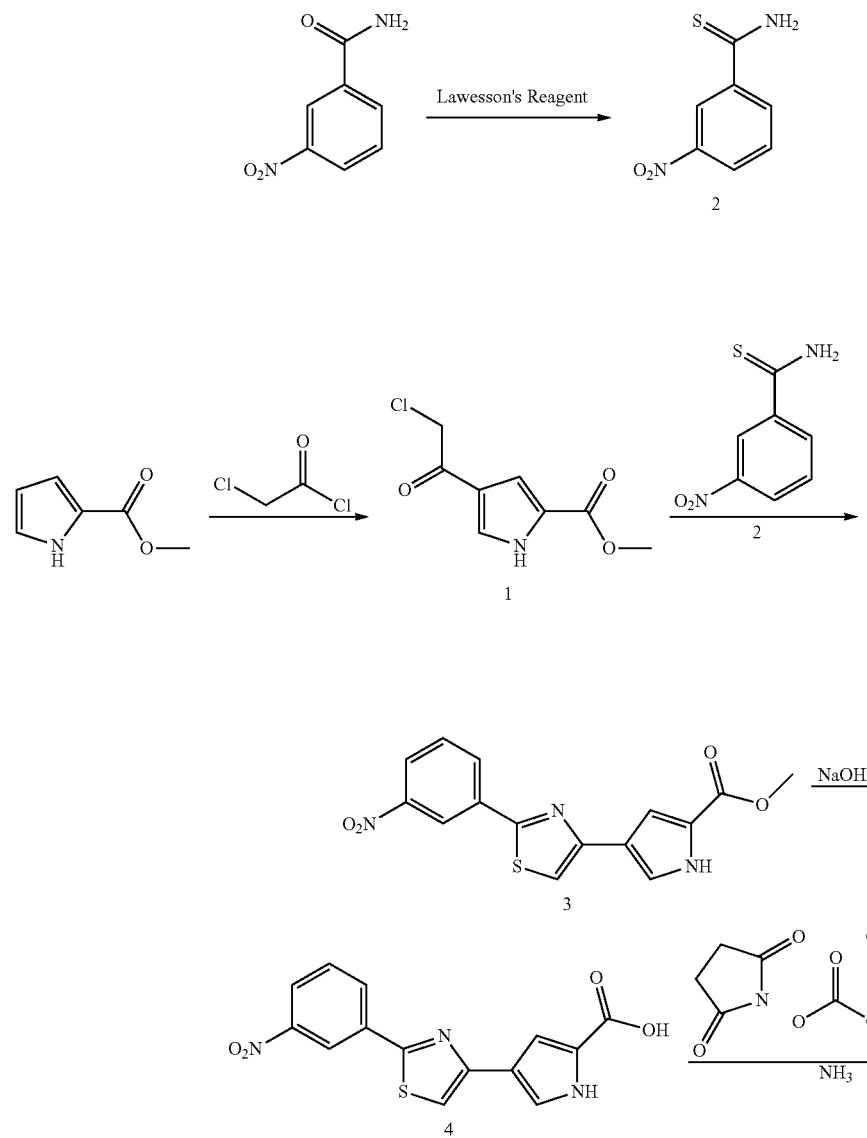

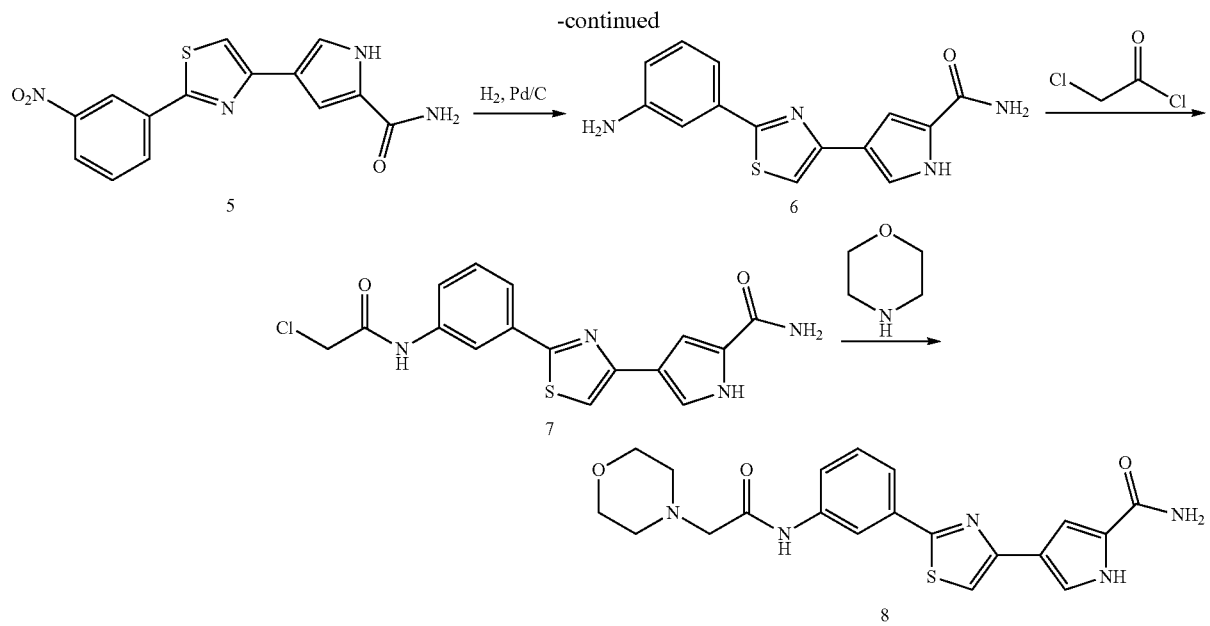

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO$_3$ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in dioxane-H$_2$O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 0.790 g | 2.5 |
| bis(2,5-Dioxopyrrolidin-1-yl)carbonate (DSC) | 256.17 | 0.64 g + 0.32 g | 2.5 + 1.25 |
| Acetonitrile-Dioxane 1:1 | — | 50 mL | — |
| Triethylamine | 101 | 1.04 mL | 7.5 |
| Ammonia in MeOH (7M) | 57.1 | 0.7 mL | 10 |

Procedure

DSC was added to a solution of the acid and triethylamine in dioxane-acetonitrile and the components were stirred at rt. Active ester formation was monitored by HPLC. Extra portions of the activating agent were added until a point of 95% conversion. Then, ammonia solution was added and an immediate formation of the amide (precipitate) was observed. Additional portions of ammonia were introduced until full conversion of the active ester was observed. The solid obtained was collected by filtration, washed with water, taken in EtOH and evaporated to dryness yielding 0.32 g (1.02 mmole, 40% yield) of yellow powder.

Reagents Table-Synthesis of 6

| Reagent/raw material | MW (gr/mole) | Quantity | mmoles |
|---|---|---|---|
| 4-(2-(3-Nitrophenyl)thiazol-4-yl)-1H-pyrrole-2-carboxamide | 314.32 | 0.32 g | 1.02 |
| Pd/C | — | 100 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (quantitative yield).

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-1H-pyrrole-2-carboxamide | 284.34 | 0.28 g | 1 |
| Chloroacetylchloride | 113 | ~0.1 mL | 1.2 |
| Triethylamine | 101 | 0.41 mL | 3 |
| Morpholine | 87.12 | 0.52 mL | 6 |
| Triethylamine* | 101 | 0.41 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with morpholine and triethylamine. The mixture was refluxed vigorously for 2 hours (morpholine is added if needed for reaction completion). When the reaction was completed, heating was stopped. The solvent was removed under reduced pressure. The filtrate was evaporated and the oily product was purified on normal phase silica (eluted by PE:THF gradient). 20 mg (5%). HPLC—96% purity. MS—(ES$^+$) Calcd. 411.14. Found 411.8 (MH$^+$).

Synthesis of Compound:

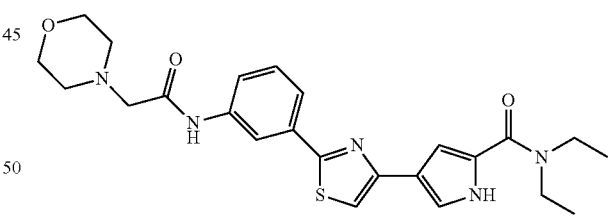

Scheme 28

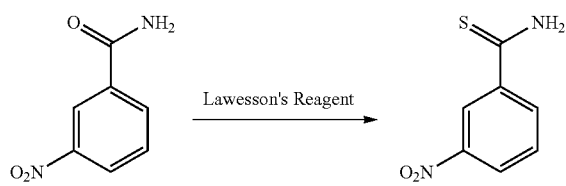

-continued
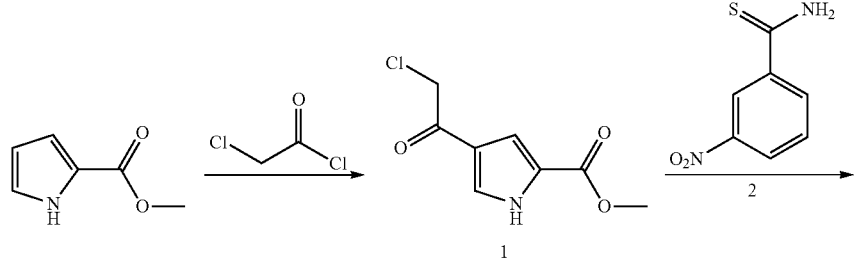
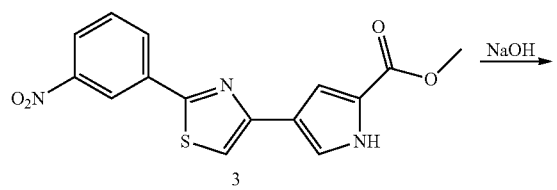
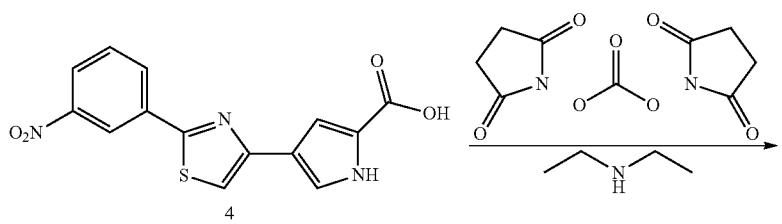
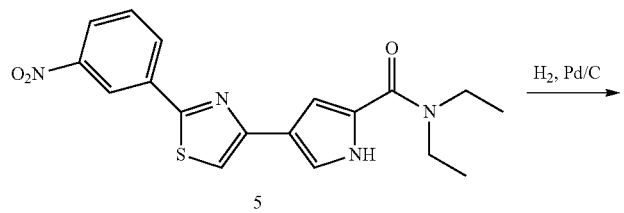
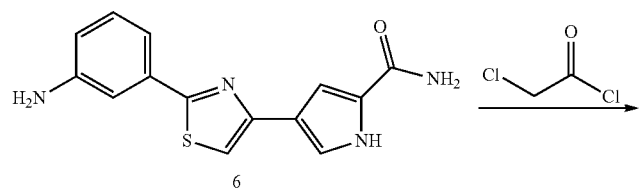
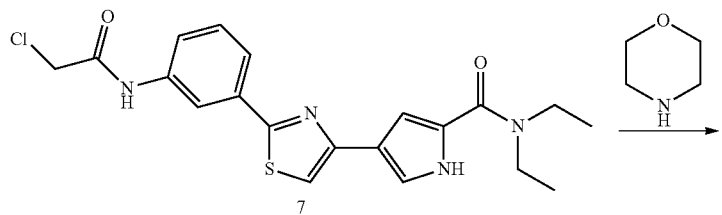
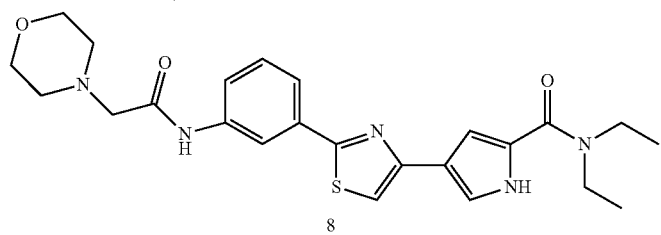

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| $NaHCO_3$ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| $H_2O$ | — | 50 mL | — |

Procedure

NaOH was added to a mixture of the ester in dioxane-$H_2O$ 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 0.780 g | 2.5 |
| bis(2,5-Dioxopyrrolidin-1-yl)carbonate (DSC) | 256.17 | 0.64 g + 0.32 g | 2.5 + 1.25 |
| Acetonitrile-Dioxane 1:1 | — | 30 mL | — |
| Triethylamine | 101 | 1.04 mL | 7.5 |
| Diethylamine | 73.14 | 0.82 mL | 8 |

Procedure

DSC was added to a solution of the acid and triethylamine in dioxane-acetonitrile and the components were stirred at rt. Active ester formation was monitored by HPLC. Extra portions of the activating agent were added until a point of 97% conversion. Then, diethylamine was added. Additional portions of diethylamine were introduced until full conversion of the active ester was observed. The solvents were removed under reduced pressure. DCM was added and the solution was washed with saturated sodium bicarbonate solution. The organic phase was dried over $Na_2SO_4$ and evaporated yielding 0.8 g (86%) of yellow powder.

Reagents Table-Synthesis of 6

| Reagent/raw material | MW (gr/mole) | Quantity | mmoles |
|---|---|---|---|
| N,N-Diethyl-4-(2-(3-nitrophenyl)thiazol-4-yl)-1H-pyrrole-2-carboxamide | 370.43 | 0.80 g | 2.2 |
| Pd/C | — | 120 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (quantitative yield).

Reagents Table-Synthesis of 7 and 8

| Reagent/raw material | MW (gr/mole) | Quantity | mmoles |
|---|---|---|---|
| 4-(2-(3-Aminophenyl)thiazol-4-yl)-N,N-diethyl-1H-pyrrole-2-carboxamide | 340 | 0.68 g | 2 |
| Chloroacetylchloride | 113 | ~0.19 mL | 2.4 |
| Triethylamine | 101 | 0.83 mL | 6 |
| Morpholine | 87.12 | 0.53 mL | 6 |
| Triethylamine* | 101 | 0.83 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of 8

Dioxane was added to the oily residue along with morpholine and triethylamine. The mixture was refluxed vigorously for 2 hours (morpholine is added if needed for reaction completion). When the reaction was completed, heating was stopped. The solvent was removed under reduced pressure. The solution was evaporated and the oily product was purified on normal phase silica (eluted by PE:THF gradient). Fractions were combined and evaporated. The oily product was further triturated using small amount of THF. (87 mg, 9.3%). HPLC—100% purity. MS—(ES$^+$) Calcd. 467.2. Found 467.9 (MH$^+$).

Synthesis of Compound:

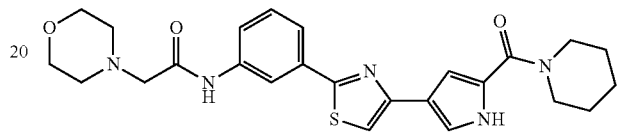

Scheme 29

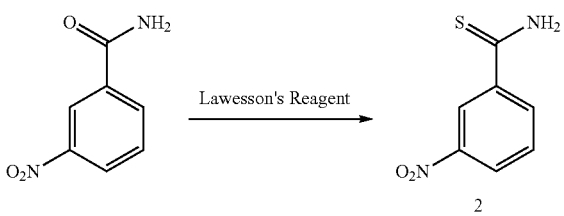

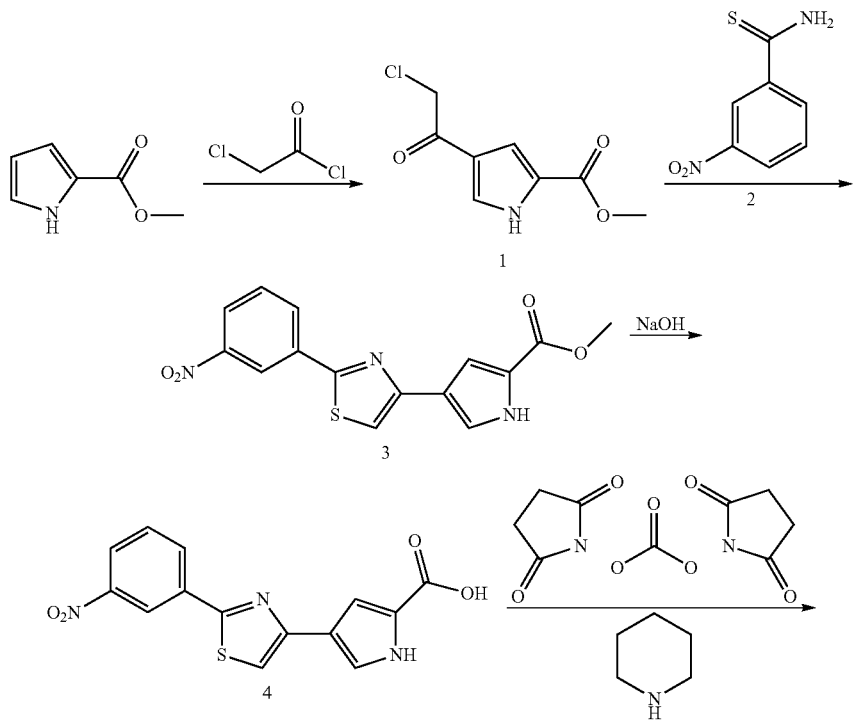

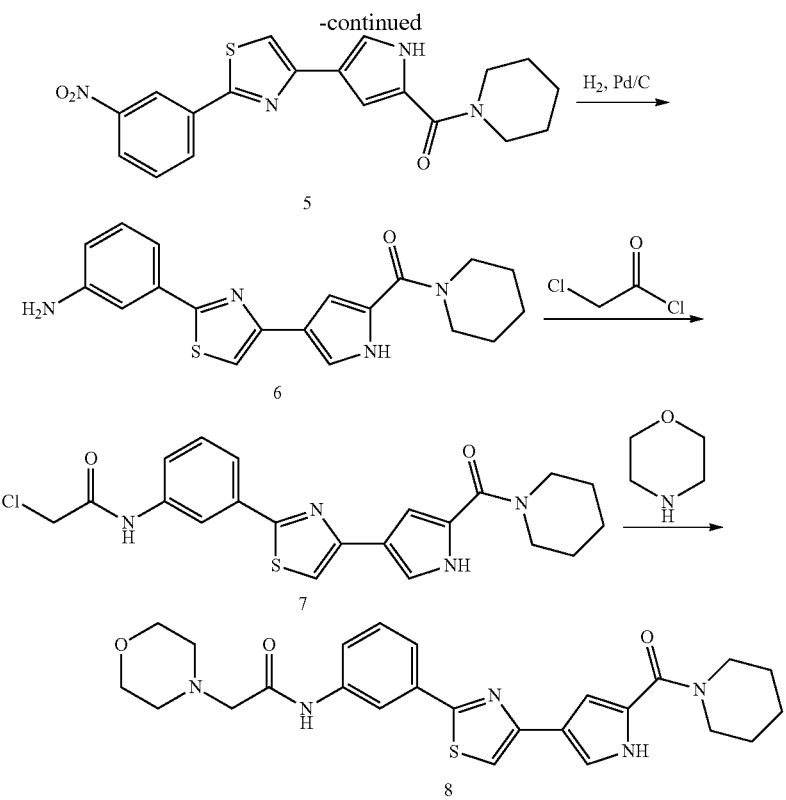

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| $NaHCO_3$ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| $H_2O$ | — | 50 mL | — |

Procedure

NaOH was added to a mixture of the ester in dioxane-$H_2O$ 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 0.78 g | 2.5 |
| bis(2,5-Dioxopyrrolidin-1-yl)carbonate (DSC) | 256.17 | 0.64 + 0.32 g | 2.5 |
| Acetonitrile-Dioxane 1:1 | — | 50 mL | — |
| Triethylamine | 101 | 1.03 mL | 7.5 |
| Piperidine | 85.15 | 0.98 mL | 10 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, piperidine was added and an immediate formation of the amide (precipitate) was observed. Additional portions of pyrrolidine were introduced until full conversion of the active ester was observed. The solid obtained was removed by filtration, and the filtrate (90% purity) was evaporated and the resulting solid was stirred in water (30 mL). Vacuum drying afforded 0.33 g (34%) of yellow solid.

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(piperidin-1-yl)methanone | 382.43 | 0.33 g | 0.86 |
| Pd/C | — | 100 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (0.3 g, quantitative yield).

Reagents Table-Synthesis of 7 and 8

| Reagent/raw material | MW (gr/mole) | Quantity | mmoles |
|---|---|---|---|
| (4-(2-(3-Aminophenyl)thiazol-4-yl)-1H-pyrrol-2-yl)(piperidin-1-yl)methanone | 352 | 0.3 g | 0.85 |
| Chloroacetylchloride | 113 | 0.82 mL | 1 |
| Triethylamine | 101 | 0.42 mL | 3 |
| Morpholine | 87.12 | 0.26 mL | 3 |
| Triethylamine* | 101 | 0.42 mL | 3 |
| DCM | — | 20 mL | — |
| Dioxane | — | 40 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with morpholine and triethylamine. The mixture was refluxed vigorously for 2 hours (morpholine is added if needed for reaction completion). When the reaction was completed, heating was stopped and the solvent was removed under reduced pressure. The residue was taken in EtOH and norit was added. The mixture was stirred for 30 minutes and charcoal was removed by filtration. The filtrate was evaporated and the oily product was purified on normal phase silica (eluted by PE:THF gradient). 104 mg (25%). HPLC—97.4% purity. MS—(ES$^+$) Calcd. 479.59. Found 480.9 (MH$^+$).

Synthesis of Compound:

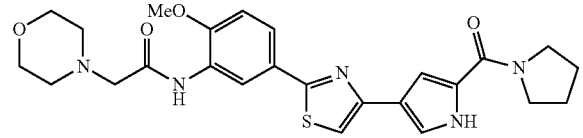 [SMILES: COc1ccc(-c2nc(-c3c[nH]c(C(=O)N4CCCC4)c3)cs2)cc1NC(=O)CN1CCOCC1]

Scheme 30
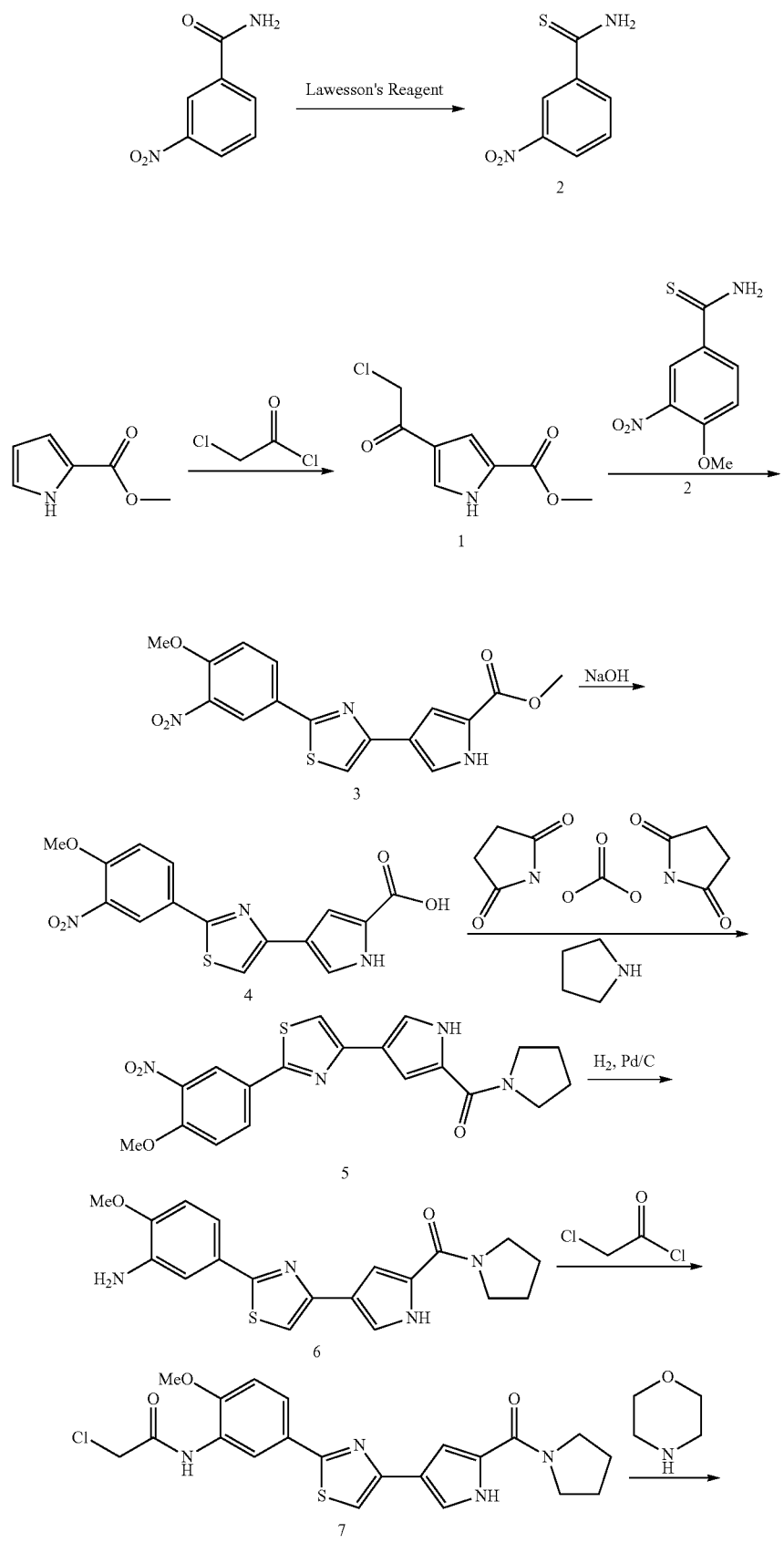

-continued

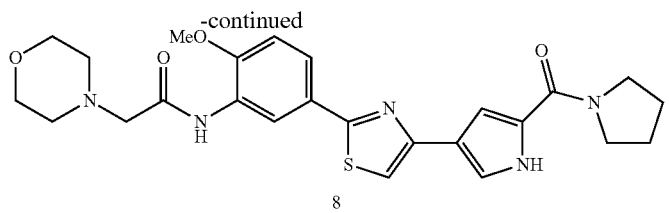

8

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 4-Methoxy-3-nitrobenzamide | 196.16 | 1.1 g | 5.6 |
| Lawesson's reagent | 404 | 1.6 g | 4.0 |
| $NaHCO_3$ | 84 | 0.53 g | 6.0 |
| 1,2 Dimethoxyethane | — | 80 mL | — |
| THF | — | 40 mL | — |

Procedure

Lawesson's reagent was added to a stirring mixture of 4-methoxy-3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (0.9 g, 76% yield).

Reagents Table-Synthesis of 3

| Reagent/raw material | MW (gr/mole) | Quantity | mmoles |
|---|---|---|---|
| 4-Methoxy-3-nitrobenzothioamide | 212.2 | 0.85 g | 4.2 |

-continued

| Reagent/raw material | MW (gr/mole) | Quantity | mmoles |
|---|---|---|---|
| Methyl 4-(2-chloroacetyl)-1H-pyrrole-2-carboxylate | 201.6 | 0.9 g | 4.2 |
| Sodium acetate | 82 | 0.7 g | 8.5 |
| Acetic acid | — | 4 mL | — |

Procedure

The reagents were stirred in acetic acid and heated to reflux resulting in a clear solution followed by precipitation formation. The mixture was refluxed for 2 hours (conversion of starting materials was monitored by HPLC). The mixture was cooled to rt, and the solid was collected by filtration, washed with ice water (80 mL), air dried and then vacuum dried. (1.04 g, 68% orange solid).

Reagents Table-Synthesis of 4

| Reagent/raw material | MW (gr/mole) | Quantity | mmoles |
|---|---|---|---|
| Methyl 4-(2-(4-methoxy-3-nitrophenyl)thiazol-4-yl)-1H-pyrrole-2-carboxylate | 359.4 | 1.04 g | 2.9 |
| NaOH | 40 | 0.46 g | 11.6 |
| Dioxane | — | 15 mL | — |
| $H_2O$ | — | 7.5 mL | — |

Procedure

NaOH was added to a mixture of the ester in a mixture of dioxane-$H_2O$ 2:1. The mixture was heated to 70-80° C. during which a dark solution was formed. When reaction was completed the organic solvent was evaporated and the residue was acidified using concentrated hydrochloric acid. The product was either extracted to ethyl acetate or collected by filtration. Orange solid (980 mg, 98% yield).

Reagents Table-Synthesis of 5

| Reagent/raw material | MW (gr/mole) | Quantity | mmoles |
|---|---|---|---|
| 4-(2-(4-Methoxy-3-nitrophenyl)thiazol-4-yl)-1H-pyrrole-2-carboxylic acid | 345.3 | 980 mg | 2.8 |
| bis(2,5-Dioxopyrrolidin-1-yl) carbonate (DSC) | 256.17 | 1.09 g | 4.2 |
| Acetonitrile-Dioxane 1:1 | — | 60 mL | — |
| Triethylamine | 101 | 1.2 mL | 8.5 |
| Pyrrolidine | 71.1 | 0.6 mL | 7.1 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide was observed (the color of the reaction changed). Additional portions of pyrrolidine were introduced until full conversion of the active ester was observed. The solid obtained was removed by filtration, washed with water and dried under high vacuum to afford the desired product as an orange solid: 1.04 g, 91.9% yield.

Reagents Table-Synthesis of 6

| Reagent/raw material | MW (gr/mole) | Quantity | mmoles |
|---|---|---|---|
| (4-(2-(4-Methoxy-3-nitrophenyl)thiazol-4-yl)-1H-pyrrol-2-yl)(pyrrolidin-1-yl)methanone | 398.4 | 1.04 g | 2.61 |
| Pd/C | — | 150 mg | cat. |
| THF | — | 100 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 950 mg, 98.8% yield.

Reagents Table-Synthesis of 7 and 8

| Reagent/raw material | MW (gr/mole) | Quantity | mmoles |
|---|---|---|---|
| (4-(2-(3-Amino-4-methoxyphenyl)thiazol-4-yl)-1H-pyrrol-2-yl)(pyrrolidin-1-yl)methanone | 368.5 | 950 mg | 2.6 |
| Chloroacetylchloride | 113 | 0.23 mL | 2.8 |
| Triethylamine | 101 | 1.09 mL | 7.7 |
| Morpholine | 87.1 | 0.17 mL | 1.94 |
| Triethylamine* | 101 | 0.27 mL | 1.94 |
| DCM | — | 40 mL | — |
| Dioxane | — | 12 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with morpholine and triethylamine. The mixture was refluxed vigorously for 1 hour (morpholine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:THF gradient) to afford the pure product as a yellow solid: 7.5 mg, 2.3% yield, 100% purity. HPLC—100% purity. MS—(ES$^+$) Calcd. 495.59. Found 496.27 (MH$^+$).

Synthesis of Compound:

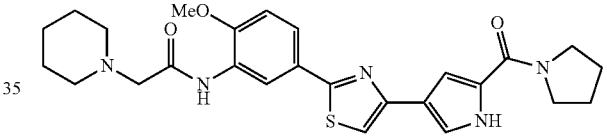

Scheme 31

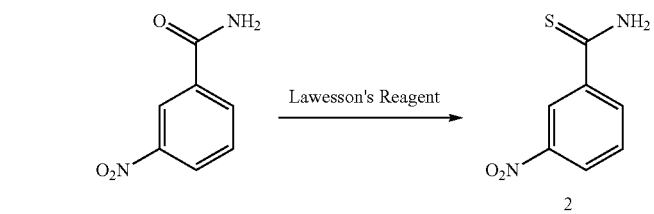

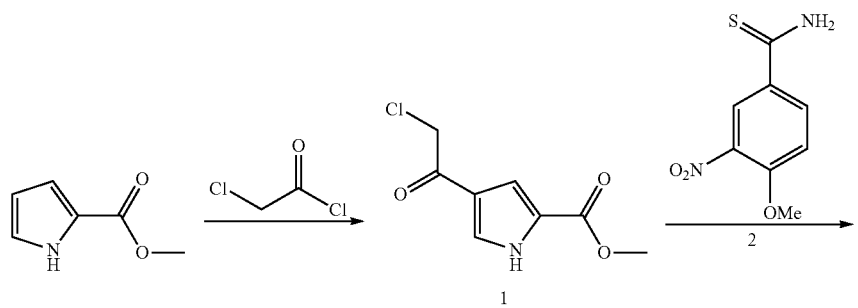

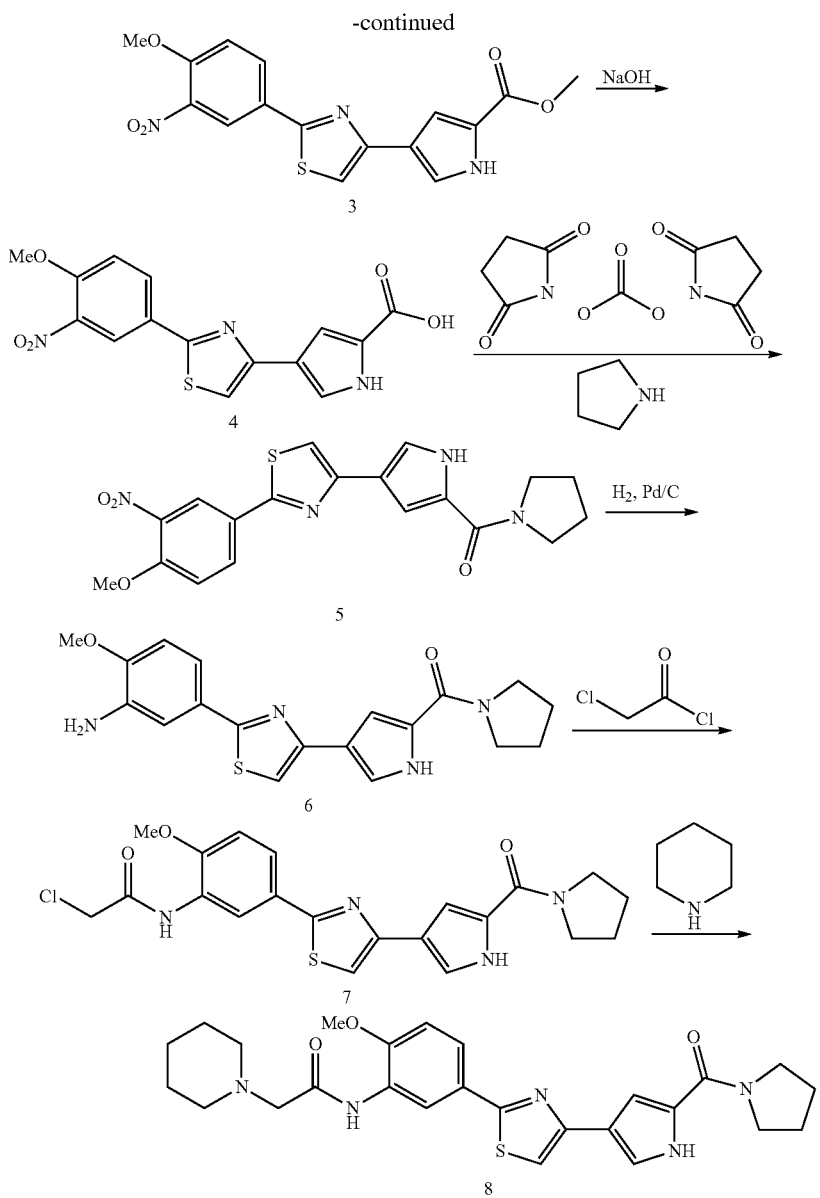

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 4-Methoxy-3-nitrobenzamide | 196.16 | 1.1 g | 5.6 |
| Lawesson's reagent | 404 | 1.6 g | 4.0 |
| NaHCO$_3$ | 84 | 0.53 g | 6.0 |
| 1,2 Dimethoxyethane | — | 80 mL | — |
| THF | — | 40 mL | — |

Procedure

Lwesson's reagent was added to a stirring mixture of 4-methoxy-3-nitrobenzamide in dimethoxyethane-THF 2:1.

The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (0.9 g, 76% yield).

Reagents Table-Synthesis of 3

| Reagent/raw material | MW (gr/mole) | Quantity | mmoles |
|---|---|---|---|
| 4-Methoxy-3-nitrobenzothioamide | 212.2 | 0.85 g | 4.2 |
| Methyl 4-(2-chloroacetyl)-1H-pyrrole-2-carboxylate | 201.6 | 0.9 g | 4.2 |
| Sodium acetate | 82 | 0.7 g | 8.5 |
| Acetic acid | — | 4 mL | — |

Procedure

The reagents were stirred in acetic acid and heated to reflux resulting in a clear solution followed by precipitation formation. The mixture was refluxed for 2 hours (conversion of starting materials was monitored by HPLC). The mixture was cooled to rt, and the solid was collected by filtration, washed with ice water (80 mL), air dried and then vacuum dried. (1.04 g, 68% orange solid).

Reagents Table-Synthesis of 4

| Reagent/raw material | MW (gr/mole) | Quantity | mmoles |
|---|---|---|---|
| Methyl 4-(2-(4-methoxy-3-nitrophenyl)thiazol-4-yl)-1H-pyrrole-2-carboxylate | 359.4 | 1.04 g | 2.9 |
| NaOH | 40 | 0.46 g | 11.6 |
| Dioxane | — | 15 mL | — |
| H$_2$O | — | 7.5 mL | — |

Procedure

NaOH was added to a suspension of the ester in a mixture of dioxane-H$_2$O 2:1. The mixture was heated to 70-80° C. during which a dark solution was formed. When reaction was completed the organic solvent was evaporated and the residue was acidified using concentrated hydrochloric acid. The product was either extracted to ethyl acetate or collected by filtration. Orange solid (980 mg, 98% yield).

Reagents Table-Synthesis of 5

| Reagent/raw material | MW (gr/mole) | Quantity | mmoles |
|---|---|---|---|
| 4-(2-(4-Methoxy-3-nitrophenyl)thiazol-4-yl)-1H-pyrrole-2-carboxylic acid | 345.3 | 980 mg | 2.8 |
| bis(2,5-Dioxopyrrolidin-1-yl) carbonate (DSC) | 256.17 | 1.09 g | 4.2 |
| Acetonitrile-Dioxane 1:1 | — | 60 mL | — |
| Triethylamine | 101 | 1.2 mL | 8.5 |
| Pyrrolidine | 71.1 | 0.6 mL | 7.1 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide was observed (the color of the reaction changed). Additional portions of pyrrolidine were introduced until full conversion of the active ester was observed. The solid obtained was removed by filtration, washed with water and dried under high vacuum to afford the desired product as an orange solid: 1.04 g, 91.9% yield.

Reagents Table-Synthesis of 6

| Reagent/raw material | MW (gr/mole) | Quantity | mmoles |
|---|---|---|---|
| (4-(2-(4-Methoxy-3-nitrophenyl)thiazol-4-yl)-1H-pyrrol-2-yl)(pyrrolidin-1-yl)methanone | 398.4 | 1.04 g | 2.61 |
| Pd/C | — | 150 mg | cat. |
| THF | — | 100 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 950 mg, 98.8% yield.

Reagents Table-Synthesis of 7 and 8

| Reagent/raw material | MW (gr/mole) | Quantity | mmoles |
|---|---|---|---|
| (4-(2-(3-Amino-4-methoxyphenyl)thiazol-4-yl)-1H-pyrrol-2-yl)(pyrrolidin-1-yl)methanone | 368.5 | 950 mg | 2.6 |
| Chloroacetylchloride | 113 | 0.23 mL | 2.8 |
| Triethylamine | 101 | 1.09 mL | 7.7 |
| Piperidine | 85.2 | 0.19 mL | 1.94 |
| Triethylamine* | 101 | 0.27 mL | 1.94 |
| DCM | — | 40 mL | — |
| Dioxane | — | 12 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with piperidine and triethylamine. The mixture was refluxed vigorously for 1 hour (piperidine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:EtOAc gradient) to afford the pure product as a yellow solid: 31 mg, 9.7% yield, 99% purity. HPLC—99% purity. MS—(ES$^+$) Calcd. 493.62. Found 494.51 (MH$^+$).

Synthesis of Compound:

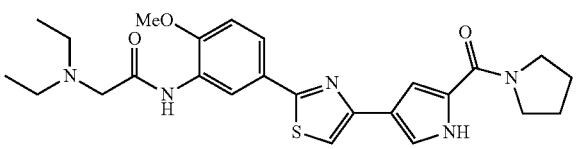 [SMILES: CCN(CC)CC(=O)Nc1cc(-c2nc(-c3c[nH]c(C(=O)N4CCCC4)c3)cs2)ccc1OC]

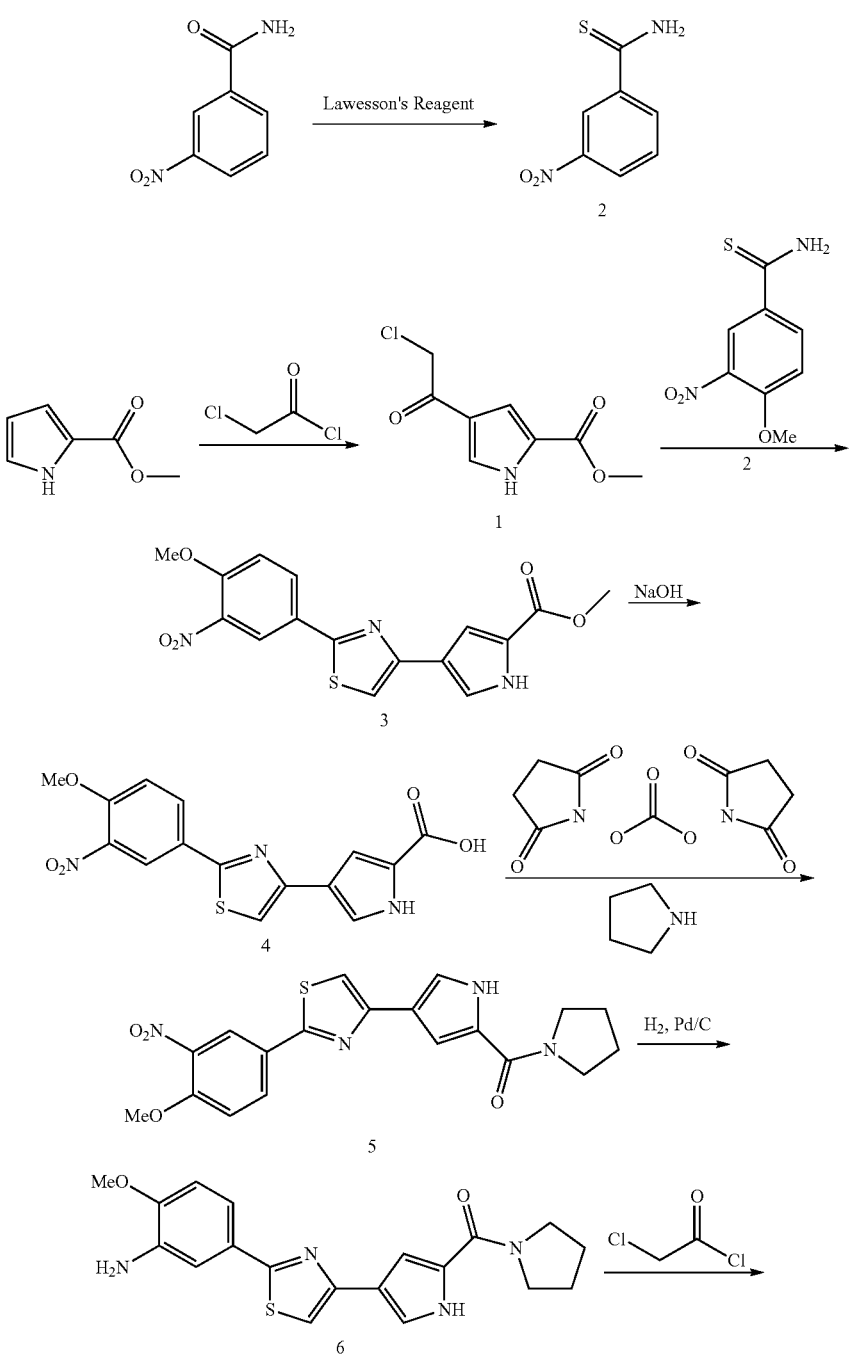

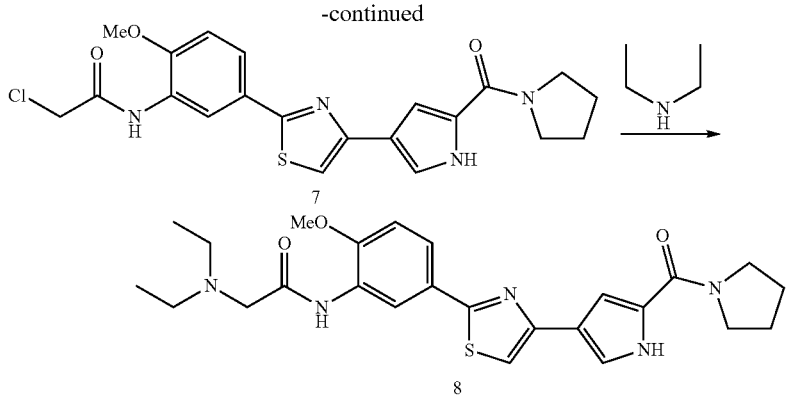

Reagents Table-Synthesis of 1

| Reagent/raw material | MW (gr/mole) | Quantity | mmoles |
| --- | --- | --- | --- |
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
| --- | --- | --- | --- |
| 4-Methoxy-3-nitrobenzamide | 196.16 | 1.1 g | 5.6 |
| Lawesson's reagent | 404 | 1.6 g | 4.0 |
| NaHCO$_3$ | 84 | 0.53 g | 6.0 |
| 1,2 Dimethoxyethane | — | 80 mL | — |
| THF | — | 40 mL | — |

Procedure

Lawesson's reagent was added to a stirring mixture of 4-methoxy-3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (0.9 g, 76% yield).

Reagents Table-Synthesis of 3

| Reagent/raw material | MW (gr/mole) | Quantity | mmoles |
| --- | --- | --- | --- |
| 4-Methoxy-3-nitrobenzothioamide | 212.2 | 0.85 g | 4.2 |
| Methyl 4-(2-chloroacetyl)-1H-pyrrole-2-carboxylate | 201.6 | 0.9 g | 4.2 |
| Sodium acetate | 82 | 0.7 g | 8.5 |
| Acetic acid | — | 4 mL | — |

Procedure

The reagents were stirred in acetic acid and heated to reflux resulting in a clear solution followed by precipitation formation. The mixture was refluxed for 2 hours (conversion of starting materials was monitored by HPLC). The mixture was cooled to rt, and the solid was collected by filtration, washed with ice water (80 mL), air dried and then vacuum dried. (1.04 g, 68% orange solid).

Reagents Table-Synthesis of 4

| Reagent/raw material | MW (gr/mole) | Quantity | mmoles |
| --- | --- | --- | --- |
| Methyl 4-(2-(4-methoxy-3-nitrophenyl)thiazol-4-yl)-1H-pyrrole-2-carboxylate | 359.4 | 1.04 g | 2.9 |
| NaOH | 40 | 0.46 g | 11.6 |
| Dioxane | — | 15 mL | — |
| H$_2$O | — | 7.5 mL | — |

Procedure

NaOH was added to a mixture of the ester in dioxane-H$_2$O (2:1). The reaction mixture was heated to 70-80° C. during which a dark solution was formed. When reaction was completed the organic solvent was evaporated and the residue was acidified using concentrated HCl. The product was either extracted to ethyl acetate or collected by filtration. Orange solid (980 mg, 98% yield).

Reagents Table-Synthesis of 5

| Reagent/raw material | MW (gr/mole) | Quantity | mmoles |
|---|---|---|---|
| 4-(2-(4-Methoxy-3-nitrophenyl)thiazol-4-yl)-1H-pyrrole-2-carboxylic acid | 345.3 | 980 mg | 2.8 |
| bis(2,5-Dioxopyrrolidin-1-yl)carbonate (DSC) | 256.17 | 1.09 g | 4.2 |
| Acetonitrile-Dioxane 1:1 | — | 60 mL | — |
| Triethylamine | 101 | 1.2 mL | 8.5 |
| Pyrrolidine | 71.1 | 0.6 mL | 7.1 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide was observed (the color of the reaction changed). Additional portions of pyrrolidine were introduced until full conversion of the active ester was observed. The solid obtained was removed by filtration, washed with water and dried under high vacuum to afford the desired product as an orange solid: 1.04 g, 91.9% yield.

Reagents Table-Synthesis of 6

| Reagent/raw material | MW (gr/mole) | Quantity | mmoles |
|---|---|---|---|
| (4-(2-(4-Methoxy-3-nitrophenyl)thiazol-4-yl)-1H-pyrrol-2-yl)(pyrrolidin-1-yl)methanone | 398.4 | 1.04 g | 2.61 |
| Pd/C | — | 150 mg | cat. |
| THF | — | 100 mL | — |

Procedure

The nitro compound was dissolved in boiling THF. The catalyst was added and the mixture was subjected to hydrogen atmosphere for 48 h. The catalyst was removed by filtration over celite and the solvent was evaporated yielding the product as a yellow solid: 950 mg, 98.8% yield.

Reagents Table-Synthesis of 7 and 8

| Reagent/raw material | MW (gr/mole) | Quantity | mmoles |
|---|---|---|---|
| (4-(2-(3-Amino-4-methoxyphenyl)thiazol-4-yl)-1H-pyrrol-2-yl)(pyrrolidin-1-yl)methanone | 368.5 | 950 mg | 2.6 |
| Chloroacetylchloride | 113 | 0.23 mL | 2.8 |
| Triethylamine | 101 | 1.09 mL | 7.7 |
| Diethyl amine | 73 | 1.35 mL | 12.9 |
| Triethylamine* | 101 | 0.27 mL | 1.94 |
| DCM | — | 40 mL | — |
| Dioxane | — | 12 mL | — |

*Synthesis of 8

Synthesis of 7

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 8

Dioxane was added to the oily residue along with diethyl amine and triethylamine. The mixture was refluxed vigorously for 1 hour (diethyl amine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was purified on normal phase silica (eluted by PE:EtOAc gradient) to afford the pure product as a yellow solid: 32 mg, 10.3% yield, 99% purity. HPLC—99% purity. MS—(ES$^+$) Calcd. 481.61. Found 482.23 (MH$^+$).

Synthesis of Compound:

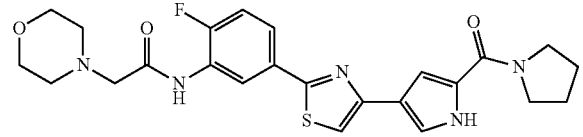 [SMILES: O=C(CN1CCOCC1)Nc1cc(-c2nc(-c3c[nH]c(C(=O)N4CCCC4)c3)cs2)ccc1F]

Scheme 33

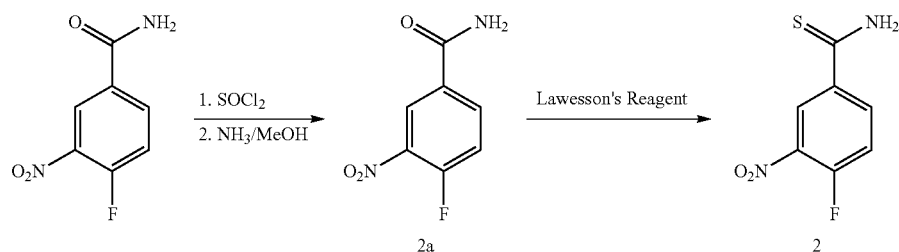

-continued
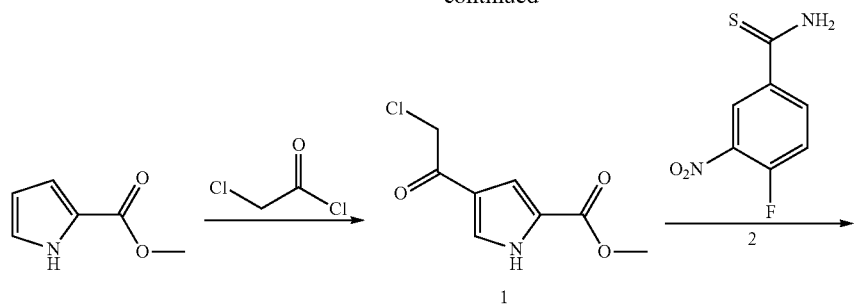
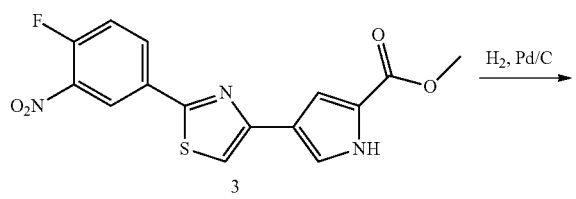
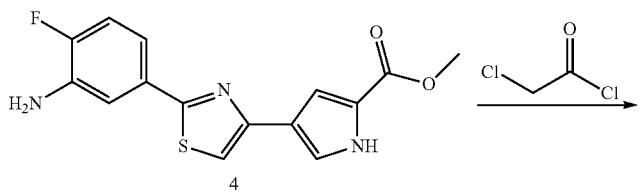
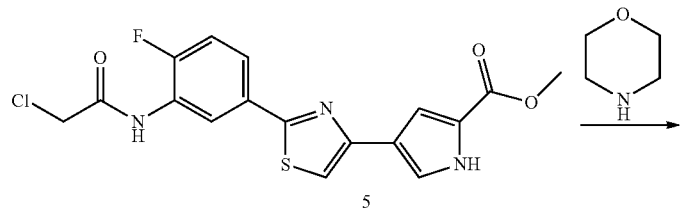
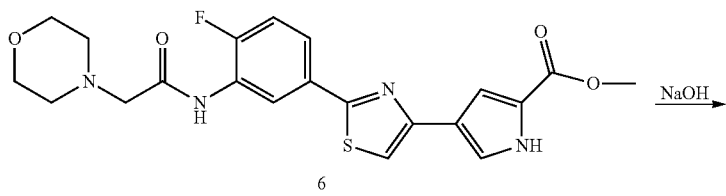
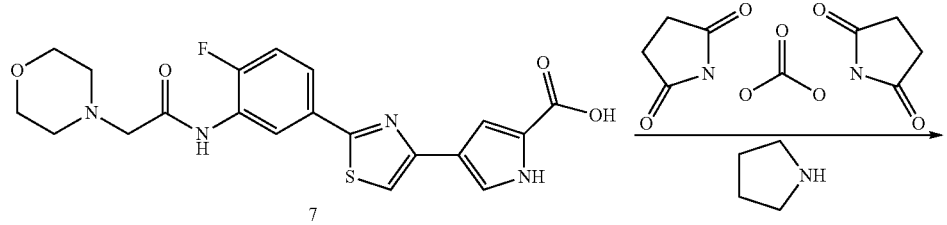
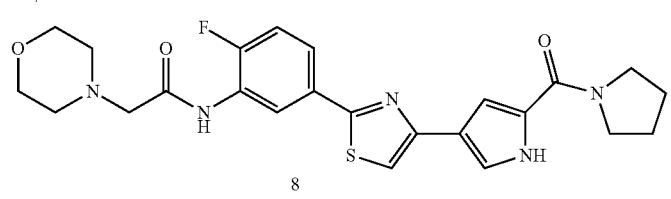

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2a

| Reagent/raw material | MW (gr/mole) | Quantity | mmoles |
|---|---|---|---|
| 4-Fluoro-3-nitrobenzoic acid | 185.1 | 1.1 g | 6.0 |
| Thionyl chloride | — | 5 mL | — |
| NH$_3$ in MeOH | 84 | 1.7 mL | 12.0 |
| Toluene | — | 15 mL | — |

Procedure

Step A: to a mixture of 4-Fluoro-3-nitrobenzoic acid in toluene, thionyl chloride was added. The mixture was stirred at 80° C. for 20 h and the solvent was evaporated to give the acyl chloride.

Step B: acyl chloride was dissolved in toluene. Ammonia in MeOH was added dropwise to the solution, resulting in yellow precipitation formation. The mixture was stirred 15 minutes at rt. Then, 1 M HCl was added. The solid was collected by filtration, washed with water and dried under vacuum to afford the pure product as yellow solid: 740 mg, 67% yield.

Reagents Table-Synthesis of 2

| Reagent/raw material | MW (gr/mole) | Quantity | mmoles |
|---|---|---|---|
| 4-Fluoro-3-nitrobenzamide | 184.1 | 1.5 g | 8.0 |
| Lawesson's reagent | 404 | 2.4 g | 6.0 |
| NaHCO$_3$ | 84 | 0.5 g | 6.0 |
| 1,2 Dimethoxyethane | — | 16 mL | — |
| THF | — | 8 mL | — |

Procedure

Lawesson's reagent was added to a stirring mixture of 4-fluoro-3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (60 mL). The milky mixture was heated to boil and then left to cool to rt. resulting in yellow crystals. (1.23 g, 75.4% yield).

Reagents Table-Synthesis of 3

| Reagent/raw material | MW (gr/mole) | Quantity | mmoles |
|---|---|---|---|
| 4-Fluoro-3-nitrobenzothioamide | 200.2 | 1.24 g | 6.14 |
| Methyl 4-(2-chloroacetyl)-1H-pyrrole-2-carboxylate | 201.6 | 1.24 g | 6.14 |
| Sodium acetate | 82 | 1.0 g | 12.3 |
| Acetic acid | — | 5 mL | — |

Procedure

The reagents were stirred in acetic acid and heated to reflux resulting in a clear solution followed by precipitation formation. The mixture was refluxed for 2 hours (conversion of starting materials was monitored by HPLC). The mixture was cooled to rt, and the solid was collected by filtration, washed with ice water (80 mL), air dried and then vacuum dried (1.5 g, 70.3% orange solid).

Reagents Table-Synthesis of 4

| Reagent/raw material | MW (gr/mole) | Quantity | mmoles |
|---|---|---|---|
| Methyl 4-(2-(4-fluoro-3-nitrophenyl)thiazol-4-yl)-1H-pyrrole-2-carboxylate | 347.3 | 700 mg | 2.0 |
| Pd/C | — | 200 mg | cat. |
| THF | — | 60 mL | — |

Procedure

The nitro compound was dissolved in boiling THF. The catalyst was added and the mixture was subjected to hydrogen atmosphere for 72 h. The catalyst was removed by filtration over celite and the solvent was evaporated yielding the product as a brown solid: 680 mg, 100% yield.

Reagents Table-Synthesis of 5 and 6

| Reagent/raw material | MW (gr/mole) | Quantity | mmoles |
|---|---|---|---|
| Methyl 4-(2-(3-amino-4-fluorophenyl)thiazol-4-yl)-1H-pyrrole-2-carboxylate | 317.3 | 680 mg | 2.14 |
| Chloroacetylchloride | 113 | 0.19 mL | 2.36 |
| Triethylamine | 101 | 0.90 mL | 6.43 |
| Morpholine | 87.1 | 0.57 mL | 6.43 |
| Triethylamine* | 101 | 0.90 mL | 6.43 |
| DCM | — | 35 mL | — |
| Dioxane | — | 35 mL | — |

*Synthesis of 6

Synthesis of 5

A solution of chloroacetylchloride in DCM was added dropwise to a mixture of aniline and triethylamine in DCM under cooling on ice bath. (The mixture turns into a clear solution upon addition) The reaction mixture was stirred for 1 h. The solvent was removed under reduced pressure and the oily residue was used as is in the next step.

Synthesis of 6

Dioxane was added to the oily residue along with morpholine and triethylamine. The mixture was refluxed vigorously for 2 hours (morpholine is added if needed for reaction completion). When the reaction was completed, heating was stopped, norit was added and the mixture was stirred for 20 minutes. The charcoal was removed by filtration and the solvent was evaporated under reduced pressure. The filtrate was evaporated and the oily product was taken to the next step without further treatment: 1.2 g, 100% yield.

Reagents Table-Synthesis of 7

| Reagent/raw material | MW (gr/mole) | Quantity | mmoles |
|---|---|---|---|
| Methyl 4-(2-(4-fluoro-3-(2-morpholinoacetamido)phenyl)thiazol-4-yl)-1H-pyrrole-2-carboxylate | 444.5 | 1.2 g | 2.7 |
| NaOH | 40 | 0.43 g | 10.8 |

-continued

| Reagent/raw material | MW (gr/mole) | Quantity | mmoles |
|---|---|---|---|
| Dioxane | — | 12 mL | — |
| H$_2$O | — | 6 mL | — |

Procedure

NaOH was added to a mixture of the ester in dioxane-H$_2$O 2:1. The mixture was heated to 80° C. for 2 h during which a dark solution was formed. When reaction was completed the organic solvent was evaporated and the residue was acidified using concentrated hydrochloric acid. The product was collected by filtration and washed with water. After drying in vacuum, the desired product was obtained as a brown solid (380 mg, 32.7% yield).

Reagents Table-Synthesis of 8

| Reagent/raw material | MW (gr/mole) | Quantity | mmoles |
|---|---|---|---|
| 4-(2-(4-Fluoro-3-(2-morpholinoacetamido)phenyl)thiazol-4-yl)-1H-pyrrole-2-carboxylic acid | 430.45 | 380 mg | 0.88 |
| bis(2,5-Dioxopyrrolidin-1-yl)carbonate (DSC) | 256.17 | 340 mg | 1.32 |
| Acetonitrile-Dioxane 1:1 | — | 18 mL | — |
| Triethylamine | 101 | 268 mg | 2.65 |
| Pyrrolidine | 71.1 | 157 mg | 2.20 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide was observed (the color of the reaction changed). Additional portions of pyrrolidine were introduced until full conversion of the active ester was observed. The solid obtained was collected by filtration, washed with water and dried under high vacuum to afford the crude product. The crude was purified by Combi-flash column to give the product with 94% purity. Crystallization from hot MeOH afforded the pure desired product as a white solid: 15 mg, 3.5% yield, 100% purity. HPLC—100% purity. MS—(ES$^+$) Calcd. 483.56. Found 484.36 (MH$^+$).

Synthesis of Compound:

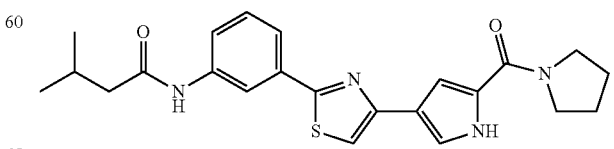

Scheme 34
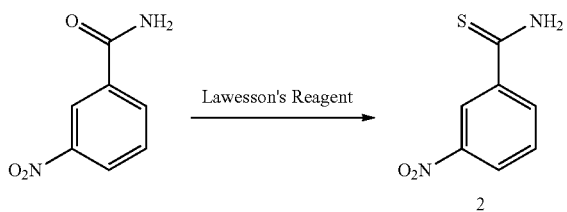
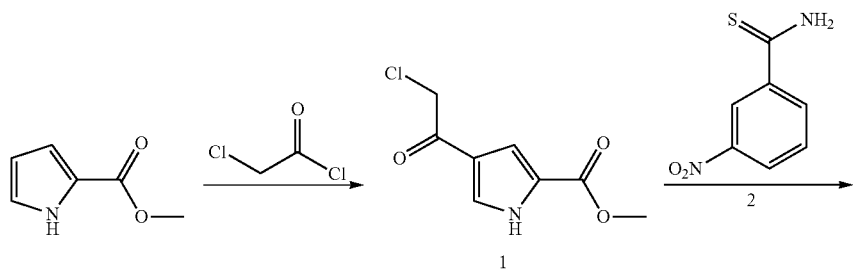
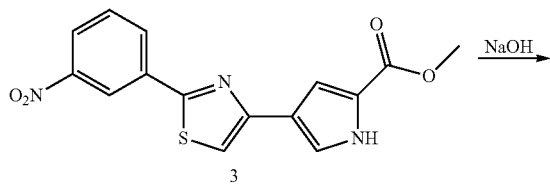
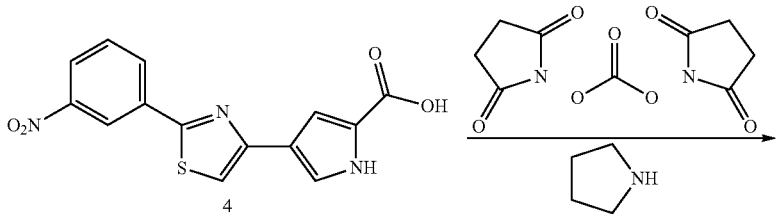
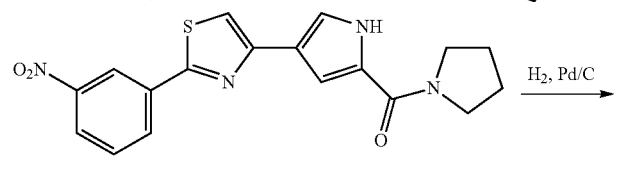
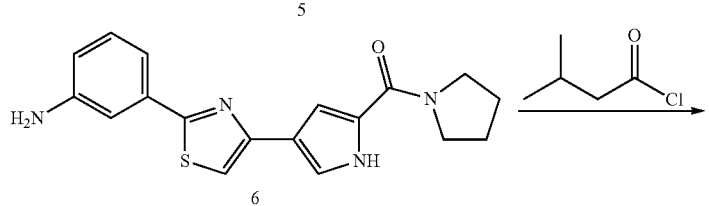
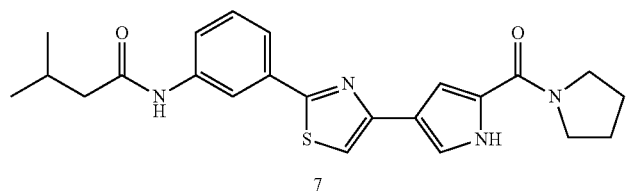

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| $NaHCO_3$ | 84 | 2 g | 12 |
| 1,2 Dimethoxyethane | — | 80 mL | — |
| THF | — | 40 mL | — |

Procedure

Lawesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| $H_2O$ | — | 50 mL | — |

Procedure

NaOH was added to a mixture of the ester in dioxane-$H_2O$ (2:1). The reaction mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.1 g | 10 |
| bis(2,5-Dioxopyrrolidin-1-yl) carbonate (DSC) | 256.17 | 2.56 + 1.28 g | 10 + 5 |
| Acetonitrile-Dioxane 1:1 | — | 50 mL | — |
| Triethylamine | 101 | 4.15 mL | 30 |
| Pyrrolidine | 71.12 | 2.5 mL | 30 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was removed by filtration, and the filtrate (90% purity) was evaporated and the resulting solid was stirred in water (30 mL). Vacuum drying afforded the pure desired product: 3.68 g, 100% yield.

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 3.68 g | 10 |
| Pd/C | — | 150 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.0 g, 80%).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338 | 1.0 g | 2.95 |
| 3-Methylbutanoyl chloride | 120 | ~0.1 mL | 1.2 |
| Triethylamine | 101 | 0.41 mL | 3 |

Synthesis of 7

A solution of 3-Methylbutanoyl chloride in DCM was added dropwise to a mixture of aniline and triethylamine in DCM under cooling on ice bath. The reaction mixture was stirred for 1 h. The product gradually precipitated from the mixture, collected by filtration and washed with water. 160 mg, 31% yield. HPLC—100% purity. MS—(ES$^+$) Calcd. 422.54. Found 423.31 (MH$^+$).

Synthesis of Compound:

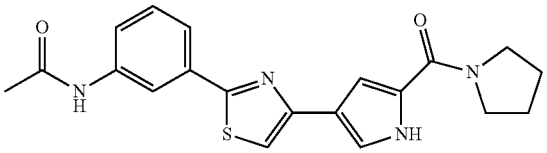

Scheme 35

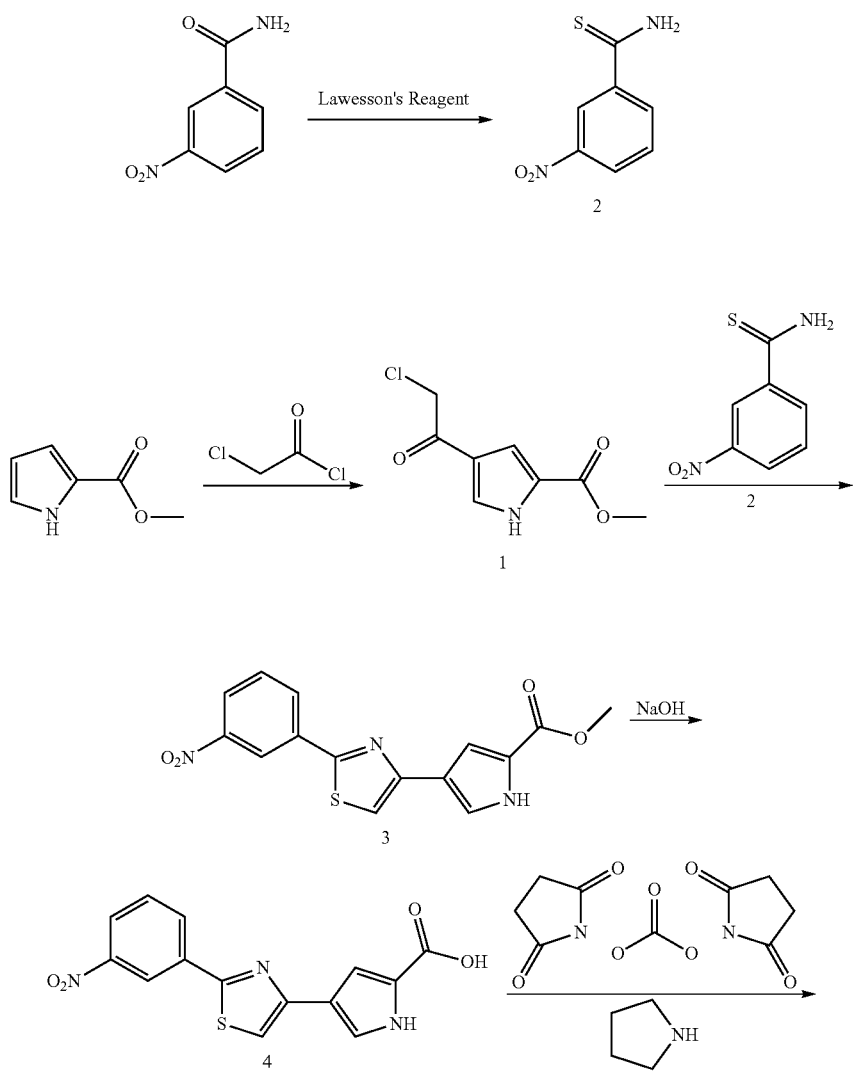

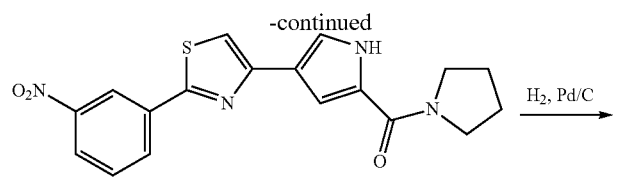

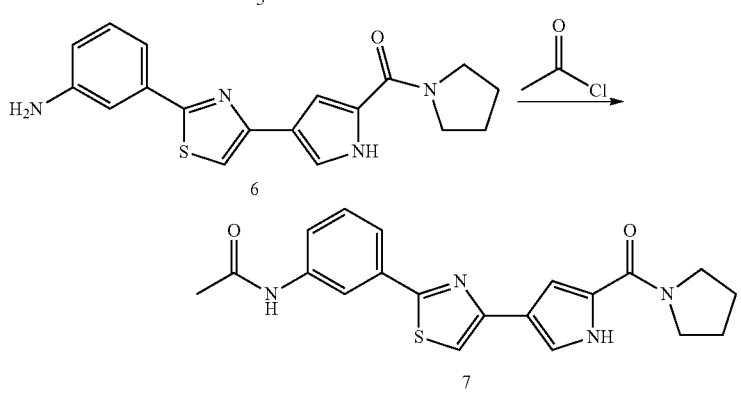

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| AlCl$_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of AlCl$_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over Na$_2$SO$_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| NaHCO$_3$ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF 2:1. The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| H$_2$O | — | 50 mL | — |

Procedure

NaOH was added to a mixture of the ester in dioxane-H$_2$O 2:1. The mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.1 g | 10 |
| bis(2,5-Dioxopyrrolidin-1-yl)carbonate (DSC) | 256.17 | 2.56 + 1.28 g | 10 + 5 |
| Acetonitrile-Dioxane 1:1 | — | 50 mL | — |
| Triethylamine | 101 | 4.15 mL | 30 |
| Pyrrolidine | 71.12 | 2.5 mL | 30 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was removed by filtration, and the filtrate (90% purity) was evaporated and the resulting solid was stirred in water (30 mL). Vacuum drying afforded the pure desired product: 3.68 g, 100% yield.

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 3.68 g | 10 |

-continued

| Reagent/raw material | MW (gr/mole) | Quantity | mmoles |
|---|---|---|---|
| Pd/C | — | 200 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.0 g, 80%).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338 | 0.338 g | 1.0 |
| Acetyl chloride | 78.5 | 0.085 mL | 1.2 |
| Triethylamine | 101 | 0.42 mL | 3.0 |

Synthesis of 7

A solution of Acetyl chloride in DCM was added dropwise to a mixture of aniline and triethylamine in DCM under cooling on ice bath. The reaction mixture was stirred for 1 h. The product gradually precipitated from the mixture, collected by filtration and washed with water. The product was crystallized from MeOH. 83 mg, 22% yield. HPLC—97.6% purity. MS—(ES$^+$) Calcd. 380.46. Found 381.30 (MH$^+$).

Synthesis of Compound:

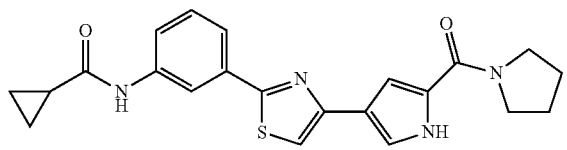 [SMILES: O=C(Nc1cccc(-c2nc(-c3c[nH]c(C(=O)N4CCCC4)c3)cs2)c1)C1CC1]

Scheme 36

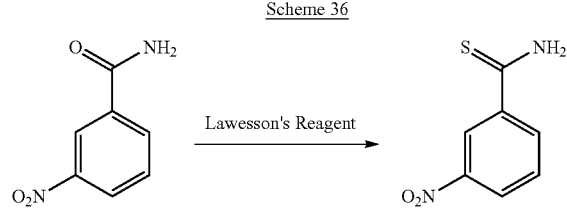

-continued
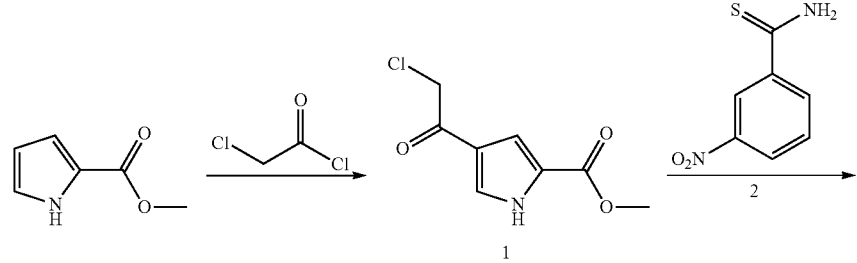
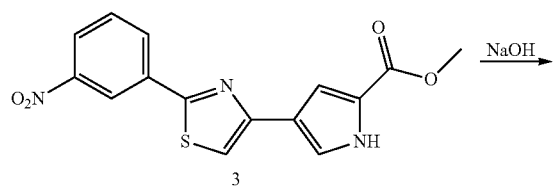
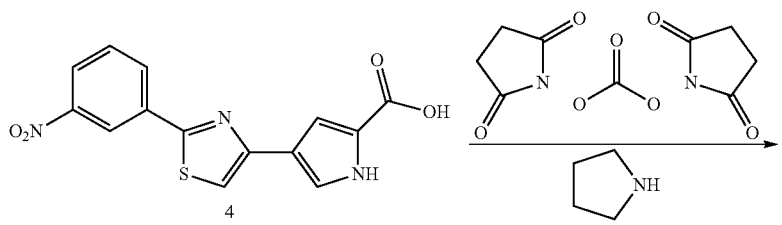
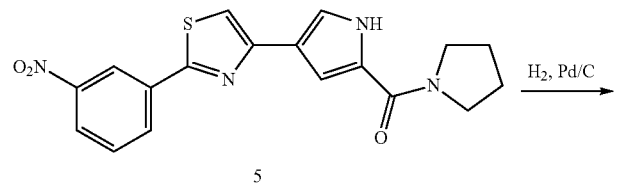
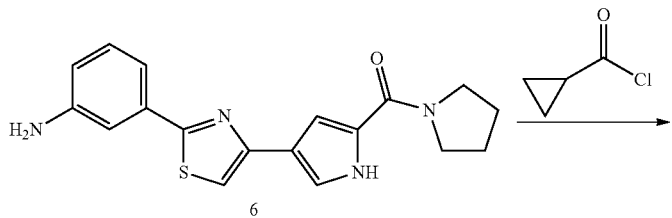
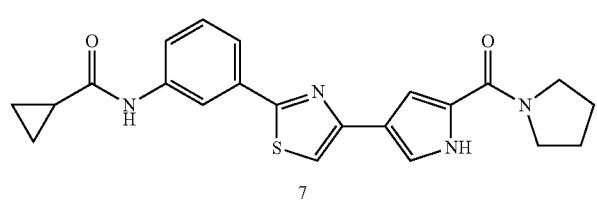

Reagents Table-Synthesis of 1

| Reagent/raw material | MW (gr/mole) | Quantity | mmoles |
|---|---|---|---|
| Methyl 1H-pyrrole-2-carboxylate | 125.13 | 6.25 g | 50 |
| $AlCl_3$ | 133.34 | 16.67 g | 125 |
| Chloroacetyl chloride | 113 | 10 mL | 125 |
| DCM | — | 100 mL | — |

Procedure

A solution of methyl 1H-pyrrole-2-carboxylate (6.25 g, 50 mmoles) in DCM (80 mL) was added dropwise to a stirring mixture of $AlCl_3$ (16.67 g, 125 mmoles) and chloroacetyl chloride (10 mL, 125 mmoles) in DCM (50 mL) under cooling on ice bath, resulting in white precipitation formation. When the addition was completed the mixture was refluxed and monitored by HPLC. When full conversion was observed the reaction was poured into a mixture of water and crushed ice (300 mL) and stirred until the organic phase was gone. The product was extracted to EA and washed 3 times with saturated bicarbonate solution; the organic phase was dried over $Na_2SO_4$ and evaporated yielding of gray solid (9 g, 90% yield).

Reagents Table-Synthesis of 2

| Reagent/raw material | MW (gr/mole) | Quantity | mmoles |
|---|---|---|---|
| 3-Nitrobenzamide | 182.2 | 3.32 g | 20 |
| Lawesson's reagent | 404 | 6.06 g | 15 |
| $NaHCO_3$ | 84 | 2 g | 12 |
| 1,2 Dimethoxyethane | — | 80 mL | — |
| THF | — | 40 mL | — |

Procedure

Lwesson's reagent was added to a stirring mixture of 3-nitrobenzamide in dimethoxyethane-THF (2:1). The reaction was stirred at 50° C. for 2 h and when completed sodium bicarbonate was added and the mixture was stirred at rt for 1 h. The solvents were removed under reduced pressure and the oily residue was slowly added to a stirring mixture of water and crushed ice (300 mL). The milky mixture was heated to boil and then left to cool to rt. resulting in yellow crystals. (2.8 g, 77% yield).

Reagents Table-Synthesis of 3

| Reagent/raw material | MW (gr/mole) | Quantity | mmoles |
|---|---|---|---|
| 3-Nitrobrhioenzamide | 182 | 4.55 g | 25 |
| Methyl 4-(2-chloroacetyl)-1H-pyrrole-2-carboxylate | 201.6 | 5.04 g | 25 |
| Sodium acetate | 82 | 4.1 g | 50 |
| Acetic acid | — | 20 mL | — |

Procedure

The reagents were stirred in acetic acid and heated to reflux resulting in a clear solution followed by precipitation formation. The mixture was refluxed for 3-5 hours (conversion of starting materials was monitored by HPLC). The mixture was cooled to rt, and the solid was collected by filtration, washed with ice water (80 mL), air dried and then vacuum dried. (90% mustard yellow powder).

Reagents Table-Synthesis of 4

| Reagent/raw material | MW (gr/mole) | Quantity | mmoles |
|---|---|---|---|
| Methyl 4-(2-(3-nitrophenyl)thiazol-4-yl)-1H-pyrrole-2-carboxylate | 329.33 | 6.6 g | 20 |
| NaOH | 40 | 3.2 g | 80 |
| Dioxane | — | 100 mL | — |
| $H_2O$ | — | 50 mL | — |

Procedure

NaOH was added to a mixture of the ester in dioxane-$H_2O$ (2:1). The reaction mixture was heated to 70-80° C. during which a dark solution is formed. When reaction was completed the organic solvent was evaporated and the residue was acidified using concentrated hydrochloric acid. The product was either extracted to ethyl acetate or collected by filtration. Yellow powder (5.8 g, 92% yield).

Reagents Table-Synthesis of 5

| Reagent/raw material | MW (gr/mole) | Quantity | mmoles |
|---|---|---|---|
| 4-(2-(3-Nitrophenyl)thiazol-4-yl)-1H-pyrrole-2-carboxylic acid | 315.3 | 3.1 g | 10 |
| bis(2,5-Dioxopyrrolidin-1-yl)carbonate (DSC) | 256.17 | 2.56 + 1.28 g | 10 + 5 |
| Acetonitrile-Dioxane 1:1 | — | 50 mL | — |
| Triethylamine | 101 | 4.15 mL | 30 |
| Pyrrolidine | 71.12 | 2.5 mL | 30 |

Procedure

DSC was added to a solution of the acid and triethylamine in dioxane-acetonitrile and the components were stirred at rt. Active ester formation was monitored by HPLC. Extra portions of the activating agent were added until a point of 90-95% conversion. Then, pyrrolidine was added and an immediate formation of the amide (precipitate) was observed. Additional portions of pyrrolidine were introduced until full conversion of the active ester was observed. The solid obtained was removed by filtration, and the filtrate (90% purity) was evaporated and the resulting solid was stirred in water (30 mL). Vacuum drying afforded the pure desired product: 3.68 g, 100% yield.

Reagents Table-Synthesis of 6

| Reagent/raw material | MW (gr/mole) | Quantity | mmoles |
|---|---|---|---|
| (4-(2-(3-Nitrophenyl)thiazol-4-yl)-1H-pyrrol-2-yl)(pyrrolidin-1-yl)methanone | 368.41 | 3.68 g | 10 |
| Pd/C | — | 200 mg | — |
| THF | — | 150 mL | — |

Procedure

The nitro compound was dissolved in boiling THF. The catalyst was added and the mixture was subjected to hydrogen atmosphere overnight. The catalyst was removed by filtration over celite and the solvent was evaporated yielding white foam (1.0 g, 80%).

Reagents Table-Synthesis of 7

| Reagent/raw material | MW (gr/mole) | Quantity | mmoles |
|---|---|---|---|
| (4-(2-(3-Aminophenyl)thiazol-4-yl)-1H-pyrrol-2-yl)(pyrrolidin-1-yl)methanone | 338 | 0.236 g | 0.7 |
| Cyclopropanecarbonyl chloride | 104.53 | 0.08 mL | 0.84 |
| Triethylamine | 101 | 0.29 mL | 2.1 |

Synthesis of 7

A solution of Cyclopropanecarbonyl chloride in DCM was added dropwise to a mixture of aniline and triethylamine in DCM under cooling on ice bath. The reaction mixture was stirred for 1 h. The product gradually precipitated from the mixture, collected by filtration and washed with water. 87.6 mg, 31% yield. HPLC—99% purity. MS—(ES$^+$) Calcd. 406.50. Found 407.40 (MH$^+$).

Example 10

Proliferation of Daudi Cells

The compounds of the invention were tested on Daudi proliferation according to the procedure in Example 4 (for Daudi cells): Proliferation of RS4; 11, Ramos, Namalwa, RL, Molt-4 and Daudi cells. The compounds of the invention were tested on Daudi proliferation (72 hr), 3 fold dilution, and 9 points in duplicates. The top concentration for compounds of the invention was 10 uM; reference compound 7A top concentration was 10 uM; and Paclitaxel was 500 nM. Cell viability was determined using the Cell Titer Glo (CTG) reagent and detected by EnVision. EC$_{50}$s were calculated by Prism 5.

The principle of the assay is depicted in the scheme below:

Scheme 37

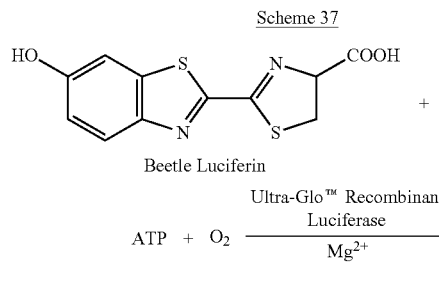

Beetle Luciferin $$ATP + O_2 \xrightarrow[Mg^{2+}]{\text{Ultra-Glo™ Recombinant Luciferase}}$$

-continued

Oxyluciferin

AMP + PP$_i$ + CO$_2$ + Light

The CellTiter-Glo™ Luminescent Cell Viability Assay uses ATP, a required co-factor of the luciferase reaction, as an indicator of metabolically active cells. The enzyme luciferase acts on luciferin in the presence of Mg$^{2+}$ and ATP to produce oxyluciferin and to release energy in the form of luminescence. Since the luciferase reaction requires ATP, the luminescence produced is proportional to the amount of ATP present, an indicator of cellular metabolic activity.

Table 7 below shows the Daudi CTG Assay results. The data is presented whereby the letter "A" means the compound has an IC$_{50}$ between 0.0000001 μM≤0.1 μM, the letter "B" means the compound has an IC$_{50}$ between 0.11 μM≤1.0 μM, the letter "C" means the compound has an IC$_{50}$ between 1.1 μM≤10 μM, and the letter "D" means the compound has an IC$_{50}$ of >10 μM.

TABLE 7

| Compound name | IC$_{50}$ |
|---|---|
| 29A | D |
| 30A | C |
| 31A | C |
| 32A | B |
| 33A | B |
| 34A | B |
| 35A | B |
| 7A | A |
| Paclitaxel | A |

Paclitaxel and compound 7A control IC$_{50}$ were 4.495 nM and 101.5 nM and were confirmed with historical data of 4.691 nM and 122.1 nM, respectively. Compounds 32A and 33A were heated to 60° C. and 70° C. to dissolve them, and there was compound precipitation after they were added to the cells. The assay was repeated and the results were comparable.

Example 11

Preparation of the Free Base 2-morpholino-N-(3-(4-(5-(pyrrolidine-1-carbonyl)-1H-pyrrol-3-yl)thiazol-2-yl)phenyl)acetamide (Compound 7A (Sample 1))

Scheme 38

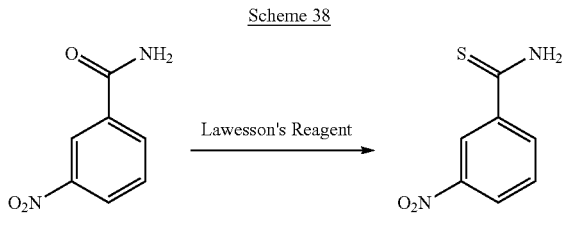

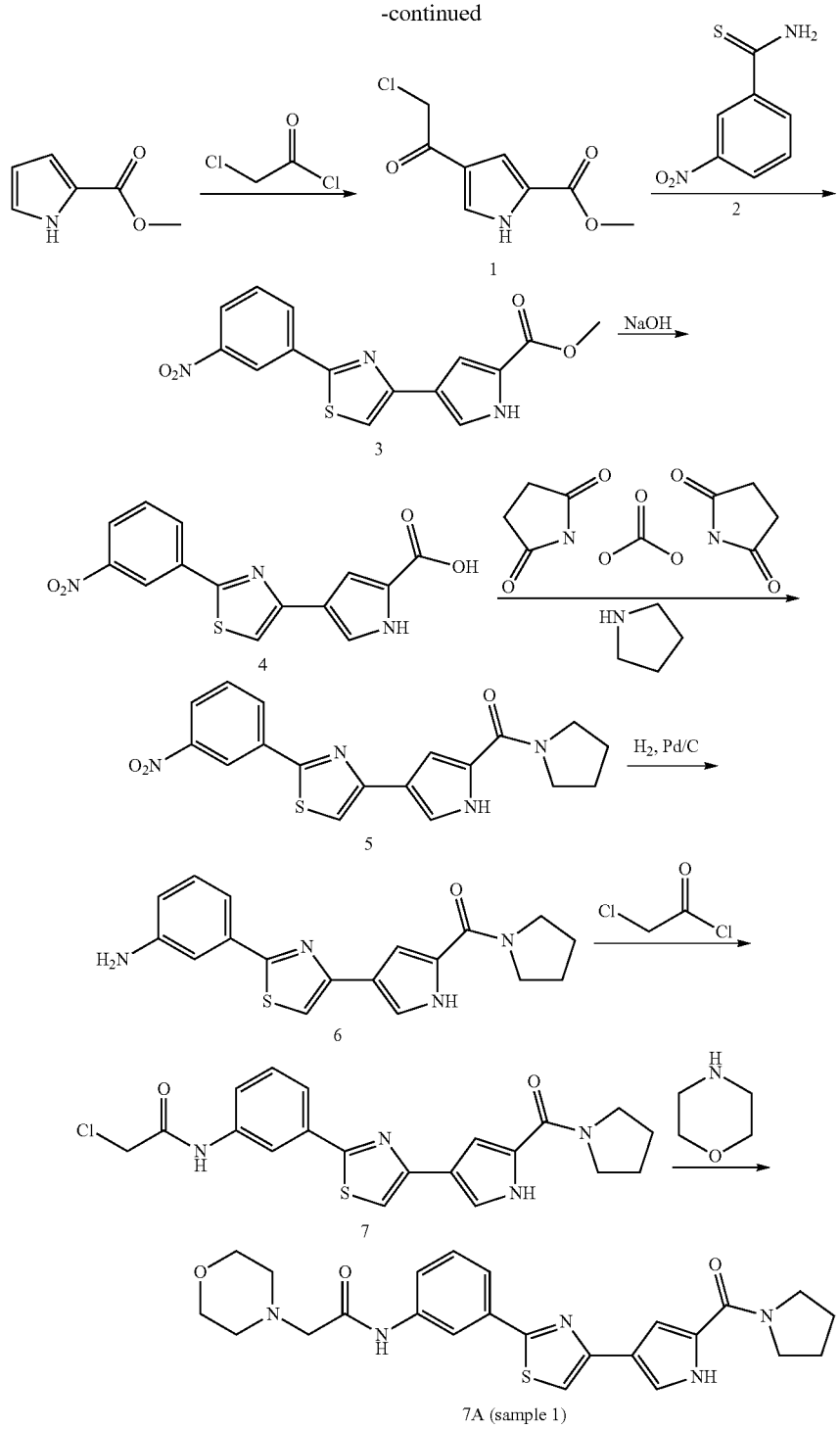
Reagents Table-Synthesis of 1
| Reagent/raw material | MW (gr/mole) | Quantity | Mmoles | Mole ratio |
|---|---|---|---|---|
| Methyl 1H-pyrrole-2-carboxylate | 125.1 | 12.5 gr | 100 | 1.0 |
| AlCl₃ | 133.3 | 33.3 gr | 250 | 2.5 |
| Chloroacetyl chloride | 112.9 | 20 mL | 250 | 2.5 |
| DCM | — | 250 mL | — | — |

421

Procedure

A solution of methyl 1H-pyrrole-2-carboxylate (12.5 gr, 100 mmoles) in DCM (150 mL) was added dropwise to a stirring mixture of $AlCl_3$ (33.3 gr, 250 mmoles) and chloroacetyl chloride (20 mL, 250 mmoles) in DCM (100 mL) under cooling on ice bath, resulting in white precipitation formation. When the addition was completed the mixture was refluxed and monitored by HPLC. When full conversion was observed the reaction was poured into a mixture of water and crushed ice (600 mL) and stirred until the organic phase was gone. The product was extracted to ethyl acetate and washed 3 times with saturated bicarbonate solution. The organic phase was dried over $Na_2SO_4$ and evaporated yielding the pure product as a gray solid (19.9 gr, 98.7% yield, 100% purity).

Reagents Table-Synthesis of 2

| Reagent/raw Material | MW (gr/mole) | Quantity | Mmoles | Mole ratio |
| --- | --- | --- | --- | --- |
| 3-Nitrobenzamide | 166.1 | 9.0 gr | 54.2 | 1.0 |
| Lawesson's reagent | 404 | 16.4 gr | 40.6 | 0.75 |
| $NaHCO_3$ | 84 | 3.41 gr | 40.6 | 0.75 |
| 1,2 Dimethoxyethane/THF (2:1) | — | 300 mL | — | — |

Procedure

Lawesson's reagent was added to a stirring mixture of 3-nitrobenzamide in a mixture of DME/THF (2:1). The reaction mixture was stirred at 50° C. for 2 h and when completed (according to HPLC) sodium bicarbonate was added and stirring was continued at rt for additional 1 h. The solvents were removed under reduced pressure and the oily residue was slowly added to a stirring mixture of water and crushed ice (400 mL) resulting in yellow crystals. The mixture was heated to 70-80° C. with stirring for 15 min. and then left to cool to rt. The solid was collected by filtration, washed with water, air dried and then vacuum dried. The pure product was obtained as a yellow crystalline solid (9.9 gr, 100% yield, 100% purity)

Reagents Table-Synthesis of 3

| Reagent/raw material | MW (gr/mole) | Quantity | mmoles | Mole ratio |
| --- | --- | --- | --- | --- |
| 3-Nitrothiobenzamide | 182.2 | 11.5 gr | 63.1 | 1.0 |
| Methyl 4-(2-chloroacetyl)-1H-pyrrole-2-carboxylate | 201.6 | 12.7 gr | 63.1 | 1.0 |
| Sodium acetate | 82 | 10.4 gr | 126.2 | 2.0 |
| Acetic acid | — | 50 mL | — | — |

Procedure

3-Nitrothiobenzamide and methyl 4-(2-chloroacetyl)-1H-pyrrole-2-carboxylate were suspended in acetic acid and sodium acetate was added. The reaction mixture was heated to reflux resulting in a clear solution followed by precipitation formation. The mixture was refluxed for 1-2 hours (conversion of starting materials was monitored by HPLC), then cooled to rt. The solid was collected by filtration, washed with ice water (200 mL), air dried and then vacuum dried affording the pure product as a mustard yellow solid (15.6 gr, 75% yield, 100% purity).

Reagents Table-Synthesis of 4

| Reagent/raw material | MW (gr/mole) | Quantity | mmoles | Mole ratio |
| --- | --- | --- | --- | --- |
| Methyl 4-(2-(3-nitrophenyl)thiazol-4-yl)-1H-pyrrole-2-carboxylate | 329.3 | 23.5 gr | 71.4 | 1.0 |
| NaOH | 40 | 11.4 gr | 285.5 | 4.0 |
| Dioxane/$H_2O$ (2:1) | — | 500 mL | — | — |

Procedure

Methyl 4-(2-(3-nitrophenyl)thiazol-4-yl)-1H-pyrrole-2-carboxylate was dissolved in a mixture of dioxane/$H_2O$ (2:1) and NaOH was added. The mixture was heated to 70-80° C. during which a dark solution was formed. Progressing was monitored using HPLC and LCMS. When reaction was completed (1 h), the volume of the organic solvent was reduced by evaporation (to ~30 mL) and then acidified using conc. HCl. The solid formed was cooled in ice bath for 10 min. then collected by filtration and washed with water. After drying in vacuum, the desired product was obtained as a yellow powder (21.4 gr, 95% yield, 100% purity).

Reagents Table-Synthesis of 5

| Reagent/raw material | MW (gr/mole) | Quantity | Mmoles | Mole ratio |
| --- | --- | --- | --- | --- |
| 4-(2-(3-Nitrophenyl)thiazol-4-yl)-1H-pyrrole-2-carboxylic acid | 315.3 | 9.46 gr | 30.0 | 1.0 |
| bis(2,5-Dioxopyrrolidin-1-yl)carbonate | 256.2 | 10.0 gr | 39.0 | 1.3 |
| Pyrrolidine | 71.1 | 6.3 mL | 75.0 | 2.5 |
| Triethylamine | 101.2 | 10.5 mL | 75.0 | 2.5 |
| Acetonitrile-Dioxane (1:1) | — | 500 mL | — | — |

Procedure

To a mixture of the acid in ACN/dioxane mixture, triethylamine was added resulting in clear solution. The activating agent was then added and the components were stirred at rt to prepare the intermediate product. Active ester formation was monitored by HPLC and LCMS. Extra portions of the activating agent were added until a point of 90-95% conversion (2 h). Then, pyrrolidine was added and an immediate formation of the amide (precipitate) was observed. Additional portions of pyrrolidine were introduced until full conversion of the active ester to the desired product was observed (1 h). The solid obtained was collected by filtration, washed with water (200 mL) and dried over vacuum to afford the pure product as a yellow solid (7.9 gr, 71.5%). The filtrate was evaporated and to the residue obtained, EtOAc and 1 M HCl were added. The formed solid in the acidic phase was isolated by filtration and washed with water to give more of the pure product (1.5 gr, 13.6% yield). The total yield of the product was: 9.4 gr, 85.1% yield, 100% purity.

Reagents Table-Synthesis of 6

| Reagent/raw material | MW (gr/mole) | Quantity | Mmoles | Mole ratio |
|---|---|---|---|---|
| (4-(2-(3-Nitrophenyl)thiazol-4-yl)-1H-pyrrol-2-yl)(pyrrolidin-1-yl)methanone | 368.4 | 11.1 gr | 30.0 | 1.0 |
| H$_2$/Pd—C (10%) | — | 0.3 gr | — | — |
| THF (HPLC) | — | 400 mL | — | — |

Procedure

The nitro compound was dissolved in boiling THF (HPLC). The catalyst reagent was added and the mixture was subjected to hydrogen atmosphere overnight. After 48 h at rt, HPLC and LCMS indicated that the starting material was fully consumed. The catalyst was removed by filtration over celite and the solvent was evaporated yielding white solid (10.0 gr, quantitative yield).

Reagents Table-Synthesis of 7 and 7A (Sample 1)

| Reagent/raw material | MW (gr/mole) | Quantity | Mmoles | Mole ratio |
|---|---|---|---|---|
| (4-(2-(3-Aminophenyl)thiazol-4-yl)-1H-pyrrol-2-yl)(pyrrolidin-1-yl)methanone | 338.4 | 1.8 gr | 5.3 | 1.0 |
| Chloroacetylchloride | 112.9 | 0.46 mL | 5.8 | 1.1 |
| Triethylamine | 101.2 | 2.2 mL | 16 | 3.0 |

-continued

| Reagent/raw material | MW (gr/mole) | Quantity | Mmoles | Mole ratio |
|---|---|---|---|---|
| Morpholine | 87.1 | 1.3 mL | 15 | 3.0 |
| Triethylamine* | 101.2 | 2.1 mL | 15 | 3.0 |
| THF | — | 80 mL | — | — |

*Synthesis of 7A (sample 1)

Synthesis of 7

A solution of chloroacetylchloride in DCM (30 mL) was added dropwise to a mixture of aniline and triethylamine in DCM (50 mL) under cooling on ice bath. (The mixture turns into a clear solution upon addition) The reaction mixture was stirred for 1 h. (additional portion of chloroacetylchloride is added on need). The solvent was removed under reduced pressure and the oily residue was used as is in the next step.

Synthesis of Compounds 7A (Sample 1), 7A (Sample 2), and 10X

Dioxane was added to the oily residue along with morpholine and triethylamine. The mixture was refluxed vigorously for 2-3 hours (morpholine is added if needed for reaction completion). When the reaction was completed, heating was stopped, norit was added and the mixture was stirred for 30 minutes.

The solids were removed by filtration and the solvent was removed under reduced pressure. The product was purified by flash chromatography (CombiFlash).

Figure 5:
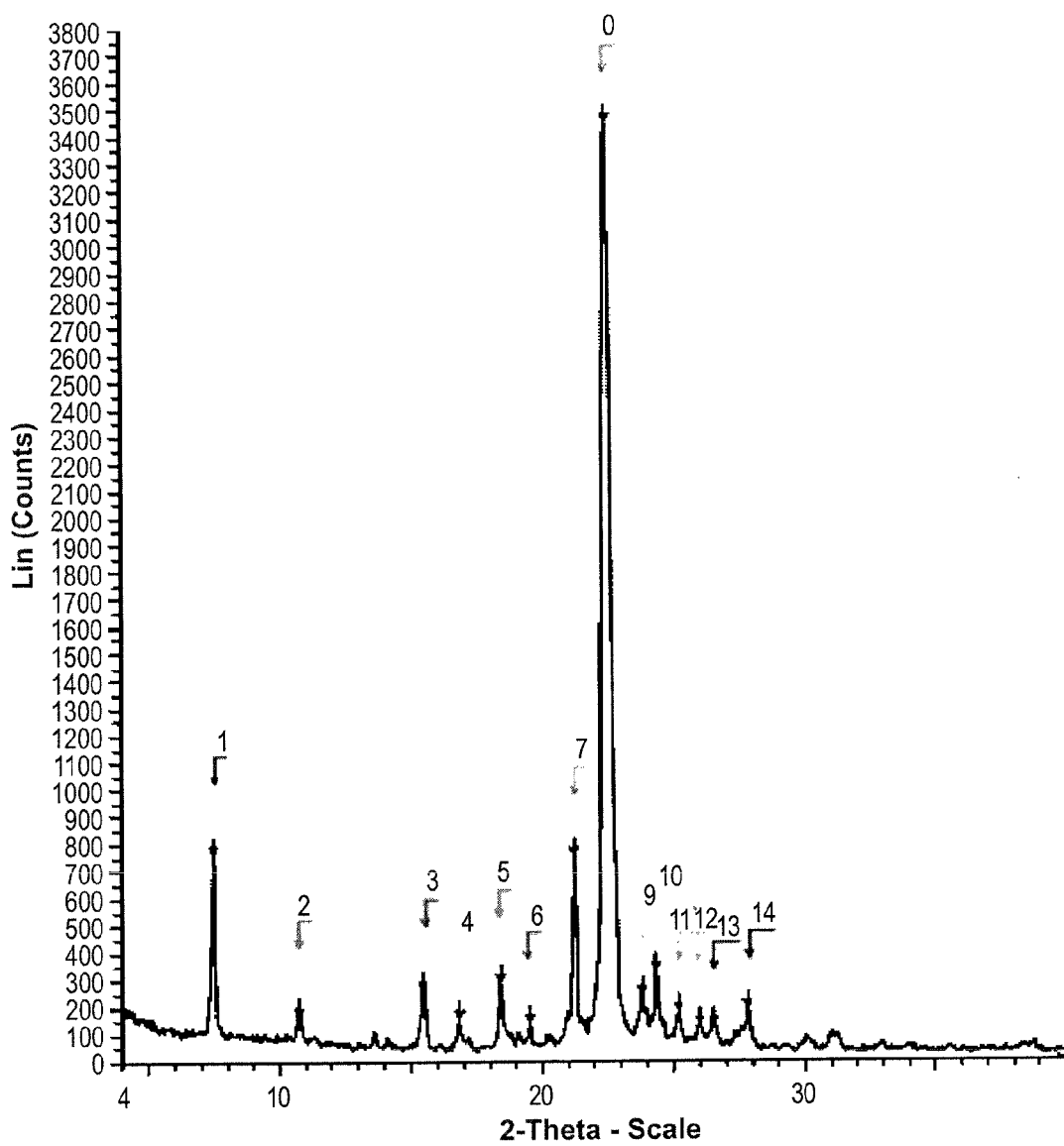
FIG. 5 is a characteristic X-ray diffraction pattern of 2-morpholino-N-(3-(4-(5-(pyrrolidine-1-carbonyl)-1H-pyrrol-3-yl)thiazol-2-yl)phenyl)acetamide (compound 7A (sample 1)) obtained by the method of Example 11 and purified by chromatography.

FIG. 5 shows a characteristic X-ray diffraction pattern of compound 7A (sample 1) prepared by the above method. Compound 7A (sample 1) is an amorphous crystal.

Compound 7A (sample 1) was recrystallized from ethanol to afford compound 10X. FIG. 15 shows a characteristic X-ray diffraction pattern of compound 10X. Table 10 lists the XRD parameter of compound 10X. FIG. 18 shows a DSC thermogram for compound 10X.

TABLE 8

A listing the XRD parameter of compound 7A (sample 1)

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 1 | 7.431 | 11.88721 | 761 | 22 | 2.444 | 9.18 | 0.169 |
| 2 | 10.704 | 8.25806 | 167 | 4.8 | 0.358 | 1.34 | 0.165 |
| 3 | 15.434 | 5.73636 | 260 | 7.5 | 1.007 | 3.78 | 0.224 |
| 4 | 16.826 | 5.26481 | 155 | 4.5 | 0.381 | 1.43 | 0.163 |
| 5 | 18.394 | 4.81946 | 292 | 8.4 | 0.876 | 3.29 | 0.172 |
| 6 | 19.494 | 4.55005 | 141 | 4.1 | 0.229 | 0.86 | 0.145 |
| 7 | 21.236 | 4.18044 | 756 | 21.8 | 1.898 | 7.13 | 0.154 |
| 8 | 22.447 | 3.95755 | 3462 | 100 | 26.63 | 100.00 | 0.37 |
| 9 | 23.79 | 3.7372 | 243 | 7 | 0.315 | 1.18 | 0.166 |
| 10 | 24.353 | 3.65198 | 331 | 9.6 | 0.629 | 2.36 | 0.16 |
| 11 | 25.189 | 3.53267 | 181 | 5.2 | 0.481 | 1.81 | 0.226 |
| 12 | 25.961 | 3.42938 | 130 | 3.8 | 0.262 | 0.98 | 0.223 |
| 13 | 26.526 | 3.35759 | 130 | 3.8 | 0.367 | 1.38 | 0.234 |
| 14 | 27.86 | 3.19973 | 190 | 5.5 | 0.293 | 1.10 | 0.141 |

Figure 6:
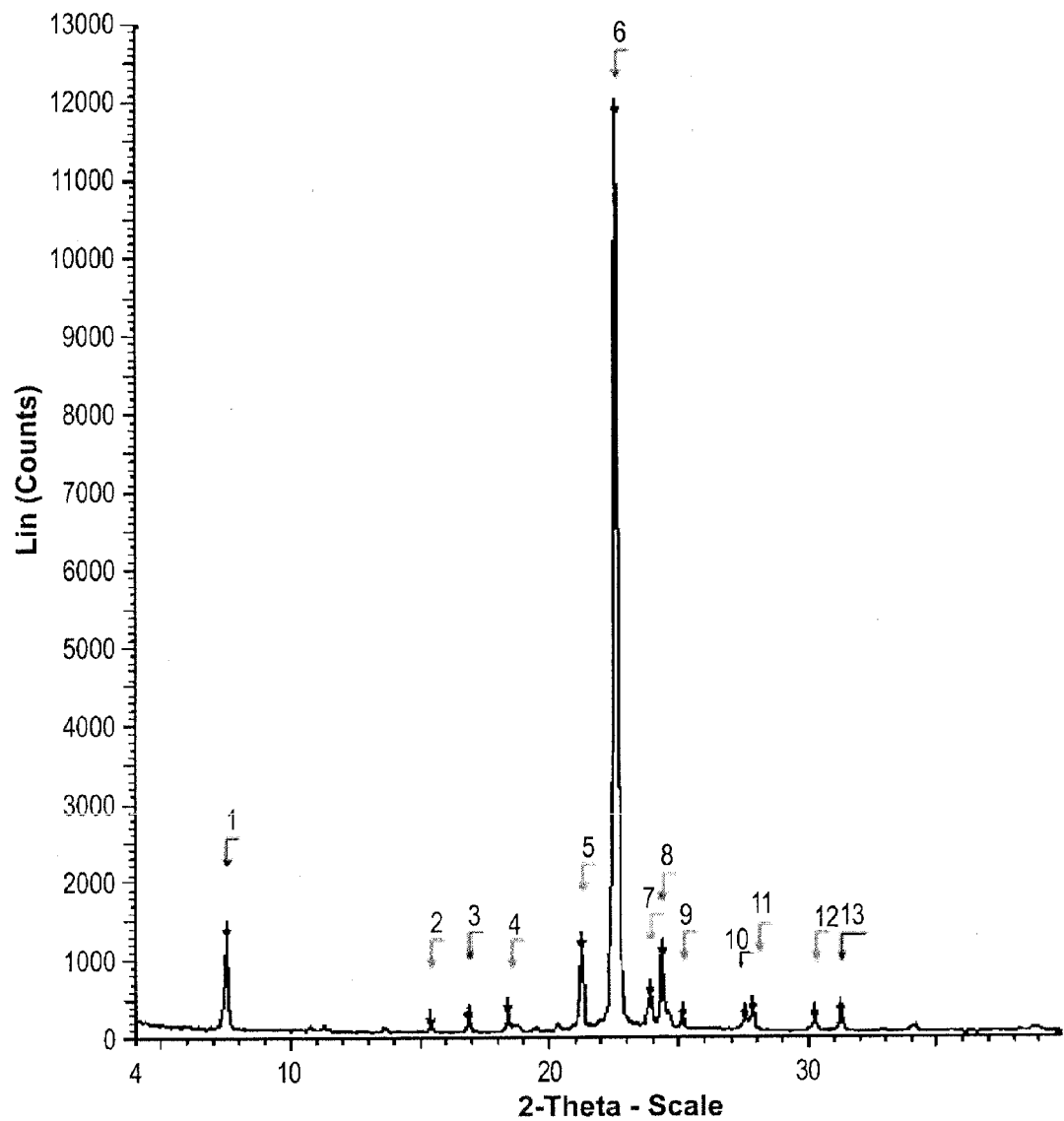
FIG. 6 is a characteristic X-ray diffraction pattern of 2-morpholino-N-(3-(4-(5-(pyrrolidine-1-carbonyl)-1H-pyrrol-3-yl)thiazol-2-yl)phenyl)acetamide (compound 7A (sample 2)).

The X-ray diffraction pattern of compound 7A (sample 1) was compared to the X-ray diffraction pattern of a sample of 2-morpholino-N-(3-(4-(5-(pyrrolidine-1-carbonyl)-1H-pyrrol-3-yl)thiazol-2-yl)phenyl)acetamide (compound 7A (sample 2) from Enamine/www.enamine.net; order number: Z134827882) (FIG. 6).

TABLE 9

A listing of the XRD parameter of 2-morpholino-N-(3-(4-(5-(pyrrolidine-1-carbonyl)-1H-pyrrol-3-yl)thiazol-2-yl)phenyl)acetamide(compound 7A (sample 2)):

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 1 | 7.469 | 11.82723 | 1291 | 10.9 | 4.525 | 9.76 | 0.171 |
| 2 | 15.357 | 5.76514 | 145 | 1.2 | 0.3 | 0.65 | 0.143 |
| 3 | 16.858 | 5.25507 | 207 | 1.7 | 0.531 | 1.15 | 0.177 |
| 4 | 18.377 | 4.82394 | 293 | 2.5 | 0.505 | 1.09 | 0.139 |
| 5 | 21.233 | 4.18115 | 1126 | 9.5 | 2.899 | 6.25 | 0.147 |
| 6 | 22.599 | 3.93127 | 11860 | 100 | 46.37 | 100.00 | 0.181 |
| 7 | 23.911 | 3.7186 | 515 | 4.3 | 1.29 | 2.78 | 0.162 |
| 8 | 24.393 | 3.64615 | 1029 | 8.7 | 2.487 | 5.36 | 0.152 |
| 9 | 25.161 | 3.5365 | 230 | 1.9 | 0.378 | 0.82 | 0.156 |
| 10 | 27.543 | 3.2359 | 209 | 1.8 | 0.31 | 0.67 | 0.175 |
| 11 | 27.891 | 3.19623 | 303 | 2.6 | 0.608 | 1.31 | 0.167 |
| 12 | 30.303 | 2.94714 | 208 | 1.8 | 0.551 | 1.19 | 0.174 |
| 13 | 31.297 | 2.85576 | 275 | 2.3 | 0.808 | 1.74 | 0.178 |

Figure 7:
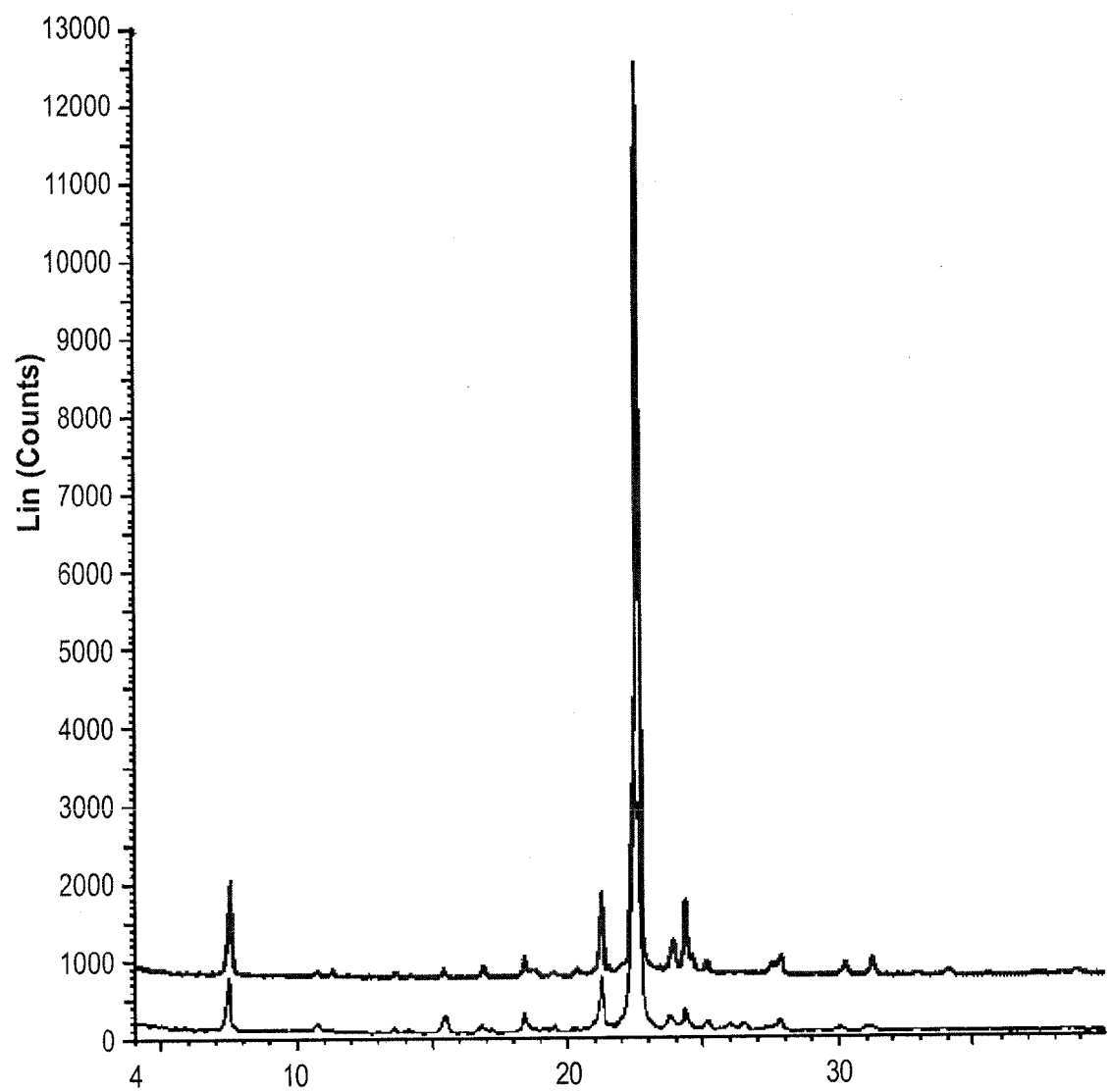
FIG. 7 is an overlay of the X-ray diffraction pattern of compound 7A (sample 1) (on the top) with the X-ray diffraction pattern of compound 7A (sample 2) (on the bottom).

FIG. 7 shows an overlay of the two spectra. The crystal forms of the two samples are identical. The XRD patterns have a 100% similarity found for peaks with intensity above 10%.

TABLE 10

A listing of the XRD parameter of 2-morpholino-N-(3-(4-(5-(pyrrolidine-1-carbonyl)-1H-pyrrol-3-yl)thiazol-2-yl)phenyl)acetamide(compound 10X):

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 1 | 7.54 | 11.71533 | 194 | 20 | 0.243 | 4.46 | 0.178 |
| 2 | 10.782 | 8.19871 | 118 | 12.1 | 0.175 | 3.21 | 0.197 |
| 3 | 14.244 | 6.21281 | 161 | 16.6 | 0.471 | 8.64 | 0.213 |
| 4 | 15.421 | 5.74124 | 358 | 36.8 | 1.419 | 26.03 | 0.216 |
| 5 | 16.907 | 5.23979 | 111 | 11.4 | 0.095 | 1.74 | 0.185 |
| 6 | 18.442 | 4.80715 | 435 | 44.8 | 2.351 | 43.12 | 0.279 |
| 7 | 19.552 | 4.53658 | 335 | 34.5 | 1.009 | 18.51 | 0.231 |
| 8 | 21.31 | 4.1662 | 972 | 100 | 5.452 | 100.00 | 0.251 |
| 9 | 22.701 | 3.91392 | 968 | 99.6 | 6.457 | 118.43 | 0.337 |
| 10 | 23.849 | 3.72811 | 212 | 21.8 | 0.437 | 8.02 | 0.263 |
| 11 | 24.457 | 3.6368 | 590 | 60.7 | 2.431 | 44.59 | 0.232 |
| 12 | 25.212 | 3.52952 | 299 | 30.8 | 0.913 | 16.75 | 0.287 |
| 13 | 27.952 | 3.1895 | 333 | 34.3 | 1.208 | 22.16 | 0.223 |
| 14 | 28.707 | 3.10728 | 105 | 10.8 | 0.031 | 0.57 | 0.055 |
| 15 | 31.472 | 2.84027 | 97 | 10 | 0.071 | 1.30 | 0.185 |
| 16 | 32.282 | 2.77083 | 93 | 9.6 | 0.032 | 0.59 | 0.059 |
| 17 | 32.98 | 2.71378 | 158 | 16.3 | 0.06 | 1.10 | 0.084 |
| 18 | 35.626 | 2.51808 | 104 | 10.7 | 0.083 | 1.52 | 0.188 |
| 19 | 37.235 | 2.41286 | 108 | 11.1 | 0.04 | 0.73 | 0.126 |
| 20 | 39.764 | 2.26504 | 95 | 9.8 | 0.077 | 1.41 | 0.14 |

Experimental:
Instrument: Bruker D8 Advance
A CuK source (=1.54056 angstrom) operating minimally at 40 kV and 200 mA, scans each sample between 4 and 40 degrees 2-theta.

Example 12

Preparation of 2-morpholino-N-(3-(4-(5-(pyrrolidine-1-carbonyl)-1H-pyrrol-3-yl)thiazol-2-yl)phenyl)acetamide hydrochloride salt (Form I) (Compound 9X)

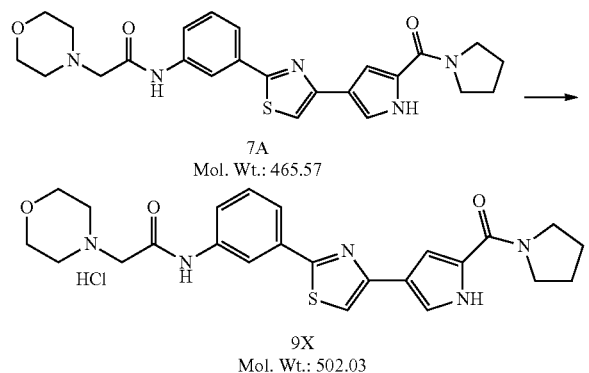

7A
Mol. Wt.: 465.57

9X
Mol. Wt.: 502.03

Reagents Table-Synthesis of 9

| Reagent/raw material | MW (gr/mole) | Quantity | mmoles | Mole ratio |
|---|---|---|---|---|
| 2-Morpholino-N-(3-(4-(5-(pyrrolidine-1-carbonyl)-1H-pyrrol-3-yl)thiazol-2-yl)phenyl)acetamide | 465.6 | 465.6 mgr | 1.0 | 1.0 |
| HCl (1.41M solution in EtOH) | 1.41M | 1.42 mL | 2.0 | 2.0 |
| Toluene | — | 30 mL | — | — |

Procedure of 9X—HCl Salt

2-Morpholino-N-(3-(4-(5-(pyrrolidine-1-carbonyl)-1H-pyrrol-3-yl)thiazol-2-yl)phenyl)acetamide (compound 7A (sample 1)) was dissolved in toluene (by heating) and HCl (1.41 M solution in EtOH) was added dropwise resulting in yellow precipitation formation. When the addition was completed, the precipitate was left to stand at rt. for 30 min., then collected by filtration, washed with water and dried in vacuum and afforded compound 9X (sample 3).

Recrystallization from hot EtOH afforded the pure product as an off-white crystalline solid: 360 mgr, 70% yield (compound 9X (sample 2)). Alternatively, recrystallization from hot methanol afforded the pure product as an off-white crystalline solid (compound 9X (sample 1)). The crystal form of all three samples of compound 9X is the same.

Analysis (Compound 7A (Sample 1))

$^1$H-NMR-DMSO-$d_6$, ppm.: 1.87-1.98 (4H, m, —CH2-CH2-); 2.45-2.55 (4H, m, —CH2-CH2-); 3.17 (2H, s, —CH2-CO—NH); 3.53 (2H, broad, —CH2-N); 3.66 (4H, t, —CH2-O—CH2-); 3.78 (2H, broad, —N—CH2-); 7.08 (1H, broad, CH Ar); 7.42 (1H, t, CH Ar); 7.67 (1H, d, CH Ar); 7.72 (1H, s, CH—S); 7.77 (1H, d, CH Ar); 8.31 (1H, s, CH—); 9.94 (1H, s, CH—NH); 11.58 (1H, s, NH). HPLC—100% purity.

MS—(ES$^+$) Calcd. 465.18. Found 466.0 (MH$^+$).

FIG. 8 shows a characteristic X-ray diffraction pattern of 2-morpholino-N-(3-(4-(5-(pyrrolidine-1-carbonyl)-1H-pyrrol-3-yl)thiazol-2-yl)phenyl)acetamide hydrochloride salt (Form I) (compound 9X (sample 1)) prepared by the above method.

TABLE 11 lists the XRD parameters of compound 9X (sample 1):

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 1 | 8.734 | 10.11647 | 101 | 6.6 | 0.134 | 2.83 | 0.104 |
| 2 | 9.8 | 9.01854 | 176 | 11.6 | 0.312 | 6.59 | 0.122 |
| 3 | 10.288 | 8.59167 | 122 | 8 | 0.158 | 3.34 | 0.084 |
| 4 | 12.324 | 7.17621 | 97 | 6.4 | 0.154 | 3.25 | 0.137 |
| 5 | 13.732 | 6.44323 | 152 | 10 | 0.268 | 5.66 | 0.091 |
| 6 | 14.403 | 6.14494 | 106 | 7 | 0.172 | 3.63 | 0.097 |
| 7 | 15.227 | 5.81385 | 71 | 4.7 | 0.067 | 1.41 | 0.111 |
| 8 | 16.025 | 5.52637 | 276 | 18.1 | 0.552 | 11.66 | 0.115 |
| 9 | 16.445 | 5.38607 | 205 | 13.5 | 0.426 | 8.99 | 0.122 |
| 10 | 16.991 | 5.21415 | 100 | 6.6 | 0.213 | 4.50 | 0.142 |
| 11 | 17.507 | 5.06171 | 83 | 5.5 | 0.085 | 1.79 | 0.086 |
| 12 | 18.023 | 4.91793 | 201 | 13.2 | 0.388 | 8.19 | 0.12 |
| 13 | 18.4 | 4.8179 | 71 | 4.7 | 0.084 | 1.77 | 0.126 |
| 14 | 18.935 | 4.6831 | 246 | 16.2 | 0.596 | 12.58 | 0.126 |
| 15 | 19.607 | 4.524 | 306 | 20.1 | 0.589 | 12.44 | 0.13 |
| 16 | 20.023 | 4.43096 | 354 | 23.3 | 0.825 | 17.42 | 0.148 |
| 17 | 20.598 | 4.3085 | 71 | 4.7 | 0.075 | 1.58 | 0.084 |
| 18 | 20.96 | 4.2349 | 142 | 9.3 | 0.292 | 6.17 | 0.113 |
| 19 | 21.429 | 4.14324 | 175 | 11.5 | 0.398 | 8.40 | 0.148 |
| 20 | 22.755 | 3.90482 | 266 | 17.5 | 0.616 | 13.01 | 0.152 |
| 21 | 23.637 | 3.76098 | 155 | 10.2 | 0.194 | 4.10 | 0.103 |
| 22 | 24.093 | 3.69082 | 1521 | 100 | 4.736 | 100.00 | 0.138 |
| 23 | 25.149 | 3.53816 | 85 | 5.6 | 0.242 | 5.11 | 0.336 |
| 24 | 25.843 | 3.4447 | 127 | 8.3 | 0.322 | 6.80 | 0.214 |
| 25 | 26.404 | 3.37278 | 324 | 21.3 | 0.72 | 15.20 | 0.144 |
| 26 | 27.087 | 3.28931 | 103 | 6.8 | 0.209 | 4.41 | 0.187 |
| 27 | 29.659 | 3.00965 | 86 | 5.7 | 0.097 | 2.05 | 0.171 |
| 28 | 31.61 | 2.82824 | 68 | 4.5 | 0.107 | 2.26 | 0.214 |
| 28 | 34.714 | 2.58206 | 84 | 5.5 | 0.138 | 2.91 | 0.152 |
| 30 | 36.225 | 2.4778 | 69 | 4.5 | 0.108 | 2.28 | 0.124 |

Figure 9:
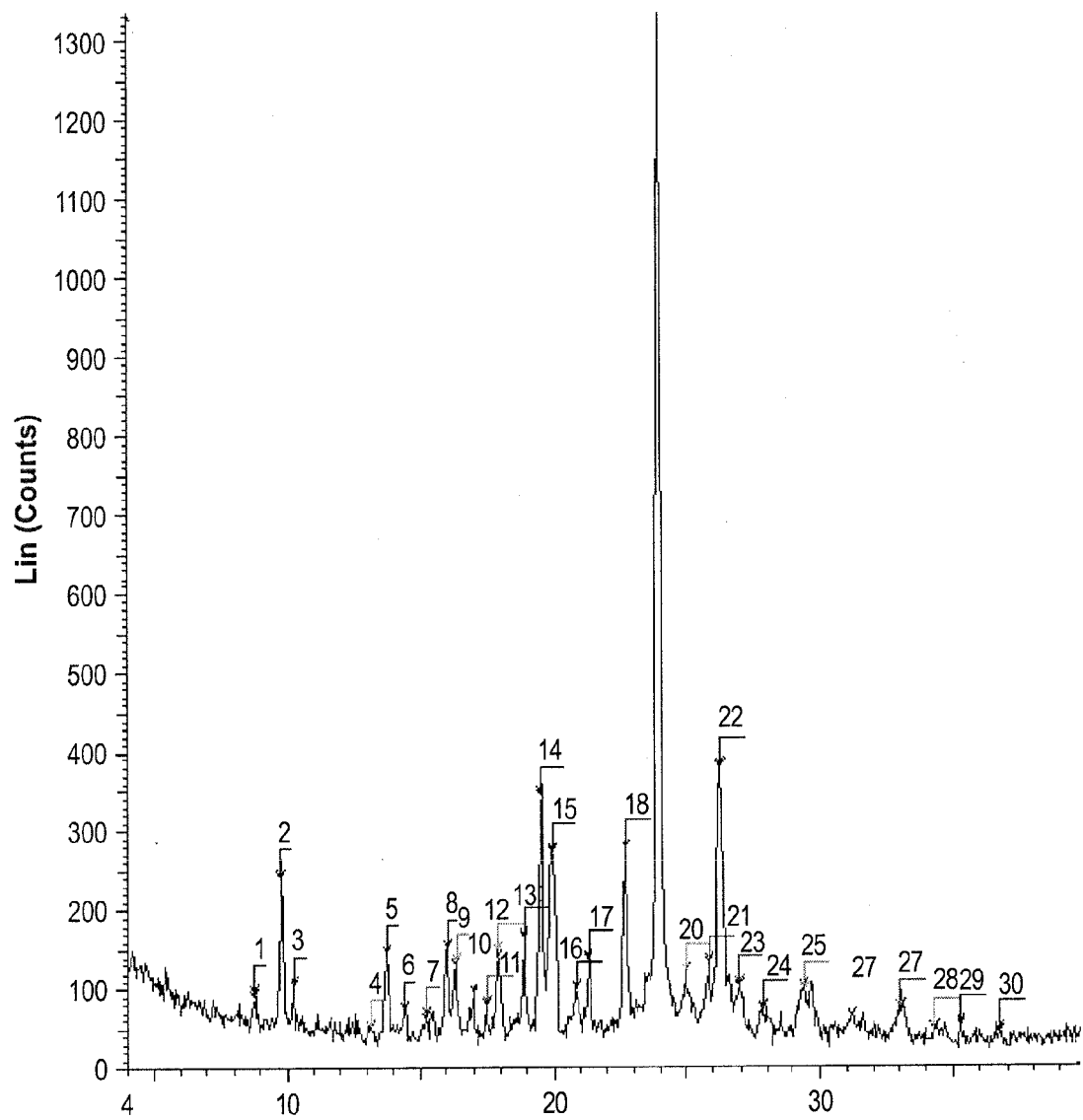
FIG. 9 is a characteristic X-ray diffraction pattern of 2-morpholino-N-(3-(4-(5-(pyrrolidine-1-carbonyl)-1H-pyrrol-3-yl)thiazol-2-yl)phenyl)acetamide hydrochloride salt (Form I), compound 9X (sample 2).

The X-ray diffraction pattern of compound 9X (sample 1) (see Table 11) was compared to the X-ray diffraction pattern of a sample of 2-morpholino-N-(3-(4-(5-(pyrrolidine-1-carbonyl)-1H-pyrrol-3-yl)thiazol-2-yl)phenyl)acetamide hydrochloride salt (Form I) (compound 9X (sample 2)) (see FIG. 9). The samples were found to have the same XRD patterns with a 92.31% similarity found for peaks with intensity above 10%.

TABLE 12 lists the XRD parameters of compound 9X (sample 3):

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 1 | 8.653 | 10.21131 | 96 | 19.3 | 0.025 | 0.86 | 0.094 |
| 2 | 9.71 | 9.10183 | 115 | 23.1 | 0.113 | 3.90 | 0.157 |
| 3 | 11.23 | 7.8725 | 78 | 15.7 | 0.064 | 2.21 | 0.103 |
| 4 | 12.037 | 7.34691 | 78 | 15.7 | 0.047 | 1.62 | 0.15 |
| 5 | 12.582 | 7.02957 | 77 | 15.5 | 0.119 | 4.11 | 0.264 |
| 6 | 13.734 | 6.44247 | 111 | 22.3 | 0.155 | 5.35 | 0.254 |
| 7 | 16.029 | 5.52485 | 172 | 34.6 | 0.542 | 18.72 | 0.283 |
| 8 | 17.837 | 4.96876 | 150 | 30.2 | 0.299 | 10.33 | 0.213 |
| 9 | 19.022 | 4.66168 | 150 | 30.2 | 0.261 | 9.02 | 0.318 |
| 10 | 19.954 | 4.44601 | 249 | 50.1 | 0.789 | 27.25 | 0.372 |

TABLE 12-continued lists the XRD parameters of compound 9X (sample 3):

| # | Angle 2-Theta ° | d value Angstrom | Intensity Count | Intensity (%) | Net Area Cps × 2-Theta ° | Area (%) | FWHM 2-Theta ° |
|---|---|---|---|---|---|---|---|
| 11 | 20.846 | 4.25782 | 129 | 26 | 0.071 | 2.45 | 0.198 |
| 12 | 21.285 | 4.17094 | 125 | 25.2 | 0.094 | 3.25 | 0.187 |
| 13 | 22.663 | 3.92033 | 185 | 37.2 | 0.08 | 2.76 | 0.108 |
| 14 | 23.058 | 3.8541 | 169 | 34 | 0.063 | 2.18 | 0.067 |
| 15 | 23.866 | 3.72549 | 497 | 100 | 2.895 | 100.00 | 0.405 |
| 16 | 25.881 | 3.43984 | 189 | 38 | 0.044 | 1.52 | 0.091 |
| 17 | 26.151 | 3.40488 | 197 | 39.6 | 0.061 | 2.11 | 0.091 |
| 18 | 26.548 | 3.35482 | 162 | 32.6 | 0.019 | 0.66 | 0.06 |
| 19 | 27.003 | 3.29936 | 141 | 28.4 | 0.04 | 1.38 | 0.092 |
| 20 | 29.459 | 3.02967 | 101 | 20.3 | 0.027 | 0.93 | 0.05 |
| 21 | 30.962 | 2.8859 | 92 | 18.5 | 0.057 | 1.97 | 0.124 |
| 22 | 36.744 | 2.44395 | 66 | 13.3 | 0.063 | 2.18 | 0.172 |
| 23 | 38.012 | 2.3653 | 71 | 14.3 | 0.055 | 1.90 | 0.102 |

The XRD for compound 9X (sample 3) is the same as for compound 9X (sample 1) and compound 9X (sample 2).

Experimental:
Instrument: Bruker D8 Advance
A CuK source (=1.54056 angstrom) operating minimally at 40 kV and 40 mA, scans each sample between 4 and 40 degrees 2-theta.

Example 13

Comparison of X-ray diffraction patterns of compound 7A (sample 1) obtained by the method of Example 11 and compound 9X (sample 1) prepared by the method of Example 12. Compared with compound 9X (sample 1), compound 7A (sample 1) has distinctive peaks at 4.262°, 19.126°, 22.072°, respectively, indicating that it has a different crystal form. The samples have different XRPD patterns with a 30.77% similarity found for peaks with intensity above 10%.

Example 14

Differential Scanning Calorimetric (DSC) analysis was performed on compound 7A (sample 1), compound 9X (samples 1 and 2), and compound 10X obtained in accordance with the process of the present invention. The DSC thermograms are shown in FIGS. 10, 11, 13, and 18. The parent compound (free base) melts at 217.6° C. In contrast, 2-morpholino-N-(3-(4-(5-(pyrrolidine-1-carbonyl)-1H-pyrrol-3-yl)thiazol-2-yl)phenyl)acetamide hydrochloride salt (Form I) undergoes decomposition before melting, and thus, there is no apparent peak to be recognized.

Equipment: DSC Q2000 V24.4 Build 116
Differential Scanning Calorimeter Conditions:
Gas 1: nitrogen 50.0 ml/min
Pan mass: 29.765 28.364 mg
Pan type: aluminum
Method log:
1: equilibrate at 25.00° C.
2: ramp 10.00° C./min to 400.00° C.
3: end of method Example 15

Aqueous Solubility Test

The kinetic solubility of test compounds was evaluated in 100 mM phosphate buffer (7.4). The test concentration was 100 µM (0% of DMSO for test compounds, 1% of DMSO for reference compounds). The test system was a 100 mM phosphate buffer (pH 7.4). Sample size was duplicates (n=2) and the bioanalytical method was LC-UV (Agilent-1200). Mobile phase A: $H_2O$-1% TFA, B: MeOH-1% TFA; column Boston Symmetrix ODS-H (2.1×50 mm, 5 µm); LC conditions 0.4 mL/Min.
For Test Compounds:

| Time (min) | Pump B |
|---|---|
| 0.1 | 30 |
| 1.6 | 95 |
| 3.8 | 95 |
| 4.0 | 30 |
| 6.0 | stop |

| | Compound name | Rentention time (min) | Wave length (nm) |
|---|---|---|---|
| Retention time and wave length | Tamoxifen | 4.7 min | 295 nm |
| | Ketoconazole | 4.6 min | 280 nm |
| | Propranolol | 4.3 min | 295 nm |
| | Compound 7A (sample 1) | 3.8 min | 260 nm |
| | Compound 9X (sample 2) | 3.8 min | 260 nm |

The results are shown in Table 13 below. Tamoxifen is a low solubility control and showed less than 1 µM in PBS; Ketoconazole, was a moderate solubility control and showed solubility of 15.9 µM in PBS; Propranolol was a high solubility control and showed solubility in PBS around dosing concentration 100 µM. The results in Table 13 show that the crystalline hydrochloride salt (compound 9X (sample 2)) exhibits superior solubility over the parent compound 7A (sample 1). Specifically, the solubility of compound is low <10 µM in PBS, whereas compound 9X (sample 2) exhibited a solubility of 10-80 µM in PBS.

TABLE 13

| | | | | Solubility (µM) | |
|---|---|---|---|---|---|
| Test article | Test system | Linear equation* | $R^2$ | Mean | RSD |
| Tamoxifen | 100 mM phosphate buffer (pH 7.4) | y = 14.843x − 1.902 | 0.9994 | <1 | N/A |
| Ketoconazole | 100 mM phosphate buffer (pH 7.4) | y = 2.5231x + 4.0853 | 0.9993 | 15.9 | 0.00 |
| Propranolol | 100 mM phosphate buffer (pH 7.4) | y = 13.605x − 10.331 | 0.9997 | >100 (112.8) | 0.01 |
| Compound 7A (sample 1) | 100 mM phosphate buffer (pH 7.4) | y = 41.583x − 2.8644 | 1.0000 | 5.9 | 0.01 |
| Compound 9X (sample 2) | 100 mM phosphate buffer (pH 7.4) | y = 35.014x − 7.7358 | 0.9997 | 51.9 | 0.03 |

Assay Procedure
1. For reference compounds:
    Add 8 μL of 10 mM DMSO stock solution into 792 μL of 100 mM phosphate buffer (n=2). Final conc.=100 μM (1% of DMSO)
    For test compounds:
    Add 8 μL of 10 mM DMSO stock solution into the tubes (n=2).
    Dry the samples under nitrogen.
    Add 800 μL of 100 mM phosphate buffer into the tubes. Final conc.=100 μM (0% of DMSO)
2. Sample tubes are shaken for 1 hour (1000 rpm) at room temperature and 37° C.
3. Samples are centrifuged (10 min-12000 rpm) to precipitate un-dissolved particles.
4. Supernatants are transferred to new tubes
5. Concentrations of the supernatants after centrifugation are determined by LC-UV detection.

Example 16

Preparation of Other Crystalline Salt Forms

Figure 13:
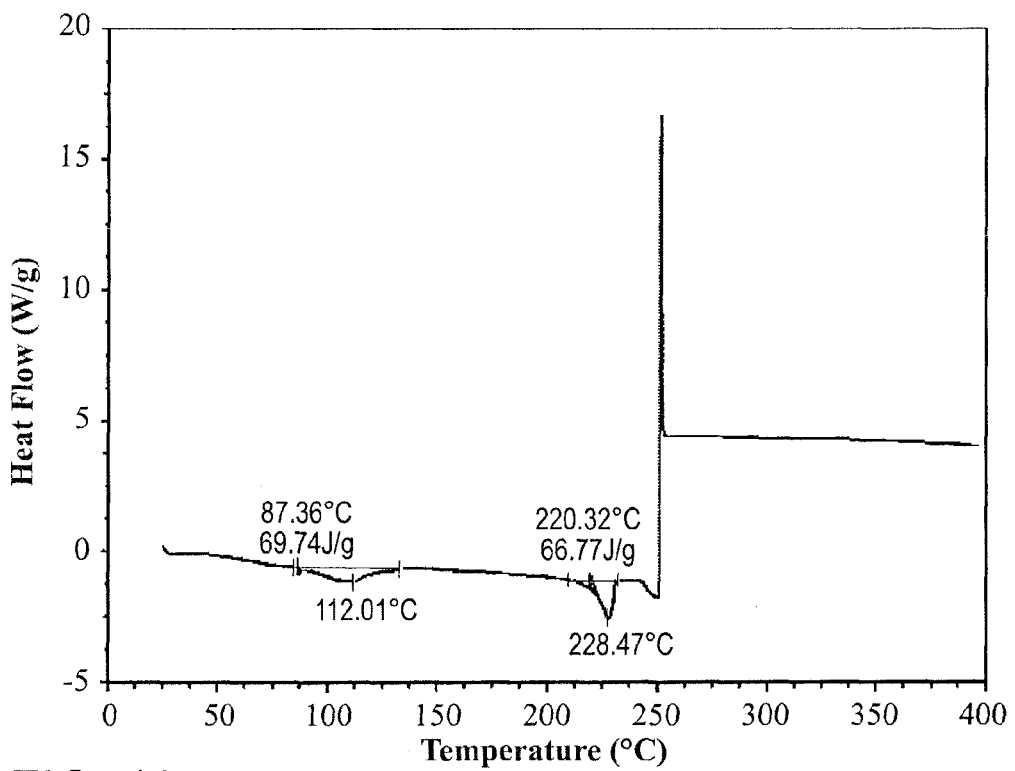
FIG. 13 is a DSC thermogram for the methanesulfonic acid salt of 2-morpholino-N-(3-(4-(5-(pyrrolidine-1-carbonyl)-1H-pyrrol-3-yl)thiazol-2-yl)phenyl)acetamide (Example 15).
Figure 14:
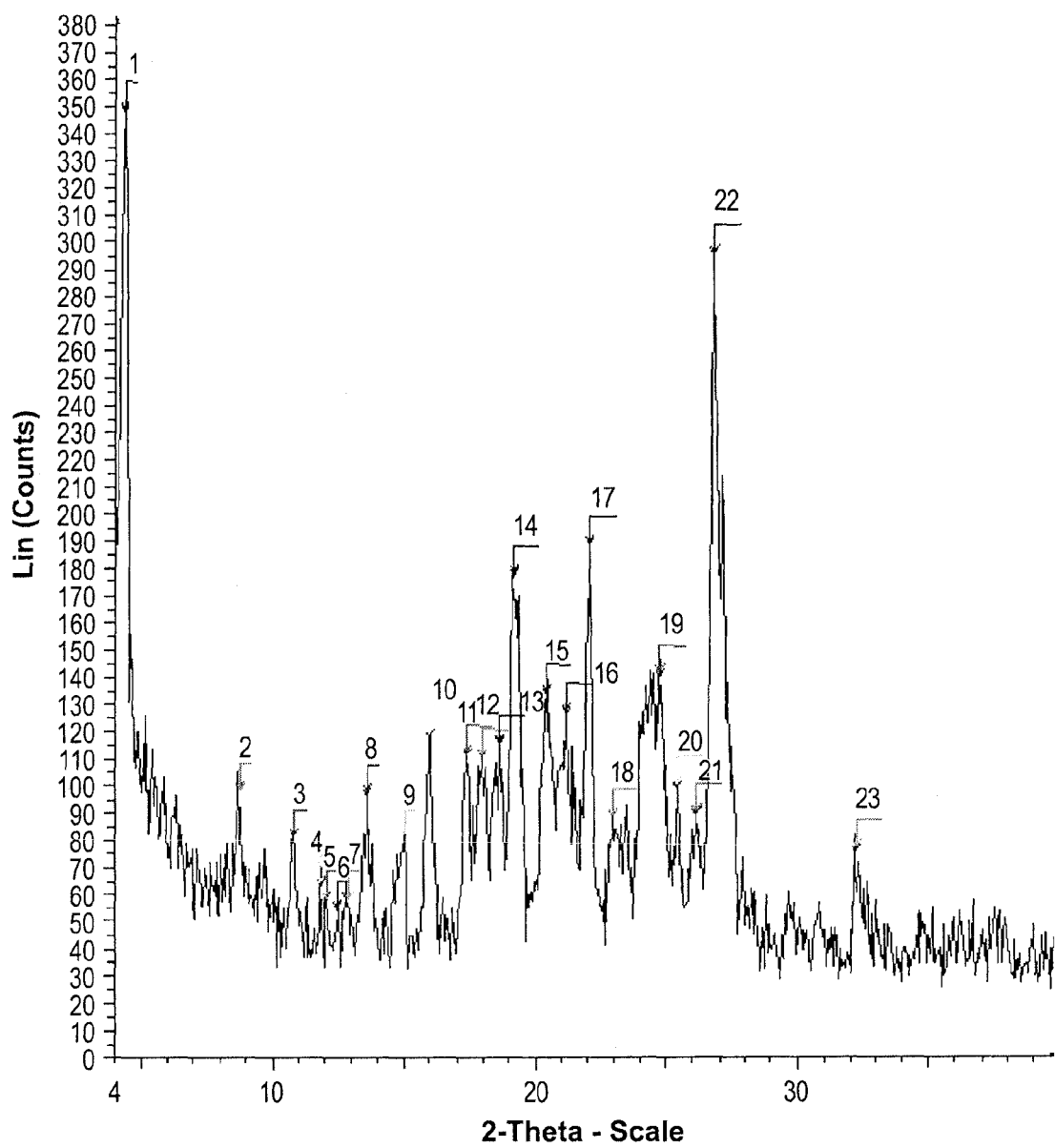
FIG. 14 is a characteristic X-ray diffraction pattern of the methane sulfonic acid salt of morpholino-N-(3-(4-(5-(pyrrolidine-1-carbonyl)-1H-pyrrol-3-yl)thiazol-2-yl)phenyl)acetamide (Example 15).

The preparation of other crystalline salt forms of 2-morpholino-N-(3-(4-(5-(pyrrolidine-1-carbonyl)-1H-pyrrol-3-yl)thiazol-2-yl)phenyl)acetamide was attempted. Specifically, attempts were made to prepare crystalline forms of the $H_2SO_4$, methanesulfonic acid, and acetic acid salts. Recrystallization of the sulfate salt and the acetate salt from toluene did not afford crystalline forms suitable for further study. Recrystallization of the methanesulfonic acid salt from toluene produced an amorphous form. FIGS. 13 and 14 show the DSC and XRPD data obtained for this methanesulfonic acid salt.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:
1. A polymorph 2-morpholino-N-(3-(4-(5-(pyrrolidine-1-carbonyl)-1H-pyrrol-3-yl)thiazol-2-yl)phenyl)acetamide hydrochloride salt (Form I) represented by the formula:

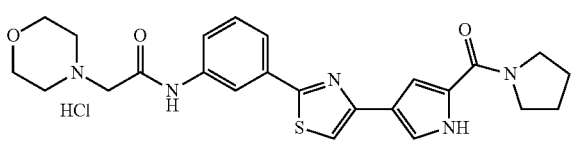

wherein, said polymorph is characterized by at least one of the following: an X-ray diffraction pattern characterized by an X-ray diffraction peak pattern substantially similar to that set forth in FIG. 8 or a Differential Scanning Calorimetry (DSC) thermogram having a decomposition trace substantially similar to that set forth in FIG. 10.

2. The polymorph according to claim 1, characterized by an X-ray diffraction pattern including characteristic peaks at about 26.4, 24.1, 22.8, 20.0, 18.9, and 9.8 degrees 2θ.

3. A polymorph 2-morpholino-N-(3-(4-(5-(pyrrolidine-1-carbonyl)-1H-pyrrol-3-yl)thiazol-2-yl)phenyl)acetamide (Form I) represented by the formula:

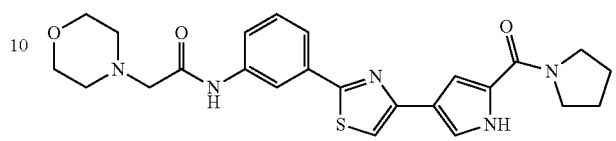

wherein, said polymorph is characterized by at least one of the following: an X-ray diffraction pattern characterized by an X-ray diffraction peak pattern substantially similar to that set forth in FIG. 15 or a Differential Scanning Calorimetry (DSC) thermogram having a decomposition trace substantially similar to that set forth in FIG. 19.

4. The polymorph according to claim 3, characterized by an X-ray diffraction pattern including characteristic peaks at about 21.3, 22.7, and 24.5 degrees 2θ.

5. A pharmaceutical composition comprising a compound according formula VII:

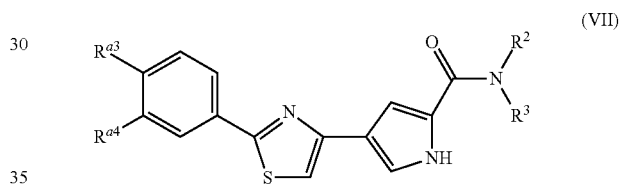

or a pharmaceutically acceptable salt, solvate, polymorph, or prodrug thereof,
wherein:
$R^2$ and $R^3$ either
(i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, $C_3$-$C_8$ cycloalkenyl, or heterocycloalkyl; or
(ii) together with the nitrogen atom to which they are attached, form a five, six, or seven membered heterocycloalkyl or heteroaromatic ring, wherein said heterocycloalkyl or heteroaromatic ring is unsubstituted; Rai and $R^{ao}$ are each independently selected from the group consisting of:
a) a linear or branched $C_1$-$C_6$ alkyl,
b) a linear or branched $C_2$-$C_6$ alkenyl,
c) a linear or branched $C_2$-$C_6$ alkynyl,
d) a linear or branched, saturated or unsaturated $C_1$-$C_6$ haloalkyl,
e) a linear or branched, saturated or unsaturated $C_1$-$C_6$ alkoxy or aryloxy,
f) a linear or branched, saturated or unsaturated $C_1$-$C_6$ haloalkoxy,
g) a linear or branched, saturated or unsaturated $C_1$-$C_6$ alkylsulfonyl, h) a linear or branched, saturated or unsaturated $C_1$-$C_6$ thioalkyl or thioaryl, wherein said alkyl, alkenyl, alkynyl, and aryl in a)-h) is unsubstituted or substituted independently at each occurrence with one or more $R^b$, i) a $C_3$-$C_8$ cycloalkyl, wherein said cycloalkyl is unsubstituted or substituted independently at each occurrence with one or more $R^b$, j) a $C_3$-$C_8$ cycloalkenyl, wherein said cycloalkenyl is unsubstituted or substituted independently at each occurrence with one or more $R^b$, k) an aryl, wherein said aryl is unsubstituted or substituted independently at each occurrence with one or more $R^b$, l) a heteroaryl, wherein said heteroaryl is unsubstituted or substituted independently at each occurrence with one or more $R^b$, m) a heterocycloalkyl, wherein said heterocycloalkyl is unsubstituted or substituted independently at each occurrence with one or more $R^b$, n) hydroxyl, o) cyano, p) amino, q) nitro, r) halogen, s) $COR^b$, t) $COOR^b$, u) $CONR^b R^c$, v) $NHCOR^b$, w) $NR^b R^c$, and x) hydrogen, or $R^{a3}$ and $R^{a4}$ together with the atoms to which they are attached, form a five or six membered heterocycloalkyl, an aryl, or heteroaromatic ring;

wherein $R^b$ and $R^c$ are, each independently, hydrogen or a group selected from halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;

wherein said alkyl, alkenyl, alkynyl, cycloalkyl, cycloalkenyl, heterocycloalkyl, aryl or heteroaryl is unsubstituted or substituted with one or more $R^d$, wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;

two $R^b$ with the atoms to which they are attached, form a five or six membered heterocycloalkyl ring and at least one pharmaceutically acceptable excipient.

6. The pharmaceutical composition according to claim 5, wherein $R^2$ and $R^3$ are each independently selected from a linear or branched $C_1$-$C_6$ alkyl, hydrogen, and $C_3$-$C_8$ cycloalkyl, or $R^2$ and $R^3$ together with the nitrogen atom to which they are attached form a five, six, or seven membered heterocycloalkyl.

7. The pharmaceutical composition according to claim 6, wherein $R^2$ and $R^3$ together with the nitrogen atom to which they are attached, form a pyrrolidine or piperidine ring.

8. A pharmaceutical composition comprising a compound of formula XII:

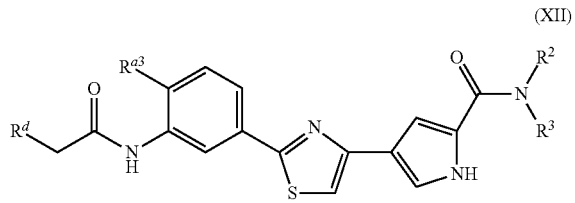

(XII)

or a pharmaceutically acceptable salt, solvate, polymorph, or prodrug thereof, wherein:

$R^2$ and $R^3$ either (i) are each independently, selected from the group consisting of a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, a heterocycloalkyl, and $COR^e$, wherein $R^e$ is selected from a hydrogen, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, $C_3$-$C_8$ cycloalkenyl, or heterocycloalkyl; or (ii) together with the nitrogen atom to which they are attached, form a five, six, or seven membered heterocycloalkyl or heteroaromatic ring, wherein said heterocycloalkyl or heteroaromatic ring is unsubstituted;

$R^{a3}$ is selected from the group consisting of:

a) a linear or branched $C_1$-$C_6$ alkyl, b) a linear or branched $C_2$-$C_6$ alkenyl, c) a linear or branched $C_2$-$C_6$ alkynyl, d) a linear or branched, saturated or unsaturated $C_1$-$C_6$ haloalkyl, e) a linear or branched, saturated or unsaturated $C_1$-$C_6$ alkoxy or aryloxy, f) a linear or branched, saturated or unsaturated $C_1$-$C_6$ haloalkoxy, g) a linear or branched, saturated or unsaturated $C_1$-$C_6$ alkylsulfonyl, h) a linear or branched, saturated or unsaturated $C_1$-$C_6$ thioalkyl or thioaryl, wherein said alkyl, alkenyl, alkynyl, and aryl in a)-h) is unsubstituted or substituted independently at each occurrence with one or more $R^b$, i) a $C_3$-$C_8$ cycloalkyl, wherein said cycloalkyl is unsubstituted or substituted independently at each occurrence with one or more $R^b$, j) a $C_3$-$C_8$ cycloalkenyl, wherein said cycloalkenyl is unsubstituted or substituted independently at each occurrence with one or more $R^b$, k) an aryl, wherein said aryl is unsubstituted or substituted independently at each occurrence with one or more $R^b$, l) a heteroaryl, wherein said heteroaryl is unsubstituted or substituted independently at each occurrence with one or more $R^b$, m) a heterocycloalkyl, wherein said heterocycloalkyl is unsubstituted or substituted independently at each occurrence with one or more $R^b$, n) hydroxyl, o) cyano, p) amino,
q) nitro,
r) halogen,
s) $COR^b$,
t) $COOR^b$,
u) $CONR^b R^c$,
v) $NHCOR^b$,
w) $NR^b R^c$, and
x) hydrogen,
wherein $R^b$ and $R^c$ are, each independently, hydrogen or a group selected from halogen, $CF_3$, $C(O)CH_3$, a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl and a heteroaryl;
wherein said alkyl, alkenyl, alkynyl, cycloalkyl, cycloalkenyl, heterocycloalkyl, aryl or heteroaryl is unsubstituted or substituted with one or more $R^d$,
wherein $R^d$ is independently at each occurrence selected from the group consisting of a linear or branched $C_1$-$C_6$ alkyl, a linear or branched $C_2$-$C_6$ alkenyl, a linear or branched $C_2$-$C_6$ alkynyl, a $C_3$-$C_8$ cycloalkyl, a $C_3$-$C_8$ cycloalkenyl, heterocycloalkyl, an aryl, a dialkylamine, a monoalkylamine, and a heteroaryl;
two $R^b$ with the atoms to which they are attached, form a five or six membered heterocycloalkyl ring and at least one pharmaceutically acceptable excipient.

9. The pharmaceutical composition according to claim 8, wherein $R^d$ is selected from heterocycloalkyl, dialkylamine, monoalkylamine, and $C_3$-$C_8$ cycloalkyl, provided that when $R^2$ and $R^3$ together with the nitrogen atom to which they are attached, form pyrrolidine, then $R^{a3}$ is not hydrogen, when $R^d$ is

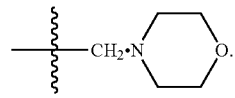

10. The pharmaceutical composition according to claim 5 comprising a compound chosen in the group consisting of

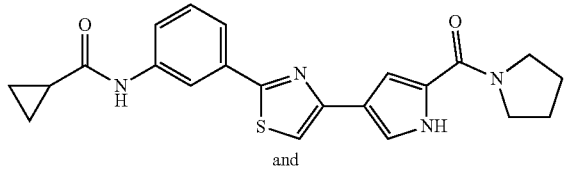

and

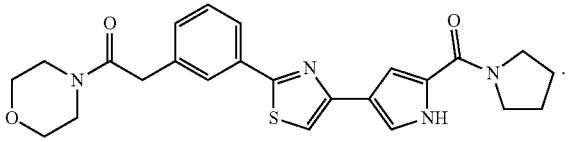

11. A compound of formula

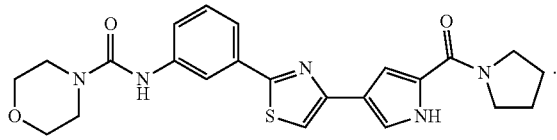 [SMILES: O=C(Nc1cccc(-c2nc(-c3c[nH]c(C(=O)N4CCCC4)c3)cs2)c1)N1CCOCC1 ; "."]

* * * * *

UNITED STATES PATENT AND TRADEMARK OFFICE
CERTIFICATE OF CORRECTION

PATENT NO. : 8,937,065 B2
APPLICATION NO. : 13/491069
DATED : January 20, 2015
INVENTOR(S) : Oren M. Becker et al.

It is certified that error appears in the above-identified patent and that said Letters Patent is hereby corrected as shown below:

In the Claims
Column 432, line 54-55, should read as follows:

-- cloalkyl or heteroaromatic ring is unsubstituted;
$R^{a3}$ and $R^{a4}$ are each independently selected from the group consisting of:
    a) a linear or branched $C_1$-$C_6$ alkyl, --.

Signed and Sealed this
Nineteenth Day of July, 2016

Michelle K. Lee
*Director of the United States Patent and Trademark Office*